US012655451B2

(12) United States Patent
Duchateau et al.

(10) Patent No.: US 12,655,451 B2
(45) Date of Patent: Jun. 16, 2026

(54) TAL-EFFECTOR NUCLEASE (TALEN)-MODIFIED ALLOGENIC CELLS SUITABLE FOR THERAPY

(71) Applicant: CELLECTIS, Paris (FR)

(72) Inventors: Philippe Duchateau, Draveil (FR); Brian Busser, New York, NY (US); Alexandre Juillerat, New York, NY (US); Anne-Sophie Gautron, Etrechy (FR); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 1704 days.

(21) Appl. No.: 16/340,412

(22) PCT Filed: Oct. 19, 2017

(86) PCT No.: PCT/EP2017/076800
§ 371 (c)(1),
(2) Date: Apr. 9, 2019

(87) PCT Pub. No.: WO2018/073393
PCT Pub. Date: Apr. 26, 2018

(65) Prior Publication Data
US 2023/0138915 A1      May 4, 2023

Related U.S. Application Data

(60) Provisional application No. 62/410,187, filed on Oct. 19, 2016.

(30) Foreign Application Priority Data

Mar. 31, 2017    (DK) ............................ PA2017 70240

(51) Int. Cl.
| | |
|---|---|
| *C12N 15/90* | (2006.01) |
| *A61K 40/11* | (2025.01) |
| *A61K 40/31* | (2025.01) |
| *A61K 40/32* | (2025.01) |
| *A61K 40/42* | (2025.01) |
| *C07K 14/705* | (2006.01) |
| *C07K 14/725* | (2006.01) |
| *C12N 5/0783* | (2010.01) |
| *C12N 9/22* | (2006.01) |
| *C12N 15/11* | (2006.01) |

(52) U.S. Cl.
CPC ............ *C12N 15/907* (2013.01); *A61K 40/11* (2025.01); *A61K 40/31* (2025.01); *A61K 40/32* (2025.01); *A61K 40/4212* (2025.01); *A61K 40/4217* (2025.01); *C07K 14/7051* (2013.01); *C12N 5/0636* (2013.01); *C12N 5/0638* (2013.01); *C12N 9/22* (2013.01); *C12N 15/11* (2013.01); *C12N 2310/20* (2017.05); *C12N 2800/80* (2013.01)

(58) Field of Classification Search
CPC ...................................................... A61K 35/17
See application file for complete search history.

(56) References Cited

U.S. PATENT DOCUMENTS

| | | | |
|---|---|---|---|
| 10,882,914 B2 * | 1/2021 | Swanson ................. | A61P 17/06 |
| 2013/0315884 A1 * | 11/2013 | Galetto .............. | C07K 14/7051 |
| | | | 435/375 |
| 2016/0272999 A1 | 9/2016 | Cellectis | |

FOREIGN PATENT DOCUMENTS

| | | | | |
|---|---|---|---|---|
| WO | 2014191128 A1 | 12/2014 | | |
| WO | 2015136001 A1 | 9/2015 | | |
| WO | 2016124765 A1 | 8/2016 | | |
| WO | 2016160721 A1 | 10/2016 | | |
| WO | WO-2017062451 A1 * | 4/2017 | ............. | A61K 35/17 |

OTHER PUBLICATIONS

Bridgeman et al. (J. Immunol. Jun. 15, 2010; 184 (12): 6938-49).*
Hudecek et al. (Clin. Cancer Res. Jun. 15, 2013; 19 (12): 3153-64).*
Long et al. (Nat. Med. Jun. 2015; 21 (6): 581-90).*
Künkele et al. (Cancer Immunol. Res. Apr. 2015; 3 (4): 368-79).*
Fujiwara et al. (Cells. May 9, 2020; 9 (5): 1182; pp. 1-17).*
Poirot et al., Multiplex Genome-Edited T-cell Manufacturing Platform for "Off-the-Shelf" Adoptive T-cell Immunotherapies, Cancer Res; 75(18) Sep. 15, 2015, 3853-3864.
Van Der Stegen et al., The pharmacology of second generation chimeric antigen receptors, Nat. Rev. Drug Discov. Jul. 2015 ; 14(7): 499-509.

* cited by examiner

*Primary Examiner* — Zachariah Lucas
*Assistant Examiner* — Sarah A Alsomairy
(74) *Attorney, Agent, or Firm* — Arrigo, Lee, Guttman & Mouta-Bellum LLP

(57) ABSTRACT

The invention relates to the fields of immunotherapy, molecular biology and recombinant nucleic acid technology. In particular, the invention relates to a TALEN-modified human primary cell comprising in its genome, a modified human T cell receptor alpha gene with an insertion comprising at least, from 5' to 3', a polynucleotide encoding a self-cleaving peptide, a chimeric antigen receptor, wherein the cell has undetectable cell-surface expression of the endogenous alpha beta T cell receptor as compared to a TCR positive control cell and expresses a receptor to target a pathological cell, use of said cell for treating a disease, including cancer. The invention further relates to methods for producing such a TALEN-modified cell, and to means for detecting such an engineered human primary cell or other genetically modified human primary cell obtained using alternative and/or additional rare cutting endonucleases.

13 Claims, 8 Drawing Sheets
Specification includes a Sequence Listing.

TCR KO, Exogenous gene inserted

Endogenous TCR maintained, Exogenous gene co-expressed

Endogenous TCR inactivated,
Recombinant TCR expressed

TCR KO, Exogenous gene expressed (IRES)

Endogenous TCR maintained, exogenous gene co-expressed (IRES)

Endogenous TCR inactivated,
Recombinant TCR expressed (IRES)

TCR KO, Exogenous gene expressed,
TALEN target site edited

SEQUENCE LISTING

```
<160> NUMBER OF SEQ ID NOS: 164

<210> SEQ ID NO 1
<211> LENGTH: 2781
<212> TYPE: DNA
<213> ORGANISM: Artificial Sequence
<220> FEATURE:
<223> OTHER INFORMATION: TALEN TRAC_T01-L1

<400> SEQUENCE: 1
atgggcgatc ctaaaaagaa acgtaaggtc atcgatatcg ccgatctacg cacgctcggc        60
tacagccagc agcaacagga gaagatcaaa ccgaaggttc gttcgacagt ggcgcagcac       120
cacgaggcac tggtcggcca cgggtttaca cacgcgcaca tcgttgcgtt aagccaacac       180
ccggcagcgt tagggaccgt cgctgtcaag tatcaggaca tgatcgcagc gttgccagag       240
gcgacacacg aagcgatcgt tggcgtcggc aaacagtggt ccggcgcacg cgctctggag       300
gccttgctca cggtggcggg agagttagaa ggtccaccgt tacagttgga cacaggccaa       360
cttctcaaga ttgcaaaacg tggcggcgtg accgcagtgg aggcagtgca tgcatggcgc       420
aatgcactga cgggtgcccc gctcaacttg acccccagc aggtggtggc catcgccagc       480
aatggcggtg gcaagcaggc gctggagacg gtccagcggc tgttgccggt gctgtgccag       540
gcccacggct tgacccccca gcaggtggtg gccatcgcca gcaataatgg tggcaagcag       600
gcgctggaga cggtccagcg gctgttgccg gtgctgtgcc aggcccacgg cttgaccccc       660
cagcaggtgg tggccatcgc cagcaatggc ggtggcaagc aggcgctgga cggtccag       720 cggctgttgc cggtgctgtg ccaggcccac ggcttgaccc cggagcaggt ggtggccatc       780
gccagccacg atggcggcaa gcaggcgctg gagacggtcc agcggctgtt gccggtgctg       840
tgccaggccc acggcttgac cccggagcag gtggtggcca tcgccagcca cgatggcggc       900
aagcaggcgc tggagacggt ccagcggctg ttgccggtgc tgtgccaggc ccacggcttg       960
accccggagc aggtggtggc catcgccagc cacgatggcg gcaagcaggc gctggagacg      1020
gtccagcggc tgttgccggt gctgtgccag gcccacggct tgaccccgga gcaggtggtg      1080
gccatcgcca gcaatattgg tggcaagcag gcgctggaga cggtgcaggc gctgttgccg      1140
gtgctgtgcc aggcccacgg cttgaccccg gagcaggtgg tggccatcgc cagccacgat      1200
ggcggcaagc aggcgctgga cggtccag cggctgttgc cggtgctgtg ccaggcccac      1260
ggcttgaccc cggagcaggt ggtggccatc gccagcaata ttggtggcaa gcaggcgctg      1320
gagacggtgc aggcgctgtt gccggtgctg tgccaggccc acggcttgac cccccagcag      1380
gtggtggcca tcgccagcaa taatggtggc aagcaggcgc tggagacggt ccagcggctg      1440
ttgccggtgc tgtgccaggc ccacggcttg accccggagc aggtggtggc catcgccagc      1500
aatattggtg gcaagcaggc gctggagacg gtgcaggcgc tgttgccggt gctgtgccag      1560
gcccacggct tgaccccca gcaggtggtg gccatcgcca gcaatggcgg tggcaagcag      1620
gcgctggaga cggtccagcg gctgttgccg gtgctgtgcc aggcccacgg cttgaccccg      1680
gagcaggtgg tggccatcgc cagcaatatt ggtggcaagc aggcgctgga cggtgcag      1740 gcgctgttgc cggtgctgtg ccaggcccac ggcttgaccc cccagcaggt ggtggccatc      1800
gccagcaatg cggtggcaa gcaggcgctg gagacggtcc agcggctgtt gccggtgctg      1860
tgccaggccc acggcttgac cccggagcag gtggtggcca tcgccagcca cgatggcggc      1920
aagcaggcgc tggagacggt ccagcggctg ttgccggtgc tgtgccaggc ccacggcttg      1980 accccctcagc aggtggtggc catcgccagc aatggcggcg gcaggccggc gctggagagc      2040
```

```
attgttgccc agttatctcg ccctgatccg gcgttggccg cgttgaccaa cgaccacctc   2100
gtcgccttgg cctgcctcgg cgggcgtcct gcgctggatg cagtgaaaaa gggattgggg   2160
gatcctatca gccgttccca gctggtgaag tccgagctgg aggagaagaa atccgagttg   2220
aggcacaagc tgaagtacgt gccccacgag tacatcgagc tgatcgagat cgcccggaac   2280
agcacccagg accgtatcct ggagatgaag gtgatggagt tcttcatgaa ggtgtacggc   2340 tacagggca agcacctggg cggctccagg aagcccgacg cgccatcta caccgtgggc    2400 tcccccatcg actacggcgt gatcgtggac accaaggcct actccggcgg ctacaacctg   2460
cccatcggcc aggccgacga aatgcagagg tacgtggagg agaaccagac caggaacaag   2520
cacatcaacc ccaacgagtg gtggaaggtg taccctcca gcgtgaccga gttcaagttc    2580
ctgttcgtgt ccggccactt caagggcaac tacaaggccc agctgaccag gctgaaccac   2640
atcaccaact gcaacggcgc cgtgctgtcc gtggaggagc tcctgatcgg cggcgagatg   2700
atcaaggccg gcaccctgac cctggaggag gtgaggagga agttcaacaa cggcgagatc   2760
aacttcgcgg ccgactgata a                                            2781

<210> SEQ ID NO 2
<211> LENGTH: 2781
<212> TYPE: DNA
<213> ORGANISM: Artificial Sequence
<220> FEATURE:
<223> OTHER INFORMATION: TALEN TRAC_T01-R1_

<400> SEQUENCE: 2
atgggcgatc ctaaaaagaa acgtaaggtc atcgatatcg ccgatctacg cacgctcggc     60
tacagccagc agcaacagga gaagatcaaa ccgaaggttc gttcgacagt ggcgcagcac    120
cacgaggcac tggtcggcca cgggtttaca cacgcgcaca tcgttgcgtt aagccaacac    180
ccggcagcgt tagggaccgt cgctgtcaag tatcaggaca tgatcgcagc gttgccagag    240
gcgacacacg aagcgatcgt tggcgtcggc aaacagtggt ccggcgcacg cgctctggag    300
gccttgctca cggtggcggg agagttgaga ggtccaccgt tacagttgga cacaggccaa    360
cttctcaaga ttgcaaaacg tggcggcgtg accgcagtgg aggcagtgca tgcatggcgc    420
aatgcactga cgggtgcccc gctcaacttg accccggagc aggtggtggc catcgccagc    480
cacgatggcg gcaagcaggc gctggagacg tccagcggc tgttgccggt gctgtgccag    540
gcccacggct tgacccccca gcaggtggtg gccatcgcca gcaatggcgg tggcaagcag    600
gcgctggaga cggtccagcg gctgttgccg gtgctgtgcc aggcccacgg cttgaccccg    660
gagcaggtgg tggccatcgc cagccacgat ggcggcaagc aggcgctgga cggtccag      720 cggctgttgc cggtgctgtg ccaggcccac ggcttgaccc cggagcaggt ggtggccatc    780
gccagcaata ttggtggcaa gcaggcgctg agacggtgc aggcgctgtt gccggtgctg    840
tgccaggccc acggcttgac cccccagcag gtggtggcca tcgccagcaa taatggtggc    900
aagcaggcgc tggagacggt ccagcggctg ttgccggtgc tgtgccaggc ccacggcttg    960
accccggagc aggtggtggc catcgccagc cacgatggcg gcaagcaggc gctggagacg   1020
gtccagcggc tgttgccggt gctgtgccag gcccacggct tgacccccca gcaggtggtg   1080
gccatcgcca gcaatggcgg tggcaagcag gcgctggaga cggtccagcg gctgttgccg   1140
gtgctgtgcc aggcccacgg cttgaccccc cagcaggtgg tggccatcgc cagcaataat   1200
ggtggcaagc aggcgctgga cggtccag cggctgttgc cggtgctgtg ccaggcccac    1260
```

-continued

```
ggcttgaccc cccagcaggt ggtggccatc gccagcaata atggtggcaa gcaggcgctg    1320
gagacggtcc agcggctgtt gccggtgctg tgccaggccc acggcttgac cccccagcag    1380
gtggtggcca tcgccagcaa tggcggtggc aagcaggcgc tggagacggt ccagcggctg    1440
ttgccggtgc tgtgccaggc ccacggcttg accccggagc aggtggtggc catcgccagc    1500
aatattggtg gcaagcaggc gctggagacg gtgcaggcgc tgttgccggt gctgtgccag    1560
gcccacggct tgaccccgga gcaggtggtg gccatcgcca gccacgatgg cggcaagcag    1620
gcgctggaga cggtccagcg gctgttgccg gtgctgtgcc aggcccacgg cttgaccccg    1680
gagcaggtgg tggccatcgc cagcaatatt ggtggcaagc aggcgctgga cacggtgcag    1740
gcgctgttgc cggtgctgtg ccaggcccac ggcttgaccc cggagcaggt ggtggccatc    1800
gccagccacg atggcggcaa gcaggcgctg gagacggtcc agcggctgtt gccggtgctg    1860
tgccaggccc acggcttgac cccccagcag gtggtggcca tcgccagcaa taatggtggc    1920
aagcaggcgc tggagacggt ccagcggctg ttgccggtgc tgtgccaggc ccacggcttg    1980 accccctcagc aggtggtggc catcgccagc aatggcggcg gcaggccggc gctggagagc    2040
attgttgccc agttatctcg ccctgatccg gcgttggccg cgttgaccaa cgaccacctc    2100
gtcgccttgg cctgcctcgg cgggcgtcct gcgctggatg cagtgaaaaa gggattgggg    2160
gatcctatca gccgttccca gctggtgaag tccgagctgg aggagaagaa atccgagttg    2220
aggcacaagc tgaagtacgt gccccacgag tacatcgagc tgatcgagat cgcccggaac    2280
agcacccagg accgtatcct ggagatgaag gtgatggagt tcttcatgaa ggtgtacggc    2340 tacagggggca agcacctggg cggctccagg aagcccgacg cgccatccta caccgtgggc    2400
tcccccatcg actacggcgt gatcgtggac accaaggcct actccggcgg ctacaacctg    2460
cccatcggcc aggccgacga aatgcagagg tacgtggagg agaaccagac caggaacaag    2520
cacatcaacc ccaacgagtg tgtggaaggtg tacccctcca gcgtgaccga gttcaagttc    2580
ctgttcgtgt ccggccactt caagggcaac tacaaggccc agctgaccag gctgaaccac    2640
atcaccaact gcaacggcgc cgtgctgtcc gtggaggagc tcctgatcgg cggcgagatg    2700
atcaaggccg gcaccctgac cctggaggag gtgaggagga gttcaacaa cggcgagatc    2760 aacttcgcgg ccgactgata a                                               2781
```

<210> SEQ ID NO 3
<211> LENGTH: 925
<212> TYPE: PRT
<213> ORGANISM: Artificial Sequence
<220> FEATURE:
<223> OTHER INFORMATION: TALEN  TRAC_T01-L1

<400> SEQUENCE: 3

```
Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95
```

```
Arg Ala Leu Glu Ala Leu Leu Thr Val Ala Gly Glu Leu Arg Gly Pro
            100                 105             110

Pro Leu Gln Leu Asp Thr Gly Gln Leu Leu Lys Ile Ala Lys Arg Gly
            115             120             125

Gly Val Thr Ala Val Glu Ala Val His Ala Trp Arg Asn Ala Leu Thr
        130             135             140

Gly Ala Pro Leu Asn Leu Thr Pro Gln Gln Val Val Ala Ile Ala Ser
145             150             155             160

Asn Gly Gly Gly Lys Gln Ala Leu Glu Thr Val Gln Arg Leu Leu Pro
                165             170             175

Val Leu Cys Gln Ala His Gly Leu Thr Pro Gln Gln Val Val Ala Ile
            180             185             190

Ala Ser Asn Asn Gly Gly Lys Gln Ala Leu Glu Thr Val Gln Arg Leu
            195             200             205

Leu Pro Val Leu Cys Gln Ala His Gly Leu Thr Pro Gln Gln Val Val
    210             215             220

Ala Ile Ala Ser Asn Gly Gly Lys Gln Ala Leu Glu Thr Val Gln
225             230             235             240

Arg Leu Leu Pro Val Leu Cys Gln Ala His Gly Leu Thr Pro Glu Gln
            245             250             255

Val Val Ala Ile Ala Ser His Asp Gly Gly Lys Gln Ala Leu Glu Thr
            260             265             270

Val Gln Arg Leu Leu Pro Val Leu Cys Gln Ala His Gly Leu Thr Pro
    275             280             285

Glu Gln Val Val Ala Ile Ala Ser His Asp Gly Gly Lys Gln Ala Leu
    290             295             300

Glu Thr Val Gln Arg Leu Leu Pro Val Leu Cys Gln Ala His Gly Leu
305             310             315             320

Thr Pro Glu Gln Val Val Ala Ile Ala Ser His Asp Gly Gly Lys Gln
            325             330             335

Ala Leu Glu Thr Val Gln Arg Leu Leu Pro Val Leu Cys Gln Ala His
            340             345             350

Gly Leu Thr Pro Glu Gln Val Val Ala Ile Ala Ser Asn Ile Gly Gly
            355             360             365

Lys Gln Ala Leu Glu Thr Val Gln Ala Leu Leu Pro Val Leu Cys Gln
    370             375             380

Ala His Gly Leu Thr Pro Glu Gln Val Val Ala Ile Ala Ser His Asp
385             390             395             400

Gly Gly Lys Gln Ala Leu Glu Thr Val Gln Arg Leu Leu Pro Val Leu
            405             410             415

Cys Gln Ala His Gly Leu Thr Pro Glu Gln Val Val Ala Ile Ala Ser
            420             425             430

Asn Ile Gly Gly Lys Gln Ala Leu Glu Thr Val Gln Ala Leu Leu Pro
            435             440             445

Val Leu Cys Gln Ala His Gly Leu Thr Pro Gln Gln Val Val Ala Ile
    450             455             460

Ala Ser Asn Asn Gly Gly Lys Gln Ala Leu Glu Thr Val Gln Arg Leu
465             470             475             480

Leu Pro Val Leu Cys Gln Ala His Gly Leu Thr Pro Glu Gln Val Val
            485             490             495

Ala Ile Ala Ser Asn Ile Gly Gly Lys Gln Ala Leu Glu Thr Val Gln
            500             505             510
```

```
Ala Leu Leu Pro Val Leu Cys Gln Ala His Gly Leu Thr Pro Gln Gln
        515                 520                 525

Val Val Ala Ile Ala Ser Asn Gly Gly Gly Lys Gln Ala Leu Glu Thr
        530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Ile Gly Gly Lys Gln Ala Leu
                565                 570                 575

Glu Thr Val Gln Ala Leu Leu Pro Val Leu Cys Gln Ala His Gly Leu
            580                 585                 590

Thr Pro Gln Gln Val Val Ala Ile Ala Ser Asn Gly Gly Gly Lys Gln
        595                 600                 605

Ala Leu Glu Thr Val Gln Arg Leu Leu Pro Val Leu Cys Gln Ala His
        610                 615                 620

Gly Leu Thr Pro Glu Gln Val Val Ala Ile Ala Ser His Asp Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
        675                 680                 685

Asp Pro Ala Leu Ala Ala Leu Thr Asn Asp His Leu Val Ala Leu Ala
        690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
        755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
            915                 920                 925
```

```
<210> SEQ ID NO 4
<211> LENGTH: 925
<212> TYPE: PRT
<213> ORGANISM: Artificial Sequence
<220> FEATURE:
<223> OTHER INFORMATION: TALEN  TRAC_T01-R1

<400> SEQUENCE: 4

Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
            115                 120                 125

Gly Val Thr Ala Val Glu Ala Val His Ala Trp Arg Asn Ala Leu Thr
        130                 135                 140

Gly Ala Pro Leu Asn Leu Thr Pro Glu Gln Val Val Ala Ile Ala Ser
145                 150                 155                 160

His Asp Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
            180                 185                 190

Ala Ser Asn Gly Gly Gly Lys Gln Ala Leu Glu Thr Val Gln Arg Leu
            195                 200                 205

Leu Pro Val Leu Cys Gln Ala His Gly Leu Thr Pro Glu Gln Val Val
        210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Glu Gln
            245                 250                 255

Val Val Ala Ile Ala Ser Asn Ile Gly Gly Lys Gln Ala Leu Glu Thr
            260                 265                 270

Val Gln Ala Leu Leu Pro Val Leu Cys Gln Ala His Gly Leu Thr Pro
        275                 280                 285

Gln Gln Val Val Ala Ile Ala Ser Asn Asn Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
            325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
        355                 360                 365

Lys Gln Ala Leu Glu Thr Val Gln Arg Leu Leu Pro Val Leu Cys Gln
```

-continued

```
        370                 375                 380

Ala His Gly Leu Thr Pro Gln Gln Val Val Ala Ile Ala Ser Asn Asn
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Gln Gln Val Val Ala Ile Ala Ser
                420                 425                 430

Asn Asn Gly Gly Lys Gln Ala Leu Glu Thr Val Gln Arg Leu Leu Pro
            435                 440                 445

Val Leu Cys Gln Ala His Gly Leu Thr Pro Gln Gln Val Val Ala Ile
        450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
                500                 505                 510

Ala Leu Leu Pro Val Leu Cys Gln Ala His Gly Leu Thr Pro Glu Gln
                515                 520                 525

Val Val Ala Ile Ala Ser His Asp Gly Gly Lys Gln Ala Leu Glu Thr
        530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Ile Gly Gly Lys Gln Ala Leu
                565                 570                 575

Glu Thr Val Gln Ala Leu Leu Pro Val Leu Cys Gln Ala His Gly Leu
                580                 585                 590

Thr Pro Glu Gln Val Val Ala Ile Ala Ser His Asp Gly Gly Lys Gln
                595                 600                 605

Ala Leu Glu Thr Val Gln Arg Leu Leu Pro Val Leu Cys Gln Ala His
        610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
                660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
        690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
                740                 745                 750

Glu Leu Ile Glu Ile Ala Arg Asn Ser Thr Gln Asp Arg Ile Leu Glu
                755                 760                 765

Met Lys Val Met Glu Phe Phe Met Lys Val Tyr Gly Tyr Arg Gly Lys
        770                 775                 780

His Leu Gly Gly Ser Arg Lys Pro Asp Gly Ala Ile Tyr Thr Val Gly
785                 790                 795                 800
```

```
Ser Pro Ile Asp Tyr Gly Val Ile Val Asp Thr Lys Ala Tyr Ser Gly
            805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
            885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925

<210> SEQ ID NO 5
<211> LENGTH: 22
<212> TYPE: DNA
<213> ORGANISM: Artificial Sequence
<220> FEATURE:
<223> OTHER INFORMATION: FORWARD

<400> SEQUENCE: 5
gctggggttt tgaagaagat cc                                               22

<210> SEQ ID NO 6
<211> LENGTH: 19
<212> TYPE: DNA
<213> ORGANISM: Artificial Sequence
<220> FEATURE:
<223> OTHER INFORMATION: REVERSE

<400> SEQUENCE: 6
gacttcctct gccctcacc                                                   19

<210> SEQ ID NO 7
<211> LENGTH: 20
<212> TYPE: DNA
<213> ORGANISM: Artificial Sequence
<220> FEATURE:
<223> OTHER INFORMATION: PROBE

<400> SEQUENCE: 7
cccttgtcca tcactggcat                                                  20

<210> SEQ ID NO 8
<211> LENGTH: 411
<212> TYPE: DNA
<213> ORGANISM: Artificial Sequence
<220> FEATURE:
<223> OTHER INFORMATION: SEQUENCE IN TRAC

<400> SEQUENCE: 8
gctggggttt tgaagaagat cctattaaat aaaagaataa gcagtattat taagtagccc     60
tgcatttcag gtttccttga gtggcaggcc aggcctggcc gtgaacgttc actgaaatca    120
tggcctcttg gccaagattg atagcttgtg cctgtccctg agtcccagtc catcacgagc    180
agctggtttc taagatgcta tttcccgtat aaagcatgag accgtgactt gccagcccca    240
```

-continued

```
cagagccccg cccttgtcca tcactggcat ctggactcca gcctgggttg gggcaaagag      300
ggaaatgaga tcatgtccta accctgatcc tcttgtccca cagatatcca gtccggtgag      360
ggcagaggaa gtcttctaac atgcggtgac gtggaggaga atccgggccc c               411

<210> SEQ ID NO 9
<211> LENGTH: 2658
<212> TYPE: DNA
<213> ORGANISM: Artificial Sequence
<220> FEATURE:
<223> OTHER INFORMATION: SEQUENCE IN TRAC ANTI-CD22 CAR

<400> SEQUENCE: 9
aagtagccct gcatttcagg tttccttgag tggcaggcca ggcctggccg tgaacgttca       60
ctgaaatcat ggcctcttgg ccaagattga tagcttgtgc ctgtccctga gtcccagtcc      120
atcacgagca gctggtttct aagatgctat ttcccgtata aagcatgaga ccgtgacttg      180
ccagccccac agagccccgc ccttgtccat cactggcatc tggactccag cctgggttgg      240
ggcaaagagg gaaatgagat catgtcctaa ccctgatcct cttgtccac agatatccag       300 tccggtgagg gcagaggaag tcttctaaca tgcggtgacg tggaggagaa tccgggcccc      360
ggatccgctc tgcccgtcac cgctctgctg ctgccactgg ccctgctgct gcacgcagca      420
agaccaggag ggggaggcag ctgcccctac agcaacccca gcctgtgcag cggaggcggc      480
ggcagcggcg gaggggtag ccaggtgcag ctgcagcaga cgcggcctgg cctggtgaag      540
ccaagccaga cactgtccct gacctgcgcc atcagcggcg attccgtgag ctccaactcc      600
gccgcctgga attggatcag gcagtcccct ctcggggcc tggagtggct gggaaggaca      660
tactatcggt ctaagtggta caacgattat gccgtgtctg tgaagagcag aatcacaatc      720
aaccctgaca cctccaagaa tcagttctct ctgcagctga atagcgtgac accagaggac      780
accgccgtgt actattgcgc cagggaggtg accggcgacc tggaggatgc ctttgacatc      840
tggggccagg gcacaatggt gaccgtgtct agcggaggag gaggatccgg aggaggagga      900
tctggcggcg gcggcagcga tatccagatg acacagtccc catcctctct gagcgcctcc      960
gtgggcgaca gagtgacaat cacctgtagg gcctcccaga ccatctggtc ttacctgaac     1020
tggtatcagc agaggcccgg caaggcccct aatctgctga tctacgcagc aagctccctg     1080
cagagcggag tgccatccag attctctggc aggggctccg gcacagactt caccctgacc     1140
atctctagcc tgcaggccga ggacttcgcc acctactatt gccagcagtc ttatagcatc     1200
ccccagacat ttggccaggg caccaagctg gagatcaagg gaagcggagg gggaggcagc     1260
tgcccctaca gcaaccccag cctgtgcagc ggaggcggcg gcagcgagct gcccacccag     1320
ggcaccttct ccaacgtgtc caccaacgtg agcccagcca gcccaccac caccgcctgt      1380 ccttattcca atccttccct gtgtgctccc accacaaccc cagcaccaag gccacctaca     1440
cctgcaccaa ccatcgcctc tcagcccctg agcctgagac ctgaggcatg taggccagca     1500
gcaggaggag cagtccatac aaggggtctg gattttgcat gcgacatcta catctgggca     1560
cctctggcag gaacatgtgg cgtgctcctg ctcagcctgg tcatcaccct gtactgcaag     1620
agaggcagga gaagctgct gtatatcttc aagcagccct tcatgcgccc cgtgcagaca     1680
acccaggagg aggatggctg ctcctgtagg ttcccagaag aggaggaggg aggatgtgag     1740
ctgcgcgtga gttttcccg gtctgccgac gcacctgcat accagcaggg ccagaaccag     1800
ctgtataacg agctgaatct gggccggaga gaggagtacg atgtgctgga caagaggcgc     1860
ggcagagatc agagatggg cggcaagccc cggagaaaga accctcagga gggcctgtac     1920
```

-continued

```
aatgagctgc agaaggataa gatggccgag gcctattctg agatcggcat gaagggagag    1980
aggcgccggg gcaagggaca cgacggactg taccagggac tgagcacagc caccaaggat    2040
acctatgacg ccctgcatat gcaggcactg cctccaaggt gatctagagg gcccgtttaa    2100
acccgctgat cagcctcgac tgtgccttct agttgccagc catctgttgt ttgcccctcc    2160
cccgtgcctt ccttgaccct ggaaggtgcc actcccactg tcctttccta ataaaatgag    2220
gaaattgcat cgcattgtct gagtaggtgt cattctattc tggggggtgg ggtggggcag    2280
gacagcaagg gggaggattg ggaagacaat agcaggcatg ctggggatgc ggtgggctct    2340
atgactagtg gcgaattccc gtgtaccagc tgagagactc taaatccagt gacaagtctg    2400
tctgcctatt caccgatttt gattctcaaa caaatgtgtc acaaagtaag gattctgatg    2460
tgtatatcac agacaaaact gtgctagaca tgaggtctat ggacttcaag agcaacagtg    2520
ctgtggcctg gagcaacaaa tctgactttg catgtgcaaa cgccttcaac aacagcatta    2580
ttccagaaga caccttcttc cccagcccag gtaagggcag ctttggtgcc ttcgcaggct    2640
gtttccttgc ttcaggaa                                                  2658
```

```
<210> SEQ ID NO 10
<211> LENGTH: 2646
<212> TYPE: DNA
<213> ORGANISM: Artificial Sequence
<220> FEATURE:
<223> OTHER INFORMATION: SEQUENCE IN TRAC ANTI-CD22 B-B7 QR3

<400> SEQUENCE: 10
```

```
aagtagccct gcatttcagg tttccttgag tggcaggcca ggcctggccg tgaacgttca      60
ctgaaatcat ggcctcttgg ccaagattga tagcttgtgc ctgtccctga gtcccagtcc     120
atcacgagca gctggtttct aagatgctat ttcccgtata aagcatgaga ccgtgacttg     180
ccagccccac agagccccgc ccttgtccat cactggcatc tggactccag cctgggttgg     240
ggcaaagagg gaaatgagat catgtcctaa ccctgatcct cttgtcccac agatatccag     300
tccggtgagg gcagaggaag tcttctaaca tgcggtgacg tggaggagaa tccgggcccc     360
ggatccgctc tgcccgtcac cgctctgctg ctgccactgg ccctgctgct gcacgccgcc     420
agacccggcg gaggaggctc ttgcccctac agcaacccca gcctgtgctc tggcggcggc     480
ggcagcggag gcggcggctc ccaggtgcag ctgcagcaga gcggccctgg cctggtggag     540
ccaagccaga cactgtccct gacctgcgcc atctctggcg acagcgtgag ctccaacagc     600
gccgcatgga attggatcag gcagtcccca tctcggggcc tggagtggct gggcagaaca     660
tactataggt ccacctggta caacgactat gccggctccg tgaagtctcg catcacaatc     720
aaccccgata ccagcaagaa tcagttctcc ctgcagctga catctgtgac ccctgaggac     780
acagccgtgt actattgcac cagaagcagg cacaatacat tcgggggaat ggacgtgtgg     840
ggacagggca cactggtgac cgtgagcgga ggaggaggat ccggcggagg aggctctggc     900
ggcggcggca gcgacatcca gctgacccag tcccccttcta gcctgagcgc ctccgtgggc     960
gatagagtga caatcacctg tagggcctct cagagcatct cctcttacct gaactggtat    1020
cagcagaagc ccggcaaggc ccctaagctg ctgatctacg cagcaagctc cctgcagtct    1080
ggagtgccaa gcagattctc cggctctggc agcggcaccg actttacact gaccatctct    1140
agcctgcagc ctgaggattt cgccacatac tattgccagc agtcctattc tacaccactg    1200 accttttggcg gcggcaccaa ggtggagatc aagggaagcg gcggcggcgg aagttgtcca    1260
```

-continued

```
tattcaaacc caagtctgtg cagcggcgga ggaggaagcg aactgcctac tcagggaacc   1320
ttcagcaacg tgtccaccaa tgtgagccca gcaaagccta ccacaaccgc atgcccatac   1380
tctaacccca gcctgtgcac aaccacacca gcacccaggc cccctacccc tgcaccaaca   1440
atcgcctccc agcctctgtc tctgcggcca gaggcctgca gacccgccgc cggcggagca   1500
gtgcacacac ggggcctgga ctttgcctgt gatatctata tctgggcacc actggccgga   1560
acatgtggcg tgctgctgct gtcactggtc attacactgt actgtaagcg aggccggaag   1620
aaactgctgt atattttcaa acagcccttt atgagacctg tgcagactac ccaggaggaa   1680
gacggctgca gctgtaggtt ccccgaggaa gaggaaggcg ggtgtgagct gagggtcaag   1740
tttagccgct ccgcagatgc ccctgcttac cagcaggggc agaatcagct gtataacgag   1800
ctgaatctgg gacggagaga ggaatacgac gtgctggata aaaggcgcgg gagagacccc   1860
gaaatgggag gcaagccacg acggaaaaac ccccaggagg gcctgtacaa tgaactgcag   1920
aaggacaaaa tggcagaggc ctatagtgaa atcgggatga agggagagag aaggcgcggc   1980
aaagggcacg atggcctgta ccaggggctg tctactgcca ccaaggacac ctatgatgct   2040
ctgcatatgc aggcactgcc tccaaggtga tctagagggc ccgtttaaac ccgctgatca   2100
gcctcgactg tgccttctag ttgccagcca tctgttgttt gcccctcccc cgtgccttcc   2160
ttgaccctgg aaggtgccac tcccactgtc ctttcctaat aaaatgagga aattgcatcg   2220
cattgtctga gtaggtgtca ttctattctg ggggtgggg tggggcagga cagcaagggg   2280
gaggattggg aagacaatag caggcatgct ggggatgcgg tgggctctat gactagtggc   2340
gaattcccgt gtaccagctg agagactcta atccagtga caagtctgtc tgcctattca   2400
ccgattttga ttctcaaaca aatgtgtcac aaagtaagga ttctgatgtg tatatcacag   2460
acaaaactgt gctagacatg aggtctatgg acttcaagag caacagtgct gtggcctgga   2520
gcaacaaatc tgactttgca tgtgcaaacg ccttcaacaa cagcattatt ccagaagaca   2580
ccttcttccc cagcccaggt aagggcagct ttggtgcctt cgcaggctgt ttccttgctt   2640
caggaa                                                              2646
```

<210> SEQ ID NO 11
<211> LENGTH: 2649
<212> TYPE: DNA
<213> ORGANISM: Artificial Sequence
<220> FEATURE:
<223> OTHER INFORMATION: SEQUENCE IN TRAC ANTI-CD22 A-D4 QR3

<400> SEQUENCE: 11

```
aagtagccct gcatttcagg tttccttgag tggcaggcca ggcctggccg tgaacgttca     60
ctgaaatcat ggcctcttgg ccaagattga tagcttgtgc ctgtccctga gtcccagtcc    120
atcacgagca gctggtttct aagatgctat ttcccgtata aagcatgaga ccgtgacttg    180
ccagccccac agagccccgc ccttgtccat cactggcatc tggactccag cctgggttgg    240
ggcaaagagg gaaatgagat catgtcctaa ccctgatcct cttgtcccac agatatccag    300
tccggtgagg gcagaggaag tcttctaaca tgcggtgacg tggaggagaa tcgggccccc    360
ggatccgctc tgcccgtcac cgctctgctg ctgccactgg ccctgctgct gcacgccgcc    420
agacccggcg gaggaggctc ttgcccctac agcaaccca gcctgtgctc tggcggcggc    480
ggcagcggag cgggcggctc ccaggtgcag ctgcagcaga cggcccccgg cctggtgaag    540
cctagccaga cactgtccct gacctgcgca atctccggcg acagcgtgtc cggaaacagg    600
gccacatgga attggatcag acagtctcca agcagggggcc tggagtggct gggaaggacc    660
```

-continued

```
tactatcggt ccgcctggta caacgactat gccgtgtctg tgaagggccg catcacattc     720
aacccagata ccagcaagaa tcagtttccc ctgcagctga attctgtgac acccgaggat     780
accgccgtgt actattgcgc cagaggcgag agcggagcag cagcagacgc cttcgatatc     840
tggggccagg gcaccacagt gacagtgagc ggaggaggag gatccggcgg aggaggctct     900
ggcggcggcg gcagcgacat ccagctgacc cagagcccac cttccctgtc tgccagcgtg     960
ggcgatcgcg tgacaatcac ctgtcgggcc tcccagtcta tcagctccta cctgaactgg    1020
tatcagcaga agccaggcaa ggcccccaag ctgctgatct acgcagcatc tagcctgcag    1080
tctggagtgc caagcagatt cagcggatcc ggattcggca cagactttac actgaccatc    1140
tcctctctgc agcccgagga tttcgccacc tactattgcc agcagtctta tagcacacct    1200
cagacctttg gccagggcac caaggtggac atcaagggaa gtggaggagg aggaagttgt    1260
ccctactcaa acccatctct gtgctcagga ggaggaggaa gtgaactgcc tactcaggga    1320
acattcagca acgtgtccac caatgtgagc ccagcaaagc ctaccacaac cgcatgccca    1380
tactctaacc ccagcctgtg cacaaccaca ccagcaccca ggcccctac ccctgcacca    1440 acaatcgcct cccagcctct gtctctgcgg ccagaggcct gcagaccgc cgccggcgga    1500 gcagtgcaca cacggggcct ggactttgcc tgtgatatct atatctgggc accactggcc    1560
ggaacatgtg gcgtgctgct gctgtcactg gtcattacac tgtactgtaa gcgaggccgg    1620
aagaaactgc tgtatatttt caaacagccc tttatgagac ctgtgcagac tacccaggag    1680
gaagacggct gcagctgtag gttccccgag aagaggaag gcgggtgtga gctgagggtc    1740
aagtttagcc gctccgcaga tgcccctgct taccagcagg ggcagaatca gctgtataac    1800
gagctgaatc tgggacggag agaggaatac gacgtgctgg ataaaaggcg cgggagagac    1860
cccgaaatgg gaggcaagcc acgacggaaa aaccccagg agggcctgta caatgaactg    1920
cagaaggaca aaatggcaga ggcctatagt gaaatcggga tgaagggaga gagaaggcgc    1980
ggcaaagggc acgatggcct gtaccagggg ctgtctactg ccaccaagga cacctatgat    2040
gctctgcata tgcaggcact gcctccaagg tgatctagag ggcccgttta aacccgctga    2100
tcagcctcga ctgtgccttc tagttgccag ccatctgttg tttgcccctc ccccgtgcct    2160
tccttgaccc tggaaggtgc cactcccact gtcctttcct aataaaatga ggaaattgca    2220
tcgcattgtc tgagtaggtg tcattctatt ctggggggtg gggtggggca ggacagcaag    2280
ggggaggatt gggaagacaa tagcaggcat gctggggatg cggtgggctc tatgactagt    2340
ggcgaattcc cgtgtaccag ctgagagact ctaaatccag tgacaagtct gtctgcctat    2400
tcaccgattt tgattctcaa acaaatgtgt cacaaagtaa ggattctgat gtgtatatca    2460
cagacaaaac tgtgctagac atgaggtcta tggacttcaa gagcaacagt gctgtggcct    2520
ggagcaacaa atctgacttt gcatgtgcaa acgccttcaa caacagcatt attccagaag    2580
acaccttctt ccccagccca ggtaagggca gctttggtgc cttcgcaggc tgtttccttg    2640
cttcaggaa                                                           2649
```

<210> SEQ ID NO 12
<211> LENGTH: 2679
<212> TYPE: DNA
<213> ORGANISM: Artificial Sequence
<220> FEATURE:
<223> OTHER INFORMATION: SEQUENCE IN TRAC ANTI-CD123 K43 QR3

<400> SEQUENCE: 12

-continued

```
aagtagccct gcatttcagg tttccttgag tggcaggcca ggcctggccg tgaacgttca       60
ctgaaatcat ggcctcttgg ccaagattga tagcttgtgc ctgtccctga gtcccagtcc      120
atcacgagca gctggtttct aagatgctat ttcccgtata aagcatgaga ccgtgacttg      180
ccagccccac agagccccgc ccttgtccat cactggcatc tggactccag cctgggttgg      240
ggcaaagagg gaaatgagat catgtcctaa ccctgatcct cttgtcccac agatatccag      300
tccggtgagg gcagaggaag tcttctaaca tgcggtgacg tggaggagaa tccgggcccc      360
ggatccgctc tgcccgtcac cgctctgctg ctgcctctgg ccctgctgct gcacgcagcc      420
agaccaggcg gaggaggctc ctgcccttac tctaacccaa gcctgtgctc cggaggagga      480
ggatccggcg gaggaggctc tgaggtgaag ctggtggaga gcggaggagg cctggtgcag      540
cctggcggct ccctgtctct gagctgcgca gcatccggct tcacctttac agactactat      600
atgtcttggg tgagacagcc ccctggcaag gccctggagt ggctggccct gatcaggtcc      660
aaggccgatg gctacaccac agagtattcc gcctctgtga agggcagatt caccctgtct      720
agggacgata gccagtccat cctgtacctg cagatgaatg cactgcgccc cgaggacagc      780
gccacatact attgtgccag agacgccgcc tactattctt actatagccc tgagggcgct      840
atggactact ggggccaggg cacctccgtg acagtgagct ccggaggagg aggaagcgga      900
ggaggaggct ccggcggcgg cggctctatg gccgactata aggatatcgt gatgacccag      960
agccacaagt ttatgtctac aagcgtgggc gaccgcgtga acatcacctg caaggccagc     1020
cagaatgtgg attccgccgt ggcctggtac cagcagaagc ctggccagag ccctaaggcc     1080
ctgatctatt ccgcctctta ccggtatagc ggagtgcctg accgcttcac cggaaggggda     1140 tccggaacag acttcaccct gacaatctct agcgtgcagg ccgaggatct ggccgtgtac     1200
tattgtcagc agtactatag cacccctgg accttcggcg gaggaaccaa gctggagatc     1260
aagagaggat ctggaggagg aggaagctgc ccatactcca acccctctct gtgcagcgga     1320
ggaggaggat ctgagctgcc aacccagggc acattttcca acgtgtctac aaatgtgagc     1380
ccagcaaagc caaccacaac cgcatgccct tatagcaatc catcctgtg cacaaccaca     1440 cctgcaccaa gaccaccaac cccagcacct acaatcgcct ctcagccact gagcctgcgc     1500
cccgaggcat gccggcctgc agcaggcggc gccgtgcaca ccaggggcct ggacttcgcc     1560
tgcgatatct acatctgggc acctctggca ggaacctgtg gcgtgctgct gctgagcctg     1620
gtcatcaccc tgtactgcaa gagaggcagg aagaagctgc tgtatatctt caagcagccc     1680
tttatgcgcc ctgtgcagac cacacaggag gaggacggct gcagctgtcg gttcccagaa     1740
gaggaggagg gcggctgtga gctgagagtg aagtttagca ggtccgccga tgcaccagca     1800
taccagcagg gacagaacca gctgtataac gagctgaatc tgggccggag agaggagtac     1860
gacgtgctgg ataagaggag gggaagggac cccgagatgg gaggcaagcc acggagaaag     1920 aaccccccagg agggcctgta caatgagctg cagaaggaca gatggccga ggcctattcc     1980 gagatcggca tgaagggaga gaggcgccgg ggcaagggac acgatggcct gtaccagggc     2040
ctgtctaccg ccacaaagga cacctatgat gccctgcata tgcaggcact gcctccaagg     2100
tgatctagag ggcccgttta aacccgctga tcagcctcga ctgtgccttc tagttgccag     2160
ccatctgttg tttgcccctc ccccgtgcct tccttgaccc tggaaggtgc cactcccact     2220
gtcctttcct aataaaatga ggaaattgca tcgcattgtc tgagtaggtg tcattctatt     2280
ctggggggtg gggtggggca ggacagcaag ggggaggatt gggaagacaa tagcaggcat     2340
gctggggatg cggtgggctc tatgactagt ggcgaattcc cgtgtaccag ctgagagact     2400
```

-continued

```
ctaaatccag tgacaagtct gtctgcctat tcaccgattt tgattctcaa acaaatgtgt      2460
cacaaagtaa ggattctgat gtgtatatca cagacaaaac tgtgctagac atgaggtcta      2520
tggacttcaa gagcaacagt gctgtggcct ggagcaacaa atctgacttt gcatgtgcaa      2580
acgccttcaa caacagcatt attccagaag acaccttctt ccccagccca ggtaagggca      2640
gctttggtgc cttcgcaggc tgtttccttg cttcaggaa                           2679

<210> SEQ ID NO 13
<211> LENGTH: 22
<212> TYPE: DNA
<213> ORGANISM: Artificial Sequence
<220> FEATURE:
<223> OTHER INFORMATION: plus strand first PCR

<400> SEQUENCE: 13
ataccgttat taacatatga ca                                                22

<210> SEQ ID NO 14
<211> LENGTH: 21
<212> TYPE: DNA
<213> ORGANISM: Artificial Sequence
<220> FEATURE:
<223> OTHER INFORMATION: plus strand second PCR

<400> SEQUENCE: 14
catatgacaa ctcaattaaa c                                                 21

<210> SEQ ID NO 15
<211> LENGTH: 34
<212> TYPE: DNA
<213> ORGANISM: Artificial Sequence
<220> FEATURE:
<223> OTHER INFORMATION: oligo rev compl - plus

<400> SEQUENCE: 15
ataccgttat taacatatga caactcaatt aaac                                   34

<210> SEQ ID NO 16
<211> LENGTH: 22
<212> TYPE: DNA
<213> ORGANISM: Artificial Sequence
<220> FEATURE:
<223> OTHER INFORMATION: 1st PCR plus

<400> SEQUENCE: 16
ataccgttat taacatatga ca                                                22

<210> SEQ ID NO 17
<211> LENGTH: 21
<212> TYPE: DNA
<213> ORGANISM: Artificial Sequence
<220> FEATURE:
<223> OTHER INFORMATION: 2nd PCR plus

<400> SEQUENCE: 17
catatgacaa ctcaattaaa c                                                 21

<210> SEQ ID NO 18
<211> LENGTH: 29
<212> TYPE: DNA
<213> ORGANISM: Artificial Sequence
<220> FEATURE:
<223> OTHER INFORMATION: minus strand first PCR
```

-continued

```
<400> SEQUENCE: 18
gtttaattga gttgtcatat gttaataac                                          29

<210> SEQ ID NO 19
<211> LENGTH: 27
<212> TYPE: DNA
<213> ORGANISM: Artificial Sequence
<220> FEATURE:
<223> OTHER INFORMATION: minus strand second PCR

<400> SEQUENCE: 19
ttgagttgtc atatgttaat aacggta                                            27

<210> SEQ ID NO 20
<211> LENGTH: 34
<212> TYPE: DNA
<213> ORGANISM: Artificial Sequence
<220> FEATURE:
<223> OTHER INFORMATION: oligo rev compl - minus

<400> SEQUENCE: 20
gtttaattga gttgtcatat gttaataacg gtat                                    34

<210> SEQ ID NO 21
<211> LENGTH: 29
<212> TYPE: DNA
<213> ORGANISM: Artificial Sequence
<220> FEATURE:
<223> OTHER INFORMATION: 1st PCR minus

<400> SEQUENCE: 21
gtttaattga gttgtcatat gttaataac                                          29

<210> SEQ ID NO 22
<211> LENGTH: 27
<212> TYPE: DNA
<213> ORGANISM: Artificial Sequence
<220> FEATURE:
<223> OTHER INFORMATION: 2nd PCR minus

<400> SEQUENCE: 22
ttgagttgtc atatgttaat aacggta                                            27

<210> SEQ ID NO 23
<211> LENGTH: 588
<212> TYPE: DNA
<213> ORGANISM: Artificial Sequence
<220> FEATURE:
<223> OTHER INFORMATION: IRES EMCV

<400> SEQUENCE: 23 gccctctcc ctcccccccc cctaacgtta ctggccgaag ccgcttggaa taaggccggt         60
gtgcgtttgt ctatatgtta ttttccacca tattgccgtc ttttggcaat gtgagggccc       120
ggaaacctgg ccctgtcttc ttgacgagca ttcctagggg tctttcccct ctcgccaaag       180
gaatgcaagg tctgttgaat gtcgtgaagg aagcagttcc tctggaagct tcttgaagac       240
aaacaacgtc tgtagcgacc ctttgcaggc agcggaaccc cccacctggc gacaggtgcc       300
tctgcggcca aaagccacgt gtataagata cacctgcaaa ggcggcacaa ccccagtgcc       360
acgttgtgag ttggatagtt gtggaaagag tcaaatggct ctcctcaagc gtattcaaca       420
aggggctgaa ggatgcccag aaggtacccc attgtatggg atctgatctg gggcctcggt       480
gcacatgctt tacatgtgtt tagtcgaggt taaaaaaacg tctaggcccc ccgaaccacg       540
```

-continued

```
gggacgtggt tttcctttga aaaacacgat gataatatgg ccacaacc              588

<210> SEQ ID NO 24
<211> LENGTH: 366
<212> TYPE: DNA
<213> ORGANISM: Artificial Sequence
<220> FEATURE:
<223> OTHER INFORMATION: modified TCR

<400> SEQUENCE: 24
aagtagccct gcatttcagg tttccttgag tggcaggcca ggcctggccg tgaacgttca       60
ctgaaatcat ggcctcttgg ccaagattga tagcttgtgc ctgtccctga gtcccagtcc      120
atcacgagca gctggtttct aagatgctat ttcccgtata aagcatgaga ccgtgacttg      180
ccagccccac agagccccgc ccttgtccat cactggcatc tggactccag cctgggttgg      240
ggcaaagagg gaaatgagat catgtcctaa ccctgatcct cttgtcccac agatatccag      300
tccggtgagg gcagaggaag tcttctaaca tgcggtgacg tggaggagaa tccgggcccc      360
ggatcc                                                              366

<210> SEQ ID NO 25
<211> LENGTH: 576
<212> TYPE: DNA
<213> ORGANISM: Artificial Sequence
<220> FEATURE:
<223> OTHER INFORMATION: modified TCR

<400> SEQUENCE: 25
tctagagggc ccgtttaaac ccgctgatca gcctcgactg tgccttctag ttgccagcca       60
tctgttgttt gcccctcccc cgtgccttcc ttgaccctgg aaggtgccac tcccactgtc      120
ctttcctaat aaaatgagga aattgcatcg cattgtctga gtaggtgtca ttctattctg      180 ggggtgggg tggggcagga cagcaagggg gaggattggg aagacaatag caggcatgct      240
ggggatgcgg tgggctctat gactagtggc gaattcccgt gtaccagctg agagactcta      300
aatccagtga caagtctgtc tgcctattca ccgattttga ttctcaaaca aatgtgtcac      360
aaagtaagga ttctgatgtg tatatcacag acaaaactgt gctagacatg aggtctatgg      420
acttcaagag caacagtgct gtggcctgga gcaacaaatc tgactttgca tgtgcaaacg      480
ccttcaacaa cagcattatt ccagaagaca ccttcttccc cagcccaggt aagggcagct      540
ttggtgcctt cgcaggctgt ttccttgctt caggaa                             576

<210> SEQ ID NO 26
<211> LENGTH: 17
<212> TYPE: DNA
<213> ORGANISM: Homo sapiens

<400> SEQUENCE: 26
ccgtgtacca gctgaga                                                   17

<210> SEQ ID NO 27
<211> LENGTH: 21
<212> TYPE: PRT
<213> ORGANISM: Artificial Sequence
<220> FEATURE:
<223> OTHER INFORMATION: 2A peptide

<400> SEQUENCE: 27

Gly Ser Gly Glu Gly Arg Gly Ser Leu Leu Thr Cys Gly Asp Val Glu
1               5                   10                  15
```

Glu Asn Pro Gly Pro
            20

<210> SEQ ID NO 28
<211> LENGTH: 22
<212> TYPE: PRT
<213> ORGANISM: Artificial Sequence
<220> FEATURE:
<223> OTHER INFORMATION: 2A peptide

<400> SEQUENCE: 28

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 29
<211> LENGTH: 23
<212> TYPE: PRT
<213> ORGANISM: Artificial Sequence
<220> FEATURE:
<223> OTHER INFORMATION: 2A peptide

<400> SEQUENCE: 29

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 30
<211> LENGTH: 25
<212> TYPE: PRT
<213> ORGANISM: Artificial Sequence
<220> FEATURE:
<223> OTHER INFORMATION: 2A peptide

<400> SEQUENCE: 30

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 31
<211> LENGTH: 20
<212> TYPE: PRT
<213> ORGANISM: Artificial Sequence
<220> FEATURE:
<223> OTHER INFORMATION: 2A peptide

<400> SEQUENCE: 31

Ser Gly Glu Gly Arg Gly Ser Leu Leu Thr Cys Gly Asp Val Glu Glu
1               5                   10                  15

Asn Pro Gly Pro
            20

<210> SEQ ID NO 32
<211> LENGTH: 21
<212> TYPE: PRT
<213> ORGANISM: Artificial Sequence
<220> FEATURE:
<223> OTHER INFORMATION: 2A peptide

<400> SEQUENCE: 32

Ser Gly Ala Thr Asn Phe Ser Leu Leu Lys Gln Ala Gly Asp Val Glu

-continued

```
1               5               10              15

Glu Asn Pro Gly Pro
            20

<210> SEQ ID NO 33
<211> LENGTH: 22
<212> TYPE: PRT
<213> ORGANISM: Artificial Sequence
<220> FEATURE:
<223> OTHER INFORMATION: 2A peptide

<400> SEQUENCE: 33

Ser Gly Gln Cys Thr Asn Tyr Ala Leu Leu Lys Leu Ala Gly Asp Val
1               5               10              15

Glu Ser Asn Pro Gly Pro
            20

<210> SEQ ID NO 34
<211> LENGTH: 24
<212> TYPE: PRT
<213> ORGANISM: Artificial Sequence
<220> FEATURE:
<223> OTHER INFORMATION: 2A peptide

<400> SEQUENCE: 34

Ser Gly Val Lys Gln Thr Leu Asn Phe Asp Leu Leu Lys Leu Ala Gly
1               5               10              15

Asp Val Glu Ser Asn Pro Gly Pro
            20

<210> SEQ ID NO 35
<211> LENGTH: 20
<212> TYPE: PRT
<213> ORGANISM: Artificial Sequence
<220> FEATURE:
<223> OTHER INFORMATION: 2A peptide

<400> SEQUENCE: 35

Ser Gly Glu Gly Arg Gly Ser Leu Leu Thr Cys Gly Asp Val Glu Glu
1               5               10              15

Asn Pro Gly Pro
            20

<210> SEQ ID NO 36
<211> LENGTH: 16
<212> TYPE: DNA
<213> ORGANISM: Artificial Sequence
<220> FEATURE:
<223> OTHER INFORMATION: recognition domain

<400> SEQUENCE: 36
ttgtcccaca gatatc                                                16

<210> SEQ ID NO 37
<211> LENGTH: 19
<212> TYPE: DNA
<213> ORGANISM: Artificial Sequence
<220> FEATURE:
<223> OTHER INFORMATION: recognition domain v

<400> SEQUENCE: 37
ttgtcccaca gatatccag                                             19

<210> SEQ ID NO 38
```

```
<211> LENGTH: 51
<212> TYPE: DNA
<213> ORGANISM: Artificial Sequence
<220> FEATURE:
<223> OTHER INFORMATION: binding domain

<400> SEQUENCE: 38
ttgtcccaca gatatccaga accctgaccc tgccgtgtac cagctgagag a            51

<210> SEQ ID NO 39
<211> LENGTH: 20
<212> TYPE: DNA
<213> ORGANISM: Artificial Sequence
<220> FEATURE:
<223> OTHER INFORMATION: oligonucleotide

<400> SEQUENCE: 39
agagtctctc agctggtaca                                              20

<210> SEQ ID NO 40
<211> LENGTH: 20
<212> TYPE: DNA
<213> ORGANISM: Artificial Sequence
<220> FEATURE:
<223> OTHER INFORMATION: oligonucleotide

<400> SEQUENCE: 40
gcaccaaagc tgcccttacc                                              20

<210> SEQ ID NO 41
<211> LENGTH: 20
<212> TYPE: DNA
<213> ORGANISM: Artificial Sequence
<220> FEATURE:
<223> OTHER INFORMATION: oligonuceotide

<400> SEQUENCE: 41
aagttcctgt gatgtcaagc                                              20

<210> SEQ ID NO 42
<211> LENGTH: 20
<212> TYPE: DNA
<213> ORGANISM: Artificial Sequence
<220> FEATURE:
<223> OTHER INFORMATION: oligonucleotide

<400> SEQUENCE: 42
ttcggaaccc aatcactgac                                              20

<210> SEQ ID NO 43
<211> LENGTH: 20
<212> TYPE: DNA
<213> ORGANISM: Artificial Sequence
<220> FEATURE:
<223> OTHER INFORMATION: oligonucleotide

<400> SEQUENCE: 43
gattaaaccc ggccactttc                                              20

<210> SEQ ID NO 44
<211> LENGTH: 20
<212> TYPE: DNA
<213> ORGANISM: Artificial Sequence
<220> FEATURE:
<223> OTHER INFORMATION: oligonucleotide

<400> SEQUENCE: 44
```

-continued

```
cgtcatgagc agattaaacc                                         20

<210> SEQ ID NO 45
<211> LENGTH: 20
<212> TYPE: DNA
<213> ORGANISM: Artificial Sequence
<220> FEATURE:
<223> OTHER INFORMATION: oligonucleotide

<400> SEQUENCE: 45
ctcaaggttc agatcagaag                                         20

<210> SEQ ID NO 46
<211> LENGTH: 20
<212> TYPE: DNA
<213> ORGANISM: Artificial Sequence
<220> FEATURE:
<223> OTHER INFORMATION: oligonucleotide

<400> SEQUENCE: 46
taggcagaca gacttgtcac                                         20

<210> SEQ ID NO 47
<211> LENGTH: 20
<212> TYPE: DNA
<213> ORGANISM: Artificial Sequence
<220> FEATURE:
<223> OTHER INFORMATION: oligonucleotide

<400> SEQUENCE: 47
aacaaatgtg tcacaaagta                                         20

<210> SEQ ID NO 48
<211> LENGTH: 20
<212> TYPE: DNA
<213> ORGANISM: Artificial Sequence
<220> FEATURE:
<223> OTHER INFORMATION: oligonucleotide

<400> SEQUENCE: 48
caccaaagct gcccttacct                                         20

<210> SEQ ID NO 49
<211> LENGTH: 20
<212> TYPE: DNA
<213> ORGANISM: Artificial Sequence
<220> FEATURE:
<223> OTHER INFORMATION: oligonucleotide

<400> SEQUENCE: 49
ctgacaggtt ttgaaagttt                                         20

<210> SEQ ID NO 50
<211> LENGTH: 20
<212> TYPE: DNA
<213> ORGANISM: Artificial Sequence
<220> FEATURE:
<223> OTHER INFORMATION: oligonucleotide

<400> SEQUENCE: 50
ttcaaaacct gtcagtgatt                                         20

<210> SEQ ID NO 51
<211> LENGTH: 20
<212> TYPE: DNA
```

-continued

```
<213> ORGANISM: Artificial Sequence
<220> FEATURE:
<223> OTHER INFORMATION: oligonucleotide

<400> SEQUENCE: 51
ccgaatcctc ctcctgaaag                                                  20

<210> SEQ ID NO 52
<211> LENGTH: 20
<212> TYPE: DNA
<213> ORGANISM: Artificial Sequence
<220> FEATURE:
<223> OTHER INFORMATION: oligonucleotide

<400> SEQUENCE: 52
ccactttcag gaggaggatt                                                  20

<210> SEQ ID NO 53
<211> LENGTH: 20
<212> TYPE: DNA
<213> ORGANISM: Artificial Sequence
<220> FEATURE:
<223> OTHER INFORMATION: oligonucleotide

<400> SEQUENCE: 53
taaacccggc cactttcagg                                                  20

<210> SEQ ID NO 54
<211> LENGTH: 25
<212> TYPE: DNA
<213> ORGANISM: Artificial Sequence
<220> FEATURE:
<223> OTHER INFORMATION: oligonucleotide

<400> SEQUENCE: 54
tctcaaacaa atgtgtcaca aagta                                            25

<210> SEQ ID NO 55
<211> LENGTH: 25
<212> TYPE: DNA
<213> ORGANISM: Artificial Sequence
<220> FEATURE:
<223> OTHER INFORMATION: oligonucleotide

<400> SEQUENCE: 55
cttacaatct tgcagatctg gaatg                                            25

<210> SEQ ID NO 56
<211> LENGTH: 20
<212> TYPE: DNA
<213> ORGANISM: Artificial Sequence
<220> FEATURE:
<223> OTHER INFORMATION: oligonucleotide

<400> SEQUENCE: 56
ttaatctgct catgacgctg                                                  20

<210> SEQ ID NO 57
<211> LENGTH: 20
<212> TYPE: DNA
<213> ORGANISM: Artificial Sequence
<220> FEATURE:
<223> OTHER INFORMATION: oligonucleotide

<400> SEQUENCE: 57
ggagaagagg ggcaatgcag                                                  20
```

-continued

```
<210> SEQ ID NO 58
<211> LENGTH: 20
<212> TYPE: DNA
<213> ORGANISM: Artificial Sequence
<220> FEATURE:
<223> OTHER INFORMATION: oligonucleotide

<400> SEQUENCE: 58
tcttctccct ctccaaacag                                               20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide

<400> SEQUENCE: 59
agcagctttc acctccttgg                                               20

<210> SEQ ID NO 60
<211> LENGTH: 20
<212> TYPE: DNA
<213> ORGANISM: Artificial Sequence
<220> FEATURE:
<223> OTHER INFORMATION: oligonucleotide

<400> SEQUENCE: 60
gtagcagctt tcacctcctt                                               20

<210> SEQ ID NO 61
<211> LENGTH: 20
<212> TYPE: DNA
<213> ORGANISM: Artificial Sequence
<220> FEATURE:
<223> OTHER INFORMATION: oligonucleotide

<400> SEQUENCE: 61
agttggtggc attgccgggg                                               20

<210> SEQ ID NO 62
<211> LENGTH: 23
<212> TYPE: DNA
<213> ORGANISM: Artificial Sequence
<220> FEATURE:
<223> OTHER INFORMATION: oligonucleotide

<400> SEQUENCE: 62
tctgtgatat acacatcaga atc                                           23

<210> SEQ ID NO 63
<211> LENGTH: 24
<212> TYPE: DNA
<213> ORGANISM: Artificial Sequence
<220> FEATURE:
<223> OTHER INFORMATION: oligonucleotide

<400> SEQUENCE: 63
tctgtgatat acacatcaga atcc                                          24

<210> SEQ ID NO 64
<211> LENGTH: 23
<212> TYPE: DNA
<213> ORGANISM: Artificial Sequence
<220> FEATURE:
```

-continued

<223> OTHER INFORMATION: oligonucleotide

<400> SEQUENCE: 64
gagtctctca gctggtacac ggc                                              23

<210> SEQ ID NO 65
<211> LENGTH: 24
<212> TYPE: DNA
<213> ORGANISM: Artificial Sequence
<220> FEATURE:
<223> OTHER INFORMATION: oligonucleotide

<400> SEQUENCE: 65
gagtctctca gctggtacac ggca                                             24

<210> SEQ ID NO 66
<211> LENGTH: 23
<212> TYPE: DNA
<213> ORGANISM: Artificial Sequence
<220> FEATURE:
<223> OTHER INFORMATION: oligonucleotide

<400> SEQUENCE: 66
attctcaaac aaatgtgtca caa                                              23

<210> SEQ ID NO 67
<211> LENGTH: 24
<212> TYPE: DNA
<213> ORGANISM: Artificial Sequence
<220> FEATURE:
<223> OTHER INFORMATION: oligonucleotide

<400> SEQUENCE: 67
attctcaaac aaatgtgtca caaa                                             24

<210> SEQ ID NO 68
<211> LENGTH: 23
<212> TYPE: DNA
<213> ORGANISM: Artificial Sequence
<220> FEATURE:
<223> OTHER INFORMATION: oligonucleotide

<400> SEQUENCE: 68
gtctgtgata tacacatcag aat                                              23

<210> SEQ ID NO 69
<211> LENGTH: 24
<212> TYPE: DNA
<213> ORGANISM: Artificial Sequence
<220> FEATURE:
<223> OTHER INFORMATION: oligonucleotide

<400> SEQUENCE: 69
gtctgtgata tacacatcag aatc                                             24

<210> SEQ ID NO 70
<211> LENGTH: 23
<212> TYPE: DNA
<213> ORGANISM: Artificial Sequence
<220> FEATURE:
<223> OTHER INFORMATION: oligonucleotide

<400> SEQUENCE: 70
gagaatcaaa atcggtgaat agg                                              23

```
<210> SEQ ID NO 71
<211> LENGTH: 23
<212> TYPE: DNA
<213> ORGANISM: Artificial Sequence
<220> FEATURE:
<223> OTHER INFORMATION: oligonucleotide

<400> SEQUENCE: 71
tgtgctagac atgaggtcta tgg                                          23

<210> SEQ ID NO 72
<211> LENGTH: 23
<212> TYPE: DNA
<213> ORGANISM: Artificial Sequence
<220> FEATURE:
<223> OTHER INFORMATION: oligonucleotide

<400> SEQUENCE: 72
tcagggttct ggatatctgt ggg                                          23

<210> SEQ ID NO 73
<211> LENGTH: 23
<212> TYPE: DNA
<213> ORGANISM: Artificial Sequence
<220> FEATURE:
<223> OTHER INFORMATION: oligonucleotide

<400> SEQUENCE: 73
gtcagggttc tggatatctg tgg                                          23

<210> SEQ ID NO 74
<211> LENGTH: 23
<212> TYPE: DNA
<213> ORGANISM: Artificial Sequence
<220> FEATURE:
<223> OTHER INFORMATION: oligonucleotide

<400> SEQUENCE: 74
aaagtcagat ttgttgctcc agg                                          23

<210> SEQ ID NO 75
<211> LENGTH: 23
<212> TYPE: DNA
<213> ORGANISM: Artificial Sequence
<220> FEATURE:
<223> OTHER INFORMATION: oligonucleotide

<400> SEQUENCE: 75
aacaaatgtg tcacaaagta agg                                          23

<210> SEQ ID NO 76
<211> LENGTH: 23
<212> TYPE: DNA
<213> ORGANISM: Artificial Sequence
<220> FEATURE:
<223> OTHER INFORMATION: oligonucleotide

<400> SEQUENCE: 76
tggatttaga gtctctcagc tgg                                          23

<210> SEQ ID NO 77
<211> LENGTH: 23
<212> TYPE: DNA
<213> ORGANISM: Artificial Sequence
<220> FEATURE:
<223> OTHER INFORMATION: oligonucleotide
```

-continued

<400> SEQUENCE: 77
taggcagaca gacttgtcac tgg                                               23

<210> SEQ ID NO 78
<211> LENGTH: 23
<212> TYPE: DNA
<213> ORGANISM: Artificial Sequence
<220> FEATURE:
<223> OTHER INFORMATION: oligonucleotide

<400> SEQUENCE: 78
agctggtaca cggcagggtc agg                                               23

<210> SEQ ID NO 79
<211> LENGTH: 23
<212> TYPE: DNA
<213> ORGANISM: Artificial Sequence
<220> FEATURE:
<223> OTHER INFORMATION: oligonucleotide

<400> SEQUENCE: 79
gctggtacac ggcagggtca ggg                                               23

<210> SEQ ID NO 80
<211> LENGTH: 23
<212> TYPE: DNA
<213> ORGANISM: Artificial Sequence
<220> FEATURE:
<223> OTHER INFORMATION: oligonucleotide

<400> SEQUENCE: 80
tctctcagct ggtacacggc agg                                               23

<210> SEQ ID NO 81
<211> LENGTH: 23
<212> TYPE: DNA
<213> ORGANISM: Artificial Sequence
<220> FEATURE:
<223> OTHER INFORMATION: oligonucleotide

<400> SEQUENCE: 81
agagtctctc agctggtaca cgg                                               23

<210> SEQ ID NO 82
<211> LENGTH: 23
<212> TYPE: DNA
<213> ORGANISM: Artificial Sequence
<220> FEATURE:
<223> OTHER INFORMATION: oligonucleotide

<400> SEQUENCE: 82
ctctcagctg gtacacggca ggg                                               23

<210> SEQ ID NO 83
<211> LENGTH: 23
<212> TYPE: DNA
<213> ORGANISM: Artificial Sequence
<220> FEATURE:
<223> OTHER INFORMATION: oligonucleotide

<400> SEQUENCE: 83
acaaaactgt gctagacatg agg                                               23

<210> SEQ ID NO 84
<211> LENGTH: 23

-continued

```
<212> TYPE: DNA
<213> ORGANISM: Artificial Sequence
<220> FEATURE:
<223> OTHER INFORMATION: oligonucleotide

<400> SEQUENCE: 84
atttgtttga gaatcaaaat cgg                                           23

<210> SEQ ID NO 85
<211> LENGTH: 23
<212> TYPE: DNA
<213> ORGANISM: Artificial Sequence
<220> FEATURE:
<223> OTHER INFORMATION: oligonucleotide

<400> SEQUENCE: 85
tggaataatg ctgttgttga agg                                           23

<210> SEQ ID NO 86
<211> LENGTH: 23
<212> TYPE: DNA
<213> ORGANISM: Artificial Sequence
<220> FEATURE:
<223> OTHER INFORMATION: oligonucleotide

<400> SEQUENCE: 86
agagcaacag tgctgtggcc tgg                                           23

<210> SEQ ID NO 87
<211> LENGTH: 23
<212> TYPE: DNA
<213> ORGANISM: Artificial Sequence
<220> FEATURE:
<223> OTHER INFORMATION: oligonucleotide

<400> SEQUENCE: 87
cttcttcccc agcccaggta agg                                           23

<210> SEQ ID NO 88
<211> LENGTH: 23
<212> TYPE: DNA
<213> ORGANISM: Artificial Sequence
<220> FEATURE:
<223> OTHER INFORMATION: oligonucleotide

<400> SEQUENCE: 88
acacggcagg gtcagggttc tgg                                           23

<210> SEQ ID NO 89
<211> LENGTH: 23
<212> TYPE: DNA
<213> ORGANISM: Artificial Sequence
<220> FEATURE:
<223> OTHER INFORMATION: oligonucleotide

<400> SEQUENCE: 89
cttcaagagc aacagtgctg tgg                                           23

<210> SEQ ID NO 90
<211> LENGTH: 23
<212> TYPE: DNA
<213> ORGANISM: Artificial Sequence
<220> FEATURE:
<223> OTHER INFORMATION: oligonucleotide

<400> SEQUENCE: 90
```

-continued

```
ctggggaaga aggtgtcttc tgg                                      23

<210> SEQ ID NO 91
<211> LENGTH: 23
<212> TYPE: DNA
<213> ORGANISM: Artificial Sequence
<220> FEATURE:
<223> OTHER INFORMATION: oligonucleotide

<400> SEQUENCE: 91
ttcttcccca gcccaggtaa ggg                                      23

<210> SEQ ID NO 92
<211> LENGTH: 23
<212> TYPE: DNA
<213> ORGANISM: Artificial Sequence
<220> FEATURE:
<223> OTHER INFORMATION: oligonucleotide

<400> SEQUENCE: 92
cttacctggg ctggggaaga agg                                      23

<210> SEQ ID NO 93
<211> LENGTH: 23
<212> TYPE: DNA
<213> ORGANISM: Artificial Sequence
<220> FEATURE:
<223> OTHER INFORMATION: oligonucleotide

<400> SEQUENCE: 93
gacaccttct tccccagccc agg                                      23

<210> SEQ ID NO 94
<211> LENGTH: 23
<212> TYPE: DNA
<213> ORGANISM: Artificial Sequence
<220> FEATURE:
<223> OTHER INFORMATION: oligonucleotide

<400> SEQUENCE: 94
ttcaaaacct gtcagtgatt ggg                                      23

<210> SEQ ID NO 95
<211> LENGTH: 23
<212> TYPE: DNA
<213> ORGANISM: Artificial Sequence
<220> FEATURE:
<223> OTHER INFORMATION: oligonucleotide

<400> SEQUENCE: 95
cgtcatgagc agattaaacc cgg                                      23

<210> SEQ ID NO 96
<211> LENGTH: 23
<212> TYPE: DNA
<213> ORGANISM: Artificial Sequence
<220> FEATURE:
<223> OTHER INFORMATION: oligonucleotide

<400> SEQUENCE: 96
ttcggaaccc aatcactgac agg                                      23

<210> SEQ ID NO 97
<211> LENGTH: 23
<212> TYPE: DNA
<213> ORGANISM: Artificial Sequence
```

-continued

```
<220> FEATURE:
<223> OTHER INFORMATION: oligonucleotide

<400> SEQUENCE: 97
taaacccggc cactttcagg agg                                                      23

<210> SEQ ID NO 98
<211> LENGTH: 23
<212> TYPE: DNA
<213> ORGANISM: Artificial Sequence
<220> FEATURE:
<223> OTHER INFORMATION: oligonucleotide

<400> SEQUENCE: 98
tttcaaaacc tgtcagtgat tgg                                                      23

<210> SEQ ID NO 99
<211> LENGTH: 23
<212> TYPE: DNA
<213> ORGANISM: Artificial Sequence
<220> FEATURE:
<223> OTHER INFORMATION: oligonucleotide

<400> SEQUENCE: 99
gattaaaccc ggccactttc agg                                                      23

<210> SEQ ID NO 100
<211> LENGTH: 23
<212> TYPE: DNA
<213> ORGANISM: Artificial Sequence
<220> FEATURE:
<223> OTHER INFORMATION: oligonucleotide

<400> SEQUENCE: 100
ctcgaccagc ttgacatcac agg                                                      23

<210> SEQ ID NO 101
<211> LENGTH: 23
<212> TYPE: DNA
<213> ORGANISM: Artificial Sequence
<220> FEATURE:
<223> OTHER INFORMATION: oligonucleotide

<400> SEQUENCE: 101
aagttcctgt gatgtcaagc tgg                                                      23

<210> SEQ ID NO 102
<211> LENGTH: 23
<212> TYPE: DNA
<213> ORGANISM: Artificial Sequence
<220> FEATURE:
<223> OTHER INFORMATION: oligonucleotide

<400> SEQUENCE: 102
atcctcctcc tgaaagtggc cgg                                                      23

<210> SEQ ID NO 103
<211> LENGTH: 23
<212> TYPE: DNA
<213> ORGANISM: Artificial Sequence
<220> FEATURE:
<223> OTHER INFORMATION: oligonucleotide

<400> SEQUENCE: 103
tgctcatgac gctgcggctg tgg                                                      23
```

<210> SEQ ID NO 104
<211> LENGTH: 23
<212> TYPE: DNA
<213> ORGANISM: Artificial Sequence
<220> FEATURE:
<223> OTHER INFORMATION: oligonucleotide

<400> SEQUENCE: 104
catcacagga actttctaaa agg                                                  23

<210> SEQ ID NO 105
<211> LENGTH: 23
<212> TYPE: DNA
<213> ORGANISM: Artificial Sequence
<220> FEATURE:
<223> OTHER INFORMATION: oligonucleotide

<400> SEQUENCE: 105
gtcgagaaaa gctttgaaac agg                                                  23

<210> SEQ ID NO 106
<211> LENGTH: 23
<212> TYPE: DNA
<213> ORGANISM: Artificial Sequence
<220> FEATURE:
<223> OTHER INFORMATION: oligonucleotide

<400> SEQUENCE: 106
ccactttcag gaggaggatt cgg                                                  23

<210> SEQ ID NO 107
<211> LENGTH: 23
<212> TYPE: DNA
<213> ORGANISM: Artificial Sequence
<220> FEATURE:
<223> OTHER INFORMATION: oligonucleotide

<400> SEQUENCE: 107
ctgacaggtt ttgaaagttt agg                                                  23

<210> SEQ ID NO 108
<211> LENGTH: 23
<212> TYPE: DNA
<213> ORGANISM: Artificial Sequence
<220> FEATURE:
<223> OTHER INFORMATION: oligonucleotide

<400> SEQUENCE: 108
agctttgaaa caggtaagac agg                                                  23

<210> SEQ ID NO 109
<211> LENGTH: 23
<212> TYPE: DNA
<213> ORGANISM: Artificial Sequence
<220> FEATURE:
<223> OTHER INFORMATION: oligonucleotide

<400> SEQUENCE: 109
ctgtggtcca gctgaggtga ggg                                                  23

<210> SEQ ID NO 110
<211> LENGTH: 23
<212> TYPE: DNA
<213> ORGANISM: Artificial Sequence
<220> FEATURE:
<223> OTHER INFORMATION: oligonucleotide -continued

<400> SEQUENCE: 110
ctgcggctgt ggtccagctg agg                                          23

<210> SEQ ID NO 111
<211> LENGTH: 23
<212> TYPE: DNA
<213> ORGANISM: Artificial Sequence
<220> FEATURE:
<223> OTHER INFORMATION: oligonucleotide

<400> SEQUENCE: 111
tgtggtccag ctgaggtgag ggg                                          23

<210> SEQ ID NO 112
<211> LENGTH: 23
<212> TYPE: DNA
<213> ORGANISM: Artificial Sequence
<220> FEATURE:
<223> OTHER INFORMATION: oligonucleotide

<400> SEQUENCE: 112
tcctcctcct gaaagtggcc ggg                                          23

<210> SEQ ID NO 113
<211> LENGTH: 23
<212> TYPE: DNA
<213> ORGANISM: Artificial Sequence
<220> FEATURE:
<223> OTHER INFORMATION: oligonucleotide

<400> SEQUENCE: 113
ttaatctgct catgacgctg cgg                                          23

<210> SEQ ID NO 114
<211> LENGTH: 23
<212> TYPE: DNA
<213> ORGANISM: Artificial Sequence
<220> FEATURE:
<223> OTHER INFORMATION: oligonucleotide

<400> SEQUENCE: 114
acccggccac tttcaggagg agg                                          23

<210> SEQ ID NO 115
<211> LENGTH: 23
<212> TYPE: DNA
<213> ORGANISM: Artificial Sequence
<220> FEATURE:
<223> OTHER INFORMATION: oligonucleotide

<400> SEQUENCE: 115
gctgtggtcc agctgaggtg agg                                          23

<210> SEQ ID NO 116
<211> LENGTH: 23
<212> TYPE: DNA
<213> ORGANISM: Artificial Sequence
<220> FEATURE:
<223> OTHER INFORMATION: oligonucleotide

<400> SEQUENCE: 116
ccgaatcctc ctcctgaaag tgg                                          23

<210> SEQ ID NO 117

```
<211> LENGTH: 941
<212> TYPE: DNA
<213> ORGANISM: Homo sapiens

<400> SEQUENCE: 117
ttggccaaga ttgatagctt gtgcctgtcc ctgagtccca gtccatcacg agcagctggt         60
ttctaagatg ctatttcccg tataaagcat gagaccgtga cttgccagcc ccacagagcc        120
ccgcccttgt ccatcactgg catctggact ccagcctggg ttggggcaaa gagggaaatg        180
agatcatgtc ctaaccctga tcctcttgtc ccacagatat ccagaaccct gaccctgccg        240
tgtaccagct gagagactct aaatccagtg acaagtctgt ctgcctattc accgattttg        300
attctcaaac aaatgtgtca caaagtaagg attctgatgt gtatatcaca gacaaaactg        360
tgctagacat gaggtctatg gacttcaaga gcaacagtgc tgtggcctgg agcaacaaat        420
ctgactttgc atgtgcaaac gccttcaaca acagcattat tccagaagac accttcttcc        480
ccagcccagg taagggcagc tttggtgcct tcgcaggctg tttccttgct tcaggaatgg        540
ccaggttctg cccagagctc tggtcaatga tgtctaaaac tcctctgatt ggtggtctcg        600
gccttatcca ttgccaccaa aaccctcttt ttactaagaa acagtgagcc ttgttctggc        660
agtccagaga atgacacggg aaaaaagcag atgaagagaa ggtggcagga gagggcacgt        720
ggcccagcct cagtctctcc aactgagttc ctgcctgcct gcctttgctc agactgtttg        780
ccccttactg ctcttctagg cctcattcta agcccctct ccaagttgcc tctccttatt        840
tctccctgtc tgccaaaaaa tctttcccag ctcactaagt cagtctcacg cagtcactca        900
ttaacccacc aatcactgat gtgccggca catgaatgca c                            941

<210> SEQ ID NO 118
<211> LENGTH: 704
<212> TYPE: DNA
<213> ORGANISM: Homo sapiens

<400> SEQUENCE: 118
ccgtgtacca gctgagagac tctaaatcca gtgacaagtc tgtctgccta ttcaccgatt         60
ttgattctca aacaaatgtg tcacaaagta aggattctga tgtgtatatc acagacaaaa        120
ctgtgctaga catgaggtct atggacttca agagcaacag tgctgtggcc tggagcaaca        180
aatctgactt tgcatgtgca aacgccttca caacagcat tattccagaa gacaccttct        240
tccccagccc aggtaagggc agctttggtg ccttcgcagg ctgtttcctt gcttcaggaa        300
tggccaggtt ctgcccagag ctctggtcaa tgatgtctaa aactcctctg attggtggtc        360
tcggccttat ccattgccac caaaaccctc tttttactaa gaaacagtga gccttgttct        420
ggcagtccag agaatgacac gggaaaaaag cagatgaaga gaaggtggca ggagagggca        480
cgtggcccag cctcagtctc tccaactgag ttcctgcctg cctgcctttg tcagactgt        540 ttgcccctta ctgctcttct aggcctcatt ctaagcccct tctccaagtt gcctctcctt        600
atttctccct gtctgccaaa aaatctttcc cagctcacta agtcagtctc acgcagtcac        660
tcattaaccc accaatcact gattgtgccg gcacatgaat gcac                         704

<210> SEQ ID NO 119
<211> LENGTH: 224
<212> TYPE: DNA
<213> ORGANISM: Artificial Sequence
<220> FEATURE:
<223> OTHER INFORMATION: Terminator

<400> SEQUENCE: 119
```

-continued

```
ctgtgccttc tagttgccag ccatctgttg tttgcccctc cccgtgcct tccttgaccc        60 tggaaggtgc cactcccact gtcctttcct aataaaatga ggaaattgca tcgcattgtc       120
tgagtaggtg tcattctatt ctggggggtg gggtggggca ggacagcaag ggggaggatt       180
gggaacacaa tagcaggcat gctggggatg cggtgggctc tatg                        224
```

```
<210> SEQ ID NO 120
<211> LENGTH: 225
<212> TYPE: DNA
<213> ORGANISM: Artificial Sequence
<220> FEATURE:
<223> OTHER INFORMATION: Terminator

<400> SEQUENCE: 120
ctgtgccttc tagttgccag ccatctgttg tttgcccctc cccgtgcct tccttgaccc        60 tggaaggtgc cactcccact gtcctttcct aataaaatga ggaaattgca tcgcattgtc       120
tgagtaggtg tcattctatt ctggggggtg gggtggggca ggacagcaag ggggaggatt       180
gggaagacaa tagcaggcat gctggggatg cggtgggctc tatgg                       225
```

```
<210> SEQ ID NO 121
<211> LENGTH: 276
<212> TYPE: DNA
<213> ORGANISM: Artificial Sequence
<220> FEATURE:
<223> OTHER INFORMATION: Termnator

<400> SEQUENCE: 121
cctcgactgt gccttctagt tgccagccat ctgttgtttg ccctccccc gtgccttcct        60 tgaccctgga aggtgccact cccactgtcc tttcctaata aaatgaggaa attgcatcgc       120
attgtctgag taggtgtcat tctattctgg ggggtggggt ggggcaggac agcaaggggg       180
aggattggga agacaatagc aggcatgctg gggatgcggt gggctctatg gcttctgagg       240
cggaaagaac cagctggggc tctaggggt atcccc                                  276
```

```
<210> SEQ ID NO 122
<211> LENGTH: 223
<212> TYPE: DNA
<213> ORGANISM: Artificial Sequence
<220> FEATURE:
<223> OTHER INFORMATION: Terminator

<400> SEQUENCE: 122
ctgtgccttc tagttgccag ccatctgttg tttgcccctc cccgtgcct tccttgaccc        60 tggaaggtgc cactcccact gtcctttcct aataaaatga ggaaattgca tcgcattgtc       120
tgagtaggtg tcattctatt ctggggggtg gggtggggca ggacagcaag ggggaggatt       180
gggaacacaa tagcaggcat gctggggatg cggtgggctc tat                         223
```

```
<210> SEQ ID NO 123
<211> LENGTH: 60
<212> TYPE: DNA
<213> ORGANISM: Artificial Sequence
<220> FEATURE:
<223> OTHER INFORMATION: binding site

<400> SEQUENCE: 123
tgatcctctt gtcccacaga tatccagaac cctgaccctg cccgtgtacc agctgagaga        60
```

```
<210> SEQ ID NO 124
```

-continued

```
<211> LENGTH: 48
<212> TYPE: DNA
<213> ORGANISM: Artificial Sequence
<220> FEATURE:
<223> OTHER INFORMATION: binding site

<400> SEQUENCE: 124
ttgtcccaca gatatcagaa ccctgaccct gccgtgtacc agctgaga              48

<210> SEQ ID NO 125
<211> LENGTH: 48
<212> TYPE: DNA
<213> ORGANISM: Artificial Sequence
<220> FEATURE:
<223> OTHER INFORMATION: probe

<400> SEQUENCE: 125
ttgtcccaca gatatcagaa ccctgaccct gccgtgtacc agctgaga              48

<210> SEQ ID NO 126
<211> LENGTH: 48
<212> TYPE: DNA
<213> ORGANISM: Artificial Sequence
<220> FEATURE:
<223> OTHER INFORMATION: probe

<400> SEQUENCE: 126
ttgtcccaca gatatcagaa ccctgaccct gccgtgtacc agctgaga              48

<210> SEQ ID NO 127
<211> LENGTH: 100
<212> TYPE: DNA
<213> ORGANISM: Homo sapiens

<400> SEQUENCE: 127
taacccccaa aactttctct tctgcaggtc aagagaaagg atttctgaag gcagccctgg    60
aagtggagtt aggagcttct aacccgtcat ggtttcaata                       100

<210> SEQ ID NO 128
<211> LENGTH: 94
<212> TYPE: DNA
<213> ORGANISM: Artificial Sequence
<220> FEATURE:
<223> OTHER INFORMATION: TALEN

<400> SEQUENCE: 128
tctgcaggtc aagagaaagg atttctgaag gcagccctgg aagtggatct gcaggtcaag    60
agaaaggatt tctgaaggca gccctggaag tgga                             94

<210> SEQ ID NO 129
<211> LENGTH: 16
<212> TYPE: DNA
<213> ORGANISM: Artificial Sequence
<220> FEATURE:
<223> OTHER INFORMATION: probe

<400> SEQUENCE: 129
ttgtcccaca gatatc                                                16

<210> SEQ ID NO 130
<211> LENGTH: 17
<212> TYPE: DNA
<213> ORGANISM: Artificial Sequence
<220> FEATURE:
<223> OTHER INFORMATION: probe
```

-continued

```
<400> SEQUENCE: 130
ccgtgtacca gctgaga                                               17

<210> SEQ ID NO 131
<211> LENGTH: 130
<212> TYPE: DNA
<213> ORGANISM: Homo sapiens

<400> SEQUENCE: 131
gatacgaacc taaactttca aaacctgtca gtgattgggt tccgaatcct cctcctgaaa    60
gtggccgggt ttaatctgct catgacgctg cggctgtggt ccagctgagg tgaggggcct   120
tgaagctggg                                                        130

<210> SEQ ID NO 132
<211> LENGTH: 100
<212> TYPE: DNA
<213> ORGANISM: Artificial Sequence
<220> FEATURE:
<223> OTHER INFORMATION: TALEN

<400> SEQUENCE: 132
tctgctcatg acgctgcggc tgtggtccag ctgaggtgag gggccttgaa tctgctcatg    60
acgctgcggc tgtggtccag ctgaggtgag gggccttgaa                        100

<210> SEQ ID NO 133
<211> LENGTH: 96
<212> TYPE: DNA
<213> ORGANISM: Artificial Sequence
<220> FEATURE:
<223> OTHER INFORMATION: TALEN

<400> SEQUENCE: 133
tgctcatgac gctgcggctg tggtccagct gaggtgaggg gccttgaatg ctcatgacgc    60
tgcggctgtg gtccagctga ggtgaggggc cttgaa                             96

<210> SEQ ID NO 134
<211> LENGTH: 98
<212> TYPE: DNA
<213> ORGANISM: Artificial Sequence
<220> FEATURE:
<223> OTHER INFORMATION: TALEN

<400> SEQUENCE: 134
tgacgctgcg gctgtggtcc agctgaggtg aggggccttg aagctgggat gacgctgcgg    60
ctgtggtcca gctgaggtga ggggccttga agctggga                           98

<210> SEQ ID NO 135
<211> LENGTH: 98
<212> TYPE: DNA
<213> ORGANISM: Artificial Sequence
<220> FEATURE:
<223> OTHER INFORMATION: TALEN

<400> SEQUENCE: 135
tggtccagct gaggtgaggg gccttgaagc tgggagtggg gtttagggat ggtccagctg    60
aggtgagggg ccttgaagct gggagtgggg tttaggga                           98

<210> SEQ ID NO 136
<211> LENGTH: 98
<212> TYPE: DNA
```

<213> ORGANISM: Artificial Sequence
<220> FEATURE:
<223> OTHER INFORMATION: TALEN

<400> SEQUENCE: 136
tttctcttct gcaggtcaag agaaaggatt tctgaaggca gccctggaat ttctcttctg      60
caggtcaaga gaaaggattt ctgaaggcag ccctggaa      98

<210> SEQ ID NO 137
<211> LENGTH: 94
<212> TYPE: DNA
<213> ORGANISM: Artificial Sequence
<220> FEATURE:
<223> OTHER INFORMATION: TALEN

<400> SEQUENCE: 137
ttctgaaggc agccctggaa gtggagttag gagcttctaa cccgtcattc tgaaggcagc      60
cctggaagtg gagttaggag cttctaaccc gtca      94

<210> SEQ ID NO 138
<211> LENGTH: 134
<212> TYPE: DNA
<213> ORGANISM: Homo sapiens

<400> SEQUENCE: 138
tagcccctga aaccctgaaa atgttctctc ttccacaggt caagagaaag gattccagag      60
gctagctcca aaaccatccc aggtcattct tcatcctcac ccactccaaa accatcccag     120
gtcattcttc atcc      134

<210> SEQ ID NO 139
<211> LENGTH: 98
<212> TYPE: DNA
<213> ORGANISM: Artificial Sequence
<220> FEATURE:
<223> OTHER INFORMATION: TALEN

<400> SEQUENCE: 139
tgaaaatgtt ctctcttcca caggtcaaga gaaaggattc cagaggctat gaaaatgttc      60
tctcttccac aggtcaagag aaaggattcc agaggcta      98

<210> SEQ ID NO 140
<211> LENGTH: 98
<212> TYPE: DNA
<213> ORGANISM: Artificial Sequence
<220> FEATURE:
<223> OTHER INFORMATION: TALEN

<400> SEQUENCE: 140
ttctctcttc cacaggtcaa gagaaaggat tccagaggct agctccaaat tctctcttcc      60
acaggtcaag agaaaggatt ccagaggcta gctccaaa      98

<210> SEQ ID NO 141
<211> LENGTH: 98
<212> TYPE: DNA
<213> ORGANISM: Artificial Sequence
<220> FEATURE:
<223> OTHER INFORMATION: TALEN

<400> SEQUENCE: 141
ttctctcttc cacaggtcaa gagaaaggat tccagaggct agctccaaat ctctcttcca      60
caggtcaaga gaaaggattc cagaggctag ctccaaaa      98

<210> SEQ ID NO 142
<211> LENGTH: 98
<212> TYPE: DNA
<213> ORGANISM: Artificial Sequence
<220> FEATURE:
<223> OTHER INFORMATION: TALEN

<400> SEQUENCE: 142
tagctccaaa accatcccag gtcattcttc atcctcaccc actccaaaat agctccaaaa        60
ccatcccagg tcattcttca tcctcaccca ctccaaaa                                98

<210> SEQ ID NO 143
<211> LENGTH: 224
<212> TYPE: DNA
<213> ORGANISM: Homo sapiens

<400> SEQUENCE: 143
ttggccaaga ttgatagctt gtgcctgtcc ctgagtccca gtccatcacg agcagctggt        60
ttctaagatg ctatttcccg tataaagcat gagaccgtga cttgccagcc ccacagagcc       120
ccgcccttgt ccatcactgg catctggact ccagcctggg ttggggcaaa gagggaaatg       180
agatcatgtc ctaaccctga tcctcttgtc ccacagatat ccag                       224

<210> SEQ ID NO 144
<211> LENGTH: 35
<212> TYPE: DNA
<213> ORGANISM: Artificial Sequence
<220> FEATURE:
<223> OTHER INFORMATION: oligonucleotide

<400> SEQUENCE: 144
cctgaccctg ccgtgtacca gctgagagac tctaa                                   35

<210> SEQ ID NO 145
<211> LENGTH: 49
<212> TYPE: DNA
<213> ORGANISM: Artificial Sequence
<220> FEATURE:
<223> OTHER INFORMATION: oligonucleotide

<400> SEQUENCE: 145
tccagtgaca agtctgtctg cctattcacc gattttgatt ctcaaacaa                    49

<210> SEQ ID NO 146
<211> LENGTH: 103
<212> TYPE: DNA
<213> ORGANISM: Artificial Sequence
<220> FEATURE:
<223> OTHER INFORMATION: oligonucleotide

<400> SEQUENCE: 146
ttgtcccaca gatatccaga accctgaccc tgccgtgtac cagctgagag actctaaatc        60
cagtgacaag tctgtctgcc tattcaccga ttttgattct caa                        103

<210> SEQ ID NO 147
<211> LENGTH: 36
<212> TYPE: DNA
<213> ORGANISM: Artificial Sequence
<220> FEATURE:
<223> OTHER INFORMATION: oligonucleotide

<400> SEQUENCE: 147

-continued

```
ttcaccgatt ttgattctca aacaaatgtg tcacaa                                  36

<210> SEQ ID NO 148
<211> LENGTH: 178
<212> TYPE: DNA
<213> ORGANISM: Artificial Sequence
<220> FEATURE:
<223> OTHER INFORMATION: oligonucleotide

<400> SEQUENCE: 148
ttgtcccaca gatatccaga accctgaccc tgccgtgtac cagctgagag actctaaatc       60
cagtgacaag tctgtctgcc tattcaccga ttttgattct caaacaaatg tgtcacaaag      120
taaggattct gatgtgtata tcacagacaa aactgtgcta gacatgaggt ctatggac        178

<210> SEQ ID NO 149
<211> LENGTH: 49
<212> TYPE: DNA
<213> ORGANISM: Artificial Sequence
<220> FEATURE:
<223> OTHER INFORMATION: oligonucleotide

<400> SEQUENCE: 149
tatatcacag acaaaactgt gctagacatg aggtctatgg acttcaaga                    49

<210> SEQ ID NO 150
<211> LENGTH: 49
<212> TYPE: DNA
<213> ORGANISM: Artificial Sequence
<220> FEATURE:
<223> OTHER INFORMATION: oligonucleotide

<400> SEQUENCE: 150
tgaggtctat ggacttcaag agcaacagtg ctgtggcctg gagcaacaa                    49

<210> SEQ ID NO 151
<211> LENGTH: 208
<212> TYPE: DNA
<213> ORGANISM: Artificial Sequence
<220> FEATURE:
<223> OTHER INFORMATION: oligonucleotide

<400> SEQUENCE: 151
ttgtcccaca gatatccaga accctgaccc tgccgtgtac cagctgagag actctaaatc       60
cagtgacaag tctgtctgcc tattcaccga ttttgattct caaacaaatg tgtcacaaag      120
taaggattct gatgtgtata tcacagacaa aactgtgcta gacatgaggt ctatggactt      180
caagagcaac agtgctgtgg cctggagc                                          208

<210> SEQ ID NO 152
<211> LENGTH: 50
<212> TYPE: DNA
<213> ORGANISM: Artificial Sequence
<220> FEATURE:
<223> OTHER INFORMATION: oligonucleotide

<400> SEQUENCE: 152
tatccagaac cctgaccctg ccgtgtacca gctgagagac tctaaatcca                   50

<210> SEQ ID NO 153
<211> LENGTH: 55
<212> TYPE: DNA
<213> ORGANISM: Artificial Sequence
<220> FEATURE:
<223> OTHER INFORMATION: oligonucleotide
```

```
<400> SEQUENCE: 153
ttgtcccaca gatatccaga accctgaccc tgccgtgtac cagctgagag actct            55

<210> SEQ ID NO 154
<211> LENGTH: 49
<212> TYPE: DNA
<213> ORGANISM: Artificial Sequence
<220> FEATURE:
<223> OTHER INFORMATION: oligonucleotide

<400> SEQUENCE: 154
tttagaaagt tcctgtgatg tcaagctggt cgagaaaagc tttgaaaca               49

<210> SEQ ID NO 155
<211> LENGTH: 156
<212> TYPE: DNA
<213> ORGANISM: Artificial Sequence
<220> FEATURE:
<223> OTHER INFORMATION: product
<220> FEATURE:
<221> NAME/KEY: misc_feature
<222> LOCATION: (59)..(68)
<223> OTHER INFORMATION: n is a, c, g, or t

<400> SEQUENCE: 155
aatgatacgg cgaccaccga gatctacact ctttccctac acgacgctct tccgatctnn   60
nnnnnnnngt ttaattgagt tgtcatatgt atcaccgact gcccatagag aggactccag  120
tcactaaggc gaatctcgta tgccgtcttc tgcttg                            156

<210> SEQ ID NO 156
<211> LENGTH: 163
<212> TYPE: DNA
<213> ORGANISM: Artificial Sequence
<220> FEATURE:
<223> OTHER INFORMATION: product
<220> FEATURE:
<221> NAME/KEY: misc_feature
<222> LOCATION: (95)..(106)
<223> OTHER INFORMATION: n is a, c, g, or t

<400> SEQUENCE: 156
caagcagaag acggcatacg agattcgcct tagtgactgg agtcctctct atgggcagtc   60
ggtgatttga gttgtcatat gttaataacg gtatnnnnnn nnnnnnagat cggaagagcg  120
tcgtgtagga aagagtgtag atctcggtgg tcgccgtatc att                    163

<210> SEQ ID NO 157
<211> LENGTH: 19
<212> TYPE: DNA
<213> ORGANISM: Artificial Sequence
<220> FEATURE:
<223> OTHER INFORMATION: oligonucleotide

<400> SEQUENCE: 157
tgctgtggcc tggagcaac                                               19

<210> SEQ ID NO 158
<211> LENGTH: 15
<212> TYPE: DNA
<213> ORGANISM: Artificial Sequence
<220> FEATURE:
<223> OTHER INFORMATION: oligonucleotide

<400> SEQUENCE: 158
```

-continued

```
gactttgcat gtgca                                                                  15

<210> SEQ ID NO 159
<211> LENGTH: 17
<212> TYPE: DNA
<213> ORGANISM: Artificial Sequence
<220> FEATURE:
<223> OTHER INFORMATION: oligonucleotide

<400> SEQUENCE: 159
ggcacatggt cgactct                                                                17

<210> SEQ ID NO 160
<211> LENGTH: 16
<212> TYPE: DNA
<213> ORGANISM: Artificial Sequence
<220> FEATURE:
<223> OTHER INFORMATION: oligonucleotide

<400> SEQUENCE: 160
aacagggtgt ctatag                                                                 16

<210> SEQ ID NO 161
<211> LENGTH: 941
<212> TYPE: DNA
<213> ORGANISM: Homo sapiens

<400> SEQUENCE: 161
ttggccaaga ttgatagctt gtgcctgtcc ctgagtccca gtccatcacg agcagctggt        60
ttctaagatg ctatttcccg tataaagcat gagaccgtga cttgccagcc ccacagagcc       120
ccgcccttgt ccatcactgg catctggact ccagcctggg ttggggcaaa gagggaaatg       180
agatcatgtc ctaaccctga tcctcttgtc ccacagatat ccagaaccct gaccctgccg       240
tgtaccagct gagagactct aaatccagtg acaagtctgt ctgcctattc accgattttg       300
attctcaaac aaatgtgtca caaagtaagg attctgatgt gtatatcaca gacaaaactg       360
tgctagacat gaggtctatg gacttcaaga gcaacagtgc tgtggcctgg agcaacaaat       420
ctgactttgc atgtgcaaac gccttcaaca acagcattat tccagaagac accttcttcc       480
ccagcccagg taagggcagc tttggtgcct tcgcaggctg tttccttgct tcaggaatgg       540
ccaggttctg cccagagctc tggtcaatga tgtctaaaac tcctctgatt ggtggtctcg       600
gccttatcca ttgccaccaa aaccctcttt ttactaagaa acagtgagcc ttgttctggc       660
agtccagaga atgacacggg aaaaaagcag atgaagagaa ggtggcagga gagggcacgt       720
ggcccagcct cagtctctcc aactgagttc ctgcctgcct gcctttgctc agactgtttg       780 cccttactg ctcttctagg cctcattcta agcccttct ccaagttgcc tctccttatt        840
tctccctgtc tgccaaaaaa tctttcccag ctcactaagt cagtctcacg cagtcactca       900
ttaacccacc aatcactgat gtgccggca catgaatgca c                            941

<210> SEQ ID NO 162
<211> LENGTH: 15
<212> TYPE: DNA
<213> ORGANISM: Artificial Sequence
<220> FEATURE:
<223> OTHER INFORMATION: oligonucleotide

<400> SEQUENCE: 162
ttgtcccaca gatat                                                                  15
```

-continued

```
<210> SEQ ID NO 163
<211> LENGTH: 15
<212> TYPE: DNA
<213> ORGANISM: Artificial Sequence
<220> FEATURE:
<223> OTHER INFORMATION: oligonucleotide

<400> SEQUENCE: 163
tctcagctgg tacac                                                            15

<210> SEQ ID NO 164
<211> LENGTH: 22
<212> TYPE: DNA
<213> ORGANISM: Artificial Sequence
<220> FEATURE:
<223> OTHER INFORMATION: oligonucleotide

<400> SEQUENCE: 164
gggctatagg aggtcttggg ac                                                    22
```

TAL-EFFECTOR NUCLEASE (TALEN)-MODIFIED ALLOGENIC CELLS SUITABLE FOR THERAPY

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Mar. 18, 2024, is named 16340412_seq_lst_ST25-2.txt and is 77,351 bytes in size.

FIELD OF THE INVENTION

The invention relates to the fields of immunotherapy, molecular biology and recombinant nucleic acid technology. In particular, the invention relates to a TALEN-modified human primary cell comprising in its genome, a modified human T cell receptor alpha gene with an insertion comprising at least, from 5' to 3', a polynucleotide encoding a self-cleaving peptide, a chimeric antigen receptor, wherein the cell has undetectable cell-surface expression of the endogenous alpha beta T cell receptor as compared to a TCR positive control cell and expresses a receptor to target a pathological cell, use of said cell for treating a disease, including cancer. The invention further relates to methods for producing such a TALEN-modified cell, and to means for detecting such an engineered human primary cell or other genetically modified human primary cell obtained using alternative and/or additional rare cutting endonucleases.

BACKGROUND OF THE INVENTION

T cell adoptive immunotherapy is a promising approach for cancer treatment. This strategy utilizes isolated human T cells, usually obtained from patients themselves that have been genetically-modified to enhance their specificity for a specific tumor associated antigen. Genetic modification may involve the expression of a chimeric antigen receptor or of an exogenous T cell receptor, the inactivation of particular cell surface proteins, to prevent inhibition of the cytolytic activity by cancer cells, gene modification to make cells sensitive or resistant to a drug.

By contrast to exogenous T cell receptors, chimeric antigen receptors derive their specificity from the variable domains of a monoclonal antibody. Thus, T cells expressing chimeric antigen receptors (CAR T cells) induce tumor immunoreactivity in a major histocompatibility complex non-restricted manner. To date, T cell adoptive immunotherapy has been utilized as a clinical therapy for a number of cancers, including B cell malignancies (e.g., acute lymphoblastic leukemia (ALL), B cell non-Hodgkin lymphoma (NHL), and chronic lymphocytic leukemia), multiple myeloma, neuroblastoma, glioblastoma, advanced gliomas, ovarian cancer, mesothelioma, melanoma, and pancreatic cancer.

Despite its potential usefulness as a cancer treatment, adoptive immunotherapy with CAR T cells has been limited, in part, by expression of the endogenous T cell receptor on the cell surface. CAR T cells expressing an endogenous T cell receptor may recognize major and minor histocompatibility antigens following administration to an allogeneic patient, which can lead to the development of graft-versus-host-disease (GVHD). As a result, clinical trials have largely focused on the use of autologous CAR T cells, wherein a patient's T cells are isolated, genetically-modified to incorporate a chimeric antigen receptor, and then re-infused into the same patient. An autologous approach provides immune tolerance to the administered CAR T cells; however, this approach is constrained by both the time and expense necessary to produce patient-specific CAR T cells after a patient's cancer has been diagnosed.

Thus, "off the shelf CAR T cells" or so called "allogenic CAR T cells" or universal CART (UCART), prepared using cells from a third-party donor, that have reduced or better, no expression of the endogenous T cell receptor and do not initiate GVHD upon administration have been prepared.

To reduce or eliminate cell surface expression of the TCR in primary T cells (isolated from healthy donors), various methods were used.

Genetic modification of genomic DNA can be performed using site-specific, rare-cutting endonucleases that are engineered to recognize DNA sequences in the locus of interest. Methods for producing engineered, site-specific endonucleases are known in the art. For example, zinc-finger nucleases (ZFNs) can be engineered to recognize and cut predetermined sites in a genome. ZFNs are chimeric proteins comprising a zinc finger DNA-binding domain fused to the nuclease domain of the FokI restriction enzyme. The zinc finger domain can be redesigned through rational or experimental means to produce a protein that binds to a predetermined DNA sequence-18 basepairs in length. By fusing this engineered protein domain to the FokI nuclease, it is possible to target DNA breaks with genome-level specificity. ZFNs have been used extensively to target gene addition, removal, and substitution in a wide range of eukaryotic organisms (reviewed in Durai et al. (2005), Nucleic Acids Res 33, 5978). Likewise, TAL-effector nucleases (TALENs) can be generated to cleave specific sites in genomic DNA. Like a ZFN, a TALEN comprises an engineered, site-specific DNA-binding domain fused to the FokI nuclease domain (reviewed in Mak et al. (2013), Curr Opin Struct Biol. 23:93-9). In this case, the DNA binding domain comprises a tandem array of TAL-effector domains, each of which specifically recognizes a single DNA basepair. Thus, TALENs are heterodimeric, so that the production of a single functional nuclease in a cell requires co-expression of two proteins, making it more reliable and specific for the locus targeted than other techniques (less off sites is measured). Compact TALENs have an alternative endonuclease architecture (Beurdeley et al. (2013), Nat Commun. 4:1762). A Compact TALEN comprises an engineered, site-specific TAL-effector DNA-binding domain fused to the nuclease domain from the I-TevI homing endonuclease. Unlike FokI, I-TevI does not need to dimerize to produce a double-strand DNA break so a Compact TALEN is functional as a monomer.

Engineered endonucleases based on the CRISPR/Cas9 system are also known in the art (Ran et al. (2013), Nat Protoc. 8:2281-2308; Mali et al. (2013), Nat Methods 10:957-63). A CRISPR endonuclease comprises two components: (1) CRISPR-associated Protein9, typically microbial Cas9; and (2) a short "guide RNA" comprising a 20 nucleotides targeting sequence that directs the nuclease to a location of interest in the genome. By expressing multiple guide RNAs in the same cell, each having a different targeting sequence, it is possible to target DNA breaks simultaneously to multiple sites in the genome. The primary drawback of the CRISPR/Cas9 system is its reported high frequency of off-target DNA breaks, which could limit the utility of the system for treating human patients (Fu et al. (2013), Nat Biotechnol. 31:822-6).

Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38:49-95). Homing endonucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), Nucleic Acids Res. 29 (18): 3757-3774). The LAGLIDADG homing endonucleases with a single copy of the LAGLIDADG motif form homodimers, whereas members with two copies of the LAGLIDADG motif are found as monomers.

I-CreI is a member of the LAGLIDADG family of homing endonucleases that recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), J. Mol. Biol. 342:31-41; Chames et al. (2005), Nucleic Acids Res. 33: el78; Seligman et al. (2002), Nucleic Acids Res. 30:3870-9, Arnould et al. (2006), J. Mol. Biol. 355:443-58). A method of rationally-designing mono-LAGLIDADG homing endonucleases was described that is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), Nucleic Acids Res. 37:1650-62; Grizot e/1 al. (2009), Nucleic Acids Res. 37:5405-19). Thus, a functional "single-chain" meganuclease can be expressed from a single transcript. The use of engineered meganucleases for cleaving DNA targets in the human T cell receptor alpha constant region was previously disclosed (WO 2014/191527). WO 2014/191527 discloses variants of the I-OnuI meganuclease that are engineered to target a recognition sequence within exon 1 of the TCR alpha constant region gene. Although the WO 2014/191527 publication discusses that a chimeric antigen receptor can be expressed in TCR knockout cells, the authors do not disclose the insertion of the chimeric antigen receptor coding sequence into the meganuclease cleavage site in the TCR alpha constant region gene.

The use of other nucleases and mechanisms for disrupting expression of the endogenous TCR has also been disclosed. For example, the use of zinc finger nucleases for disrupting TCR genes in human T cells was described by U.S. Pat. No. 8,95,828 and by U.S. Patent Application Publication No. US2014/034902. U.S. Publication No. US2014/0301990 describes the use of zinc finger nucleases and transcription-activator like effector nucleases (TALENs), and of a CRISPR Cas system with an engineered single guide RNA for targeting TCR genes in an isolated T cell. U.S. Patent Application Publication No. US2012/0321667 discloses the use of small-hairpin RNAs that target nucleic acids encoding specific TCRs and/or CD3 chains in T cells.

Similarly, WO2017062451, WO2015057980, WO2017106528 or U.S. Pat. No. 7,910,332 B2 describes TCR negative T cells obtained using various tools of gene editing, in particular Crispr/cas 9 system, or a meganuclease targeting various sequences of the constant region of the T cell receptor gene (TRAC gene).

Each type of endonuclease, when used in optimized conditions, generates a double strand cut of the DNA and either a new DNA sequence at the site of insertion or a deletion is created. Further, the frequency of off target gene modifications is directly related to the endonuclease used and to the sequence of the TRAC gene bound and cut by the endonuclease used, making the final product more or less reliable as a medicament.

There is still a need for providing off the shelve products, in particular for immunotherapy, with more stable gene modification(s), less off site, and means of detecting engineered cells, measuring the quality of such products, identifying their integrity and stability.

The present inventors are the first to teach a TALEN-modified human primary cells with a TALEN-mediated specific insertion into the TCR-encoding gene allowing a CAR targeting CD123 or CD22 to be expressed at the cell surface and a TALEN-induced off site target below detection as measured by a guide seq technique. They are also the first to report means and method of detecting such genetically-modified human primary cells over cells engineered using other endonucleases designed to cleave the TCR, in particular on site and off site cleavages.

SUMMARY OF THE INVENTION

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a coding sequence such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second TALEN recognition domain, (d) a 3' region of the genomic TRAC gene.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) a gap (c') optionally a second TALEN recognition domain, (d) a 3' region of the genomic TRAC gene.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a coding sequence such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second TALEN recognition domain, (d) a 3' region of the genomic TRAC gene.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) an insertion as compared to the wild type TRAC gene affecting the cell surface expression of the extracellular domain or transmembrane domain of the alpha beta TCR, said insertion comprising an exogenous polynucleotide comprising a sequence coding for a self-cleaving peptide in frame with the TRAC open reading frame, a sequence coding a chimeric antigen receptor (CAR), a termination sequence.

(c') optionally a second TALEN recognition domain, (d) a 3' region of the genomic TRAC gene.

A CAR means chimeric antigen receptor and may be a recombinant TCR.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN,

(c) an insertion as compared to the wild type TRAC gene affecting the cell surface expression of the extracellular domain or transmembrane domain of the alpha beta TCR, said insertion comprising an IRES, a chimeric antigen receptor (CAR), a termination sequence, a combination thereof, (c') optionally a second TALEN recognition domain, (d) a 3' region of the genomic TRAC gene.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) an insertion as compared to the wild type TRAC gene affecting the cell surface expression of the extracellular domain or transmembrane domain of the alpha beta TCR, said insertion comprising a self-cleaving peptide in frame with the TRAC open reading frame, a sequence coding a protein conferring sensitivity to a drug, a termination sequence, (c') optionally a second TALEN recognition domain, (d) a 3' region of the genomic TRAC gene.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) an insertion as compared to the wild type TRAC gene affecting the cell surface expression of the extracellular domain or transmembrane domain of the alpha beta TCR, said insertion comprising a self-cleaving peptide in frame with the TRAC open reading frame, a sequence coding a protein conferring resistance to a drug, a termination sequence, (c') optionally a second TALEN recognition domain, (d) a 3' region of the genomic TRAC gene.

The present invention provides a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a TALEN, (c) an insertion as compared to the wild type TRAC gene affecting the cell surface expression of the extracellular domain or transmembrane domain of the alpha beta TCR, said insertion comprising a self-cleaving peptide in frame with the TRAC open reading frame, a sequence coding a cytokine, a termination sequence, (c') optionally a second TALEN recognition domain, (d) a 3' region of the genomic TRAC gene.

Here; a "cytokine" encompasses any factor influencing the functioning (activity, capacity to migrate, adhere, resists to tumor environment) of immune cells.

In one aspect, the present invention provides a TALEN-modified endogenous αβ-TCR negative human primary cell according to the above embodiments, wherein said human primary cell is a human primary T cell or a human primary cell derived from a human primary T cell, or a human lymphoid primary cell, or a human primary stem cell, or a human primary progenitor cell.

In one aspect, the present invention provides a TALEN-modified endogenous αβ-TCR negative human primary cell according to any one of according to the above embodiments, wherein said human primary cell is a human primary T cell or a population of human primary T cells.

In one aspect, the present invention provides a TALEN-modified endogenous αβ-TCR negative human primary cell according to any one of according to the above embodiments, wherein said human T primary cell or population thereof comprises or consists in human primary CD8 T cell, human primary CD4 T cell, a combination thereof.

In still another aspect, the present invention provides a TALEN-modified endogenous αβ-TCR negative human primary cell according to any one of the above embodiments, wherein said recognition domain for a TALEN comprises the following sequence ttgtcccacagATATC (SEQ ID NO: 36), or ttgtcccacagATATCCAG (SEQ ID NO: 37), and optionally CCGTGTACCAGCTGAGA (SEQ ID NO: 26). In one aspect, the present invention provides a TALEN-modified endogenous αβ-TCR negative human primary cell comprising the following sequence: AAGTAGCCCTGCAT-TTCAGGTTTCCTTGAGTGG-CAGGCCAGGCCTG-GCCGTGAACGTTCAC-TGAAATCATGGCCTCTTG-GCCAAGATTGATAGCTTGTGCCTGTCCCTGAGTCC-CAGTCCATCACGAGCAGCTGGTTTCTAAGATGCT-ATTTCCCGTATAAAGCATGAGACCGTGACTT-GCC-AGCCCCACAGAGCCCCGCCCTTGTCCATCACTGG-CATCTGGACTCCAGCCTGGGTTGGGGCAAAGAGG-GA AATGAGATCATGTCCTAACCCTGATCCTCT-TGTCCCACAGATATCCAGTCCGGTGAGGG-CAGAG-GAAGTCTTCTAACATGCGGTGACGTGGAGGAG-AATCCGGGCCCCGGATCC (SEQ ID NO: 24) coding sequence TCTAGAGGGCCCGTTTAAACCCGCTGATC-AGCCTCGACTGTGCCTTCTAGTT-GCCAGCCATCT-GTTGTTTGCCCCTCCCCCGTGCCTTCCTTGACCCTG-GAAGGTGCCACTCCCACTGTCCTTTCCTAA TAAA-ATGAGGAAATTGCATCGCATTGTCTGAGTAGGTGT-CATTC-TATTCTGGGGGGTGGGGGGGGCAGGACA-GCAAGGGGGAGGATTGGGAAGACAATAGCAGG-CATGCTGGGG ATGCGGTGGGCTCTATGACTAGT-GGCGAATTCCCGTGTACCAGCTGAGA-GACTCTAA-ATCCAGTGACAAGTCTGTCTGCCTATTCACCGAT-TTTGATTCTCAAACAAATGTGTCACAAAGTAAGG ATTCTGATGTGTATATCACAGACAAAACTGTGCTA-GACATGAGGTCTATGGACTTCAAGAG-CAACAGTG-CTGTGGCCTGGAGCAACAAATCTGACTTTGCATG-TGCAAACGCCTTCAACAACAGCATTATTCCAGA AGACACCTTCTTCCCCAGCCCAGGTAAGGGCAG-CTTTGGTGCCTTCGCAGGCTGTTTCCTTGCTTCAG-GAA (SEQ ID NO: 25) in the TRAC gene, [wherein underlined sequences represent a homology arm, italic bold sequences represent a self-cleaving peptide, preferably a 2A peptide, italic sequences represent a termination sequence (BGH polyA), The "codingsequence" represents a sequence coding a protein, such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a combination thereof, preferably "codingsequence" represents a chimeric antigen receptor, even more preferably an anti-CD22 or anti-CD123 CAR, even more more preferably a sequence of SEQ ID NO: 9, 10, 11, or 12 (corresponding to an anti-CD22 CAR, an anti-CD22 CAR B-B7 QR3, an anti-CD22 CAR A-D4 QR3, anti-CD123 CAR, respectively).

The present invention contemplates any of these particular CARs comprising two epitopes recognized by the rituximab molecular antibody (R2) or 3 epitopes recognized by the rituximab and one recognized by QBEN (CD34), designed QR3 above.

The present invention provides a TALEN-modified endogenous αβ-TCR negative human primary cell according to any one of, wherein said human T primary cell or population thereof comprising a sequence of SEQ ID NO: 9

The present invention provides a TALEN-modified endogenous αβ-TCR negative human primary cell according to any one of, wherein said human T primary cell or population thereof comprising a sequence of SEQ ID NO: 10.

The present invention provides a TALEN-modified endogenous αβ-TCR negative human primary cell according to any one of, wherein said human T primary cell or population thereof comprising a sequence of SEQ ID NO: 11.

The present invention provides a TALEN-modified endogenous αβ-TCR negative human primary cell according to any one of, wherein said human T primary cell or population thereof comprising a sequence of SEQ ID NO: 12.

The present invention provides a TALEN-modified endogenous αβ-TCR negative human primary cell according to any one of, wherein said human T primary cell or population thereof comprising a sequence having at least from 99%, 98%, 97%, 96%, 95% 94% 93% 92% 91% 90% 89% 88% 87% 86% 85% 84% 83% 82% 81% to 80% identity with of SEQ ID NO: 9.

The present invention provides a TALEN-modified endogenous αβ-TCR negative human primary cell according to any one of, wherein said human T primary cell or population thereof comprising a sequence having at least from 99%, 98%, 97%, 96%, 95% 94% 93% 92% 91% 90% 89% 88% 87% 86% 85% 84% 83% 82% 81% to 80% identity with of SEQ ID NO: 10.

The present invention provides a TALEN-modified endogenous αβ-TCR negative human primary cell according to any one of, wherein said human T primary cell or population thereof comprising a sequence having at least from 99%, 98%, 97%, 96%, 95% 94% 93% 92% 91% 90% 89% 88% 87% 86% 85% 84% 83% 82% 81% to 80% identity with of SEQ ID NO: 11.

The present invention provides a TALEN-modified endogenous αβ-TCR negative human primary cell according to any one of, wherein said human T primary cell or population thereof comprising a sequence having at least from 99%, 98%, 97%, 96%, 95% 94% 93% 92% 91% 90% 89% 88% 87% 86% 85% 84% 83% 82% 81% to 80% identity with of SEQ ID NO: 12.

The present invention provides a TALEN-modified endogenous αβ-TCR negative human primary T cell according to any one of the above comprising a sequence of SEQ ID NO: 9.

The present invention provides a TALEN-modified endogenous αβ-TCR negative human primary T cell according to any one of the above comprising a sequence of SEQ ID NO: 10.

The present invention provides a TALEN-modified endogenous αβ-TCR negative human primary T cell according to any one of the above comprising a sequence of SEQ ID NO: 11.

The present invention provides a TALEN-modified endogenous αβ-TCR negative human primary T cell according to any one of the above comprising a sequence of SEQ ID NO: 12.

The present invention provides a TALEN-modified endogenous αβ-TCR negative human primary T cell according to any one of the above comprising a sequence of SEQ ID NO: 9 and expressing undetectable level of MHC molecules.

The present invention provides a TALEN-modified endogenous αβ-TCR negative human primary T cell according to any one of the above comprising a sequence of SEQ ID NO: 10 and expressing undetectable level of MHC molecules.

The present invention provides a TALEN-modified endogenous αβ-TCR negative human primary T cell according to any one of the above comprising a sequence of SEQ ID NO: 11 and expressing undetectable level of MHC molecules.

The present invention provides a TALEN-modified endogenous αβ-TCR negative human primary T cell according to any one of the above comprising a sequence of SEQ ID NO: 12 and expressing undetectable level of MHC molecules.

In one aspect, the present invention provides a TALEN-modified endogenous αβ-TCR negative human primary cell according to any one of the above embodiments, wherein said CAR sequence comprises an anti-CD22 CAR sequence, anti-CD123 CAR sequence, anti-CD30 CAR sequence, anti-HSP-70 CAR sequence, anti-o-acetyl-GD2 CAR sequence, anti-CS-1 CAR sequence, anti-CLL-1 CAR sequence. In one aspect, the present invention provides a TALEN-modified endogenous αβ-TCR negative human primary cell according to any one of the above embodiments, wherein said CAR sequence comprises an anti-CD22 CAR sequence, anti-CD123 CAR sequence, anti-CD30 CAR sequence, anti-HSP-70 CAR sequence, anti-o-acetyl-GD2 CAR sequence, anti-CS-1 CAR sequence, anti-CLL-1 CAR sequence.

In one aspect, the present invention provides a TALEN-modified endogenous DO-TCR negative human primary cell according to any one of the above embodiments, wherein said CAR sequence comprises an Anti-BCMA CAR sequence, anti-CD33 CAR sequence, anti-EGFRVIII CAR sequence, anti Flt3 CAR sequence, anti-WT1 CAR sequence, anti-CD70 CAR sequence, anti-MUC16 CAR sequence, anti-PRAME CAR sequence, anti-TSPAN10 CAR sequence, anti-CLAUDIN18.2 CAR sequence, anti-DLL3 CAR sequence, anti-LY6G6D CAR sequence. anti-Liv-1 CAR sequence, anti-CHRNA2 CAR sequence, anti-ADAM10 CAR sequence.

The present invention provides a TALEN-modified endogenous αβ-TCR negative human cell according to any one of the above embodiments, further comprising undetectable level of MHC molecules as compared to an unmodified (eg non-engineered) control cell and a deletion functionally affecting cell surface expression of a beta 2 microglobulin molecule or of a CIITA molecule.

The present invention provides a TALEN-modified endogenous αβ-TCR negative human cell according to any one of the above embodiments, wherein said insertion resulted in an inactivation of the gene coding the TCR alpha and an undetectable cell surface expression of endogenous αβ-TCR in at least 96% of the total cells, in at least 97% of the total cells, in at least 98% of the total cells, in at least 99% of the total cells, as compared to a positive control.

A positive control may be non-engineered mature T cells expressing a detectable level of alpha beta TCR at the surface that may be detected for example by flow cytometry using an antibody specific for the alpha TCR, beta TCR, alpha beta TCR.

The present invention provides the TALEN-modified endogenous αβ-TCR negative human cell according to any one of the above embodiments, comprising a TALEN binding domain and or a sequence upstream a TALEN binding domain present in the wt TRAC gene.

The present invention provides a TALEN-modified endogenous αβ-TCR negative human cell according to any one of the above embodiments, wherein said TALEN comprises a first TALEN subunit:

```
MGDPKKKRKVIDIADLRTLGYSQQQQEKIKPKVRSTVAQHHEALVGHGFT
HAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNL
TPQQVVAIASNGGGKQALETVQRLLPVLCQAHGLTPQQVVAIASNNGGKQ
ALETVQRLLPVLCQAHGLTPQQVVAIASNGGGKQALETVQRLLPVLCQAH
GLTPEQVVAIASHDGGKQALETVQRLLPVLCQAHGLTPEQVVAIASHDGG
KQALETVQRLLPVLCQAHGLTPEQVVAIASHDGGKQALETVQRLLPVLCQ
AHGLTPEQVVAIASNIGGKQALETVQALLPVLCQAHGLTPEQVVAIASHD
GGKQALETVQRLLPVLCQAHGLTPEQVVAIASNIGGKQALETVQALLPVL
CQAHGLTPQQVVAIASNNGGKQALETVQRLLPVLCQAHGLTPEQVVAIAS
NIGGKQALETVQALLPVLCQAHGLTPQQVVAIASNGGGKQALETVQRLLP
VLCQAHGLTPEQVVAIASNIGGKQALETVQALLPVLCQAHGLTPQQVVAI
ASNGGGKQALETVQRLLPVLCQAHGLTPEQVVAIASHDGGKQALETVQRL
LPVLCQAHGLTPQQVVAIASNGGGRPALESIVAQLSRPDPALAALTNDHL
VALACLGGRPALDAVKKGLGDPISRSQLVKSELEEKKSELRHKLKYVPHE
YIELIEIARNSTQDRILEMKVMEFFMKVYGYRGKHLGGSRKPDGAIYTVG
SPIDYGVIVDTKAYSGGYNLPIGQADEMQRYVEENQTRNKHINPNEWWKV
YPSSVTEFKFLFVSGHFKGNYKAQLTRLNHITNCNGAVLSVEELLIGGEM
IKAGTLTLEEVRRKFNNGEINFAAD, of SEQ ID NO: 3,
``` and a second TALEN subunit:

```
MGDPKKKRKVIDIADLRTLGYSQQQQEKIKPKVRSTVAQHHEALVGHGFT
HAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNL
TPEQVVAIASHDGGKQALETVQRLLPVLCQAHGLTPQQVVAIASNGGGKQ
```

-continued

```
ALETVQRLLPVLCQAHGLTPEQVVAIASHDGGKQALETVQRLLPVLCQAH

GLTPEQVVAIASNIGGKQALETVQALLPVLCQAHGLTPQQVVAIASNNGG

KQALETVQRLLPVLCQAHGLTPEQVVAIASHDGGKQALETVQRLLPVLCQ

AHGLTPQQVVAIASNGGGKQALETVQRLLPVLCQAHGLTPQQVVAIASNN

GGKQALETVQRLLPVLCQAHGLTPQQVVAIASNNGGKQALETVQRLLPVL

CQAHGLTPQQVVAIASNGGGKQALETVQRLLPVLCQAHGLTPEQVVAIAS

NIGGKQALETVQALLPVLCQAHGLTPEQVVAIASHDGGKQALETVQRLLP

VLCQAHGLTPEQVVAIASNIGGKQALETVQALLPVLCQAHGLTPEQVVAI

ASHDGGKQALETVQRLLPVLCQAHGLTPQQVVAIASNNGGKQALETVQRL

LPVLCQAHGLTPQQVVAIASNGGGRPALESIVAQLSRPDPALAALTNDHL

VALACLGGRPALDAVKKGLGDPISRSQLVKSELEEKKSELRHKLKYVPHE

YIELIEIARNSTQDRILEMKVMEFFMKVYGYRGKHLGGSRKPDGAIYTVG

SPIDYGVIVDTKAYSGGYNLPIGQADEMQRYVEENQTRNKHINPNEWWKV

YPSSVTEFKFLFVSGHFKGNYKAQLTRLNHITNCNGAVLSVEELLIGGEM

IKAGTLTLEEVRRKFNNGEINFAAD, or SEQ ID NO: 4,
```

In another embodiment, said first TALEN subunit comprises a sequence having at least from 99%, 98%, 97%, 96%, 95% 94% 93% 92% 91% 90% 89% 88% 87% 86% 85% 84% 83% 82% 81% to 80% identity with SEQ ID NO: 3, provided that said first TALEN subunit binds to said a TALEN recognition domain, preferably to tigteccacagATATC (SEQ ID NO: 35), and a second TALEN subunit sequence having at least from 99%, 98%, 97%, 96%, 95% 94% 93% 92% 91% 90% 89% 88% 87% 86% 85% 84% 83% 82% 81% to 80% identity with SEQ ID NO: 4 provided that said second TALEN subunit binds to a second TALEN recognition domain, preferably to CCGTGTACCAGCTGAGA (SEQ ID NO: 26), and provided that the frequency of off target binding is below detection;

Off target may be measured by "guide-seq" analysis using for example an adapted version for TALEN guide seq. for TALEN engineered cells.

The present invention provides a TALEN-modified endogenous αβ-TCR negative human cell according to any one of the above embodiments, wherein said at least one insertion comprises an exogenous polynucleotide sequence located downstream a TALEN binding domain of sequence ttgtcccacagATATC (SEQ ID NO: 36), or ttgtcccacagA-TATCCAG (SEQ ID NO: 37), (present in the native TRAC).

In another embodiment, the present invention provides a TALEN-modified endogenous αβ-TCR negative human cell according to any one of the above embodiments, wherein said at least one insertion comprises an IRES, an exogenous polynucleotide sequence coding a chimeric antigen receptor, a terminator sequence of polyadenylation signal, optionally a TALEN binding domain.

The present invention provides a TALEN-modified endogenous αβ-TCR negative human cell according to any one of the above embodiments, wherein said at least one insertion comprises a sequence encoding a self-cleaving peptide in frame with the genomic TRAC coding sequence.

The present invention provides a TALEN-modified endogenous αβ-TCR negative human cell according to any one of the above embodiments, wherein said at least one insertion comprises a sequence encoding a self-cleaving peptide in frame with the genomic TRAC coding sequence, an exogenous polynucleotide sequence coding a product conferring resistance to a drug, a terminator sequence of polyadenylation signal, optionally a TALEN binding domain.

The present invention provides a TALEN-modified endogenous αβ-TCR negative human cell according to any one of the above embodiments, wherein said at least one insertion comprises a sequence encoding a self-cleaving peptide in frame with the genomic TRAC coding sequence, an exogenous polynucleotide sequence coding a product conferring sensitivity to a drug, a terminator sequence of polyadenylation signal, optionally a TALEN binding domain.

The present invention provides a TALEN-modified endogenous αβ-TCR negative human cell according to any one of the above embodiments, wherein said at least one insertion comprises a sequence encoding a self-cleaving peptide in frame with the genomic TRAC coding sequence, an exogenous polynucleotide sequence coding a cytokine, a terminator sequence of polyadenylation signal, optionally a TALEN binding domain.

The present invention provides a TALEN-modified endogenous αβ-TCR negative human cell according to any one of the above embodiments, wherein said at least one insertion comprises a sequence encoding a self-cleaving peptide in frame with the genomic TRAC coding sequence, an exogenous polynucleotide sequence coding at least a chimeric antigen receptor, a terminator sequence of poly-adenylation signal, optionally a TALEN binding domain.

The present invention provides a TALEN-modified endogenous αβ-TCR negative human cell according to any one of the above embodiments, wherein said at least one insertion comprises a sequence encoding a self-cleaving peptide in frame with the genomic TRAC coding sequence, said self-cleaving peptide is a self-cleaving peptide selected from a 2A peptide, a 2A like peptide, a P2A peptide, a E2A peptide, a F2A peptide, preferably a 2A peptide, more preferably a 2A peptide, of sequence GSGEGRGSLLTCGDVEENPGP (SEQ ID NO: 27), GSGATNFSLLKQAGDVEENPGP (SEQ ID NO: 28), GSGQCTNYALLKLAGDVESNPGP (SEQ ID NO: 29), GSGVKQTLNFDLLKLAGDVESNPGP (SEQ ID NO: 30), SGEGRGSLLTCGDVEENPGP (SEQ ID NO: 31), SGATNFSLLKQAGDVEENPGP (SEQ ID NO: 32), SGQCTNYALLKLAGDVESNPGP (SEQ ID NO: 33), SGVKQTLNFDLLKLAGDVESNPGP (SEQ ID NO: 34), even more preferably a 2A peptide of sequence SGEGRGSLLTCGDVEENPGP (SEQ ID NO: 35).

The present invention provides a TALEN-modified endogenous αβ-TCR negative human cell according to any one of the above embodiments, wherein said at least one insertion comprises a sequence coding a 2A peptide of sequence SGEGRGSLLTCGDVEENPGP (SEQ ID NO: 35) encoded by a sequence in frame with the genomic TRAC coding sequence, an exogenous polynucleotide sequence coding a chimeric antigen receptor, a terminator sequence of polyadenylation signal, optionally a TALEN binding domain.

The present invention provides a TALEN-modified endogenous αβ-TCR negative human cell according to any one of the above embodiments, wherein said exogenous polynucleotide sequence comprises a chimeric antigen receptor (CAR) selected from a CAR specific for at least one of the following antigen The CAR molecule of the invention comprises an antigen binding domain wherein said antigen binding domain binds to the tumor antigen associated with a disease, and said tumor antigen is selected from a group consisting of: CD19 molecule (CD19); membrane spanning 4-domains A1 (MS4A1 also known as CD20); CD22 molecule (CD22); CD24 molecule (CD24); CD248 molecule (CD248); CD276 molecule (CD276 or B7H3); CD33 molecule (CD33); CD38 molecule (CD38); CD44v6; CD70 molecule (CD70); CD72; CD79a; CD79b; interleukin 3 receptor subunit alpha (IL3RA also known as CD123); TNF receptor superfamily member 8 (TNFRSF8 also known as CD30); KIT proto-oncogene receptor tyrosine kinase (CD117); V-set pre-B cell surrogate light chain 1 (VPREB1 or CD179a); adhesion G protein-coupled receptor E5 (ADGRE5 or CD97); TNF receptor superfamily member 17 (TNFRSF17 also known as BCMA); SLAM family member 7 (SLAMF7 also known as CS1); L1 cell adhesion molecule (L1CAM); C-type lectin domain family 12 member A (CLEC12A also known as CLL-1); tumor-specific variant of the epidermal growth factor receptor (EGFRvlll); thyroid stimulating hormone receptor (TSHR); Fms related tyrosine kinase 3 (FLT3); ganglioside GD3 (GD3); Tn antigen (Tn Ag); lymphocyte antigen 6 family member G6D (LY6G6D); Delta like canonical Notch ligand 3 (DLL3); Interleukin-13 receptor subunit alpha-2 (IL-13RA2); Interleukin 11 receptor subunit alpha (IL11RA); mesothelin (MSLN); Receptor tyrosine kinase like orphan receptor 1 (ROR1); Prostate stem cell antigen (PSCA); erb-b2 receptor tyrosine kinase 2 (ERBB2 or Her2/neu); Protease Serine 21 (PRSS21); Kinase insert domain receptor (KDR also known as VEGFR2); Lewis y antigen (LewisY); Solute carrier family 39 member 6 (SLC39A6); Fibroblast activation protein alpha (FAP); Hsp70 family chaperone (HSP70); Platelet-derived growth factor receptor beta (PDGFR-beta); Cholinergic receptor nicotinic alpha 2 subunit (CHRNA2); Stage-Specific Embryonic Antigen-4 (SSEA-4); Mucin 1, cell surface associated (MUC1); mucin 16, cell surface associated (MUC16); claudin 18 (CLDN18); claudin 6 (CLDN6); Epidermal Growth Factor Receptor (EGFR); Preferentially expressed antigen in melanoma (PRAME); Neural Cell Adhesion Molecule (NCAM); ADAM metallopeptidase domain 10 (ADAM10); Folate receptor 1 (FOLR1); Folate receptor beta (FOLR2); Carbonic Anhydrase IX (CA9); Proteasome subunit beta 9 (PSMB9 or LMP2); Ephrin receptor A2 (EphA2); Tetraspanin 10 (TSPAN10); Fucosyl GM1 (Fuc-GM1); sialyl Lewis adhesion molecule (sLe); TGS5; high molecular weight-melanoma-associated antigen (HMW-MAA); o-acetyl-GD2 ganglioside (OAcGD2); tumor endothelial marker 7-related (TEM7R); G protein-coupled receptor class C group 5, member D (GPRC5D); chromosome X open reading frame 61 (CXORF61); ALK receptor tyrosine kinase (ALK); Polysialic acid; Placenta-specific 1 (PLAC1); hexasaccharide portion of globoH glycoceramide (GloboH); NY-BR-1 antigen; uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 family member K (LY6K); olfactory receptor family 51 subfamily E member 2 (OR51E2); TCR Gamma Alternate Reading Frame Protein (TARP); Wilms tumor protein (WT1); ETV6-AML1 fusion protein due to 12;21 chromosomal translocation (ETV6-AML1); sperm autoantigenic protein 17 (SPA17); X Antigen Family, Member 1E (XAGE1E); TEK receptor tyrosine kinase (Tie2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL1), and Heat shock protein 70 (HSP70).

Preferably said wherein said exogenous polynucleotide sequence comprises a CAR specific for CD22, CD123, CS-1, CLL-1, CD38, HSP70, MUC-1, CD30, o-acetyl-GD2 and a sequence SGEGRGSLLTCGDVEENPGP (SEQ ID NO: 35) in frame with the genomic TRAC coding sequence, a terminator sequence of polyadenylation signal.

More Preferably said wherein said exogenous polynucleotide sequence comprises a CAR specific for CD123, and a sequence SGEGRGSLLTCGDVEENPGP (SEQ ID NO: 35) in frame with the genomic TRAC coding sequence, a terminator sequence of polyadenylation signal. More Preferably said wherein said exogenous polynucleotide sequence comprises a CAR specific for CD22, and a sequence SGEGRGSLLTCGDVEENPGP (SEQ ID NO: 35) in frame with the genomic TRAC coding sequence, a terminator sequence of polyadenylation signal.

The present invention provides a TALEN-modified endogenous αβ-TCR negative human cell according to any one of the above embodiments wherein said (CAR) comprises an extracellular ligand-binding domain comprising an epitope specific for a monoclonal antibody, a transmembrane domain and one or more intracellular signaling domains.

The present invention provides a TALEN-modified endogenous αβ-TCR negative human cell according to any one of the above embodiments, wherein said at least one insertion comprises an IRES, an exogenous polynucleotide sequence comprising a chimeric antigen receptor (CAR), a terminator sequence of polyadenylation signal, optionally a TALEN binding domain.

The present invention provides the TALEN-modified endogenous αβ-TCR negative human cell according to any one of the above embodiments, wherein said chimeric antigen receptor (CAR), comprise at least one antigen specific for a monoclonal antibody, preferably two antigens specific for a monoclonal antibody.

The present invention provides a TALEN-modified endogenous αβ-TCR negative human cell according to any one of the above embodiments wherein said exogenous polynucleotide comprises a transcription termination signal stopping the activity of RNA polymerase.

The present invention provides a TALEN-modified endogenous αβ-TCR negative human cell according to any one of the above embodiments comprising at least one additional disruption in an endogenous gene wherein said disrupted or inactivated endogenous gene is selected from the group consisting of an endogenous beta subunit gene of the TCR, an endogenous cytokine inducible SH2-containing (CISH) gene, an adenosine A2a receptor (ADORA) gene, a CD276 gene, a V-set domain containing T cell activation inhibitor 1 (VTCNI) gene, a B and T lymphocyte associated (BTLA) gene, a cytotoxic T-lymphocyte-associated protein 4 (CTLA4) gene, an indoleamine 2,3-dioxygenase 1 (IDO I) gene, a killer cell immunoglobulin-like receptor, three domains, long cytoplasmic tail, 1 (KIR3DL1) gene, a lymphocyte-activation gene 3 (LAG3) gene, a programmed cell death 1 (PD-1) gene, an hepatitis A virus cellular receptor 2 (HAVCR2) gene, a V-domain immunoglobulin suppressor of T-cell activation (VISTA) gene, a natural killer cell receptor 2B4 (CD244) gene, a hypoxanthine phosphoribosyltransferase 1 (HPRT) gene, an adeno-associated virus integration site (AAVS I), and chemokine (C-C motif) receptor 5 (gene/pseudogene) (CCR5) gene, a combination thereof.

The present invention provides a TALEN-modified endogenous αβ-TCR negative human cell according to any one of the above embodiments, for use to alter the survival of pathological cells responsible for a pathological condition, said pathological condition may be a cancer, a viral infection in any individual regardless of his MHC or TCR molecules.

The present invention provides a population of human cells comprising a TALEN-modified endogenous αβ-TCR negative human cell according to any one of the above embodiments.

The present invention provides a pharmaceutical composition comprising a TALEN-modified endogenous αβ-TCR negative human cell according to any one of the above embodiments or a population of human cells according to the above embodiments and a pharmaceutically acceptable excipient.

The present invention provides a TALEN-modified endogenous αβ-TCR negative human cell according to any one of the above embodiments or the population of human cells according to the above embodiments or the pharmaceutical composition according to the above embodiments for use as a medicament.

The present invention provides a TALEN-modified endogenous αβ-TCR negative human cell according to any one of the above embodiments or the population of human cells according to the above embodiments the above or the pharmaceutical composition according to the above, for use in the treatment of cancer.

The present invention provides the TALEN-modified endogenous αβ-TCR negative human cell according to any one of the above embodiments or the population of human cells according to the above or the pharmaceutical composition according to the above for use in the treatment of a cancer selected from the group consisting of carcinoma, lymphoma, sarcoma, blastomas, and leukemia.

The present invention provides a TALEN-modified endogenous αβ-TCR negative human cell according to any one of the above embodiments or the population of human cells according to the above or the pharmaceutical composition according to the above for use in the treatment of cancer wherein the cancer is selected from the group consisting of a cancer of B-cell origin, a cancer of T cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma.

The present invention provides a TALEN-modified endogenous αβ-TCR negative human cell according to any one of the above or the population of human cells according to the above embodiments or the pharmaceutical composition according to the above embodiments for use in the treatment of cancer wherein the cancer of B-cell origin is selected from the group consisting of B-lineage acute lymphoblastic leukemia, B-cell chronic lymphocytic leukemia, and B-cell non-Hodgkin's lym-*phoma.*

The present invention provides a TALEN-modified endogenous αβ-TCR negative human cell according to any one of the above embodiments or a population of human cells according to the above embodiments or a pharmaceutical composition according to the above embodiments for use in the treatment of a cancer wherein the cancer is AML, ALL, a T cell lymphoma, CLL.

The present invention provides a means for detecting an endonuclease-modified endogenous ???TCR negative human cell.

More particularly, the present invention provides a means for detecting an endonuclease-modified endogenous αβ-TCR negative human cell, wherein said endonuclease-modified endogenous αβ-TCR negative human cell comprises an endonuclease modified genomic TRAC gene as compared to the wild type TRAC gene.

In advantageous embodiments, a means according to the invention allows detecting a modified human genomic TRAC gene comprising from 5' to 3': a gap or an insertion as compared to the wild type TRAC gene, said insertion comprising an exogenous polynucleotide selected from a noncoding sequence, such as a stop codon, a termination sequence, an IRES, a sequence coding for a protein such as a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a combination thereof.

In one embodiment said gap or insertion is affecting the expression of the extracellular domain of the alpha beta TCR, or affecting the transmembrane domain of the alpha beta TCR, and ultimately affecting the cell surface expression of the alpha beta TCR.

The present invention provides a means for detecting an endonuclease-modified endogenous αβ-TCR negative human cell, said endonuclease-modified endogenous dB-TCR negative human cell comprising an endonuclease modified genomic TRAC gene as compared to the wild type TRAC gene, wherein said modified human genomic TRAC gene comprises from 5' to 3'!

(a) a 5' region of said human genomic TRAC gene upstream a recognition domain for a rare cutting endonuclease present in the wild type TRAC gene, (b) a gap or an insertion as compared to the wild type TRAC gene affecting the cell surface expression of the extracellular domain or transmembrane domain of the alpha beta TCR, said insertion comprising an exogenous polynucleotide selected from a noncoding sequence, a stop codon, a sequence coding for a self-cleaving peptide in frame with the TRAC open reading frame, an IRES, a sequence coding a chimeric antigen receptor (CAR), a sequence coding a TCR, a sequence coding a protein conferring sensitivity to a drug, a sequence coding a protein conferring resistance to a drug, a termination sequence, a combination thereof, (c') optionally a second rare cutting endonuclease recognition domain, (d) a 3' region of the genomic TRAC gene.

The present invention provides a means according to the above wherein said endonuclease is selected from the group consisting of: Crispr/Cas 9, Cpf1, TALEN, transposase, ZEN, Zinc finger endonuclease, meganuclease, MegaTAL, a combination thereof, and said means binds to a sequence of the endonuclease-modified TRAC gene specific for said endonuclease and/or upstream a sequence specific for said endonuclease.

The present invention provides a means according to the above wherein said endonuclease is selected from the group consisting of: Crispr/Cas 9, TALEN, Zinc finger endonuclease, meganuclease, MegaTAL, a combination thereof, and said means binds to a sequence of the endonuclease modified TRAC, which is specific for said nuclease or located upstream said sequence specific for said endonuclease.

In advantageous embodiments, the TALEN-modified endogenous αβ-TCR negative human cell according to the above comprises an inactivated genomic TCRA gene wherein an exogenous sequence coding a CAR was integrated into the genomic TCRA gene using a vector, such as for example a lentiviral vector or a AAV vector, and said genomic disruption(s) performed using an endonuclease selected from a CRISPR/CAS9, meganuclease, MegaTAL, Zn Finger, TALEN, combination thereof.

The present invention provides a means according to the above embodiments wherein said endonuclease is a TALEN.

The present invention provides a means according to the above embodiments for detecting a TALEN modified endogenous αβ-TCR negative human cell comprising a probe wherein said probe binds to a sequence in the modified genomic TRAC gene, preferably to a sequence in the modified genomic TRAC gene upstream the endonuclease binding domain, or to a sequence in the modified genomic TRAC gene at the endonuclease recognition domain, and/or to a sequence encoding a tag.

The present invention provides a means according to the above embodiments wherein said TALEN modified genomic TRAC gene comprises, (a) a 5' region of said human genomic TRAC gene;
(b) a recognition domain for a TALEN, preferably a recognition domain for a TALEN comprising the following sequence ttgtcccacagATATC (SEQ ID NO: 36), or ttgtcccacagATATCCAG (SEQ ID NO: 37), or
(c) a gap or an insertion as compared to the wild type TRAC gene affecting the cell surface expression of the extracellular domain or transmembrane domain of the alpha beta TCR,
said insertion comprising an exogenous polynucleotide selected from a stop codon, a sequence coding for a self-cleaving peptide in frame with the TRAC open reading frame, an IRES, a sequence coding a chimeric antigen receptor (CAR), a sequence coding a TCR, a sequence coding a protein conferring sensitivity to a drug, a sequence coding a protein conferring resistance to a drug, a termination se-quence, a combination thereof,
(c') optionally a second TALEN recognition domain.
(d) a 3' region of the genomic TRAC gene;
and said means binds specifically to said TALEN-modified genomic TRAC gene.

The present invention provides a means according to any one of the above embodiments for detecting a TALEN modified endogenous DR-TCR negative human cell comprising a probe wherein said probe binds to at least 10 bases of the sequence ttgtcccacagATATC (SEQ ID NO: 36), or ttgtcccacagATATCCAG (SEQ ID NO: 37), in the modified genomic TRAC gene.

The present invention provides a means according to any one of the above embodiments for detecting an endonuclease-modified endogenous αβ-TCR negative human cell by polymerase chain reaction (pcr) or off sites modifications, preferably by guide sequence analysis.

The present invention provides a means according to any one of the above embodiments for detecting a TALEN-modified endogenous αβ-TCR negative human cell according to any one of the above embodiments.

The present invention provides a TALEN-modified endogenous αβ-TCR negative human cell according to any one of the above embodiments comprising an inactivated genomic TCRA gene wherein an exogenous coding sequence was integrated into the genomic TCRA gene using one or more endonucleases and/or a viral vector.

The present invention provides a TALEN-modified endogenous αβ-TCR negative human cell according to any one of the above embodiments comprising an inactivated genomic TCRA gene wherein an exogenous sequence coding a CAR was integrated into the genomic TCRA gene using a lentiviral vector or a AAV vector and said genomic disruptions are performed using a CRISPR/CAS9, meganuclease, MEGATAL or TALEN endonuclease system.

Under particular aspects, the present invention provides a method for treating a patient in need thereof, the method comprising administering a cell according to any one of the preceding embodiments.

Under particular aspects, the present invention provides a kit comprising at least one TALEN that binds to the genomic TRAC gene, and a TALEN that binds a gene coding one of the products selected from an endogenous cytokine inducible SH2-containing (CISH), adenosine A2a receptor (ADORA), CD276, V-set domain containing T cell activation inhibitor 1 (VTCN1), B and T lymphocyte associated (BTLA), cytotoxic T-lymphocyte-associated protein 4 (CTLA4), indoleamine 2,3-dioxygenase 1 (IDOI), killer cell immunoglobulin-like receptor, three domains, long cytoplasmic tail, 1 (KIR3DL1), lymphocyte-activation gene 3 (LAG3), programmed cell death 1 (PD-1), hepatitis A virus cellular receptor 2 (HAVCR2), V-domain immunoglobulin suppressor of T-cell activation (VISTA), natural killer cell receptor 2B4 (CD244), hypoxanthine phosphoribosyltransferase 1 (HPRT), adeno-associated virus integration site (AAVS SITE (E.G. AAVS 1, AAVS2, ETC.)), or chemokine (C-C motif) receptor 5 (gene/pseudogene) (CCR5).

The present invention provides a method of producing an endonuclease-modified endogenous αβ-TCR negative human cell said method comprising:
(a) introducing into a human cell:
(i) a first nucleic acid sequence encoding an engineered nuclease; or an engineered nuclease protein; optionally, a nucleic acid guiding said endonuclease,
wherein said engineered nuclease produces a cleavage at a recognition sequence within said human TCR alpha constant region gene; said cleavage resulting in an inhibition of cell surface expression of the αβ-TCR to undetectable level as compared to adequate control (eg non engineered immune T cell).
(ii) a second nucleic acid sequence comprising an exogenous polynucleotide encoding a CAR,
(iii) optionally a probe,
wherein the sequence of said exogenous polynucleotide is inserted into said human TCR alpha constant region gene at said cleavage site; by homologous recombination (HR) and further wherein said genetically-modified cell has reduced cell-surface expression of the endogenous TCR when compared to an unmodified control cell.

In particular embodiments, the present invention provides a method of producing an endonuclease-modified endogenous αβ-TCR negative human cell wherein a probe is introduced into the human cell at the same time as the endonuclease so that said probe may be inserted into any dsDNA cutting sites, unless a sequence is inserted by HR. This is performed (in parallel to or during the manufacturing of T cells as an internal control for identifying any off site cutting of the endonuclease.

Above a threshold of integration of said probe into the genome, the endonuclease-modified endogenous αβ-TCR negative human cell may not be used for immunotherapy.

The present invention provides a method for producing an endonuclease-modified endogenous αβ-TCR negative human cell according to any one of the above embodiments said method comprises a step of detecting endonuclease-induced on site and off site(s), preferably by pcr and/or by guide sequence.

The present invention provides a method of any one of the above embodiments, wherein said engineered nuclease is a meganuclease, a zinc-finger nuclease (ZFN), a transcription activator-like effector nuclease (TALEN), a CRISPR/Cas nuclease, or a megaTAL nuclease.

The present invention provides a method for producing an endonuclease-modified endogenous αβ-TCR negative human cell according to any one of the above embodiments said method comprising the following steps:

Providing a cell according to the invention and a control cell(s)

Removing DNA and RNA using a mixture of nucleases,

Extracting Genomic DNA, (gDNA),

Incubating gDNA with a forward primer, a reverse primer and a probe.

Performing a PCR with an annealing/extension time of more than 45 seconds, preferably of more than 60 seconds, more preferably of more than 90 seconds.

A control cell(s) may be a non-engineered T cell.

The step of providing a cell according to the invention comprises a step of:

Providing a primary cell,

Introducing a mRNA encoding said endonuclease and/or a guide conferring specificity to a cutting site in the genomic DNA (that may be an endonuclease as such and/or a polynucleotide), said cutting site resulting in a KO of the TRAC gene and undetectable level of cell surface expression of alpha beta TCR, Introducing a polynucleotide comprising at least a self cleaving peptide or an IRES, a gene encoding a CAR, sequence homology with the gene to be KO, resulting in a KO by KI of the TRAC gene and the production of a TCR negative CAR positive cells Purifying said resulting TCR negative CAR positive cells, Providing said resulting TCR negative CAR positive cells according to the invention and a control cell(s) Removing DNA and RNA using a mixture of nucleases, Extracting Genomic DNA, (gDNA), Incubating gDNA with a forward primer, a reverse primer and a probe.

Performing a PCR with an annealing/extension time of more than 45 seconds, preferably of more than 60 seconds, more preferably of more than 90 seconds.

detecting endonuclease-specific on and off site cutting.

In a preferred embodiment, introducing a mRNA encoding said endonuclease conferring specificity to a cutting site in the genomic DNA (that may be an endonuclease as such and/or a polynucleotide), said cutting site resulting in a KO of the TRAC gene and undetectable level of cell surface expression of alpha beta TCR, is introducing a mRNA encoding a TALEN conferring specificity to a cutting site in the genomic DNA (that may be an endonuclease as such and/or a polynucleotide), said cutting site resulting in a KO of the TRAC gene and undetectable level of cell surface expression of alpha beta TCR.

The same method applies to any genes that is intended to be KO and in which an exogenous coding sequence is introduced. In that embodiment, the step of introducing a mRNA encoding said endonuclease and/or a guide conferring specificity to a cutting site in the genomic DNA (that may be an endonuclease as such and/or a polynucleotide), said cutting site resulting in a KO of the TRAC gene and undetectable level of cell surface expression of alpha beta TCR, is generalized to introducing a mRNA encoding said endonuclease and/or a guide conferring specificity to a cutting site in the genomic DNA (that may be an endonuclease as such and/or a polynucleotide), said cutting site resulting in a KO of the said gene and undetectable level expression of the product encoded by said gene.

The present invention also provides a method for detecting an endonuclease-modified endogenous αβ-TCR negative human cell according to any one of the above embodiments said method comprises:

Providing a cell according to the invention, a control cell(s)

Removing DNA and RNA using benzonase,

Extracting Genomic DNA, (gDNA),

Incubating gDNA with a forward primer, a reverse primer and a probe.

Performing a PCR with an annealing/extension time increased by 2.

The present invention provides a method for detecting an endonuclease-modified endogenous αβ-TCR negative human cell according to any one of the above embodiments said method comprising:

Providing a cell according to the invention, a control cell(s)

Removing DNA and RNA using a mixture of nucleases, such as benzonase,

Extracting Genomic DNA, (gDNA),

Incubating from 20 to 30 ng of gDNA, with 300 nM of forward primer, 900 nM of reverse primer and 220 nM of probe.

Performing a PCR with an annealing/extension time increased by 2, preferably of more than 45 sec.

The present invention provides a method for detecting an endonuclease-modified endogenous αβ-TCR negative human cell according to any one of the above embodiments said method comprises Providing a cell according to the invention, a control cell(s)

Removing DNA and RNA using benzonase,

Extracting Genomic DNA, (gDNA),

Incubating gDNA with a forward primer of (SEQ ID NO: 5), a reverse primer of (SEQ ID NO: 6) and a probe of (SEQ ID NO: 7).

Performing a PCR with an annealing/extension time increased by 2.

The present invention provides a method as disclosed in the above embodiments, wherein said endonuclease is a TALEN.

The present invention provides a method as disclosed in the above embodiments, wherein said exogenous polynucleotide comprises a nucleic acid sequence encoding a self-cleaving peptide and a chimeric antigen receptor.

The present invention provides a method as disclosed in the above embodiments wherein said chimeric antigen receptor comprises an extracellular ligand-binding domain and one or more intracellular signaling domains.

The present invention provides a method as disclosed in the above embodiments wherein said chimeric antigen receptor comprises an extracellular ligand-binding domain and one or more intracellular signaling domains and a costimulatory domain.

The present invention provides a method as disclosed in the above embodiments, wherein said exogenous polynucleotide comprises a first promoter sequence that drives expression of said exogenous polynucleotide.

The present invention provides the method as disclosed in the above embodiments, wherein at least said second nucleic acid sequence is introduced into said cell by contacting said cell with a recombinant adeno-associated virus (AAV) vector comprising said second nucleic acid sequence.

The present invention provides the method of any one of the above embodiments, wherein said recombinant AAV vector is a self-complementary AAV vector.

A method of any one of the above is provided, wherein said recombinant AAV vector derived at least in part from an AAV6.

The method of any one of the above, wherein said recombinant AAV vector derived from an AAV6/AAV2 particles.

The method of any one of the above, wherein said recombinant AAV vector comprises AAV6 particles and a DNA sequence between inverted terminal repeats (ITRs) from AAV2.

The method of any one of the above, wherein said recombinant TALEN comprises a first subunit and a second subunit, wherein said first subunit binds to a first recognition half-site, and wherein said second subunit binds to a second recognition half-site.

The method as any one of the above is provided, wherein said recombinant TALEN recognizes a se-quence ttgtcc-cacagATATCCAG (SEQ ID NO: 37) in the wild-type human TCR alpha constant region.

The present invention further provides a method of as the general method above, wherein said meganuclease recognizes and cleaves a recognition sequence within residues 93-208 of the wild-type human TCR alpha constant region, wherein said recombinant meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region.

The present invention provides a method as any one of the above, wherein said meganuclease is a single-chain meganuclease comprising a linker, wherein said linker covalently joins said first subunit and said second subunit.

In general, the present invention provides a means of detection of cells obtained according to any of one the methods above.

Others Embodiments

The present invention is useful to improve the therapeutic outcome of CAR T-cell (TCRneg, CAR+) therapies by integrating exogenous genetic attributes/circuits under the control of endogenous T-cell promoters influenced by tumor microenvironment (TME). TME features, including as non-limiting examples, arginine, cysteine, tryptophan and oxygen deprivation as well as extracellular acidosis (lactate build up), are known to upregulate specific endogenous genes. Pursuant to the invention, up-regulation of endogenous genes can be "hijacked" to re-express relevant exogenous coding sequences to improve the antitumor activity of CAR T-cells in certain tumor microenvironment.

In preferred embodiments, the method of the invention comprises the step of generating a double-strand break at a locus highly transcribed under tumor microenvironment, by expressing se-quence-specific nuclease reagents, such as TALEN, ZFN or RNA-guided endonucleases as non-limiting examples, in the presence of a DNA repair matrix preferably set into an AAV6 based vector. This DNA donor template generally includes two homology arms embedding unique or multiple Open Reading Frames and regulatory genetic elements (stop codon and polyA sequences) referred to herein as exogenous coding sequences.

In another aspect, said exogenous sequence is introduced into the genome by deleting or mod-ifying the endogenous coding sequence(s) present at said locus (knock-out by knock-in), so that a gene inactivation is combined with transgenesis.

Depending on the locus targeted and its involvement in immune cells activity, the targeted endogenous gene may be inactivated or maintained in its original function. Should the targeted gene be essential for immune cells activity, this insertion procedure can generate a single knock-in (KI) without gene inactivation. In the opposite, if the targeted gene is deemed involved in immune cells inhibi-tion/exhaustion, the insertion procedure is designed to prevent expression of the endogenous gene, preferably by knocking-out the endogenous sequence, while enabling expression of the introduced exogenous coding sequence(s).

In more specific aspects, the invention relies on up-regulating, with various kinetics, the target gene expression upon activation of the CAR signaling pathway by targeted integration (with or without the native gene disruption) at the specific loci such as, as non-limiting example, PD1, PDL1, CTLA-4, TIM3, LAG3, TNFalpha or IFNgamma.

In an even more specific aspect, it is herein described engineered immune cells, and preferably primary immune cells for infusion into patients, comprising exogenous sequences encoding IL-15 or IL-12 polypeptide(s), which are integrated at the PD1, CD25 or CD69 endogenous locus for their expression under the control of the endogenous promoters present at these loci.

In an even more specific aspect, it is herein described engineered immune cells, and preferably primary immune cells for infusion into patients, comprising exogenous sequences encoding IL2
IL12
IL15
IL15_IL15R
Tbet
CTLA4 AB soluble
PD1 AB soluble
CD40L (CD154)
NGR-TNF IL-7, an antibody, preferably a neutralizing antibody.

The immune cells according to the present invention can be [CAR]positive, [CAR]negative, [TCR]positive, or [TCR] negative, depending on the therapeutic indications and recipient patients. In one preferred aspect, the immune cells are further made [TCR]negative for allogeneic transplantation. This can be achieved especially by genetic disruption of at least one endogenous sequence encoding at least one component of TCR, such as TRAC (locus encoding TCRalpha), preferably by integration of an exogenous sequence encoding a chimeric antigen receptor (CAR) or a recombinant TCR, or component(s) thereof.

According to a further aspect of the invention, the immune cells are transfected with an exogenous sequence coding for a polypeptide which can associate and preferably interfere with a cytokine receptor of the IL-6 receptor family, such as a mutated GP130, In particular, the invention provides immune cells, preferably T-cells, which secrete soluble mutated GP130, aiming at reducing cytokine release syndrome (CRS) by interfering, and ideally block, interleukine-6 (IL-6) signal transduction. CRS is a well-known complication of cell immunotherapy leading to auto immunity that appears when the transduced immune cells start to be active in-vivo. Following binding of IL-6 to its receptor IL-6R, the complex associate with the GP130 subunit, initiating signal transduction and a cascade of inflammatory responses. According to a particular aspect, a dimeric protein comprising the extracellular domain of GP130 fused to the Fc portion of a IgG1 antibody (sgp130Fc) is expressed in the engineered immune cells to bind specifically soluble IL-R/IL-6 complex to achieve partial or complete blockade of IL-6 trans signaling. The present invention thus refers to a method for limiting CRS in immunotherapy, wherein immune cells are genetically modified to express a soluble polypeptide which can associate and preferably interfere with a cytokine receptor of the IL-6 receptor family, such as sgp130Fc. According to a preferred aspect, this sequence encoding said soluble polypeptide which can associate and preferably interfere with a cytokine receptor of the IL-6 receptor family, is integrated under control of an endogenous promoter, preferably at one locus responsive to T-cells activation, such as one selected from Tables below, more especially PD1, CD25 or CD69. Polynucleotide sequences of the vectors, donor templates comprising the exogenous coding sequences and/or sequences homologous to the endogenous loci, the sequences pertaining to the resulting engineered cells, as well as those permitting the detection of said engineered cells are all part of the present disclosure.

The present invention provides an endonuclease-modified endogenous αβ-TCR negative human cell wherein the constant region of the genomic TCR gene (TRAC gene) comprises a genetic modification generated by a rare a cutting endonuclease and affecting cell surface expression of the alpha beta TCR, said genomic TRAC gene further comprising from 5' to 3':

(a) a 5' region of said human genomic TRAC gene upstream (b) a recognition domain for a rare cutting endonuclease, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second rare cutting endonuclease recognition domain, (d) a 3' region of the genomic TRAC gene.

TCR means T cell receptor. TRAC means T cell receptor alpha constant region.

According to the present invention, the endonuclease-modified endogenous αβ-TCR negative human cell (hereafter "a cell" or "a human cell") may be "a population of human cells", preferably, a primary cell or a population of human primary cells, or more preferably a primary endonuclease-modified endogenous αβ-TCR negative human cell or a population of primary endonuclease-modified endogenous αβ-TCR negative human cells.

In particular embodiments, a cell of the invention is a primary, endonuclease-modified, endogenous αβ-TCR negative, human T cell or a population of primary endonuclease-modified endogenous αβ-TCR negative human T cells.

The present invention provides a TALEN-modified endogenous αβ-TCR negative human primary cell wherein the constant region of the genomic TCR gene (TRAC gene) comprises a genetic modification generated by a TALEN and affecting cell surface expression of the alpha beta TCR, said genomic TRAC gene comprising from 5' to 3':

(a) a 5' region of said human genomic TRAC gene upstream (b) a recognition domain for a TALEN, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second TALEN recognition domain, (d) a 3' region of the genomic TRAC gene.

In particular embodiments, the TALEN-modified endogenous αβ-TCR negative primary human cell obtained comprises undetectable level of off-site cut as determined using an adapted guide seq technique and a TALEN binding to the following sequence: TTGTCCCACAGA-TATCCagaac-cctgaccctgCCGTGTACCAGCTGAGAGA (SEQ ID NO: 38).

The present invention provides a TALEN-modified endogenous αβ-TCR negative human primary cell wherein the constant region of the genomic TCR gene (TRAC gene) comprises a genetic modification generated by a TALEN and affecting cell surface expression of the alpha beta TCR, said genomic TRAC gene comprising from 5' to 3':

(a) a 5' region of said human genomic TRAC gene upstream (b) a recognition domain for a TALEN comprising the following sequence ttgtcccacagATATC (SEQ ID NO: 36), or ttgtcccacagATATCCAG (SEQ ID NO: 37)

(c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second TALEN recognition domain, comprising the following sequence CCGTGTAC-CAGCTGAGA (SEQ ID NO: 26)

(d) a 3' region of the genomic TRAC gene.

The present invention provides a TALEN-modified endogenous αβ-TCR negative human primary cell wherein the constant region of the genomic TCR gene (TRAC gene) comprises an insertion generated by a TALEN and affecting cell surface expression of the alpha beta TCR, said genomic TRAC gene comprising from 5' to 3':

(a) a 5' region of said human genomic TRAC gene upstream (b) a recognition domain for a TALEN comprising the following sequence ttgtcccacagATATC (SEQ ID NO: 36), or ttgtcccacagATATCCAG (SEQ ID NO: 37)

(c) an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second TALEN recognition domain, comprising the following sequence CCGTGTAC-CAGCTGAGA (SEQ ID NO: 26)

(d) a 3' region of the genomic TRAC gene.

The present invention provides a TALEN-modified endogenous αβ-TCR negative human primary cell wherein the constant region of the genomic TCR gene (TRAC gene) comprises an insertion generated by a TALEN and affecting cell surface expression of the alpha beta TCR, said genomic TRAC gene comprising from 5' to 3':

(a) a 5' region of said human genomic TRAC gene upstream (b) a recognition domain for a TALEN comprising the following sequence ttgtcccacagATATC (SEQ ID NO: 36), or ttgtcccacagATATCCAG (SEQ ID NO: 37)

(c) an insertion as compared to the wild type TRAC gene affecting the cell surface expression of the extracellular domain or transmembrane domain of the alpha beta TCR, said insertion comprising an exogenous polynucleotide comprising an IRES, a coding sequence coding a chimeric antigen receptor (CAR), a termination sequence, (c') optionally a second TALEN recognition domain, comprising the following sequence CCGTGTAC-CAGCTGAGA (SEQ ID NO: 26)

(d) a 3' region of the genomic TRAC gene.

The present invention provides a TALEN-modified endogenous αβ-TCR negative human primary cell wherein the constant region of the genomic TCR gene (TRAC gene) comprises an insertion generated by a TALEN and affecting cell surface expression of the alpha beta TCR, said genomic TRAC gene comprising from 5' to 3':

(a) a 5' region of said human genomic TRAC gene upstream (b) a recognition domain for a TALEN comprising the following sequence ttgtcccacagATATC (SEQ ID NO: 36), or ttgtcccacagATATCCAG (SEQ ID NO: 37)

(c) an insertion as compared to the wild type TRAC gene affecting the cell surface expression of the extracellular domain or transmembrane domain of the alpha beta TCR, said insertion comprising a self-cleaving peptide in frame with the TRAC open reading frame, a se-quence coding a chimeric antigen receptor (CAR), a termination sequence, (c') optionally a second TALEN recognition domain, comprising the following sequence CCGTGTAC-CAGCTGAGA (SEQ ID NO: 26)

(d) a 3' region of the genomic TRAC gene.

More particularly, the present invention provides a TALEN-modified endogenous αβ-TCR negative human primary cell comprising in the genomic TRAC gene one of the following sequences:

```
                              (SEQ ID NO: 24-SEQ ID NO: 25)
AAGTAGCCCTGCATTTCAGGTTTCCTTGAGTGGCAGGCCAGGCCTGGC

CGTGAACGTTCACTGAAATCATGGCCTCTTGGCCAAGATTGATAGCTT

GTGCCTGTCCCTGAGTCCCAGTCCATCACGAGCAGCTGGTTTCTAAGA

TGCTATTTCCCGTATAAAGCATGAGACCGTGACTTGCCAGCCCCACAG

AGCCCCGCCCTTGTCCATCACTGGCATCTGGACTCCAGCCTGGGTTGG

GGCAAAGAGGGAAATGAGATCATGTCCTAACCCTGATCCTCTTGTCCC

ACAGATATCCAGTCCGGTGAGGGCAGAGGAAGTCTTCTAACATGCGG

TGACGTGGAGGAGAATCCGGGCCCCGGATCCcodingsequenceTCT

AGAGGGCCCGTTTAAACCCGCTGATCAGCCTCGACTGTGCCTTCTAGT

TGCCAGCCATCTGTTGTTTGCCCCTCCCCCGTGCCTTCCTTGACCCTG

GAAGGTGCCACTCCCACTGTCCTTTCCTAATAAAATGAGGAAATTGCA

TCGCATTGTCTGAGTAGGTGTCATTCTATTCTGGGGGGTGGGGTGGGG

CAGGACAGCAAGGGGGAGGATTGGGAAGACAATAGCAGGCATGCTGGG

GATGCGGTGGGCTCTATGACTAGTGGCGAATTCCCGTGTACCAGCTGA

GAGACTCTAAATCCAGTGACAAGTCTGTCTGCCTATTCACCGATTTTG

ATTCTCAAACAAATGTGTCACAAAGTAAGGATTCTGATGTGTATATCA

CAGACAAAACTGTGCTAGACATGAGGTCTATGGACTTCAAGAGCAACA

GTGCTGTGGCCTGGAGCAACAAATCTGACTTTGCATGTGCAAACGCCT

TCAACAACAGCATTATTCCAGAAGACACCTTCTTCCCCAGCCCAGGTA

AGGGCAGCTTTGGTGCCTTCGCAGGCTGTTTCCTTGCTTCAGGAA,
``` wherein underlined sequences are sequences of endogenous genomic TRAC gene that may be used for homologous recombination, bold italic sequence corresponds to a sequence encoding a self-cleaving peptide, Italic sequence corresponds to termination signal such as poly A sequences, codingsequence corresponds to at least one open reading frame encoding a protein, said protein may be for example a chimeric antigen receptor (CAR);

(SEQ ID NO: 9)

AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

*TCCGGTGAGGGCAGAGGAAGTCTTCTAACATGCGGTGACGTGGAGGAGAATCCGGGCCCC*GGATCCGCTCTG

CCCGTCACCGCTCTGCTGCTGCCACTGGCCCTGCTGCTGCACGCAGCAAGACCAGGAGGGGGAGGCAGCTGCC

CCTACAGCAACCCCAGCCTGTGCAGCGGAGGCGGCGGCAGCGGCGGAGGGGGTAGCCAGGTGCAGCTGCAG

CAGAGCGGCCCCTGGCCTGGTGAAGCCAAGCCAGACACTGTCCCTGACCTGCGCCATCAGCGGCGATTCCGTGA

GCTCCAACTCCGCCGCCTGGAATTGGATCAGGCAGTCCCCTTCTCGGGGCCTGGAGTGGCTGGGAAGGACATAC

TATCGGTCTAAGTGGTACAACGATTATGCCGTGTCTGTGAAGAGCAGAATCACAATCAACCCTGACACCTCCAAG

AATCAGTTCTCTCTGCAGCTGAATAGCGTGACACCAGAGGACACCGCCGTGTACTATTGCGCCAGGGAGGTGAC

CGGCGACCTGGAGGATGCCTTTGACATCTGGGGCCAGGGCACAATGGTGACCGTGTCTAGCGGAGGAGGAGG

ATCCGGAGGAGGAGGATCTGGCGGCGGCGGCAGCGATATCCAGATGACACAGTCCCCATCCTCTCTGAGCGCCT

CCGTGGGCGACAGAGTGACAATCACCTGTAGGGCCTCCCAGACCATCTGGTCTTACCTGAACTGGTATCAGCAG

AGGCCCGGCAAGGCCCCTAATCTGCTGATCTACGCAGCAAGCTCCCTGCAGAGCGGAGTGCCATCCAGATTCTCT

GGCAGGGGCTCCGGCACAGACTTCACCCTGACCATCTCTAGCCTGCAGGCCGAGGACTTCGCCACCTACTATTGC

CAGCAGTCTTATAGCATCCCCCAGACATTTGGCCAGGGCACCAAGCTGGAGATCAAGGGAAGCGGAGGGGGAG

GCAGCTGCCCCTACAGCAACCCCAGCCTGTGCAGCGGAGGCGGCGGCAGCGAGCTGCCCACCCAGGGCACCTT

CTCCAACGTGTCCACCAACGTGAGCCCAGCCAAGCCCACCACCACCGCCTGTCCTTATTCCAATCCTTCCCTGTGT

GCTCCCACCACAACCCCAGCACCAAGGCCACCTACACCTGCACCAACCATCGCCTCTCAGCCCCTGAGCCTGAGA

CCTGAGGCATGTAGGCCAGCAGCAGGAGGAGCAGTCCATACAAGGGGTCTGGATTTTGCATGCGACATCTACAT

CTGGGCACCTCTGGCAGGAACATGTGGCGTGCTCCTGCTCAGCCTGGTCATCACCCTGTACTGCAAGAGAGGCA

GGAAGAAGCTGCTGTATATCTTCAAGCAGCCCTTCATGCGCCCCGTGCAGACAACCCAGGAGGAGGATGGCTGC

TCCTGTAGGTTCCCAGAAGAGGAGGAGGGAGGATGTGAGCTGCGCGTGAAGTTTTCCCGGTCTGCCGACGCAC

CTGCATACCAGCAGGGCCAGAACCAGCTGTATAACGAGCTGAATCTGGGCCGGAGAGAGGAGTACGATGTGCT

GGACAAGAGGCGCGGCAGAGATCCAGAGATGGGCGGCAAGCCCCGGAGAAAGAACCCTCAGGAGGGCCTGT

ACAATGAGCTGCAGAAGGATAAGATGGCCGAGGCCTATTCTGAGATCGGCATGAAGGGAGAGAGGCGCCGGG

GCAAGGGACACGACGGACTGTACCAGGGACTGAGCACAGCCACCAAGGATACCTATGACGCCCTGCATATGCAG

GCACTGCCTCCAAGGTGATCTAGAGGGCCCGTTTAAACCCGCTGATCAGCCTCGA*CTGTGCCTTCTAGTTGCCAG*

*CCATCTGTTGTTTGCCCCTCCCCCGTGCCTTCCTTGACCCTGGAAGGTGCCACTCCCACTGTCCTTTCCTAATAAAAT*

*GAGGAAATTGCATCGCATTGTCTGAGTAGGTGTCATTCTATTCTGGGGGGTGGGGTGGGGCAGGACAGCAAGG*

*GGGAGGATTGGGAAGACAATAGCAGGCATGCTGGGGATGCGGTGGGCTCTATGACTAGTGGCGAATT*CCGTGT

ACCAGCTGAGAGACTCTAAATCCAGTGACAAGTCTGTCTGCCTATTCACCGATTTTGATTCTCAAACAAATGTGTC

ACAAAGTAAGGATTCTGATGTGTATATCACAGACAAAACTGTGCTAGACATGAGGTCTATGGACTTCAAGAGCAA

CAGTGCTGTGGCCTGGAGCAACAAATCTGACTTTGCATGTGCAAACGCCTTCAACAACAGCATTATTCCAGAAGA

CACCTTCTTCCCCAGCCCAGGTAAGGGCAGCTTTGGTGCCTTCGCAGGCTGTTTCCTTGCTTCAGGAA,, or

-continued (CD22 B-B7 QR3)

(SEO ID NO: 10)

AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

*TCCGGTGAGGGCAGAGGAAGTCTTCTAACATGCGGTGACGTGGAGGAGAATCCGGGCCCC*GGATCCGCTCTG

CCCGTCACCGCTCTGCTGCTGCCACTGGCCCTGCTGCTGCACGCCGCCAGACCCGGCGGAGGAGGCTCTTGCCC

CTACAGCAACCCCAGCCTGTGCTCTGGCGGCGGCGGCAGCGGAGGCGGCGGCTCCCAGGTGCAGCTGCAGCA

GAGCGGCCCTGGCCTGGTGGAGCCAAGCCAGACACTGTCCCTGACCTGCGCCATCTCTGGCGACAGCGTGAGC

TCCAACAGCGCCGCATGGAATTGGATCAGGCAGTCCCCATCTCGGGGCCTGGAGTGGCTGGGCAGAACATACTA

TAGGTCCACCTGGTACAACGACTATGCCGGCTCCGTGAAGTCTCGCATCACAATCAACCCCGATACCAGCAAGAA

TCAGTTCTCCCTGCAGCTGACATCTGTGACCCCTGAGGACACAGCCGTGTACTATTGCACCAGAAGCAGGCACAA

TACATTTCGGGGAATGGACGTGTGGGGACAGGGCACACTGGTGACCGTGAGCGGAGGAGGAGGATCCGGCGG

AGGAGGCTCTGGCGGCGGCGGCAGCGACATCCAGCTGACCCAGTCCCCTTCTAGCCTGAGCGCCTCCGTGGGC

GATAGAGTGACAATCACCTGTAGGGCCTCTCAGAGCATCTCCTCTTACCTGAACTGGTATCAGCAGAAGCCCGGC

AAGGCCCCTAAGCTGCTGATCTACGCAGCAAGCTCCCTGCAGTCTGGAGTGCCAAGCAGATTCTCCGGCTCTGG

CAGCGGCACCGACTTTACACTGACCATCTCTAGCCTGCAGCCTGAGGATTTCGCCACATACTATTGCCAGCAGTCC

TATTCTACACCACTGACCTTTGGCGGCGGCACCAAGGTGGAGATCAAGGGAAGCGGCGGCGGCGGAAGTTGTC

CATATTCAAACCCAAGTCTGTGCAGCGGCGGAGGAGGAAGCGAACTGCCTACTCAGGGAACCTTCAGCAACGT

GTCCACCAATGTGAGCCCAGCAAAGCCTACCACAACCGCATGCCCATACTCTAACCCCAGCCTGTGCACAACCAC

ACCAGCACCCAGGCCCCCTACCCCTGCACCAACAATCGCCTCCCAGCCTCTGTCTCTGCGGCCAGAGGCCTGCAG

ACCCGCCGCCGGCGGAGCAGTGCACACACGGGGCCTGGACTTTGCCTGTGATATCTATATCTGGGCACCACTGG

CCGGAACATGTGGCGTGCTGCTGCTGTCACTGGTCATTACACTGTACGTAAGCGAGGCCGGAAGAAACTGCTG

TATATTTTCAAACAGCCCTTTATGAGACCTGTGCAGACTACCCAGGAGGAAGACGGCTGCAGCTGTAGGTTCCCC

GAGGAAGAGGAAGGCGGGTGTGAGCTGAGGGTCAAGTTTAGCCGCTCCGCAGATGCCCCTGCTTACCAGCAG

GGGCAGAATCAGCTGTATAACGAGCTGAATCTGGGACGGAGAGAGGAATACGACGTGCTGGATAAAAGGCGCG

GGAGAGACCCCGAAATGGGAGGCAAGCCACGACGGAAAAACCCCCAGGAGGGCCTGTACAATGAACTGCAGA

AGGACAAAATGGCAGAGGCCTATAGTGAAATCGGGATGAAGGGAGAGAGAAGGCGCGGCAAAGGGCACGAT

GGCCTGTACCAGGGGCTGTCTACTGCCACCAAGGACACCTATGATGCTCTGCATATGCAGGCACTGCCTCCAAGG

TGATCTAGAGGGCCCGTTTAAACCCGCTGATCAGCCTCGA*CTGTGCCTTCTAGTTGCCAGCCATCTGTTGTTTGCC*

*CCTCCCCCGTGCCTTCCTTGACCCTGGAAGGTGCCACTCCCACTGTCCTTTCCTAATAAAATGAGGAAATTGCATCG*

*CATTGTCTGAGTAGGTGTCATTCTATTCTGGGGGGTGGGGTGGGGCAGGACAGCAAGGGGGAGGATTGGGAAG*

*ACAATAGCAGGCATGCTGGGGATGCGGTGGGCTCTATGACTAGTGGCGAATT*CCCGTGTACCAGCTGAGAGACT

CTAAATCCAGTGACAAGTCTGTCTGCCTATTCACCGATTTTGATTCTCAAACAAATGTGTCACAAAGTAAGGATTCT

GATGTGTATATCACAGACAAAACTGTGCTAGACATGAGGTCTATGGACTTCAAGAGCAACAGTGCTGTGGCCTGG

AGCAACAAATCTGACTTTGCATGTGCAAACGCCTTCAACAACAGCATTATTCCAGAAGACACCTTCTTCCCCAGCC

CAGGTAAGGGCAGCTTTGGTGCCTTCGCAGGCTGTTTCCTTGCTTCAGGAA,, (CD22 A-D4 QR3)

(SEO ID NO: 11)

AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

-continued

TCCAGCCTGGGTTGGGGCAAAGAGGGAAATGAGATCATGTCCTAACCCTGATCCTCTTGTCCCACAGATATCCAG

*TCCGGTGAGGGCAGAGGAAGTCTTCTAACATGCGGTGACGTGGAGGAGAATCCGGGCCCC*GGATCCGCTCTG

CCCGTCACCGCTCTGCTGCTGCCACTGGCCCTGCTGCTGCACGCCGCCAGACCCGGCGGAGGAGGCTCTTGCCC

CTACAGCAACCCCAGCCTGTGCTCTGGCGGCGGCGGCAGCGGAGGCGGCGGCTCCCAGGTGCAGCTGCAGCA

GAGCGGCCCCGGCCTGGTGAAGCCTAGCCAGACACTGTCCCTGACCTGCGCAATCTCCGGCGACAGCGTGTCCG

GAAACAGGGCCACATGGAATTGGATCAGACAGTCTCCAAGCAGGGGCCTGGAGTGGCTGGGAAGGACCTACTA

TCGGTCCGCCTGGTACAACGACTATGCCGTGTCTGTGAAGGGCCGCATCACATTCAACCCAGATACCAGCAAGAA

TCAGTTTTCCCTGCAGCTGAATTCTGTGACACCCGAGGATACCGCCGTGTACTATTGCGCCAGAGGCGAGAGCG

GAGCAGCAGCAGACGCCTTCGATATCTGGGGCCAGGGCACCACAGTGACAGTGAGCGGAGGAGGAGGATCCG

GCGGAGGAGGCTCTGGCGGCGGCGGCAGCGACATCCAGCTGACCCAGAGCCCACCTTCCCTGTCTGCCAGCGT

GGGCGATCGCGTGACAATCACCTGTCGGGCCTCCCAGTCTATCAGCTCCTACCTGAACTGGTATCAGCAGAAGCC

AGGCAAGGCCCCCAAGCTGCTGATCTACGCAGCATCTAGCCTGCAGTCTGGAGTGCCAAGCAGATTCAGCGGAT

CCGGATTCGGCACAGACTTTACACTGACCATCTCCTCTCTGCAGCCCGAGGATTTCGCCACCTACTATTGCCAGCA

GTCTTATAGCACACCTCAGACCTTTGGCCAGGGCACCAAGGTGGACATCAAGGGAAGTGGAGGAGGAGGAAG

TTGTCCCTACTCAAACCCATCTCTGTGCTCAGGAGGAGGAGGAAGTGAACTGCCTACTCAGGGAACATTCAGCA

ACGTGTCCACCAATGTGAGCCCAGCAAAGCCTACCACAACCGCATGCCCATACTCTAACCCCAGCCTGTGCACAA

CCACACCAGCACCCAGGCCCCCTACCCCTGCACCAACAATCGCCTCCCAGCCTCTGTCTCTGCGGCCAGAGGCCT

GCAGACCCGCCGCCGGCGGAGCAGTGCACACACGGGGCCTGGACTTTGCCTGTGATATCTATATCTGGGCACCA

CTGGCCGGAACATGTGGCGTGCTGCTGCTGTCACTGGTCATTACACTGTACTGTAAGCGAGGCCGGAAGAAACT

GCTGTATATTTTCAAALAGLCCTTTATGAGACCTGTGLAGACTACCCAGGAGGAAGACGGCTGCAGCTGTAGGTT

CCCCGAGGAAGAGGAAGGCGGGTGTGAGCTGAGGGTCAAGTTTAGCCGCTCCGCAGATGCCCCTGCTTACCAG

CAGGGGCAGAATCAGCTGTATAACGAGCTGAATCTGGGACGGAGAGAGGAATACGACGTGCTGGATAAAAGGC

GCGGGAGAGACCCCGAAATGGGAGGCAAGCCACGACGGAAAAACCCCAGGAGGGCCTGTACAATGAACTGC

AGAAGGACAAAATGGCAGAGGCCTATAGTGAAATCGGGATGAAGGGAGAGAGAAGGCGCGGCAAAGGGCAC

GATGGCCTGTACCAGGGGCTGTCTACTGCCACCAAGGACACCTATGATGCTCTGCATATGCAGGCACTGCCTCCA

AGGTGATCTAGAGGGCCCGTTTAAACCCGCTGATCAGCCTCGA*CTGTGCCTTCTAGTTGCCAGCCATCTGTTGTTT*

*GCCCCTCCCCCGTGCCTTCCTTGACCCTGGAAGGTGCCACTCCCACTGTCCTTTCCTAATAAAATGAGGAAATTGC*

*ATCGCATTGTCTGAGTAGGTGTCATTCTATTCTGGGGGGTGGGGTGGGGCAGGACAGCAAGGGGGAGGATTGG*

*GAAGACAATAGCAGGCATGCTGGGGATGCGGTGGGCTCTATGACTAGTGGCGAATT*CCCGTGTACCAGCTGAGA

GACTCTAAATCCAGTGACAAGTCTGTCTGCCTATTCACCGATTTTGATTCTCAAACAAATGTGTCACAAAGTAAGG

ATTCTGATGTGTATATCACAGACAAAACTGTGCTAGACATGAGGTCTATGGACTTCAAGAGCAACAGTGCTGTGG

CCTGGAGCAACAAATCTGACTTTGCATGTGCAAACGCCTTCAACAACAGCATTATTCCAGAAGACACCTTCTTCCC

CAGCCCAGGTAAGGGCAGCTTTGGTGCCTTCGCAGGCTGTTTCCTTGCTTCAGGAA,;
or (CD123 K43 QR3)

(SEQ ID NO: 12)

AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

*TCCGGTGAGGGCAGAGGAAGTCTTCTAACATGCGGTGACGTGGAGGAGAATCCGGGCCCC*GGATCCGCTCTG

CCCGTCACCGCTCTGCTGCTGCCTCTGGCCCTGCTGCTGCACGCAGCCAGACCAGGCGGAGGAGGCTCCTGCCC

-continued

TTACTCTAACCCAAGCCTGTGCTCCGGAGGAGGAGGATCCGGCGGAGGAGGCTCTGAGGTGAAGCTGGTGGA

GAGCGGAGGAGGCCTGGTGCAGCCTGGCGGCTCCCTGTCTCTGAGCTGCGCAGCATCCGGCTTCACCTTTACAG

ACTACTATATGTCTTGGGTGAGACAGCCCCCTGGCAAGGCCCTGGAGTGGCTGGCCCTGATCAGGTCCAAGGCC

GATGGCTACACCACAGAGTATTCCGCCTCTGTGAAGGGCAGATTCACCCTGTCTAGGGACGATAGCCAGTCCATC

CTGTACCTGCAGATGAATGCACTGCGCCCCGAGGACAGCGCCACATACTATTGTGCCAGAGACGCCGCCTACTAT

TCTTACTATAGCCCTGAGGGCGCTATGGACTACTGGGGCCAGGGCACCTCCGTGACAGTGAGCTCCGGAGGAGG

AGGAAGCGGAGGAGGAGGCTCCGGCGGCGGCGGCTCTATGGCCGACTATAAGGATATCGTGATGACCCAGAGC

CACAAGTTTATGTCTACAAGCGTGGGCGACCGCGTGAACATCACCTGCAAGGCCAGCCAGAATGTGGATTCCGC

CGTGGCCTGGTACCAGCAGAAGCCTGGCCAGAGCCCTAAGGCCCTGATCTATTCCGCCTCTTACCGGTATAGCGG

AGTGCCTGACCGCTTCACCGGAAGGGGATCCGGAACAGACTTCACCCTGACAATCTCTAGCGTGCAGGCCGAG

GATCTGGCCGTGTACTATTGTCAGCAGTACTATAGCACCCCCTGGACCTTCGGCGGAGGAACCAAGCTGGAGATC

AAGAGAGGATCTGGAGGAGGAGGAAGCTGCCCATACTCCAACCCCTCTCTGTGCAGCGGAGGAGGAGGATCTG

AGCTGCCAACCCAGGGCACATTTTCCAACGTGTCTACAAATGTGAGCCCAGCAAAGCCAACCACAACCGCATGC

CCTTATAGCAATCCATCCCTGTGCACAACCACACCTGCACCAAGACCACCAACCCCAGCACCTACAATCGCCTCTC

AGCCACTGAGCCTGCGCCCCGAGGCATGCCGGCCTGCAGCAGGCGGCGCCGTGCACACCAGGGGCCTGGACT

TCGCCTGCGATATCTACATCTGGGCACCTCTGGCAGGAACCTGTGGCGTGCTGCTGCTGAGCCTGGTCATCACCC

TGTACTGCAAGAGAGGCAGGAAGAAGCTGCTGTATATCTTCAAGCAGCCCTTTATGCGCCCTGTGCAGACCACAC

AGGAGGAGGACGGCTGCAGCTGTCGGTTCCCAGAAGAGGAGGAGGGCGGCTGTGAGCTGAGAGTGAAGTTT

AGCAGGTCCGCCGATGCACCAGCATACCAGCAGGGACAGAACCAGCTGTATAACGAGCTGAATCTGGGCCGGA

GAGAGGAGTACGACGTGCTGGATAAGAGGAGGGGAAGGGACCCCGAGATGGGAGGCAAGCCACGGAGAAA

GAACCCCCAGGAGGGCCTGTACAATGAGCTGCAGAAGGACAAGATGGCCGAGGCCTATTCCGAGATCGGCATG

AAGGGAGAGAGGCGCCGGGGCAAGGGACACGATGGCCTGTACCAGGGCCTGTCTACCGCCACAAAGGACACC

TATGATGCCCTGCATATGCAGGCACTGCCTCCAAGGTGATCTAGAGGGCCCGTTTAAACCCGCTGATCAGCCTCG

*ACTGTGCCTTCTAGTTGCCAGCCATCTGTTGTTTGCCCCTCCCCCGTGCCTTCCTTGACCCTGGAAGGTGCCACTCC*

*CACTGTCCTTTCCTAATAAAATGAGGAAATTGCATCGCATTGTCTGAGTAGGTGTCATTCTATTCTGGGGGGTGGG*

*GTGGGGCAGGACAGCAAGGGGGAGGATTGGGAAGACAATAGCAGGCATGCTGGGGATGCGGTGGGCTCTATG*

ACTAGTGGCGAATT<u>CCCGTGTACCAGCTGAGAGACTCTAAATCCAGTGACAAGTCTGTCTGCCTATTCACCGATTT</u>

<u>TGATTCTCAAACAAATGTGTCACAAAGTAAGGATTCTGATGTGTATATCACAGACAAAACTGTGCTAGACATGAGG</u>

<u>TCTATGGACTTCAAGAGCAACAGTGCTGTGGCCTGGAGCAACAAATCTGACTTTGCATGTGCAAACGCCTTCAAC</u>

<u>AACAGCATTATTCCAGAAGACACCTTCTTCCCCAGCCCAGGTAAGGGCAGCTTTGGTGCCTTCGCAGGCTGTTTC</u>

<u>CTTGCTTCAGGAA</u>, .

The insertion may comprise a sequence having at least from 99%, 98%, 97%, 96%, 95% 94% 93% 92% 91% 90% 89% 88% 87% 86% 85% 84% 83% 82% 81% to 80% identity with SEQ ID NO: 9

The insertion may comprise a sequence having at least from 99%, 98%, 97%, 96%, 95% 94% 93% 92% 91% 90% 89% 88% 87% 86% 85% 84% 83% 82% 81% to 80% identity with SEQ ID NO: 10

The insertion may comprise a sequence having at least from 99%, 98%, 97%, 96%, 95% 94% 93% 92% 91% 90% 89% 88% 87% 86% 85% 84% 83% 82% 81% to 80% identity with SEQ ID NO: 11

The insertion may comprise a sequence having at least from 99%, 98%, 97%, 96%, 95% 94% 93% 92% 91% 90%

89% 88% 87% 86% 85% 84% 83% 82% 81% to 80% identity with SEQ ID NO: 12.

The insertion may comprise a sequence having at least 80% identity with SEQ ID NO: 9

The insertion may comprise a sequence having at least 80% identity with SEQ ID NO: 10

The insertion may comprise a sequence having at least 80% identity with SEQ ID NO: 11

The insertion may comprise a sequence having at least 80% identity with SEQ ID NO: 12

The insertion may comprise a sequence having at least 90% identity with SEQ ID NO: 9

The insertion may comprise a sequence having at least 90% identity with SEQ ID NO: 10

The insertion may comprise a sequence having at least 90% identity with SEQ ID NO: 11

The insertion may comprise a sequence having at least 90% identity with SEQ ID NO: 12

The insertion may comprise a sequence having at least 95% identity with SEQ ID NO: 9

The insertion may comprise a sequence having at least 95% identity with SEQ ID NO: 10

The insertion may comprise a sequence having at least 95% identity with SEQ ID NO: 11

The insertion may comprise a sequence having at least 95% identity with SEQ ID NO: 12.

In particular embodiments, the insertion may comprise a sequence encoding a CAR having the desired function of said CAR that is to say binding to any one of the target listed herein, preferably an antigen expressed at the surface of pathological cells directly or indirectly responsible for a disease.

Cell

By cell or cells is intended any eukaryotic living cell, any primary cell or cell line.

By "primary cell" or "primary cells" are intended cells, a homogenous population of cells taken (isolated) from a living tissue (i.e. biopsy material including blood) and established for growth, that have undergone very few population doublings and are therefore more representative of the main functional components and characteristics of tissues from which they are derived from, in comparison to continuous tumorigenic or artificially immortalized cell lines.

The cell of the invention (ie TALEN-modified endogenous αβ-TCR negative human primary cell) according to any one of the above embodiments may be a human T-cell, a human cell derived from a human T cell, a human lymphoid cell, a human stem cell, a human progenitor cell, a human induced pluripotent stem cell (iPSC), a human embryonic stem cell, a human mesenchymal stem cell (MSC), a human hematopoietic stem cell (HSC).

Preferably, the cell (TALEN-modified endogenous αβ-TCR negative human primary cell) according to any of the embodiments of the present invention, may be (ultimately) a human T-cell, more preferably a human lymphoid T cell, a human progenitor T cell, a human CD4+ T cell, a human CD8+ T cell, a human regulatory T cell, a human NKT cell, a human naïve T cell, a human memory T cell, a human TIL, a combination thereof.

In preferred embodiments, the cell or human cell of the invention is a TALEN-modified endogenous αβ-TCR negative human primary cell.

In lore preferred embodiments, the cell or human cell of the invention is a TALEN-modified endogenous αβ-TCR negative human primary T cell.

The human cell of the present invention may be even more preferably a primary human T cell isolated from the blood or from a tissue or a population of primary human T cell isolated from the blood or from a tissue and cultured in vitro for few passages before and/or after being engineered.

In particular embodiments, the human T cell of the present invention may be a human T cell line, a primary human T cell line, a primary human T cell line means derived from one human primary cell or a homogenous population of human primary cells.

In particular embodiments, the human cell of the invention is part of a population of human cells comprising said human cell.

In particular embodiments, the human cell of the invention is a population of human cells, preferably a homogenous population of human immune cells, more preferably a homogenous population of human T cells, even more preferably a homogenous population of human T cells with cytolytic activity.

In particular embodiments, the human cell of the invention is a population of human primary cells, preferably a homogenous population of human immune primary cells, more preferably a homogenous population of human primary T cells, even more preferably a homogenous population of human primary T cells with cytolytic activity.

The human cell of the present invention is engineered, meaning that said human cell comprises a genetic modification, in particular an insertion of an exogenous polynucleotide, into the genomic DNA, induced by an endonuclease, preferably a rare cutting endonuclease, more preferably a rare cutting endonuclease selected from TALEN, CRISPR CAS9, Meganuclease, MegaTAL, Zn Finger, or a combination thereof, even more preferably at least by a TALEN.

In preferred embodiments, the human cell of the present invention is engineered, meaning that said human cell comprises at least one genetic modification, preferably an insertion affecting the TRAC gene, said insertion comprising an exogenous polynucleotide encoding a CAR, said cell express a CAR at the cell surface, and undetectable level of alpha beta TCR at the cell surface.

In preferred embodiments, the human cell of the present invention is engineered, meaning that said human cell comprises at least one genetic modification, preferably an insertion affecting the TRAC gene, said insertion comprising an exogenous polynucleotide encoding a TCR (here an exogenous TCR), said cell express said exogenous TCR at the cell surface, and undetectable level of alpha beta TCR at the cell surface.

In particular embodiments, the human cell of the present invention is engineered, meaning that said human cell comprises at least one genetic modification, preferably an insertion within the TRAC gene, said insertion comprising an exogenous polynucleotide encoding a tag or a protein, said insertion does not prevent the endogenous TCR to be translated and transduced and expressed at the cell surface, said cell express said endogenous TCR at the cell surface.

1. A TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a half TALEN, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a coding sequence such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a recognition domain for another half TALEN, (d) a 3' region of the genomic TRAC gene.

The TALEN-modified endogenous αβ-TCR negative human primary cell of embodiment 1 comprising a level of off target cutting below detection by a guide seq analysis is provided.

2. The TALEN-modified endogenous αβ-TCR negative human primary cell according to embodiment 1 wherein said human primary cell is a human primary T cell, or a human lymphoid primary cell, or a human primary stem cell, or a human primary progenitor cell.

3. The TALEN-modified endogenous αβ-TCR negative human primary cell according to any one of embodiments 1 to 2 wherein said human primary cell is a human primary T cell or a population of human primary T cells.

4. The TALEN-modified endogenous αβ-TCR negative human primary cell according to any one of embodiments 1 to 3 wherein said human T primary cell or population thereof comprises or consists in human primary CD8 T cell, human primary CD4 T cell, a combination thereof.

5. The TALEN-modified endogenous αβ-TCR negative human primary cell according to any one of embodiments 1 to 4 wherein said recognition domain for a TALEN comprises the following sequence ttgtcccacagATATC (SEQ ID NO: 36), or ttgtcccacagATATCCAG (SEQ ID NO: 37), and optionally CCGTG-TACCAGCTGAGA (SEQ ID NO: 26).

6. The TALEN-modified endogenous αβ-TCR negative human primary cell according to any one of embodiments 1 to 5 comprising the following sequence: AAGTAGCCCTG-CATTTCAGGTTTCCTTGAGTGGCAGGCCAGGCC TGGCCGTGAACGTTCACTGAAATCATGGCC TCTTGGCCAAGATTGATAGCTTGTGCCTGTCCCT-GAGTCCCAGTCCATCACGAGCAGCTGGTTTCTAA-GATGCTAT TTCCCGTATAAAGCATGAGACCGTG ACTTGCCAGCCCCACAGAGCCCCGCCCTTGTCCAT-CACTGGCATCTGGAC TCCAGCCTGGGTTGGGGCA AAGAGGGAAATGAGATCATGTCCTAACCCTGATC CTCTTGTCCCACAGATATCCAG TCCGGTGAGGG CAGAGGAAGTCTTCTAACATGCGGTGACGTGGAG-GAGAATCCGGGCCCCGGATCCcodingse quenceTCTA GAGGGCCCGTTTAAACCCGCTGATCAGCCTCG ACTGTGCCTTCTAGTTGCCAGCCATCTGTTGTTT GCCCCTCCCCCGTGCCTTCCTTGACCCTGGAAG GTGCCACTCCCACTGTCCTTTCCTAATAAAATGAG-GAAATTGC ATCGCATTGTCTGAGTAGGTGTCATTC-TATTCTGGGGGGTGGGGTGGGGCAGGACAGC AAGGGGGAGGATTGG GAAGACAATAGCAGG-CATGCTGGGGATGCGGTGGGGCTCTATGACTAGT GGCGAATTCCCGTGTACCAGCTGAGA GACTCT AAATCCAGTGACAAGTCTGTCTGCCTATTCACC-GATTTTGATTCTCAAACAAATGTGTCACAAAG TAAGG ATTCTGATGTGTATATCACAGACAAAACT GTGCTAGACATGAGGTCTATGGACTTCAAGAGC AACAGTGCTGTGG CCTGGAGCAACAAATCT GAC TTTGCATGTGCAAACGCCTTCAACAACAGCATTAT-TCCAGAAGACACCTTCTTCCC CAGCCCAGGTAAG GGCAGCTTTGGTGCCTTCGCAGGCTGTTTCCTTG-CTTCAGGAA (SEQ ID NO: 24-SEQ ID NO: 25) in the TRAC gene, The TALEN-modified endogenous DE-TCR negative human primary cell according to any one of embodiments 1 to 5 wherein said recognition domain for a TALEN comprises a homology arm, a se-quence coding a protein, such as a sequence coding for a self-cleaving peptide in frame with the TRAC open reading frame, preferably a 2A peptide; a sequence coding a chimeric antigen receptor (CAR), preferably a CAR, more preferably an anti-CD123 CAR or an anti-CD22 CAR; a sequence coding a TCR, a sequence coding a protein conferring sensitivity to a drug, a sequence coding a protein conferring resistance to a drug, a cytokine, a termination sequence.

In a preferred embodiment said coding sequence is fol-lowed by a termination sequence such as a BGH poly A.

7. The TALEN-modified endogenous αβ-TCR negative human primary cell according to any one of embodiments 1 to 6 wherein said CAR sequence comprises an anti-CD22 CAR sequence, anti-CD123 CAR sequence, anti-CD30 CAR sequence, anti-HSP-70 CAR sequence, anti-o-acetyl-GD2 CAR se-quence, anti-CS-1 CAR sequence, anti-CLL-1 CAR sequence, an anti-CD38 CAR sequence, anti-5T4 CAR sequence, anti-MUC1 CAR sequence, anti-FAP CAR sequence, anti-HER2 CAR sequence, anti-CD79a CAR sequence, anti-CD79b CAR.

The TALEN-modified endogenous αβ-TCR negative human primary cell according to any one of embodiments 1 to 7, wherein said polynucleotide sequence comprises one of the following sequences: SEQ ID NO: 9, SEQ ID NO: 10, SEQ ID NO: 11, SEQ ID NO: 12.

The TALEN-modified endogenous αβ-TCR negative human primary cell according to any one of embodiments 1 to 7, wherein said polynucleotide sequence comprises one of the following sequences: SEQ ID NO: 9, SEQ ID NO: 10, SEQ ID NO: 11, SEQ ID NO: 12 which are respectively:

```
                                                      (SEQ ID NO: 9)
AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

TCCGGTGAGGGCAGAGGAAGTCTTCTAACATGCGGTGACGTGGAGGAGAATCCGGGCCCCGGATCCGCTCTGC

CCGTCACCGCTCTGCTGCTGCCACTGGCCCTGCTGCTGCACGCAGCAAGACCAGGAGGGGGAGGCAGCTGCCC

CTACAGCAACCCCAGCCTGTGCAGCGGAGGCGGCGGCAGCGGCGGAGGGGGTAGCCAGGTGCAGCTGCAGC

AGAGCGGCCCTGGCCTGGTGAAGCCAAGCCAGACACTGTCCCTGACCTGCGCCATCAGCGGCGATTCCGTGAG

CTCCAACTCCGCCGCCTGGAATTGGATCAGGCAGTCCCCTTCTCGGGGCCTGGAGTGGCTGGGAAGGACATACT

ATCGGTCTAAGTGGTACAACGATTATGCCGTGTCTGTGAAGAGCAGAATCACAATCAACCCTGACACCTCCAAGA

ATCAGTTCTCTCTGCAGCTGAATAGCGTGACACCAGAGGACACCGCCGTGTACTATTGCGCCAGGGAGGTGACC
```

-continued

GGCGACCTGGAGGATGCCTTTGACATCTGGGGCCAGGGCACAATGGTGACCGTGTCTAGCGGAGGAGGAGGA

TCCGGAGGAGGAGGATCTGGCGGCGGCGGCAGCGATATCCAGATGACACAGTCCCCATCCTCTCTGAGCGCCTC

CGTGGGCGACAGAGTGACAATCACCTGTAGGGCCTCCCAGACCATCTGGTCTTACCTGAACTGGTATCAGCAGA

GGCCCGGCAAGGCCCCTAATCTGCTGATCTACGCAGCAAGCTCCCTGCAGAGCGGAGTGCCATCCAGATTCTCTG

GCAGGGGCTCCGGCACAGACTTCACCCTGACCATCTCTAGCCTGCAGGCCGAGGACTTCGCCACCTACTATTGCC

AGCAGTCTTATAGCATCCCCCCAGACATTTGGCCAGGGCACCAAGCTGGAGATCAAGGGAAGCGGAGGGGGAG

GCAGCTGCCCCTACAGCAACCCCAGCCTGTGCAGCGGAGGCGGCGGCAGCGAGCTGCCCACCCAGGGCACCTT

CTCCAACGTGTCCACCAACGTGAGCCCAGCCAAGCCCACCACCACCGCCTGTCCTTATTCCAATCCTTCCCTGTGT

GCTCCCACCACAACCCCAGCACCAAGGCCACCTACACCTGCACCAACCATCGCCTCTCAGCCCCTGAGCCTGAGA

CCTGAGGCATGTAGGCCAGCAGCAGGAGGAGCAGTCCATACAAGGGGTCTGGATTTTGCATGCGACATCTACAT

CTGGGCACCTCTGGCAGGAACATGTGGCGTGCTCCTGCTCAGCCTGGTCATCACCCTGTACTGCAAGAGAGGCA

GGAAGAAGCTGCTGTATATCTTCAAGCAGCCCTTCATGCGCCCCGTGCAGACAACCCAGGAGGAGGATGGCTGC

TCCTGTAGGTTCCCAGAAGAGGAGGAGGGAGGATGTGAGCTGCGCGTGAAGTTTTCCCGGTCTGCCGACGCAC

CTGCATACCAGCAGGGCCAGAACCAGCTGTATAACGAGCTGAATCTGGGCCGGAGAGAGGAGTACGATGTGCT

GGACAAGAGGCGCGGCAGAGATCCAGAGATGGGCGGCAAGCCCCGGAGAAAGAACCCTCAGGAGGGCCTGT

ACAATGAGCTGCAGAAGGATAAGATGGCCGAGGCCTATTCTGAGATCGGCATGAAGGGAGAGAGGCGCCGGG

GCAAGGGACACGACGGACTGTACCAGGGACTGAGCACAGCCACCAAGGATACCTATGACGCCCTGCATATGCAG

GCACTGCCTCCAAGGTGATCTAGAGGGCCCGTTTAAACCCGCTGATCAGCCTCGA*CTGTGCCTTCTAGTTGCCAG*

*CCATCTGTTGTTTGCCCCTCCCCCGTGCCTTCCTTGACCCTGGAAGGTGCCACTCCCACTGTCCTTTCCTAATAAAAT*

*GAGGAAATTGCATCGCATTGTCTGAGTAGGTGTCATTCTATTCTGGGGGGTGGGGTGGGGCAGGACAGCAAGG*

*GGGAGGATTGGGAAGACAATAGCAGGCATGCTGGGGATGCGGTGGGCTCTATGACTAGTGGCGAATTCCCGTG*

TACCAGCTGAGAGACTCTAAATCCAGTGACAAGTCTGTCTGCCTATTCACCGATTTTGATTCTCAAACAAATGTGT

CACAAAGTAAGGATTCTGATGTGTATATCACAGACAAAACTGTGCTAGACATGAGGTCTATGGACTTCAAGAGCA

ACAGTGCTGTGGCCTGGAGCAACAAATCTGACTTTGCATGTGCAAACGCCTTCAACAACAGCATTATTCCAGAAG

ACACCTTCTTCCCCAGCCCAGGTAAGGGCAGCTTTGGTGCCTTCGCAGGCTGTTTCCTTGCTTCAGGAA, (SEQ ID NO: 10)
AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

TCCGGTGAGGGCAGAGGAAGTCTTCTAACATGCGGTGACGTGGAGGAGAATCCGGGCCCCGGATCCGCTCTGC

CCGTCACCGCTCTGCTGCTGCCACTGGCCCTGCTGCTGCACGCCGCCAGACCCGGCGGAGGAGGCTCTTGCCCC

TACAGCAACCCCAGCCTGTGCTCTGGCGGCGGCGGCAGCGGAGGCGGCGGCTCCCAGGTGCAGCTGCAGCAG

AGCGGCCCTGGCCTGGTGGAGCCAAGCCAGACACTGTCCCTGACCTGCGCCATCTCTGGCGACAGCGTGAGCTC

CAACAGCGCCGCATGGAATTGGATCAGGCAGTCCCCATCTCGGGGCCTGGAGTGGCTGGGCAGAACATACTATA

GGTCCACCTGGTACAACGACTATGCCGGCTCCGTGAAGTCTCGCATCACAATCAACCCCGATACCAGCAAGAATC

AGTTCTCCCTGCAGCTGACATCTGTGACCCCTGAGGACACAGCCGTGTACTATTGCACCAGAAGCAGGCACAATA

CATTTCGGGGAATGGACGTGTGGGGACAGGGCACACTGGTGACCGTGAGCGGAGGAGGAGGATCCGGCGGA

GGAGGCTCTGGCGGCGGCGGCAGCGACATCCAGCTGACCCAGTCCCCTTCTAGCCTGAGCGCCTCCGTGGGCG

ATAGAGTGACAATCACCTGTAGGGCCTCTCAGAGCATCTCCTCTTACCTGAACTGGTATCAGCAGAAGCCCGGCA

-continued

AGGCCCCTAAGCTGCTGATCTACGCAGCAAGCTCCCTGCAGTCTGGAGTGCCAAGCAGATTCTCCGGCTCTGGC

AGCGGCACCGACTTTACACTGACCATCTCTAGCCTGCAGCCTGAGGATTTCGCCCACATACTATTGCCAGCAGTCCT

ATTCTACACCACTGACCTTTGGCGGCGGCACCAAGGTGGAGATCAAGGGAAGCGGCGGCGGCGGAAGTTGTCC

ATATTCAAACCCAAGTCTGTGCAGCGGCGGAGGAGGAAGCGAACTGCCTACTCAGGGAACCTTCAGCAACGTG

TCCACCAATGTGAGCCCAGCAAAGCCTACCACAACCGCATGCCCATACTCTAACCCCAGCCTGTGCACAACCACA

CCAGCACCCAGGCCCCCTACCCCTGCACCAACAATCGCCTCCCAGCCTCTGTCTCTGCGGCCAGAGGCCTGCAGA

CCCGCCGCCGGCGGAGCAGTGCACACACGGGGCCTGGACTTTGCCTGTGATATCTATATCTGGGCACCACTGGC

CGGAACATGTGGCGTGCTGCTGCTGTCACTGGTCATTACACTGTACTGTAAGCGAGGCCGGAAGAAACTGCTGT

ATATTTTCAAACAGCCCTTTATGAGACCTGTGCAGACTACCCAGGAGGAAGACGGCTGCAGCTGTAGGTTCCCCG

AGGAAGAGGAAGGCGGGTGTGAGCTGAGGGTCAAGTTTAGCCGCTCCGCAGATGCCCCTGCTTACCAGCAGG

GGCAGAATCAGCTGTATAACGAGCTGAATCTGGGACGGAGAGAGGAATACGACGTGCTGGATAAAAAGGCGCGG

GAGAGACCCCGAAATGGGAGGCAAGCCACGACGGAAAAACCCCCAGGAGGGCCTGTACAATGAACTGCAGAA

GGACAAAATGGCAGAGGCCTATAGTGAAATCGGGATGAAGGGAGAGAGAAGGCGCGGCAAAGGGCACGATG

GCCTGTACCAGGGGCTGTCTACTGCCACCAAGGACACCTATGATGCTCTGCATATGCAGGCACTGCCTCCAAGGT

GATCTAGAGGGCCCGTTTAAACCCGCTGATCAGCCTCGACTGTGCCTTCTAGTTGCCAGCCATCTGTTGTTTGCCC

CTCCCCCGTGCCTTCCTTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGGCAGGACAGCAAGGGGGAGGATTGGGAA

GACAATAGCAGGCATGCTGGGGATGCGGTGGGCTCTATGACTAGTGGCGAATTCCCGTGTACCAGCTGAGAGAC

TCTAAATCCAGTGACAAGTCTGTCTGCCTATTCACCGATTTTGATTCTCAAACAAATGTGTCACAAAGTAAGGATTC

TGATGTGTATATCACAGACAAAACTGTGCTAGACATGAGGTCTATGGACTTCAAGAGCAACAGTGCTGTGGCCTG

GAGCAACAAATCTGACTTTGCATGTGCAAACGCCTTCAACAACAGCATTATTCCAGAAGACACCTTCTTCCCCAG

CCCAGGTAAGGGCAGCTTTGGTGCCTTCGCAGGCTGTTTCCTTGCTTCAGGAA, (SEQ ID NO: 11)
AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

TCCGGTGAGGGCAGAGGAAGTCTTCTAACATGCGGTGACGTGGAGGAGAATCCGGGCCCCGGATCCGCTCTGC

CCGTCACCGCTCTGCTGCTGCCACTGGCCCTGCTGCTGCACGCCGCCAGACCCGGCGGAGGAGGCTCTTGCCCC

TACAGCAACCCCAGCCTGTGCTCTGGCGGCGGCGGCAGCGGAGGCGGCGGCTCCCAGGTGCAGCTGCAGCAG

AGCGGCCCCGGCCTGGTGAAGCCTAGCCAGACACTGTCCCTGACCTGCGCAATCTCCGGCGACAGCGTGTCCGG

AAACAGGGCCACATGGAATTGGATCAGACAGTCTCCAAGCAGGGGCCTGGAGTGGCTGGGAAGGACCTACTAT

CGGTCCGCCTGGTACAACGACTATGCCGTGTCTGTGAAGGGCCGCATCACATTCAACCCAGATACCAGCAAGAAT

CAGTTTTCCCTGCAGCTGAATTCTGTGACACCCGAGGATACCGCCGTGTACTATTGCGCCAGAGGCGAGAGCGG

AGCAGCAGCAGACGCCTTCGATATCTGGGGCCAGGGCACCACAGTGACAGTGAGCGGAGGAGGAGGATCCGG

CGGAGGAGGCTCTGGCGGCGGCGGCAGCGACATCCAGCTGACCCAGAGCCCACCTTCCCTGTCTGCCAGCGTG

GGCGATCGCGTGACAATCACCTGTCGGGCCTCCCAGTCTATCAGCTCCTACCTGAACTGGTATCAGCAGAAGCCA

GGCAAGGCCCCCAAGCTGCTGATCTACGCAGCATCTAGCCTGCAGTCTGGAGTGCCAAGCAGATTCAGCGGATC

CGGATTCGGCACAGACTTTACACTGACCATCTCCTCTCTGCAGCCCGAGGATTTCGCCACCTACTATTGCCAGCAG

TCTTATAGCACACCTCAGACCTTTGGCCAGGGCACCAAGGTGGACATCAAGGGAAGTGGAGGAGGAGGAAGTT

GTCCCTACTCAAACCCATCTCTGTGCTCAGGAGGAGGAGGAAGTGAACTGCCTACTCAGGGAACATTCAGCAAC

-continued

GTGTCCACCAATGTGAGCCCAGCAAAGCCTACCACAACCGCATGCCCATACTCTAACCCCAGCCTGTGCACAACC

ACACCAGCACCCAGGCCCCCTACCCCTGCACCAACAATCGCCTCCCAGCCTCTGTCTCTGCGGCCAGAGGCCTGC

AGACCCGCCGCCGGCGGAGCAGTGCACACACGGGGCCTGGACTTTGCCTGTGATATCTATATCTGGGCACCACT

GGCCGGAACATGTGGCGTGCTGCTGCTGTCACTGGTCATTACACTGTACTGTAAGCGAGGCCGGAAGAAACTGC

TGTATATTTTCAAACAGCCCTTTATGAGACCTGTGCAGACTACCLAGGAGGAAGACGGCTGCAGCTGTAGGTTCC

CCGAGGAAGAGGAAGGCGGGTGTGAGCTGAGGGTCAAGTTTAGCCGCTCCGCAGATGCCCCTGCTTACCAGCA

GGGGCAGAATCAGCTGTATAACGAGCTGAATCTGGGACGGAGAGAGGAATACGACGTGCTGGATAAAAGGCGC

GGGAGAGACCCCGAAATGGGAGGCAAGCCACGACGGAAAAACCCCCAGGAGGGCCTGTACAATGAACTGCAG

AAGGACAAAATGGCAGAGGCCTATAGTGAAATCGGGATGAAGGGAGAGAGAAGGCGCGGCAAAGGGCACGA

TGGCCTGTACCAGGGGCTGTCTACTGCCACCAAGGACACCTATGATGCTCTGCATATGCAGGCACTGCCTCCAAG

GTGATCTAGAGGGCCCGTTTAAACCCGCTGATCAGCCTCGACTGTGCCTTCTAGTTGCCAGCCATCTGTTGTTTGC

CCCTCCCCCGTGCCTTCCTTGACCCTGGAAGGTGCCACTCCCACTGTCCTTTCCTAATAAAATGAGGAAATTGCAT

CGCATTGTCTGAGTAGGTGTCATTCTATTCTGGGGGGTGGGGTGGGGCAGGACAGCAAGGGGGAGGATTGGG

AAGACAATAGCAGGCATGCTGGGGATGCGGTGGGCTCTATGACTAGTGGCGAATTCCCGTGTACCAGCTGAGAG

ACTCTAAATCCAGTGACAAGTCTGTCTGCCTATTCACCGATTTTGATTCTCAAACAAATGTGTCACAAAGTAAGGA

TTCTGATGTGTATATCACAGACAAAACTGTGCTAGACATGAGGTCTATGGACTTCAAGAGCAACAGTGCTGTGGC

CTGGAGCAACAAATCTGACTTTGCATGTGCAAACGCCTTCAACAACAGCATTATTCCAGAAGACACCTTCTTCCCC

AGCCCAGGTAAGGGCAGCTTTGGTGCCTTCGCAGGCTGTTTCCTTGCTTCAGGAA,
or (SEQ ID NO: 12)

AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

TCCGGTGAGGGCAGAGGAAGTCTTCTAACATGCGGTGACGTGGAGGAGAATCCGGGCCCCGGATCCGCTCTGC

CCGTCACCGCTCTGCTGCTGCCTCTGGCCCTGCTGCTGCACGCAGCCAGACCAGGCGGAGGAGGCTCCTGCCCT

TACTCTAACCCAAGCCTGTGCTCCGGAGGAGGAGGATCCGGCGGAGGAGGCTCTGAGGTGAAGCTGGTGGAG

AGCGGAGGAGGCCTGGTGCAGCCTGGCGGCTCCCTGTCTCTGAGCTGCGCAGCATCCGGCTTCACCTTTACAGA

CTACTATATGTCTTGGGTGAGACAGCCCCCTGGCAAGGCCCTGGAGTGGCTGGCCCTGATCAGGTCCAAGGCCG

ATGGCTACACCACAGAGTATTCCGCCTCTGTGAAGGGCAGATTCACCCTGTCTAGGGACGATAGCCAGTCCATCC

TGTACCTGCAGATGAATGCACTGCGCCCCGAGGACAGCGCCACATACTATTGTGCCAGAGACGCCGCCTACTATT

CTTACTATAGCCCTGAGGGCGCTATGGACTACTGGGGCCAGGGCACCTCCGTGACAGTGAGCTCCGGAGGAGG

AGGAAGCGGAGGAGGAGGCTCCGGCGGCGGCGGCTCTATGGCCGACTATAAGGATATCGTGATGACCCAGAGC

CACAAGTTTATGTCTACAAGCGTGGGCGACCGCGTGAACATCACCTGCAAGGCCAGCCAGAATGTGGATTCCGC

CGTGGCCTGGTACCAGCAGAAGCCTGGCCAGAGCCCTAAGGCCCTGATCTATTCCGCCTCTTACCGGTATAGCGG

AGTGCCTGACCGCTTCACCGGAAGGGGATCCGGAACAGACTTCACCCTGACAATCTCTAGCGTGCAGGCCGAG

GATCTGGCCGTGTACTATTGTCAGCAGTACTATAGCACCCCCTGGACCTTCGGCGGAGGAACCAAGCTGGAGATC

AAGAGAGGATCTGGAGGAGGAGGAAGCTGCCCATACTCCAACCCCTCTCTGTGCAGCGGAGGAGGAGGATCTG

AGCTGCCAACCCAGGGCACATTTTCCAACGTGTCTACAAATGTGAGCCCAGCAAAGCCAACCACAACCGCATGC

CCTTATAGCAATCCATCCCTGTGCACAACCACACCTGCACCAAGACCACCAACCCCAGCACCTACAATCGCCTCTC

AGCCACTGAGCCTGCGCCCCGAGGCATGCCGGCCTGCAGCAGGCGGCGCCGTGCACACCAGGGGCCTGGACT

TCGCCTGCGATATCTACATCTGGGCACCTCTGGCAGGAACCTGTGGCGTGCTGCTGCTGAGCCTGGTCATCACCC

-continued

```
TGTACTGCAAGAGAGGCAGGAAGAAGCTGCTGTATATCTTCAAGCAGCCCTTTATGCGCCCTGTGCAGACCACAC

AGGAGGAGGACGGCTGCAGCTGTCGGTTCCCAGAAGAGGAGGAGGGCGGCTGTGAGCTGAGAGTGAAGTTT

AGCAGGTCCGCCGATGCACCAGCATACCAGCAGGGACAGAACCAGCTGTATAACGAGCTGAATCTGGGCCGGA

GAGAGGAGTACGACGTGCTGGATAAGAGGAGGGGAAGGGACCCCGAGATGGGAGGCAAGCCACGGAGAAA

GAACCCCCAGGAGGGCCTGTACAATGAGCTGCAGAAGGACAAGATGGCCGAGGCCTATTCCGAGATCGGCATG

AAGGGAGAGAGGCGCCGGGGCAAGGGACACGATGGCCTGTACCAGGGCCTGTCTACCGCCACAAAGGACACC

TATGATGCCCTGCATATGCAGGCACTGCCTCCAAGGTGATCTAGAGGGCCCGTTTAAACCCGCTGATCAGCCTCG

ACTGTGCCTTCTAGTTGCCAGCCATCTGTTGTTTGCCCCTCCCCCGTGCCTTCCTTGACCCTGGAAGGTGCCACTC

CCACTGTCCTTTCCTAATAAAATGAGGAAATTGCATCGCATTGTCTGAGTAGGTGTCATTCTATTCTGGGGGGTGG

GGTGGGGCAGGACAGCAAGGGGGAGGATTGGGAAGACAATAGCAGGCATGCTGGGGATGCGGTGGGCTCTAT

GACTAGTGGCGAATTCCCGTGTACCAGCTGAGAGACTCTAAATCCAGTGACAAGTCTGTCTGCCTATTCACCGATT

TTGATTCTCAAACAAATGTGTCACAAAGTAAGGATTCTGATGTGTATATCACAGACAAAACTGTGCTAGACATGAG

GTCTATGGACTTCAAGAGCAACAGTGCTGTGGCCTGGAGCAACAAATCTGACTTTGCATGTGCAAACGCCTTCAA

CAACAGCATTATTCCAGAAGACACCTTCTTCCCCAGCCCAGGTAAGGGCAGCTTTGGTGCCTTCGCAGGCTGTTT

CCTTGCTTCAGGAA.
```

8. The TALEN-modified endogenous αβ-TCR negative human cell according to any one of embodiments 1 to 7, further comprising undetectable level of MHC molecules as compared to an unmodified control cell and a deletion functionally affecting cell surface expression of a beta 2 microglobulin molecule or of a CIITA molecule.

9. The TALEN-modified endogenous αβ-TCR negative human cell according to any one of embodiments 1 to 8, wherein said insertion resulted in an inactivation of the gene coding the TCR alpha and an undetectable cell surface expression of endogenous αβ-TCR in at least 96% of the total cells, in at least 97% of the total cells, in at least 98% of the total cells, in at least 99% of the total cells.

10. The TALEN-modified endogenous αβ-TCR negative human cell according to any one of embodiments 1 to 9, comprising:

a first half TALEN having a sequence having at least from 100%, 99%, 98%, 97%, 96%, 95% 94% 93% 92% 91% 90% 89% 88% 87% 86% 85% 84% 83% 82% 81% to 80% identity with SEQ ID NO: 3, provided that said first TALEN binding domain binds to ttgtcccacagATATC (SEQ ID NO: 36), and a second half TALEN having a sequence having at least from 100%, 99%, 98%, 97%, 96%, 95% 94% 93% 92% 91% 90% 89% 88% 87% 86% 85% 84% 83% 82% 81% to 80% identity with SEQ ID NO: 4, provided that said second half TALEN binds to CCGTGTACCAGCTGAGA (SEQ ID NO: 26) and the frequency of off target cleavage of said TALEN is below detection.

11. The TALEN-modified endogenous αβ-TCR negative human cell according to any one of embodiments 1 to 10, wherein said at least one insertion comprises an exogenous polynucleotide sequence located downstream a TALEN binding domain of sequence ttgtcccacagATATC (SEQ ID NO: 36), or ttgtcccacagATATCCAG (SEQ ID NO: 37), present in the wt TRAC.

12. The TALEN-modified endogenous αβ-TCR negative human cell according to any one of embodiments 1 to 11, wherein said at least one insertion comprises a sequence encoding a self-cleaving peptide in frame with the genomic TRAC coding sequence selected from a 2A peptide, a 2A like peptide, a P2A peptide, a E2A peptide, a F2A peptide, preferably a 2A peptide, more preferably a 2A peptide, of sequence GSGEGRGSLLTCGDVEENPGP (SEQ ID NO: 27), GSGATNFSLLKQAGDVEENPGP (SEQ ID NO: 28), GSGQCTNYALLKLAGDVESNPGP (SEQ ID NO: 29), GSGVKQTLNFDLLKLAGDVESNPGP (SEQ ID NO: 30), SGEGRGSLLTCGDVEENPGP (SEQ ID NO: 31), SGATNFSLLKQAGDVEENPGP (SEQ ID NO: 32), SGQCTNYALLKLAGDVESNPGP (SEQ ID NO: 33), SGVKQTLNFDLLKLAGDVESNPGP (SEQ ID NO: 34), even more preferably a 2A peptide of sequence SGEGRGSLLTCGDVEENPGP (SEQ ID NO: 35).

13. The TALEN-modified endogenous αβ-TCR negative human cell according to any one of embodiments 1 to 12, wherein said at least one insertion comprises a sequence coding a 2A peptide, of sequence SGEGRGSLLTCGD-VEENPGP (SEQ ID NO: 35) in frame with the genomic TRAC coding sequence, an exogenous polynucleotide sequence coding a chimeric antigen receptor, a terminator sequence of polyadenylation signal, optionally a TALEN binding domain.

14. The TALEN-modified endogenous αβ-TCR negative human cell according to any one of embodiments 1 to 13, wherein said exogenous polynucleotide sequence comprises a chimeric antigen receptor (CAR) selected from a CAR specific for at least one of the following antigen: Preferably CD22, CD123, CS-1, CLL-1, CD38, HSP70, MUC-1, CD30, o-acetyl-GD2nd a sequence SGEGRGSLLTCGD-VEENPGP (SEQ ID NO: 35) in frame with the genomic TRAC coding sequence, a terminator sequence of polyadenylation signal.

15. The TALEN-modified endogenous αβ-TCR negative human cell according to any one of embodiments 1 to 14 wherein said (CAR) comprises an extracellular ligand-binding domain, an epitope specific for a monoclonal antibody, a transmembrane domain and one or more intracellular signaling domains.

16. The TALEN-modified endogenous αβ-TCR negative human cell according to any one of embodiments 1 to 10, wherein said at least one insertion comprises an IRES, an exogenous polynucleotide sequence comprising a chimeric antigen receptor (CAR), a terminator sequence of polyade-nylation signal, optionally a TALEN binding domain.

17. The TALEN-modified endogenous αβ-TCR negative human cell according to any one of embodiments 1 to 15, wherein said chimeric antigen receptor (CAR), comprise at least one antigen specific for a monoclonal antibody, pref-erably two antigens specific for a monoclonal antibody.

18. The TALEN-modified endogenous αβ-TCR negative human cell according to any one of embodiments 1 to 12 wherein said exogenous polynucleotide comprises a tran-scription termination signal stopping the activity of RNA polymerase.

19. The TALEN-modified endogenous αβ-TCR negative human cell according to any one of embodiments 1 to 18 comprising at least one additional disruption in an endog-enous gene wherein said endogenous gene is selected from the group consisting CD52, dCK GR, beta subunit gene of the TCR (TCRB1 or TCRB2), a cytokine inducible SH2-containing (CISH) gene, an adenosine A2a receptor (ADORA) gene, a CD276 gene, a V-set domain containing T cell activation inhibitor 1 (VTCNI) gene, a B and T lymphocyte associated (BTLA) gene, a cytotoxic T-lympho-cyte-associated protein 4 (CTLA4) gene, an indoleamine 2,3-dioxygenase 1 (IDO I) gene, a killer cell immunoglobu-lin-like receptor, three domains, long cytoplasmic tail, 1 (KIR3DL1) gene, a lymphocyte-activation gene 3 (LAG3) gene, a programmed cell death 1 (PD-1) gene, an hepatitis A virus cellular receptor 2 (HAVCR2) gene, a V-domain immunoglobulin suppressor of T-cell activation (VISTA) gene, a natural killer cell receptor 284 (CD244) gene, a hypoxanthine phosphoribosyltransferase 1 (HPRT) gene, and chemokine (C-C motif) receptor 5 (gene/pseudogene) (CCR5) gene, CXCR4, a combination thereof.

20. A population of human cells comprising a TALEN-modified endogenous αβ-TCR negative human cell accord-ing to any one of embodiments 1 to 19.

21. A pharmaceutical composition comprising a TALEN-modified endogenous αβ-TCR negative human cell accord-ing to any one of embodiments 1 to 19 or a population of human cells according to embodiment 20 and a pharmaceu-tically acceptable excipient.

22. The TALEN-modified endogenous af-TCR negative human cell according to any one of embodiments 1 to 19 or the population of human cells according to embodiment 20 or the pharmaceutical composition according to embodi-ment 21 for use as a medicament.

23. The TALEN-modified endogenous ap-TCR negative human cell according to any one of embodiments 1 to 19 or the population of human cells according to embodiment 19 or the pharmaceutical composition according to embodi-ment 21 for use in the treatment of cancer.

24. The TALEN-modified endogenous αβ-TCR negative human cell according to any one of embodiments 1 to 19 or the population of human cells according to embodiments 20 or the pharmaceutical composition according to embodi-ments 21 for use in the treatment of a cancer selected from the group consisting of carcinoma, lymphoma, sarcoma, blastomas, and leukemia.

25. The TALEN-modified endogenous αβ-TCR negative human cell according to any one of embodiments 1 to 19 or the population of human cells according to embodiment 20 or the pharmaceutical composition according to embodi-ment 21 for use in the treatment of cancer wherein the cancer is selected from the group consisting of a cancer of B-cell origin, a cancer of T cell origin, breast cancer, gastric cancer, neuroblastoma, osteosarcoma, lung cancer, melanoma, pros-tate cancer, colon cancer, renal cell carcinoma, ovarian cancer, rhabdomyo sarcoma, leukemia, and Hodgkin's lym-phoma.

26. The TALEN-modified endogenous αβ-TCR negative human cell according to any one of embodiments 1 to 19 or the population of human cells according to embodiment 20 or the pharmaceutical composition according to embodi-ment 21 for use in the treatment of cancer wherein the cancer of B-cell origin is selected from the group consisting of B-lineage acute lymphoblastic leukemia, B-cell chronic lymphocytic leukemia, and B-cell non-Hodgkin's lym-phoma.

27. The TALEN-modified endogenous αβ-TCR negative human cell according to any one of embodiments 1 to 19 or the population of human cells according to embodiment 20 or the pharmaceutical composition according to embodi-ment 21 for use in the treatment of a cancer wherein the cancer is AML, ALL, a T cell lymphoma, CLL.

28. A means for detecting an endonuclease-modified endogenous αβ-TCR negative human cell, said endonu-clease-modified endogenous αβ-TCR negative human cell comprising an endonuclease modified genomic TRAC gene as compared to the wild type TRAC gene, wherein said modified human genomic TRAC gene comprises from 5' to 3':

(a) a 5' region of said human genomic TRAC gene upstream a recognition domain for a rare cutting endo-nuclease present in the wild type TRAC gene, (b) a gap or an insertion as compared to the wild type TRAC gene affecting the cell surface expression of the extracellular domain or transmembrane domain of the alpha beta TCR, said insertion comprising an exogenous polynucleotide selected from a noncoding sequence, a stop codon, a sequence coding for a self-cleaving peptide in frame with the TRAC open reading frame, an IRES, a sequence coding a chimeric antigen receptor (CAR), a sequence coding a TCR, a sequence coding a protein conferring sensitivity to a drug, a sequence coding a protein conferring resistance to a drug, a sequence coding for a cytokine, a termination sequence, a com-bination thereof, (c') optionally a second rare cutting endonuclease recog-nition domain, (d) a 3' region of the genomic TRAC gene.

29. The means according to embodiment 28 wherein said endonuclease is selected from the group consisting of: CRISPR/Cas 9, CRISPR/Cpf1, TALEN, transposase, ZEN, Zinc finger endonuclease, meganuclease, or MegaTAL and said means binds to a sequence of the endonuclease modi-fied TRAC, specific for said nuclease and/or upstream said sequence specific for said nuclease.

30. The means according to embodiments 28 or 29 wherein said endonuclease is a TALEN.

31. The means according to embodiment 30 for detecting a TALEN modified endogenous αβ-TCR negative human cell comprising a probe wherein said probe binds to a sequence in the modified genomic TRAC gene, upstream the endonuclease binding domain or endonuclease recognition domain, and/or to a sequence encoding a tag.

32. The MEANS according to embodiments 30 or 31 wherein said TALEN modified genomic TRAC gene com-prises, (a) a 5' region of said human genomic TRAC gene;

(b) a recognition domain for a (half?) TALEN, preferably a recognition domain for a (half?) TALEN comprising the following sequence ttgtcccacagATATC (SEQ ID
NO: 36), or ttgtcccacagATATCCAG (SEQ ID NO: 37),
or (c) a gap or an insertion as compared to the wild type
TRAC gene affecting the cell surface expression of the
extracellular domain or transmembrane domain of the
alpha beta TCR, said insertion comprising an exogenous polynucleotide
selected from a noncoding sequence, s stop codon, a
sequence coding for a self-cleaving peptide in frame
with the TRAC open reading frame, an IRES, a
sequence coding a chimeric antigen receptor (CAR), a
sequence coding a TCR, a sequence coding a protein
conferring sensitivity to a drug, a sequence coding a
protein conferring resistance to a drug, a termination
sequence, a combination thereof, (c') optionally a second (half?) TALEN recognition
domain.

(d) a 3' region of the genomic TRAC gene;
and said means binds specifically to said TALEN-modi-
fied genomic TRAC gene.

33. The means according to any one of embodiments 30
to 32 for detecting a TALEN modified endogenous αβ-TCR
negative human cell comprising a probe wherein said probe
binds to at least 10 bases of the sequence ttgtcccacagATATC
(SEQ ID NO: 36), or ttgtcccacagATATCCAG (SEQ ID NO:
37), in the modified genomic TRAC gene.

34. The means according to any one of embodiments 30
to 33 for detecting an endonuclease-modified endogenous
αβ-TCR negative human cell by polymerase chain reaction
(pcr) or potential off sites modifications, preferably by guide
sequence.

35. The means according to any one of embodiments 30
to 34 for detecting a TALEN-modified endogenous αβ-TCR
negative human cell according to any one of embodiments
1 to 19.

36. The TALEN-modified endogenous αβ-TCR negative
human cell according to any one of 1 to 15 comprising an
inactivated genomic TCRA gene wherein an exogenous
sequence coding a CAR was integrated into the genomic
TCRA gene using a lentiviral vector or a AAV vector and
said genomic disruptions were performed using an endonu-
clease selected from a CRISPR/CAS9, CRISPR/Cpf1 mega-
nuclease, MegaTAL, ZFN, TALEN, combination thereof.

37. A method for producing an endonuclease-modified
endogenous αβ-TCR negative human cell said method com-
prising:

(a) introducing into a human cell:
(i) a first nucleic acid sequence encoding an engineered
nuclease; or an engineered nuclease protein;
wherein said engineered nuclease produces a cleavage at
a recognition sequence within said human TCR alpha
constant region gene; said cleavage resulting in an
inhibition of cell surface expression of the αβ-TCR to
undetectable level.
(ii) a second nucleic acid sequence comprising an exog-
enous polynucleotide encoding a CAR,
(iii) optionally a probe,
wherein the sequence of said exogenous polynucleotide is
inserted into said genomic human TCR alpha constant
region gene at said cleavage site; and further wherein
said genetically-modified cell has reduced cell-surface
expression of the endogenous TCR when compared to
an unmodified control cell.

38. A method for producing an endonuclease-modified
endogenous αβ-TCR negative human cell according to
embodiment 37 said method comprising:

detecting endonuclease(s)-induced on site and off site,
preferably by pcr and/or by guide sequence.

39. The method of any one of embodiments 37 to 38,
wherein said engineered nuclease is a meganuclease, a
zinc-finger nuclease (ZFN), a transcription activator-like
effector nuclease (TALEN), a CRISPR/Cas nuclease, or a
megaTAL nuclease.

40. The method of embodiments 37 to 39, wherein said
engineered nuclease is a TALEN.

41. The method of embodiments 37 to 40, wherein said
exogenous polynucleotide comprises a nucleic acid
sequence encoding a self-cleaving peptide and a chimeric
antigen receptor.

42. The method of any one of embodiments 37 to 41
wherein said chimeric antigen receptor comprises an extra-
cellular ligand-binding domain and one or more intracellular
signaling domains.

43. The method of any one of embodiments 37 to 42,
wherein said exogenous polynucleotide comprises a pro-
moter sequence that drives expression of said exogenous
polynucleotide.

44. The method of any one of embodiments 37 to 43,
wherein at least said second nucleic acid se-quence is
introduced into said cell by contacting said cell with a
recombinant adeno-associated virus (AAV6) vector com-
prising said second nucleic acid sequence.

45. The method of any one of embodiments 39 to 44,
wherein said recombinant AAV vector is a self-complemen-
tary AAV vector.

46. The method of any one of embodiments 39 to 45,
wherein said recombinant AAV vector derived at least in part
from an AAV6.

47. The method of embodiments 39 to 46, wherein said
recombinant TALEN comprises a first subunit and a second
subunit, wherein said first subunit binds to a first recognition
half-site, and wherein said second subunit binds to a second
recognition half-site.

48. The method of embodiments 39 to 47, wherein said
recombinant TALEN recognizes a sequence ttgtcccacagA-
TATC (SEQ ID NO: 36) in the wild-type human TCR alpha
constant region.

49. The method of 37-39, wherein said endonuclease is a
Zing finger that recognizes from 5' to 3'
TGCTGTGGCCTGGAGCAAC (SEQ ID NO: 157) and
GACTTTGCATGTGCA (SEQ ID NO: 158) and cleaves
within AAATCT (aa 12-16 of SEQ ID NO: 36), a Crispr/Cas
9 that recognizes a complementary se-quence to any one of
the following sequences:

```
                                    (SEQ ID NO: 39)
    AGAGTCTCTCAGCTGGTACA, (SEQ ID NO: 40)
    GCACCAAAGCTGCCCTTACC, (SEQ ID NO: 41)
    AAGTTCCTGTGATGTCAAGC, (SEQ ID NO: 42)
    TTCGGAACCCAATCACTGAC, (SEQ ID NO: 43)
    GATTAAACCCGGCCACTTTC, (SEQ ID NO: 44)
    CGTCATGAGCAGATTAAACC, (SEQ ID NO: 45)
    CTCAAGGTTCAGATCAGAAG,
```

-continued (SEQ ID NO: 46)
TAGGCAGACAGACTTGTCAC, (SEQ ID NO: 47)
AACAAATGTGTCACAAAGTA, (SEQ ID NO: 48)
CACCAAAGCTGCCCTTACCT, (SEQ ID NO: 49)
CTGACAGGTTTTGAAAGTTT, (SEQ ID NO: 50)
TTCAAAACCTGTCAGTGATT, (SEQ ID NO: 51)
CCGAATCCTCCTCCTGAAAG, (SEQ ID NO: 52)
CCACTTTCAGGAGGAGGATT, (SEQ ID NO: 53)
TAAACCCGGCCACTTTCAGG, (SEQ ID NO: 54)
TCTCAAACAAATGTGTCACAAAGTA, (SEQ ID NO: 55)
CTTACAATCTTGCAGATCTGGAATG, (SEQ ID NO: 56)
TTAATCTGCTCATGACGCTG, (SEQ ID NO: 57)
GGAGAAGAGGGGCAATGCAG, (SEQ ID NO: 58)
TCTTCTCCCTCTCCAAACAG, (SEQ ID NO: 59)
AGCAGCTTTCACCTCCTTGG, (SEQ ID NO: 60)
GTAGCAGCTTTCACCTCCTT, (SEQ ID NO: 61)
AGTTGGTGGCATTGCCGGGG, (SEQ ID NO: 62)
TCTGTGATATACACATCAGAATC, (SEQ ID NO: 63)
TCTGTGATATACACATCAGAATCC, (SEQ ID NO: 64)
GAGTCTCTCAGCTGGTACACGGC, (SEQ ID NO: 65)
GAGTCTCTCAGCTGGTACACGGCA, (SEQ ID NO: 66)
ATTCTCAAACAAATGTGTCACAA, (SEQ ID NO: 67)
ATTCTCAAACAAATGTGTCACAAA, (SEQ ID NO: 68)
GTCTGTGATATACACATCAGAAT, (SEQ ID NO: 69)
GTCTGTGATATACACATCAGAATC, (SEQ ID NO: 70)
GAGAATCAAAATCGGTGAATAGG, (SEQ ID NO: 71)
TGTGCTAGACATGAGGTCTATGG, (SEQ ID NO: 72)
TCAGGGTTCTGGATATCTGTGGG, -continued (SEQ ID NO: 73)
GTCAGGGTTCTGGATATCTGTGG, (SEQ ID NO: 74)
AAAGTCAGATTTGTTGCTCCAGG, (SEQ ID NO: 75)
AACAAATGTGTCACAAAGTAAGG, (SEQ ID NO: 76)
TGGATTTAGAGTCTCTCAGCTGG, (SEQ ID NO: 77)
TAGGCAGACAGACTTGTCACTGG, (SEQ ID NO: 78)
AGCTGGTACACGGCAGGGTCAGG, (SEQ ID NO: 79)
GCTGGTACACGGCAGGGTCAGGG, (SEQ ID NO: 80)
TCTCTCAGCTGGTACACGGCAGG, (SEQ ID NO: 81)
AGAGTCTCTCAGCTGGTACACGG, (SEQ ID NO: 82)
CTCTCAGCTGGTACACGGCAGGG, (SEQ ID NO: 83)
ACAAAACTGTGCTAGACATGAGG, (SEQ ID NO: 84)
ATTTGTTTGAGAATCAAAATCGG, (SEQ ID NO: 85)
TGGAATAATGCTGTTGTTGAAGG, (SEQ ID NO: 86)
AGAGCAACAGTGCTGTGGCCTGG, (SEQ ID NO: 87)
CTTCTTCCCCAGCCCAGGTAAGG, (SEQ ID NO: 88)
ACACGGCAGGGTCAGGGTTCTGG, (SEQ ID NO: 89)
CTTCAAGAGCAACAGTGCTGTGG, (SEQ ID NO: 90)
CTGGGGAAGAAGGTGTCTTCTGG, (SEQ ID NO: 91)
TTCTTCCCCAGCCCAGGTAAGGG, (SEQ ID NO: 92)
CTTACCTGGGCTGGGGAAGAAGG, (SEQ ID NO: 93)
GACACCTTCTTCCCCAGCCCAGG, (SEQ ID NO: 94)
TTCAAAACCTGTCAGTGATTGGG, (SEQ ID NO: 95)
CGTCATGAGCAGATTAAACCCGG, (SEQ ID NO: 96)
TTCGGAACCCAATCACTGACAGG, (SEQ ID NO: 97)
TAAACCCGGCCACTTTCAGGAGG, (SEQ ID NO: 98)
TTTCAAAACCTGTCAGTGATTGG, (SEQ ID NO: 99)
GATTAAACCCGGCCACTTTCAGG, -continued

```
                              (SEQ ID NO: 100)
CTCGACCAGCTTGACATCACAGG, (SEQ ID NO: 101)
AAGTTCCTGTGATGTCAAGCTGG, (SEQ ID NO: 102)
ATCCTCCTCCTGAAAGTGGCCGG, (SEQ ID NO: 103)
TGCTCATGACGCTGCGGCTGTGG, (SEQ ID NO: 104)
CATCACAGGAACTTTCTAAAAGG, (SEQ ID NO: 105)
GTCGAGAAAAGCTTTGAAACAGG, (SEQ ID NO: 106)
CCACTTTCAGGAGGAGGATTCGG, (SEQ ID NO: 107)
CTGACAGGTTTTGAAAGTTTAGG, (SEQ ID NO: 108)
AGCTTTGAAACAGGTAAGACAGG, (SEQ ID NO: 109)
CTGTGGTCCAGCTGAGGTGAGGG, (SEQ ID NO: 110)
CTGCGGCTGTGGTCCAGCTGAGG, (SEQ ID NO: 111)
TGTGGTCCAGCTGAGGTGAGGGG, (SEQ ID NO: 112)
TCCTCCTCCTGAAAGTGGCCGGG, (SEQ ID NO: 113)
TTAATCTGCTCATGACGCTGCGG, (SEQ ID NO: 114)
ACCCGGCCACTTTCAGGAGGAGG, (SEQ ID NO: 115)
GCTGTGGTCCAGCTGAGGTGAGG, (SEQ ID NO: 116)
CCGAATCCTCCTCCTGAAAGTGG.
``` a MegaTAL, a meganuclease that recognizes and cleaves a recognition sequence within residues 93-208 of the wild-type human TCR alpha constant region, wherein said recombinant meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region.

50. The method of embodiment 49, wherein said meganuclease is a single-chain meganuclease comprising a linker, wherein said linker covalently joins said first subunit and said second subunit.

51. A means for detecting cells obtained according to any of one the method of embodiments 37-50.

52. The means of embodiment 51 selected from a sequence of SEQ ID NO: 5, SEQ ID NO: 6, SEQ ID NO: 7, a combination thereof or any degenerated SEQ ID NO: 5, SEQ ID NO: 6, SEQ ID NO: 7, a combination thereof.

53. The means of embodiment 51 for detecting on site and/or off site cleavage by endonuclease.

54. The means of embodiment 53 for detecting on site and/or off site cleavage by endonuclease having any one of SEQ ID N° 13 to 22, a combination thereof.

The means of embodiment 53 for detecting on site and/or off site cleavage by a TALEN comprising a sequence selected from any one GAGAATCAAAATCGGT-GAATAGG (SEQ ID NO: 70), TTCAAAACCTGTCAGT-GATTGGG (SEQ ID NO: 94), TGTGCTAGACAT-GAGGTCTATGG (SEQ ID NO: 71), CGTCATGAGCAGATTAAACCCGG (SEQ ID NO: 95), TCAGGGTTCTGGATATCTGTGGG (SEQ ID NO: 72), GTCAGGGTTCTGGATATCTGTGG (SEQ ID NO: 73), TTCGGAACCCAATCACTGACAGG (SEQ ID NO: 96), TAAACCCGGCCACTTTCAGGAGG (SEQ ID NO: 97), AAAGTCAGATTTGTTGCTCCAGG (SEQ ID NO: 74), AACAAATGTGTCACAAAGTAAGG (SEQ ID NO: 75), TGGATTTAGAGTCTCTCAGCTGG (SEQ ID NO: 76), TAGGCAGACAGACTTGTCACTGG (SEQ ID NO: 77), AGCTGGTACACGGCAGGGTCAGG (SEQ ID NO: 78), GCTGGTACACGGCAGGGTCAGGG (SEQ ID NO: 79), TCTCTCAGCTGGTACACGGCAGG (SEQ ID NO: 80), TTTCAAAACCTGTCAGTGATTGG (SEQ ID NO: 98), GATTAAACCCGGCCACTTTCAGG (SEQ ID NO: 99), CTCGACCAGCTTGACATCACAGG (SEQ ID NO: 100), AGAGTCTCTCAGCTGGTACACGG (SEQ ID NO: 81), CTCTCAGCTGGTACACGGCAGGG (SEQ ID NO: 82), AAGTTCCTGTGATGTCAAGCTGG (SEQ ID NO: 101), ATCCTCCTCCTGAAAGTGGCCGG (SEQ ID NO: 102), TGCTCATGACGCTGCGGCTGTGG (SEQ ID NO: 103), ACAAAACTGTGCTAGACATGAGG (SEQ ID NO: 83), ATTTGTTTGAGAATCAAAATCGG (SEQ ID NO: 84), CATCACAGGAACTTTCTAAAAGG (SEQ ID NO: 104), GTCGAGAAAAGCTTTGAAACAGG (SEQ ID NO: 105), CCACTTTCAGGAGGAGGATTCGG (SEQ ID NO: 106), CTGACAGGTTTTGAAAGTTTAGG (SEQ ID NO: 107), AGCTTTGAAACAGGTAAGACAGG (SEQ ID NO: 108), TGGAATAATGCTGTTGTTGAAGG (SEQ ID NO: 85), AGAGCAACAGTGCTGTGGCCTGG (SEQ ID NO: 86), CTGTGGTCCAGCTGAGGTGAGGG (SEQ ID NO: 109), CTGCGGCTGTGGTCCAGCTGAGG (SEQ ID NO: 110), TGTGGTCCAGCTGAGGTGAGGGG (SEQ ID NO: 111), CTTCTTCCCCAGCCCAGGTAAGG (SEQ ID NO: 87), ACACGGCAGGGTCAGGGTiCTGG (SEQ ID NO: 88), CTTCAAGAGCAACAGTGCTGTGG (SEQ ID NO: 89), CTGGGGAAGAAGGTGTCTTCTGG (SEQ ID NO: 90), TCCTCCTCCTGAAAGTGGCCGGG (SEQ ID NO: 112), TTAATCTGCTCATGACGCTGCGG (SEQ ID NO: 113), ACCCGGCCACTTTCAGGAGGAGG (SEQ ID NO: 114), TTCTTCCCCAGCCCAGGTAAGGG (SEQ ID NO: 91), CTTACCTGGGCTGGGGAAGAAGG (SEQ ID NO: 92), GACACCTTCTTCCCCAGCCCAGG (SEQ ID NO: 93), GCTGTGGTCCAGCTGAGGTGAGG (SEQ ID NO: 115), CCGAATCCTCCTCCTGAAAGTGG (SEQ ID NO: 116), a complementary sequence thereof; said mean may be associated for example for a mean binding to the CAR sequence of peptide 2A sequence, and allowing a PCR according to the present invention.

55. A means comprising a sequence comprising at least one of the following sequences: AGAGTCTCTCAGCTGGTACA (SEQ ID NO: 39), GCACCAAAGCTGCCCTTACC (SEQ ID NO: 40), AAGTTCCTGTGATGTCAAGC (SEQ ID NO: 41), TTCG-GAACCCAATCACTGAC (SEQ ID NO: 42), GAT-TAAACCCGGCCACTTTC (SEQ ID NO: 43), CGTCAT-GAGCAGATTAAACC (SEQ ID NO: 44), CTCAAGGTTCAGATCAGAAG (SEQ ID NO: 45), TAGGCAGACAGACTTGTCAC (SEQ ID NO: 46), AACAAATGTGTCACAAAGTA (SEQ ID NO: 47), CAC-CAAAGCTGCCCTTACCT (SEQ ID NO: 48), CTGACAGGTTTTGAAAGTIT (SEQ ID NO: 49), TTCAAAACCTGTCAGTGATT (SEQ ID NO: 50), CCGAATCCTCCTCCTGAAAG (SEQ ID NO: 51), CCACTTTCAGGAGGAGGATT (SEQ ID NO: 52), TAAACCCGGCCACTTTCAGG (SEQ ID NO: 53), TCT-CAAACAAATGTGTCACAAAGTA (SEQ ID NO: 54), CTTACAATCTTGCAGATCTGGAATG (SEQ ID NO: 55), TTAATCTGCTCATGACGCTG (SEQ ID NO: 56), GGA-GAAGAGGGGCAATGCAG (SEQ ID NO: 57), TCTTCTCCCTCTCCAAACAG (SEQ ID NO: 58), AG-CAGCTTTCACCTCCTTGG (SEQ ID NO: 59), GTAGCAGCTTTCACCTCCTT (SEQ ID NO: 60), AGTTGGTGG-CATTGCCGGGG (SEQ ID NO: 61), TCTGTGATATACACATCAGAATC (SEQ ID NO: 62), TCTGTGA-TATACACATCAGAATCC (SEQ ID NO: 63), GAGTCTCTCAGCTGGTACACGGC (SEQ ID NO: 64), GAG-TCTCTCAGCTGGTACACGGCA (SEQ ID NO: 65), ATTCTCAAACAAATGTGTCACAA (SEQ ID NO: 66), ATTCTCAAACAAATGTGTCACAAA (SEQ ID NO: 67), GTCTGTGATATACACATCAGAAT (SEQ ID NO: 68), GTCTGTGATATACACATCAGAATC (SEQ ID NO: 69), GAGAATCAAAATCGGTGAATAGG (SEQ ID NO: 70), TGTGCTAGACATGAGGTCTATGG (SEQ ID NO: 71), TCAGGGTTCTGGATATCTGTGGG (SEQ ID NO: 72), GTCAGGGTTCTGGATATCTGTGG (SEQ ID NO: 73), AAAGTCAGATTTGTTGCTCCAGG (SEQ ID NO: 74), AACAAATGTGTCACAAAGTAAGG (SEQ ID NO: 75), TGGATTTAGAGTCTCTCAGCTGG (SEQ ID NO: 76), TAGGCAGACAGACTTGTCACTGG (SEQ ID NO: 77), AGCTGGTACACGGCAGGGTCAGG (SEQ ID NO: 78), GCTGGTACACGGCAGGGTCAGGG (SEQ ID NO: 79), TCTCTCAGCTGGTACACGGCAGG (SEQ ID NO: 80), AGAGTCTCTCAGCTGGTACACGG (SEQ ID NO: 81), CTCTCAGCTGGTACACGGGAGGG (SEQ ID NO: 82), ACAAAACTGTGCTAGACATGAGG (SEQ ID NO: 83), ATTTGTTTGAGAATCAAAATCGG (SEQ ID NO: 84), TGGAATAATGCTGTTGTTGAAGG (SEQ ID NO: 85), AGAGCAACAGTGCTGTGGCCTGG (SEQ ID NO: 86), CTTCTTCCCCAGCCCAGGTAAGG (SEQ ID NO: 87), ACACGGCAGGGTCAGGGTTCTGG (SEQ ID NO: 88), CTTCAAGAGCAACAGTGCTGTGG (SEQ ID NO: 89), CTGGGGAGGAAGGTGTCTTCTGG (SEQ ID NO: 90), TTCTTCCCCAGCCCAGGTAAGGG (SEQ ID NO: 91), CTTACCTGGGCTGGGGAAGAAGG (SEQ ID NO: 92), GACACCTTCTTCCCCAGCCCAGG (SEQ ID NO: 93), TTCAAAACCTGTCAGTGATTGGG (SEQ ID NO: 94), CGTCATGAGCAGATTAAACCCGG (SEQ ID NO: 95), TTCGGAACCCAATCACTGACAGG (SEQ ID NO: 96), TAAACCCGGCCACTTTCAGGAGG (SEQ ID NO: 97), TTTCAAAACCTGTCAGTGATTGG (SEQ ID NO: 98), GATTAAACCCGGCCACTTTCAGG (SEQ ID NO: 99), CTCGACCAGCTTGACATCACAGG (SEQ ID NO: 100), AAGTTCCTGTGATGTCAAGCTGG (SEQ ID NO: 101), ATCCTCCTCCTGAAAGTGGCCGG (SEQ ID NO: 102), TGCTCATGACGCTGCGGCTGTGG (SEQ ID NO: 103), CATCACAGGAACTTTCTAAAAGG (SEQ ID NO: 104), GTCGAGAAAAGCTTTGAAACAGG (SEQ ID NO: 105), CCACTTTCAGGAGGAGGATTCGG (SEQ ID NO: 106), CTGACAGGTTTTGAAAGTTTAGG (SEQ ID NO: 107), AGCTTTGAAACAGGTAAGACAGG (SEQ ID NO: 108), CTGTGGTCCAGCTGAGGTGAGGG (SEQ ID NO: 109), CTGCGGCTGTGGTCCAGCTGAGG (SEQ ID NO: 110), TGTGGTCCAGCTGAGGTGAGGGG (SEQ ID NO: 111), TCCTCCTCCTGAAGTGGCCGGGG (SEQ ID NO: 112), TTAATCTGCTCATGACGCTGCGG (SEQ ID NO: 113), ACCCGGCCACTTTCAGGAGGAGG (SEQ ID NO: 114), GCTGTGGTCCAGCTGAGGTGAGG (SEQ ID NO: 115), CCGAATCCTCCTCCTGAAAGTGG (SEQ ID NO: 116) and complementary sequence of any one thereof.

56. The present invention also provides a Method for preparing engineered primary immune cells for cell immunotherapy, said method comprising:

providing a population of primary CAR positive (CAR+) TCR negative (TCR−) immune cells as above (comprising within the endogenous TCR alpha gene an insertion encoding any one of the CAR described herein), introducing into said CAR+TCR− primary immune cells:

At least one nucleic acid comprising an exogenous nucleotide or polynucleotide sequence to be integrated at an endogenous locus to encode at least one molecule improving the therapeutic potential of said immune cells population;

At least one sequence-specific reagent that specifically targets said selected endogenous locus, wherein said exogenous nucleotide or polynucleotide sequence is inserted by targeted gene integration into said endogenous locus, so that said exogenous nucleotide or polynucleotide sequence forms an exogenous coding sequence under transcriptional control of an endogenous promoter present at said locus.

57. In the Method according to item 1, said sequence specific reagent is a nuclease, preferably an endonuclease selected from the group consisting of: Crispr/Cas 9, TALEN, Zinc finger endonuclease, meganuclease, MegaTAL, a combination thereof.

58. Accordingly, the Method according to item 1 or 2, wherein said targeted gene integration is operated by homologous recombination or NHEJ into said CAR+TCR− primary immune cells.

59. The present invention provides a Method according to any one of items 1 to 3, wherein said endogenous promoter is selected to be active during CAR+TCR− primary immune cells activation.

60. The present invention provides a Method according to any one of items 1 to 4, wherein said molecule encoded by said exogenous coding sequence is a RNA transcript, such as a RNAi, or a polypeptide, such as a functional protein.

61. The present invention provides a Method according to any one of items 1 to 5, wherein said molecule improving the therapeutic potential activity or said population of CAR+ TCR− primary immune cells, confers resistance of the CAR+TCR− immune cells to a drug, increases persistence of the CAR+TCR− immune cells (in-vivo or in-vitro) or its safety.

62. The present invention provides a Method according to item 6, wherein said molecule enhancing the persistence of the CAR+TCR− primary immune cells is selected from a cytokine receptor, a protein conferring resistance to a drug or a secreted antibody directed against inhibitory peptides or proteins.

63. The present invention provides a Method according to any one of item 1 to 6, wherein said exogenous coding sequence encodes an IL-2, IL-12 or IL-15 receptor.

64. The present invention provides a Method according to any one of items 1 to 6, wherein said exogenous coding sequence conferring drug resistance encodes dihydrofolate reductase (DHFR), inosine monophosphate dehydrogenase 2 (IMPDH2), calcineurin or methylguanine transferase (MGMT), mTORmut and Lckmut.

65. The present invention provides a Method according to any one of items 1 to 6, wherein said exogenous sequence encodes a chemokine or a cytokine, such as IL-2, IL-12 and IL-15.

66. The present invention provides a Method according any one of items 1 to 6, wherein said exogenous sequence enhancing the therapeutic activity encodes an inhibitor of FOXP3.

67. The present invention provides a Method according to any one of items 1 to 6, wherein said exogenous sequence enhancing the therapeutic activity of the CAR+TCR− primary T-cell encodes a secreted inhibitor of Tumor Associated Macrophages (TAM), such as a CCR2/CCL2 neutralization agent.

68. The present invention provides a Method according to any one of items 1 to 6, wherein said exogenous sequence enhancing the safety of the CAR+TCR− primary immune cell encodes a component of a chimeric antigen receptor (CAR).

69. The present invention provides a Method according to item 13, wherein said CAR is an inhibitory CAR that contributes to an improved specificity of the CAR+TCR-immune cell against a given cell type.

70. The present invention provides a Method according to any one of items 1 to 6, wherein said exogenous sequence enhancing the safety of the CAR+TCR− primary immune cell encodes a factor that has the capability to kill the cell, directly, in combination with, or by activating other compound(s).

71. The present invention provides a Method according to any one of items 1 to 6, wherein said exogenous sequence enhancing the safety of the CAR+TCR− primary immune cell encodes a component of an apoptosis CAR.

72. The present invention provides a Method according to item 16, wherein said apoptosis CAR comprises FasL (CD95).

73. The present invention provides a Method according to any one of items 1 to 6, wherein said exogenous sequence enhancing the safety of the CAR+TCR− primary immune cell encodes cytochrome(s) P450, CYP2D6-1, CYP2D6-2, CYP2C9, CYP3A4, CYP2C19 or CYP1A2, conferring hypersensitivity of said immune cells to a drug, such as cyclophosphamide and/or isophosphamide.

The present invention provides a Method according to any one of items 1 to 6, wherein said exogenous sequence enhancing the safety of the CAR+TCR− primary immune cell encodes cytochrome(s) P450, CYP2D6-1, CYP2D6-2, CYP2C9, CYP3A4, CYP2C19 or CYP1A2, conferring hypersensitivity of said immune cells to a drug, such as cyclophosphamide and/or isophosphamide combined to the drug to which said cell is hypersensitive.

74. The present invention provides a Method according to any one of items 1 to 18, wherein said gene is under transcriptional control of an endogenous promoter that is constantly active during CAR+TCR-immune cell activation.

75. The present invention provides a Method according to item 19, wherein said gene is selected from CD3G, Rn28s1, Rn18s, Rn7sk, Actg1, B2m, Rpl18a, Pabpc1, Gapdh, Rpl17, Rpl19, Rplp0, Cfl1 and Pfn1.

76. The present invention provides a Method according to item 19, wherein the transcriptional activity of said endogenous promoter is stable and independent from immune cell activation.

77. The present invention provides a Method according to item 21, wherein said gene under control of said endogenous promoter stable and independent from CAR+TCR-immune cell activation is CD3.

78. The present invention provides a Method according to item 22, wherein said sequence introduced into said gene encodes a TCR binding domain, optionally in fusion with a polypeptide CD3, CD28 or 4-1BB.

79. The present invention provides a Method according to item 21, wherein said coding sequence introduced into said gene under control of said endogenous promoter with an activity that is stable and independent from CAR+TCR-immune cell activation, encodes a cytokine, a chemokine receptor, a molecule conferring resistance to a product, a co-stimulation ligand, such as 4-1BRL and OX40L, or a secreted antibody.

80. The present invention provides a Method according to any one of items 1 to 18, wherein the transcriptional activity of said endogenous promoter is dependent from immune cell activation.

81. The present invention provides a Method according to item 25, wherein said transcriptional activity of said endogenous promoter is transient upon CAR+TCR-immune cell activation.

82. The present invention provides a Method according to item 25, wherein said transcriptional activity of said endogenous promoter is up-regulated.

83. The present invention provides a Method according to item 27, wherein said transcriptional activity is strongly up-regulated.

84. The present invention provides a Method according to item 28, wherein said exogenous sequence introduced into said gene whose transcriptional activity is up regulated more particularly encodes cytokine(s), immunogenic peptide(s) or a secreted antibody, such as an anti-IDO1, anti-IL10, anti-PD1, anti-PDL1, anti-IL6 or anti-PGE2 antibody.

85. The present invention provides a Method according to item 27, wherein said transcriptional activity is weakly up-regulated.

86. The present invention provides a Method according to item 30, wherein said sequence introduced into said gene whose transcriptional activity is transient up regulated more particularly encodes a constituent of an inhibitory CAR or an apoptotic CAR, to improve the specificity of the safety of said immune cells.

87. The present invention provides a Method according to item 26, wherein said promoter is up-regulated over less than 12 hours upon immune cell activation.

Up regulated means that the gene expression is increased by at least a factor 2 as compared to a non activated T cellls 88. The present invention provides a Method according to item 32, wherein said gene is selected from Spata6, Itga6, Rcbtb2, Cd1d1, St8sia4, Itgae and Fam214a.

89. The present invention provides a Method according to item 26, wherein said promoter is up-regulated over less than 24 hours upon immune cell activation.

90. The present invention provides a Method according to item 34, wherein said gene is selected from IL3, IL2, Ccl4, IL21, Gp49a, Nr4a3, Lilrb4, Cd200, Cdkn1a, Gzmc, Nr4a2, Cish, Ccr8, Lad1 and Crabp2.

91. The present invention provides a Method according to item 26, wherein said gene is up-regulated over more than 24 hours upon CAR+TCR-immune cell activation.

92. he present invention provides a Method according to item 36, wherein said gene is selected from Gzmb, Tbx21, Plek, Chek1, Slamf7, Zbtb32, Tigit, Lag3, Gzma, Wee1, IL12rb2, Eea1 and Dtl.

93. The present invention provides a Method according to any one of items 1 to 37, wherein a modified TCR is being independently expressed in the transfected immune cells.

94. The present invention provides a Method according to item 42, wherein said CAR is directed against a CD22 antigen.

95. The present invention provides a Method according to item 38 or item39, wherein said endogenous promoter activity is dependent on said CAR expressed into the transfected immune cells.

96. The present invention provides a Method according to any one of items 1 to 40, wherein said specific endonuclease reagent is selected from a RNA of DNA-guided endonuclease, such as Cas9 or Cpf1, a RNA or DNA guide, a TAL-endonuclease, a zing finger nuclease, a homing endonuclease or any combination thereof.

97. The present invention provides a Method according to any one of items 1 to 41, wherein said specific endonuclease reagent is introduced by electroporation as a polypeptide or under a mRNA, which is translated into the cell.

98. The present invention provides a Method according to item 42, wherein said exogenous nucleic acid comprising said coding sequence is included in a DNA vector.

99. The present invention provides a Method according to item 43, wherein said DNA vector is a viral vector such as an AAV vector.

100. The present invention provides a Method according to item 43, wherein the nucleic acid encoding said sequence-specific endonuclease reagent and said exogenous nucleic acid are both included into said DNA vector.

101. The present invention provides a Method according to any one of items 1 to 45, wherein the gene sequence that is introduced into the CAR+TCR-immune cell is preceded or followed by a sequence encoding a 2A peptide to enable the transcription of said gene sequence along with at least one part of the endogenous gene.

102. The present invention provides a Method according to any one of items 1 to 46, wherein the gene sequence is introduced with the effect of inactivating the expression of at least one endogenous genomic sequence initially present in said gene.

103. The present invention provides a Method according to any one of items 1 to 47, wherein said endogenous promoter does not control the transcriptional activity of a TCR gene.

104. The present invention provides a Method according to item 47, wherein said endogenous genomic sequence that is being inactivated encodes suppressive cytokines, kinases or their receptors thereof, such as TGFb, TGFbR, IL-10, IL-10R, GCN2 or PRDM1.

105. The present invention provides a Method according to item 49, wherein said endogenous genomic sequence that is being inactivated encodes a protein acting as an immune checkpoint, such as PD1, PDL1, CTLA4, TIM3 or LAG3.

106. The present invention provides a Method according to item 47, wherein said endogenous genomic sequence that is being inactivated expresses an enzyme that activates a prodrug, such as DCK, HPRT or GGH.

The present invention provides a Method according to item 47, wherein said endogenous genomic sequence that is being inactivated is CD25, CD95 or PD1.

107. The present invention provides a Method according to item 47, wherein said endogenous genomic sequence that is being inactivated expresses a receptor to immune depletion treatments, such a Glucocorticoid receptors and CD52.

108. The present invention provides a Method according to item 47, wherein said endogenous genomic sequence that is being inactivated expresses a surface antigen which has an affinity with a CAR expressed by said CAR+TCR-immune cell or another CAR+TCR-immune cell from said population of immune cells.

109. The present invention provides a Method according to any one of items 1 to 53, wherein said CAR+TCR-immune cell is a hematopoietic stem cell HSC.

110. The present invention provides a Method according to any one of items 1 to 53, wherein said immune cell is a CAR+TCR-T-cell or CAR+TCR-NKT cell.

111. The present invention provides an engineered primary immune cell obtainable by the method of any of items 1 to 55.

112. The present invention provides an engineered primary immune CAR+TCR- cell, which comprises an exogenous coding sequence under transcriptional control of an endogenous gene promoter.

113. The present invention provides an engineered primary immune CAR+TCR- cell according to item59 or 60, wherein said endogenous gene promoter is active during the activation of said immune cell.

114. The present invention provides An engineered primary immune CAR+TCR- cell according to any one items 59 to 61, wherein said endogenous gene promoter is responsive to the activation of said immune cell, preferably upregulated.

115. The present invention provides an engineered primary immune CAR+TCR- cell according to any one items 59 to 62, wherein said endogenous gene is selected among those listed herein below.

116. The present invention provides an engineered primary immune cell according to any one items 59 to 63, wherein said primary immune cell is a T-cell or a NKT-cell.

117. The present invention provides an engineered primary immune CAR+TCR- cell according to any one items 59 to 64, wherein said primary cell is endowed with a second chimeric antigen receptor 118. The present invention provides an engineered primary immune CAR+TCR- cell according to item 65, wherein said transcriptional control of said endogenous gene is responsive to the signal activation of said chimeric antigen receptor (CAR).

119. The present invention provides a therapeutically effective population of primary immune cells, comprising at least 30%, preferably 50%, more preferably 80% of cells according to any one of items 59 to 66.

120. The present invention provides a population of primary immune cells according to item64, wherein at least 30%, preferably 50%, more preferably 80% of cells originate from a donor, preferably one single donor.

121. The present invention provides a population of primary immune CAR+TCR- cells according to item64, wherein more than 50% of said immune cells are TCR negative CAR positive T-cells.

122. The present invention provides a population of primary immune CAR+TCR- cells according to any one of items 64 to 66, wherein more than 50% of said immune cells are CAR positive and TCR negative cells and comprise another inactivated gene comprising a coding sequence, preferably a coding sequence coding for IL-7, IL-12, IL-15, IL-21 or il-IL-27.

123. The present invention provides a pharmaceutical composition comprising an engineered primary immune CAR+TCR- cell or immune CAR+TCR- cell population according to any one of the above items 56 to 67.

124. The present invention provides a method for treating a patient in need thereof, wherein said method comprises:
preparing a population of TCR-CAR-engineered primary immune CAR+TCR- cells according to any one of items 56 to 67;
optionally, purifying or sorting said engineered primary immune CAR+TCR- cells;

activating said population of engineered primary immune CAR+TCR− cells upon or after infusion of said cells into said patient.

125. The present invention provides a method according to item 69, wherein said patient is treated for cancer.

126. The present invention provides a method according to item 69, wherein said patient is treated for an infection.

In particular embodiments, said engineered primary human cells of the invention temporarily expressed a TALEN specific for at least one genomic sequence that introduced a genetic modification into the TRAC gene and/or into another genomic sequence. Preferably human cells temporarily expressed a TALEN specific for the TRAC gene and/or an endonuclease such as a TALEN, a CRISPR/CAS9, meganuclease, Zn Finger nuclease, specific for in another genomic sequence. More preferably, human cells temporarily expressed a TALEN specific for the sequence (SEQ ID NO: 38)
TTGTCCCACAGATATCCagaaccctgaccctgCCGTGTACCAGCTGAGA
GA of the TRAC gene and/or another TALEN specific for another genomic sequence selected from a genomic sequence coding a T cell antigen such as CD38, CS-1, CLL-1, CD70, a genomic sequence coding a molecule (or immune checkpoint) selected from CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF108, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, SERCA3, IL27RA, STAT1, STAT3, ILT2 ILT4, SEMA7A, SHARPIN, STAT1, PEA15, RICTOR, JAK2, AURKA, DNMT3, miRNA31, MT1A, MT2A, PTGER2, a gene generating a miR101, mir26A, mir21.

PD1, PDL1, CTLA-4, TIM3, LAG3, TNFα or IFNγ may be preferred gene(s) engineered into the cells of the present invention.

Immune checkpoints are molecules that either turn up a signal (co-stimulatory molecules) or turn down a signal, said signal is involved in the functioning of immune cells, in particular the functioning of immune cells against cancer cells or against the connective tissue in solid cancer.

In particular embodiments, the human cell of the present invention may be a human cell line, a primary human cell line, a primary human cell line means derived from one human primary cell or from a homogenous population of human primary cells.

In general, the human cell of the present invention or the population of human cells of the present invention for used in immunotherapy comprises no or undetectable off target cleavage(s) in the genome.

In particular embodiments, off sites may be determined using an adapted GUIDE-Seq analysis for each of the TALEN moiety and/or for TALEN used to engineered human cells.

In particular embodiments, off sites may be determined using an adapted GUIDE-Seq analysis for each of the TALEN moiety and/or for TALEN used to engineered human cells and compared to off targets induced by another endonuclease.

In particular embodiments, off sites may be determined using an adapted GUIDE-Seq analysis for meganuclease(s) used to engineered human cells.

In particular embodiments, off sites may be determined using an adapted GUIDE-Seq analysis for megaTAL used to engineered human cells.

In particular embodiments, off sites may be determined using an adapted GUIDE-Seq analysis for Zn Finger(s) used to engineered human cells.

In particular embodiments, off sites may be determined using an adapted GUIDE-Seq analysis for Crispr/cas 9 used to engineered human cells.

Off target sites determination may be as determined for example using guide-seq analysis as described and adapted to TALEN (as in cellectis.com/uploads/files/ASGCT_2017.pdf).

Guide-sequence (or guide-seq) analysis was first described in GUIDE-sequences enables genome-wide profiling of off-target cleavage by CRISPR-Cas nucleases.

Tsai S Q, Zheng Z, Nguyen N T, Liebers M, Topkar V V, Thapar V, Wyvekens N, Khayter C, lafrate A J, Le L P, Aryee M J, Joung J K. Nat Biotechnol. 2015 February; 33 (2): 187-197. doi: 10.1038/nbt.3117. Epub 2014 Dec. 16, and used as described in cellectis.com/uploads/files/ASGCT_2017.pdf adapted version to TALEN).

A GUIDE-Seq read count or GUIDE-Seq score for a given site by a given endonuclease, represents a quantitative measurement of the cleavage efficiency of that sequence by an RNA or protein guided nuclease. Preferably the RNA or protein guided nuclease of the invention affecting the TRAC gene have a score near zero (below detection threshold or undetectable).

The invention further provides a human cell which is an endonuclease-modified endogenous αβ-TCR negative human cell, preferably a TALEN-modified endogenous αβ-TCR negative human cell as in any of the preceding embodiments wherein said endonuclease-modified endogenous αβ-TCR negative human cell, or TALEN modified endogenous αβ-TCR negative human cell can be expanded at least over 10×in a period of 12 days.

The invention further provides a human cell which is an endonuclease-modified endogenous αβ-TCR negative human cell, preferably a TALEN-modified endogenous αβ-TCR negative human cell as in any of the preceding embodiments wherein said endonuclease-modified endogenous αβ-TCR negative human cell, or TALEN modified endogenous αβ-TCR negative human cell can be expanded without clonal expansion.

The present invention provides a TALEN-modified endogenous αβ-TCR negative human cell according to the above further comprising undetectable level of MHC molecules as compared to an unmodified (non engineered) control cell and a deletion functionally affecting cell surface expression of a beta 2 microglobulin molecule.

The present invention provides a TALEN-modified endogenous αβ-TCR negative human cell according to the above further comprising undetectable level of MHC molecules as compared to an unmodified (non engineered) control cell and a genomic deletion, a mutation or an insertion affecting the expression of a CIITA molecule, preferably a CIITA molecule of Gene ID: 4261.

The present invention provides the TALEN-modified endogenous αβ-TCR negative human cell according to the above wherein said insertion resulted in an inactivation of the gene coding the TCR alpha and an undetectable cell surface expression of endogenous αβ-TCR in at least 96% of the cells, in at least 97% of the cells, in at least 98% of the cells, or in at least 99% of the cells.

Inactivation of the TRAC gene means that cells with an inactivated TRAC gene have undetectable level of cell surface TCR alpha, preferably due to a disruption of the TRAC gene, more preferably a disruption of the sequence coding for an extracellular domain and/or transmembrane domain of the TRC alpha subunit of the alpha beta TCR, and therefore no extracellular alpha beta TCR can be addressed to the membrane, resulting in an undetectable level of cell surface TCR alpha beta as compared to a positive control.

In one embodiment, cell surface expression may be measured by flow cytometry using a monoclonal anti human alpha beta TCR, a control isotype antibody.

In addition, human cells (engineered human cells) of the invention express a detectable level of the product encoded by the gene(s) inserted into the TRAC, (unless the expression is a conditional expression controlled by a promotor, itself activated by a protein or a drug), for example of a CAR or a TCR.

The present invention provides the TALEN-modified endogenous αβ-TCR negative human cell according to the above wherein said insertion resulted in an inactivation of the gene coding the TCR alpha and an undetectable cell surface expression of endogenous αβ-TCR in at least 96% of the cells, in at least 97% of the cells, in at least 98% of the cells, in at least 99% of the cells as determined by flow cytometry 4 days after introduction of said TALEN cutting said TRAC into said human cells.

In particular embodiments, a TALEN-modified endogenous αβ-TCR negative human cell according to the above comprises a TALEN binding domain and/or a sequence upstream a TALEN binding domain present in the wild type (wt) TRAC gene, preferably said TALEN binding domain in the wt TRAC gene has the following sequence: TTGTCC-CACAGATATCCagaaccctgaccctgCCGTGTACCAGCT-GAGAGA (SEQ ID NO: 38).

In particular embodiments, the engineered TRAC gene may contain any one of the following of sequence TTGTCC-CACAGATATCC (nt 1-17 of SEQ ID NO: 38), TTGTCC-CACAGATATCCa (nt 1-18 of SEQ ID NO: 38) TTGTCC-CACAGATATCCag (nt 1-19 of SEQ ID NO: 38) TTGTCCCACAGATATCCaga (nt 1-20 of SEQ ID NO: 38) TTGTCCCACAGATATCCagaa (nt 1-21 of SEQ ID NO: 38) TTGTCCCACAGATATCCagaac (nt 1-22 of SEQ ID NO: 38) TTGTCCCACAGATATCCagaacc nt 1-23 of SEQ ID NO: 38) (TTGTCCCACAGATATCCagaaccc (nt 1-24 of SEQ ID NO: 38) TTGTCCCACAGATATCCagaaccct (nt 1-25 of SEQ ID NO: 38) TTGTCCCACAGA-TATCCagaaccctg (nt 1-26 of SEQ ID NO: 38) TTGTCC-CACAGATATCCagaaccctga (nt 1-27 of SEQ ID NO: 38) TTGTCCCACAGATATCCagaaccctgac (nt 1-28 of SEQ ID NO: 38) TTGTCCCACAGATATCCagaaccctgacc (nt 1-29 of SEQ ID NO: 38) TTGTCCCACAGA-TATCCagaaccctgaccc (nt 1-30 of SEQ ID NO: 38) TTGTCCCACAGATATCCagaaccctgaccct (nt 1-31 of SEQ ID NO: 38) TTGTCCCACAGATATCCagaaccctgaccctg (nt 1-32 of SEQ ID NO: 38), The present invention encompasses a TALEN-modified endogenous αβ-TCR negative human cell obtained using any rare cutting endonuclease binding to ttgtcccacagATATC (nt 1-17 of SEQ ID NO: 38), or to ttgtcccacagATATCCAG (SEQ ID NO: 37), preferably a TALEN as described in WO2014184741.

The present invention provides a TALEN-modified endogenous αβ-TCR negative human primary cell according to any one of the above, obtained using a TALEN binding to ttgtcccacagATATC, or to ttgtcccacagATATCCAG (SEQ ID NO: 37) or to a sequence having at least from 93.75%, 87.5%, 81.25%, 75%, 68.75% 62.5% 56.25% 5% 43.75% 37.5% 31.25% 25% 18.75% 12.5% 6.25% identity with ttgtcccacagATATC (nt 1-17 of SEQ ID NO: 38), or with ttgtcccacagATATCCAG, provided that said TALEN cleaves the TRAC gene inducing an inactivation of the TCR alpha gene, undetectable cell surface expression of the TCR alpha beta, and off target sites for said TALEN below detection using a guide-seq method).

The present invention provides a TALEN-modified endogenous αβ-TCR negative human primary cell according to any one of the above, wherein said at least one insertion comprises an exogenous polynucleotide sequence located downstream any one of the following of sequence TTGTCCCACAGATATCC (nt 1-17 of SEQ ID NO: 38), TTGTCCCACAGATATCCa (nt 1-18 of SEQ ID NO: 38) TTGTCCCACAGATATCCag (nt 1-19 of SEQ ID NO: 38) TTGTCCCACAGATATCCaga (nt 1-20 of SEQ ID NO: 38) TTGTCCCACAGATATCCagaa (nt 1-21 of SEQ ID NO: 38) TTGTCCCACAGATATCCagaac (nt 1-22 of SEQ ID NO: 38) TTGTCCCACAGATATCCagaacc (nt 1-23 of SEQ ID NO: 38) TTGTCCCACAGATATCCagaaccc (nt 1-24 of SEQ ID NO: 38) TTGTCCCACAGATATCCagaaccct (nt 1-25 of SEQ ID NO: 38) TTGTCCCACAGA-TATCCagaaccctg (nt 1-26 of SEQ ID NO: 38) TTGTCC-CACAGATATCCagaaccctga (nt 1-27 of SEQ ID NO: 38) TTGTCCCACAGATATCCagaaccctgac (nt 1-28 of SEQ ID NO: 38) TTGTCCCACAGATATCCagaaccctgacc (nt 1-29 of SEQ ID NO: 38) TTGTCCCACAGA-TATCCagaaccctgaccc (nt 1-30 of SEQ ID NO: 38) TTGTCCCACAGATATCCagaaccctgaccct (nt 1-31 of SEQ ID NO: 38) TTGTCCCACAGATATCCagaaccctgaccctg (nt 1-32 of SEQ ID NO: 38), The present invention provides a TALEN-modified endogenous αβ-TCR negative human primary cell according to any one of the above, wherein said at least one insertion comprises an exogenous polynucleotide sequence located downstream any one of the following of sequence TTGTCCCACAGATATCC (nt 1-17 of SEQ ID NO: 38), TTGTCCCACAGATATCCa (nt 1-18 of SEQ ID NO: 38) TTGTCCCACAGATATCCag (nt 1-19 of SEQ ID NO: 38) TTGTCCCACAGATATCCaga (nt 1-20 of SEQ ID NO: 38) TTGTCCCACAGATATCCagaa (nt 1-21 of SEQ ID NO: 38) TTGTCCCACAGATATCCagaac (nt 1-22 of SEQ ID NO: 38) TTGTCCCACAGATATCCagaacc (nt 1-23 of SEQ ID NO: 38) TTGTCCCACAGATATCCagaaccc (nt 1-24 of SEQ ID NO: 38) TTGTCCCACAGATATCCagaaccct (nt 1-25 of SEQ ID NO: 38) TTGTCCCACAGA-TATCCagaaccctg (nt 1-26 of SEQ ID NO: 38) TTGTCC-CACAGATATCCagaaccctga (nt 1-27 of SEQ ID NO: 38) TTGTCCCACAGATATCCagaaccctgac (nt 1-28 of SEQ ID NO: 38) TTGTCCCACAGATATCCagaaccctgacc (nt 1-29 of SEQ ID NO: 38) TTGTCCCACAGA-TATCCagaaccctgaccc (nt 1-30 of SEQ ID NO: 38) TTGTCCCACAGATATCCagaaccctgaccct (nt 1-31 of SEQ ID NO: 38), and TTGTCCCACAGA-TATCCagaaccctgaccctg (nt 1-32 of SEQ ID NO: 38), and upstream any one of the following sequence CCGTGTACCAGCTGAGAGA (nt 33-51 of SEQ ID NO: 38), gCCGTGTACCAGCTGAGAGA (nt 32-51 of SEQ ID NO: 38), tgCCGTGTACCAGCTGAGAGA (nt 31-51 of SEQ ID NO: 38), ctgCCGTGTACCAGCTGAGAGA (nt 30-51 of SEQ ID NO: 38), cctgCCGTGTACCAGCT-GAGAGA (nt 29-51 of SEQ ID NO: 38), ccctgCCGTGTACCAGCTGAGAGA (nt 28-51 of SEQ ID NO: 38), accctgCCGTGTACCAGCTGAGAGA (nt 27-51 of SEQ ID NO: 38), gaccctgCCGTGTACCAGCT-GAGAGA (nt 26-51 of SEQ ID NO: 38), tgaccctgCCGTGTACCAGCTGAGAGA (nt 25-51 of SEQ ID NO: 38), ctgaccctgCCGTGTACCAGCTGAGAGA (nt 24-51 of SEQ ID NO: 38), cctgaccctgCCGTGTACCAGCT-GAGAGA (nt 23-51 of SEQ ID NO: 38), ccctgaccctgCCGTGTACCAGCTGAGAGA (nt 22-51 of SEQ ID NO: 38), accctgaccctgCCGTGTACCAGCT-GAGAGA (nt 21-51 of SEQ ID NO: 38), aaccctgaccctgCCGTGTACCAGCTGAGAGA (nt 20-51 of SEQ ID NO: 38), gaaccctgaccctgCCGTGTACCAGCT-GAGAGA (nt 19-51 of SEQ ID NO: 38), and agaaccctgaccctgCCGTGTACCAGCTGAGAGA (nt 18-51 of SEQ ID NO: 38).

A means according to the present invention allows the detection of any one the sequences below.

The present invention provides a TALEN-modified endogenous αβ-TCR negative human primary cell according to any one of the above wherein said at least one insertion comprises a sequence encoding a self-cleaving peptide in frame with the genomic TRAC coding sequence selected from a 2A peptide, a 2A like peptide, a P2A peptide, a E2A peptide, a F2A peptide, preferably a 2A peptide, more preferably a 2A peptide of sequence GSGEGRGSLLTCGD-VEENPGP (SEQ ID NO: 27), GSGATNFSLLKQAGD-VEENPGP (SEQ ID NO: 28), GSGQCTNYALLKLAGD-VESNPGP (SEQ ID NO: 29), GSGVKQTLNFDLLKLAGDVESNPGP (SEQ ID NO: 30), SGEGRGSLLTCGDVEENPGP (SEQ ID NO: 31), SGATNFSLLKQAGDVEENPGP (SEQ ID NO: 32), SGQCTNYALLKLAGDVESNPGP (SEQ ID NO: 33), SGVKQTLNFDLLKLAGDVESNPGP (SEQ ID NO: 34), even more preferably a 2A peptide of sequence SGEGRGSLLTCGDVEENPGP (SEQ ID NO: 35).

Any polynucleotide sequence encoding a 2A peptide, preferably 2A peptide of sequence SGEGRGSLLTCGD-VEENPGP (SEQ ID NO: 35) may be inserted into the genomic TRAC gene of a cell according to the present invention.

The present invention provides a TALEN-modified endogenous αβ-TCR negative human primary cell according to any one of the above, wherein said at least one insertion comprises a sequence coding a 2A peptide, of sequence SGEGRGSLLTCGDVEENPGP (SEQ ID NO: 35) in frame with the genomic TRAC coding sequence, an exogenous polynucleotide sequence coding a chimeric antigen receptor, a terminator sequence (a terminator sequence of polyadenylation signal), optionally a TALEN binding domain.

The present invention provides a TALEN-modified endogenous αβ-TCR negative human primary cell according to any one of the above, wherein said exogenous polynucleotide sequence comprises a chimeric antigen receptor (CAR), specific for at least one of the following antigen: CD19, CD123, CD20, CD22, CD38, CD30, CS-1, CLL-1, HSP70, BCMA, VEGF, DR4, GD2, the cancer testis (CT) antigens, MUC1, GD2, o acetyl GD2, HM1.24 (CD317), CYP1B1, SP17, PRAME, Wilms' Tumour 1 (WT1), heat shock protein gp96, thyroid stimulating hormone receptor (TSHR); CD171; CS-1 (CD2 subset 1, CRACC, SLAMF7, CD319, and 19A24); C-type lectin-like molecule-1 (CLL-1); ganglioside GD3 (aNeu5Ac (2-8) aNeu5Ac (2-3) bDGalp (1-4) bDGlcp (1-1) Cer); Tn antigen (Tn Ag); Fms-Like Tyrosine Kinase 3 (FLT3); CD38; CD44v6; B7H3 (CD276); KIT (CD117); Interleukin-13 receptor subunit alpha-2 (IL-13Ra2); Interleukin 11 receptor alpha (IL-I IRa); prostate stem cell antigen (PSCA); Protease Serine 21 (PRSS21); vascular endothelial growth factor receptor 2 (VEGFR2); Lewis (Y) antigen; CD24; Platelet-derived growth factor receptor beta (PDGFR-beta); stage-specific embryonic antigen-4 (SSEA-4); Mucin 1, cell surface associated (MUC1); epidermal growth factor receptor (EGFR); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Fucosyl GM1; sialyl Lewis adhesion molecule (sLe); ganglioside GM3 (aNeu5Ac (2-3) bDGalp (1-4) bDGlcp (1-I) Cer; TGS5; high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1) and a combination thereof.

The CAR may preferably be a CAR selected from the list consisting of a CAR specific for CD19, CD123, CD20, CD22, CD38, CD30, CS-1, CLL-1, HSP70, BCMA, VEGF, DR4, GD2, O-acethyl GD2, the cancer testis (CT) antigens, MUC1, MUC16, HM1.24 (CD317), CYP1B1, SP17, PRAME, Wilms' tumour 1 (WT1), heat shock protein gp96, claudine18.2, CEA, FAP-HER2-CD79a, CD79b and a combination thereof.

The CAR may be more preferably a CAR selected from the list consisting of a CAR specific for CD123, CD22, CD38, CD30, CS-1, CLL-1, HSP70, BCMA, GD2, O-acethyl GD2, MUC1, FAP, HER2, CD79a, CD79b and a combination thereof.

In a preferred embodiment, the CAR is directed against one of the following target antigen mesothelin FRα, L1-CAM, CAIX, GD2, O-acethyl GD2, FAP, Lewis Y, EGFRVIII, HER2, CD20, PSMA, KLC, CD30, CEA, FAP-HER2-CD79a, CD79b.

In another preferred embodiment, the CAR is directed against one of the following target: a-folate receptor (FRa); L1-cell adhesion molecule (L1-CAM); carboxy-anhydrase-IX (CAIX,); Fibroblast activation protein (FAP), human epidermal growth factor receptor 2 (HER2); carcinoembryonic antigen (CEA); Prostate Specific Membrane Antigen (PSMA); CD79a, CD79b, CD20 or CD268, C type lectin domain family 14 member A; also EGFR5 (CLEC14a), Epithelial cell adhesion molecule (EPCAM), Liv-1, or Zinc transporter LIV-1 (SLC39A6), Cholinergic Receptor Nicotinic Alpha 2 Subunit (CHRNA2), A Disintegrin and metalloproteinase domain-containing protein 10, (ADAM10) or CDw156 or CD156cADAM10, Delta-like 3 (DLL3), C type lectin domain family 14 member A; also EGFR5, (CLEC14a).

CLEC14a is a 51 kDa (predicted) member of the C type lectin domain family of proteins. It is a type transmembrane protein, expressed in brain. Mature human CLEC14A is 469 amino acids in length.

In a more preferred embodiment, the CAR is directed against one of the following target antigen CD123, CD22, CD30, CLL-1, CS-1, O-Acetyl GD2, FAP, HER2, CD79a, CD79b.

On a more more preferred embodiment the CAR is directed against one of the following target antigen CD123, CD22, CD30, CLL-1, CS-1, O-Acetyl GD2, FAP, HER2, CD79a, CD79b expressed (or over expressed on tumor cells. This is achieved by using specific scfv domains, in the present invention.

The CAR molecule of the invention comprises an antigen binding domain, preferably a scfv, a transmembrane domain, and an intracellular domain comprising a costimulatory domain and/or a primary signaling domain.

The CAR molecule of the invention comprises an antigen binding domain wherein said antigen binding domain binds to the tumor antigen associated with a disease, and said tumor antigen is selected from a group consisting of: CD19 molecule (CD19); membrane spanning 4-domains A1 (MS4A1 also known as CD20); CD22 molecule (CD22); CD24 molecule (CD24); CD248 molecule (CD248); CD276 molecule (CD276 or B7H3); CD33 molecule (CD33); CD38 molecule (CD38); CD44v6; CD70 molecule (CD70); CD72; CD79a; CD79b; interleukin 3 receptor subunit alpha (IL3RA also known as CD123); TNF receptor superfamily member 8 (TNFRSF8 also known as CD30); KIT proto-oncogene receptor tyrosine kinase (CD117); V-set pre-B cell surrogate light chain 1 (VPREB1 or CD179a); adhesion G protein-coupled receptor E5 (ADGRE5 or CD97); TNF receptor superfamily member 17 (TNFRSF17 also known as BCMA); SLAM family member 7 (SLAMF7 also known as CS1); L1 cell adhesion molecule (L1CAM); C-type lectin domain family 12 member A (CLEC12A also known as CLL-1); tumor-specific variant of the epidermal growth factor receptor (EGFRvIII); thyroid stimulating hormone receptor (TSHR); Fms related tyrosine kinase 3 (FLT3); ganglioside GD3 (GD3); Tn antigen (Tn Ag); lymphocyte antigen 6 family member G6D (LY6G6D); Delta like canonical Notch ligand 3 (DLL3); Interleukin-13 receptor subunit alpha-2 (IL-13RA2); Interleukin 11 receptor subunit alpha (IL11RA); mesothelin (MSLN); Receptor tyrosine kinase like orphan receptor 1 (ROR1); Prostate stem cell antigen (PSCA); erb-b2 receptor tyrosine kinase 2 (ERBB2 or Her2/neu); Protease Serine 21 (PRSS21); Kinase insert domain receptor (KDR also known as VEGFR2); Lewis y antigen (LewisY); Solute carrier family 39 member 6 (SLC39A6); Fibroblast activation protein alpha (FAP); Hsp70 family chaperone (HSP70); Platelet-derived growth factor receptor beta (PDGFR-beta); Cholinergic receptor nicotinic alpha 2 subunit (CHRNA2); Stage-Specific Embryonic Antigen-4 (SSEA-4); Mucin 1, cell surface associated (MUC1); mucin 16, cell surface associated (MUC16); claudin 18 (CLDN18); claudin 6 (CLDN6); Epidermal Growth Factor Receptor (EGFR); Preferentially expressed antigen in melanoma (PRAME); Neural Cell Adhesion Molecule (NCAM); ADAM metallopeptidase domain 10 (ADAM10); Folate receptor 1 (FOLR1); Folate receptor beta (FOLR2); Carbonic Anhydrase IX (CA9); Proteasome subunit beta 9 (PSMB9 or LMP2); Ephrin receptor A2 (EphA2); Tetraspanin 10 (TSPAN10); Fucosyl GM1 (Fuc-GM1); sialyl Lewis adhesion molecule (sLe); TGS5; high molecular weight-melanoma-associated antigen (HMW-MAA); o-acetyl-GD2 ganglioside (OAcGD2); tumor endothelial marker 7-related (TEM7R); G protein-coupled receptor class C group 5, member D (GPRC5D); chromosome X open reading frame 61 (CXORF61); ALK receptor tyrosine kinase (ALK); Polysialic acid; Placenta-specific 1 (PLAC1); hexasaccharide portion of globoH glycoceramide (GloboH); NY-BR-1 antigen; uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 family member K (LY6K); olfactory receptor family 51 subfamily E member 2 (OR51E2); TCR Gamma Alternate Reading Frame Protein (TARP); Wilms tumor protein (WT1); ETV6-AML1 fusion protein due to 12;21 chromosomal translocation (ETV6-AML1); sperm autoantigenic protein 17 (SPA17); X Antigen Family, Member 1E (XAGE1E); TEK receptor tyrosine kinase (Tie2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL1), and Heat shock protein 70 (HSP70).

In another aspect, the CAR molecule of the invention comprises an antigen binding domain wherein said antigen binding domain binds to an antigen associated with a disease, and said tumor antigen is selected from a group consisting of: CD19 molecule (CD19); membrane spanning 4-domains A1 (MS4A1 also known as CD20); CD22 molecule (CD22); CD24 molecule (CD24); CD248 molecule (CD248); CD276 molecule (CD276 or B7H3); CD33 molecule (CD33); CD38 molecule (CD38); CD44v6; CD70 molecule (CD70); CD72; CD79a; CD79b; interleukin 3 receptor subunit alpha (IL3RA also known as CD123); TNF receptor superfamily member 8 (TNFRSF8 also known as CD30); KIT proto-oncogene receptor tyrosine kinase (CD117); V-set pre-B cell surrogate light chain 1 (VPREB1 or CD179a); adhesion G protein-coupled receptor E5 (ADGRES or CD97); TNF receptor superfamily member 17 (TNFRSF17 also known as BCMA); SLAM family member 7 (SLAMF7 also known as CS1); L1 cell adhesion molecule (L1CAM); C-type lectin domain family 12 member A (CLEC12A also known as CLL-1); tumor-specific variant of the epidermal growth factor receptor (EGFRvlll); thyroid stimulating hormone receptor (TSHR); Fms related tyrosine kinase 3 (FLT3); ganglioside GD3 (GD3); In antigen (Tn Ag); lymphocyte antigen 6 family member G6D (LY6G6D); Delta like canonical Notch ligand 3 (DLL3); Interleukin-13 receptor subunit alpha-2 (IL-13RA2); Interleukin 11 receptor subunit alpha (IL11RA); mesothelin (MSLN); Receptor tyrosine kinase like orphan receptor 1 (ROR1); Prostate stem cell antigen (PSCA); erb-b2 receptor tyrosine kinase 2 (ERBB2 or Her2/neu); Protease Serine 21 (PRSS21); Kinase insert domain receptor (KDR also known as VEGFR2); Lewis y antigen (LewisY); Solute carrier family 39 member 6 (SLC39A6); Fibroblast activation protein alpha (FAP); Hsp70 family chaperone (HSP70); Platelet-derived growth factor receptor beta (PDGFR-beta); Cholinergic receptor nicotinic alpha 2 subunit (CHRNA2); Stage-Specific Embryonic Antigen-4 (SSEA-4); Mucin 1, cell surface associated (MUC1); mucin 16, cell surface associated (MUC16); claudin 18 (CLDN18); claudin 6 (CLDN6); Epidermal Growth Factor Receptor (EGFR); Preferentially expressed antigen in melanoma (PRAME); Neural Cell Adhesion Molecule (NCAM); ADAM metallopeptidase domain 10 (ADAM10); Folate receptor 1 (FOLR1); Folate receptor beta (FOLR2); Carbonic Anhydrase IX (CA9); Proteasome subunit beta 9 (PSMB9 or LMP2); Ephrin receptor A2 (EphA2); Tetraspanin 10 (TSPAN10); Fucosyl GM1 (Fuc-GM1); sialyl Lewis adhesion molecule (sLe); TGS5; high molecular weight-melanoma-associated antigen (HMW-MAA); o-acetyl-GD2 ganglioside (OAcGD2); tumor endothelial marker 7-related (TEM7R); G protein-coupled receptor class C group 5, member D (GPRCSD); chromosome X open reading frame 61 (CXORF61); ALK receptor tyrosine kinase (ALK); Polysialic acid; Placenta-specific 1 (PLAC1); hexasaccharide portion of globoH glyceramide (GloboH); NY-BR-1 antigen; uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 family member K (LY6K); olfactory receptor family: 51 subfamily E member 2 (OR51E2); TCR Gamma Alternate Reading Frame Protein (TARP); Wilms tumor protein (WT1); ETV6-AML1 fusion protein due to 12;21 chromosomal translocation (ETV6-AML1); sperm autoantigenic protein 17 (SPA17); X Antigen Family, Member 1E (XAGE1E); TEK receptor tyrosine kinase (Tie2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL1), and Heat shock protein 70 (HSP70).

Under particular aspects, the cells of the invention are used for the treatment of a disease wherein said antigen against which the CAR is directed to is expressed or over expressed by pathological cells or tissue responsible for the disease.

The TCR molecule of the present invention comprises an antigen binding domain, wherein said antigen binding domain binds to a tumor antigen associated with a disease, and said tumor antigen is selected from a group consisting of PCTA-I/Galectin 8, CD171, TAG72, CEA, EPCAM, PSCA, PRSS21, PDGFR-beta, Prostase, PAP, ELF2M, Ephrin B2, IGF-I receptor, CAIX,gp100, bcr-abl, tyrosinase, GM3, NY-ESO-1, LAGE-la, MAGE-A1, legumain, HPV E6,E7, MAGE AI, prostein, survivin and telomerase, PCTA-I/Galectin 8, MelanA/MARTI, Ras mutant, TRP-2, RAGE-1, RU1, RU2, and intestinal carboxyl esterase.

Preferably the CAR of the invention comprises an antigen binding domain, that binds to a tumor antigen associated with a disease, and said tumor antigen is selected from a group consisting of CD22, CD123, CS-1, CLL-1, CD38, HSP70, MUC-1, CD30, FAP, HER2, CD79a and CD79b.

In preferred embodiments the CAR of the invention comprises an antigen binding domain, that binds to a tumor antigen associated with a disease, and said tumor antigen is selected from a group consisting of BCMA, CD33, EGFRVIII, Fit3, WT1, CD70, MUC16, PRAME, TSPAN10 CLAUDIN18.2, DLL3, LY6G6D, Liv-1, CHRNA2, ADAM10.

Preferably the CAR expressed at the cell surface of the cell of the invention comprises an antigen binding domain that binds to CD22.

Preferably the CAR expressed at the cell surface of the cell of the invention comprises an antigen binding domain that binds to CD123.

Preferably the CAR expressed at the cell surface of the cell of the invention comprises an antigen binding domain, that binds to CD30.

Preferably the CAR expressed at the cell surface of the cell of the invention comprises an antigen binding domain that binds to CD38.

Preferably the CAR expressed at the cell surface of the cell of the invention comprises an antigen binding domain that binds to CS-1.

Preferably the CAR expressed at the cell surface of the cell of the invention comprises an antigen binding domain that binds to CLL-1.

Preferably the CAR expressed at the cell surface of the cell of the invention comprises an antigen binding domain that binds to O-acethyl GD2.

Preferably the CAR expressed at the cell surface of the cell of the invention comprises an antigen binding domain that binds to FAP Preferably the CAR expressed at the cell surface of the cell of the invention comprises an antigen binding domain that binds to HER2

Preferably the CAR expressed at the cell surface of the cell of the invention comprises an antigen binding domain that binds to CD79a Preferably the CAR expressed at the cell surface of the cell of the invention comprises an antigen binding domain that binds to CD79b.

Preferably the CAR expressed at the cell surface of the cell of the invention comprises an antigen binding domain that binds to BCMA, Preferably the CAR expressed at the cell surface of the cell of the invention comprises an antigen binding domain that binds to CD33, Preferably the CAR expressed at the cell surface of the cell of the invention comprises an antigen binding domain that binds to EGFRVIII, Preferably the CAR expressed at the cell surface of the cell of the invention comprises an antigen binding domain that binds to Flt3, Preferably the CAR expressed at the cell surface of the cell of the invention comprises an antigen binding domain that binds to WT1, Preferably the CAR expressed at the cell surface of the cell of the invention comprises an antigen binding domain that binds to CD70, Preferably the CAR expressed at the cell surface of the cell of the invention comprises an antigen binding domain that binds to MUC16, Preferably the CAR expressed at the cell surface of the cell of the invention comprises an antigen binding domain that binds to PRAME, Preferably the CAR expressed at the cell surface of the cell of the invention comprises an antigen binding domain that binds to TSPAN10, Preferably the CAR expressed at the cell surface of the cell of the invention comprises an antigen binding domain that binds to CLAUDIN18.2, Preferably the CAR expressed at the cell surface of the cell of the invention comprises an antigen binding domain that binds to DLL3, Preferably the CAR expressed at the cell surface of the cell of the invention comprises an antigen binding domain that binds to LY6G6D, Preferably the CAR expressed at the cell surface of the cell of the invention comprises an antigen binding domain that binds to Liv-1, Preferably the CAR expressed at the cell surface of the cell of the invention comprises an antigen binding domain that binds to CHRNA2, Preferably the CAR expressed at the cell surface of the cell of the invention comprises an antigen binding domain that binds to ADAM10.

The invention provides a TALEN-modified endogenous αβ-TCR negative human cell according to any one of above embodiments, wherein said CAR comprises an extracellular ligand-binding domain, at least one epitope specific for a monoclonal antibody, a transmembrane domain and one or more intracellular signaling domains.

The invention provides a TALEN-modified endogenous αβ-TCR negative human cell according to any one of above embodiments, wherein said CAR comprises an extracellular ligand-binding domain, at least one epitope specific for a monoclonal antibody, a transmembrane domain from CD8 alpha, and one or more intracellular signaling domains from CD3 zeta and costimulatory domain from 4-1BB (human CD137).

The invention provides a TALEN-modified endogenous αβ-TCR negative human cell according to any one of above embodiments, wherein said CAR comprises an extracellular ligand-binding domain, a hinge from CD8alpha, at least one epitope specific for a monoclonal antibody, a transmembrane domain from CD8 alpha, and one or more intracellular signaling domains from CD3 zeta and costimulatory domain from 4-1BB.

The invention provides a TALEN-modified endogenous αβ-TCR negative human cell according to any one of above embodiments, wherein said CAR comprises an extracellular ligand-binding domain, a hinge from IgG1, at least one epitope specific for a monoclonal antibody, a transmembrane domain from CD8 alpha, and one or more intracellular signaling domains from CD3 zeta and costimulatory domain from 4-1BB.

The invention provides a TALEN-modified endogenous αβ-TCR negative human cell according to any one of above embodiments, wherein said CAR comprises an extracellular ligand-binding domain, no hinge, a hinge from CD8alpha, a hinge from IgG1, a hinge from FcγRIIIa, at least one epitope specific for a monoclonal antibody, a transmembrane domain from CD8 alpha, and one or more intracellular signaling domains from CD3 zeta and costimulatory domain from 4-1BB.

The invention provides a TALEN-modified endogenous αβ-TCR negative human cell according to any one of above embodiments wherein said anti-CD123 CAR comprises an extracellular ligand-binding domain, at least one epitope specific for a monoclonal antibody, a transmembrane domain and one or more intracellular signaling domains.

The invention provides a TALEN-modified endogenous αβ-TCR negative human cell according to any one of above embodiments wherein said anti-CD22 CAR comprises an extracellular ligand-binding domain, at least one epitope specific for a monoclonal antibody, a transmembrane domain and one or more intracellular signaling domains.

The invention provides a TALEN-modified endogenous αβ-TCR negative human cell according to any one of above embodiments wherein said anti-CD30 CAR comprises an extracellular ligand-binding domain, at least one epitope specific for a monoclonal antibody, a transmembrane domain and one or more intracellular signaling domains.

The invention provides a TALEN-modified endogenous αβ-TCR negative human cell according to any one of above embodiments wherein said anti-CLL-1 CAR comprises an extracellular ligand-binding domain, at least one epitope specific for a monoclonal antibody, a transmembrane domain and one or more intracellular signaling domains.

The invention provides a TALEN-modified endogenous αβ-TCR negative human cell according to any one of above embodiments wherein said anti-CS-1 CAR comprises an extracellular ligand-binding domain, at least one epitope specific for a monoclonal antibody, a transmembrane domain and one or more intracellular signaling domains.

In particular embodiments, the invention provides a TALEN-modified endogenous αβ-TCR negative human cell wherein said at least one insertion comprises a first a TALEN binding domain, an IRES, an exogenous polynucleotide sequence comprising a chimeric antigen receptor (CAR), a terminator sequence of polyadenylation signal, optionally a TALEN binding domain.

In particular embodiments, the invention provides a TALEN-modified endogenous αβ-TCR negative human cell according to the above, wherein said chimeric antigen receptor (CAR), comprises at least one antigen specific for a monoclonal antibody, preferably two antigens specific for a monoclonal antibody.

In particular embodiments, the invention provides a TALEN-modified endogenous αβ-TCR negative human cell as above wherein said exogenous polynucleotide comprises a terminator sequence or a signal terminating the transcription by stopping the activity of RNA polymerase.

TERMINATOR SEQUENCE

The TALEN-modified endogenous αβ-TCR negative human cell according to the invention comprises an insertion into the TRAC gene comprising a termination or terminator sequence, preferably the TALEN-modified endogenous αβ-TCR negative human cell invention may comprise, from 5' to 3,' an insertion comprising an open reading frame encoding a protein, preferably a CAR and a termination sequence.

Thus, a termination or terminator sequence may be inserted into the TRAC locus allowing a CAR to be expressed and preventing cell surface expression of the endogenous alpha beta TCR.

In general, a terminator is a sequence-based element defining the end of a transcriptional unit (such as a gene) and initiating the process of releasing the newly synthesized RNA from the transcription machinery. Terminators are found downstream of a gene to be transcribed, and typically occur directly after any 3' regulatory elements, such as the polyadenylation or poly (A) signal. Polyadenylation is the post-transcriptional additional of multiple adenine (A) nucleotides to the tail of a messenger RNA transcript. The purpose and mechanism of polyadenylation vary among cell types, but polyadenylation generally serves to promote transcript longevity in eukaryotes.

Accordingly, terminators regulate RNA processing and contribute to variability in RNA half-life, and ultimately gene-expression.

The following terminators available in eukaryotes at parts.

igem.org/Terminators/Catalog #Eukaryotic_terminators is part of the present invention.

The terminators of the present invention include a terminator selected from SV40, hGH, BGH, and rbGlob terminators.

The terminators of the present invention include a terminator selected from SV40, hGH, BGH, and rbGlob terminators and comprise the sequence motif AAUAAA which promotes both polyadenylation and termination. Advantageously, the SV40 late polyA and rbGlob polyA are preferred when termination of transcription is due to the presence of additional helper sequences.

In a preferred embodiment terminator sequence of the present invention may be a terminator sequence selected from SV40 polyA, BGH polyA, hGH polyA, rbGlob polyA. In a more preferred embodiment, a terminator sequence of the present invention comprises a BGH polyA and includes the consensus sequence AATAAA, in an even more preferred embodiment, A terminator sequence according to the present invention comprises a BGH polyA of sequence:

CTGTGCCTTCTAGTTGCCAGCCATCTGTTGTT TGCCCCTCCCCCGTGCCTTCCTTGACCCTG-GAAGGTGCCACTCC CACTGTCCTTT CCTAATA AAATGAGGAAATTGCATCGCATTGTCT-GAGTAGGTGTCATTCTATTCTGGGGGGTGGG GTGGGGCAGGACAGCAAGGGGGAGGATTGG-GAACACAATAGCAGGCATGCTGGGGATGC GGTGGGCTCTATG (SEQ ID NO: 119),

CTGTGCCTTCTAGTTGCCAGCCATCTGTTGTTTG CCCCTCCCCCGTGCCTTCCTTGACCCTG-GAAGGTGCCACTCCCACTGTCCTTTCC TAATAAAATGAGGAAATTGCATCGCATTGTCT-GAGTAGGTGTCATTC TATTCTGGGGGGTGGGG TGGGGCAGGACAGCAAGGGGGAGGATTGG-GAAGACAA-TAGCAGGCATGCTGGGGAT GCGGTGGGCTCTATGG (SEQ ID NO: 120), or

CCTCGACTGTGCCTTCTAGTTGCCAGCCATCTGT TGTTTGCCCCTCCCCCGTGCCTTCCTTGACCC-TGGAAGGTGC CACTCCCACTGTCCTTTCCT AATAAAATGAGGAAATTGCATCGCATTGTCT-GAGTAGGTGTCATTCTATTCTGGGG GGTG GGGTGGGGCAGGACAGCAAGGGGGAGGAT-TGGGAAGACAATAGCAGGCATGCTGGGGAT GCGGTGG GCTCTATGGCTTCTGAGGCGGAAA GAACCAGCTGGGGCTCTAGGGGGTATCCCC (SEQ ID NO: 121). The even more more preferred terminator sequence according to the present invention comprises the following sequence:

(SEQ ID NO: 122)
CTGTGCCTTCTAGTTGCCAGCCATCTGTTGTTTGCCCCTCCCCCGTGCC

TTCCTTGACCCTGGAAGGTGCCACTCCCACTGTCCTTTCCTAATAAAAT

GAGGAAATTGCATCGCATTGTCTGAGTAGGTGTCATTCTATTCTGGGGG

GTGGGGTGGGGCAGGACAGCAAGGGGGAGGATTGGGAACACAATAGCAG

GCATGCTGGGGATGCGGTGGGCTCTAT

Immune Check Point Factors

In particular embodiments, the invention provides a TALEN-modified endogenous αβ-TCR negative human cell according to any one of the above wherein at least one additional endogenous genomic gene is endonuclease-inactivated, preferably TALEN-inactivated said endogenous genomic gene is selected from the group consisting of an endogenous genomic beta subunit gene of the TCR, an endogenous genomic cytokine inducible SH2-containing (CISH) gene, an adenosine A2a receptor (ADORA) genomic gene, an endogenous genomic CD276 gene, an endogenous genomic V-set domain containing T cell activation inhibitor 1 (VTCNI) gene, an endogenous genomic B and T lymphocyte associated (BTLA) gene, an endogenous genomic cytotoxic T-lymphocyte-associated protein 4 (CTLA4) gene, an endogenous genomic indoleamine 2,3-dioxygenase 1 (IDO I) gene, an endogenous genomic killer cell immunoglobulin-like receptor, three domains, long cytoplasmic tail, 1 (KIR3DL1) gene, an endogenous genomic lymphocyte-activation gene 3 (LAG3) gene, an endogenous genomic programmed cell death 1 (PD-1) gene, an endogenous genomic hepatitis A virus cellular receptor 2 (HAVCR2) gene, an endogenous genomic V-domain immunoglobulin suppressor of T-cell activation (VISTA) gene, an endogenous genomic natural killer cell receptor 2B4 (CD244) gene, an endogenous genomic hypoxanthine phosphoribosyltransferase 1 (HPRT) gene, an endogenous genomic adeno-associated virus integration site (AAVS I), and an endogenous genomic chemokine (C—C motif) receptor 5 (gene/pseudogene) (CCR5) gene, a combination thereof.

The present invention provides a TALEN-modified endogenous αβ-TCR negative human cell expressing a CAR or a TCR, in particular any of the CAR described above, wherein one gene selected from the genes CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, is inactivated as in WO2014/184741 incorporated herein by reference.

The present invention provides a TALEN-modified endogenous αβ-TCR negative human cell according to any one of the above, expressing a CAR or a TCR, in particular any of the CAR described above, and wherein the level of expression of at least one additional factor selected from:

a) a factor which expression is involved in the reduction of glycolysis and/or calcium signaling, such as SERCA3, miR101 and mir26A to increase glycolysis, BCAT to mobilize glycolytic reserves; and/or b) a factor which expression up regulate(s) immune checkpoint proteins (e.g.TIM3, CEACAM, LAG3, TIGIT), such as IL27RA, STAT1, STAT3; and/or c) a factor which expression mediates interaction with HLA-G, such as ILT2 or ILT4; and/or d) a factor which expression is involved into the down regulation of T-cell proliferation such as SEMA7A, SHARPIN to reduce Treg proliferation, STAT1 to lower apoptosis, PEA15 to increase IL-2 secretion and RICTOR to favor CD8 memory differentiation; and/or e) polynucleotide sequence(s), which expression is (are) involved into the down regulation of T-cell activation, such as mir21; and/or f) polynucleotide sequence(s), which expression is (are) involved in signaling pathways responding to cytokines, such as JAK2 and AURKA; and/or g) polynucleotide sequence(s), which expression is (are) involved in T-cell exhaustion, such as DNMT3, miRNA31, MT1A, MT2A, PTGER2.

In particular embodiments, the invention provides a TALEN-modified endogenous αβ-TCR negative human cell according to any one of the above wherein said cell has been genetically modified, as described in PA2017 70603 which is incorporated herein by reference in its entirety.

In particular embodiments, the invention provides a TALEN-modified endogenous αβ-TCR negative human cell according to any one of the above wherein said cell has been genetically modified to reduce or inactivate the expression of SERCA3.

In particular embodiments, the invention provides a TALEN-modified endogenous αβ-TCR negative human cell according to any one of the above wherein said cell has been genetically modified to reduce or inactivate the expression of miR101.

In particular embodiments, the invention provides a TALEN-modified endogenous αβ-TCR negative human cell according to any one of the above wherein said cell has been genetically modified to reduce or inactivate the expression of mir26A to increase glycolysis.

In particular embodiments, the invention provides a TALEN-modified endogenous αβ-TCR negative human cell according to any one of the above wherein said cell has been genetically modified to reduce or inactivate the expression of BCAT to mobilize glycolytic reserves.

In particular embodiments, the invention provides a TALEN-modified endogenous αβ-TCR negative human cell according to any one of the above wherein said cell has been genetically modified to reduce or inactivate the expression of IL27RA.

In particular embodiments, the invention provides a TALEN-modified endogenous αβ-TCR negative human cell according to any one of the above wherein said cell has been genetically modified to reduce or inactivate the expression of STAT1.

In particular embodiments, the invention provides a TALEN-modified endogenous αβ-TCR negative human cell according to any one of the above wherein said cell has been genetically modified to reduce or inactivate the expression of STAT3.

In particular embodiments, the invention provides a TALEN-modified endogenous αβ-TCR negative human cell according to any one of the above wherein said cell has been genetically modified to reduce or inactivate the expression of ILT2.

In particular embodiments, the invention provides a TALEN-modified endogenous αβ-TCR negative human cell according to any one of the above wherein said cell has been genetically modified to reduce or inactivate the expression of ILT4.

In particular embodiments, the invention provides a TALEN-modified endogenous αβ-TCR negative human cell according to any one of the above wherein said cell has been genetically modified to reduce or inactivate the expression of SEMA7.

In particular embodiments, the invention provides a TALEN-modified endogenous αβ-TCR negative human cell according to any one of the above wherein said cell has been genetically modified to reduce or inactivate the expression of SHARPIN.

In particular embodiments, the invention provides a TALEN-modified endogenous αβ-TCR negative human cell according to any one of the above wherein said cell has been genetically modified to reduce or inactivate the expression of STAT1.

In particular embodiments, the invention provides a TALEN-modified endogenous αβ-TCR negative human cell according to any one of the above wherein said cell has been genetically modified to reduce or inactivate the expression PEA15.

In particular embodiments, the invention provides a TALEN-modified endogenous αβ-TCR negative human cell according to any one of the above wherein said cell has been genetically modified to reduce or inactivate the expression of RICTOR.

In particular embodiments, the invention provides a TALEN-modified endogenous αβ-TCR negative human cell according to any one of the above wherein said cell has been genetically modified to reduce or inactivate the expression of mir21

In particular embodiments, the invention provides a TALEN-modified endogenous αβ-TCR negative human cell according to any one of the above wherein said cell has been genetically modified to reduce or inactivate the expression of JAK2.

In particular embodiments, the invention provides a TALEN-modified endogenous αβ-TCR negative human cell according to any one of the above wherein said cell has been genetically modified to reduce or inactivate the expression of AURKA.

In particular embodiments, the invention provides a TALEN-modified endogenous αβ-TCR negative human cell according to any one of the above wherein said cell has been genetically modified to reduce or inactivate the expression of DNMT3.

In particular embodiments, the invention provides a TALEN-modified endogenous αβ-TCR negative human cell according to any one of the above wherein said cell has been genetically modified to reduce or inactivate the expression of miRNA31.

In particular embodiments, the invention provides a TALEN-modified endogenous αβ-TCR negative human cell according to any one of the above wherein said cell has been genetically modified to reduce or inactivate the expression of MT1A.

In particular embodiments, the invention provides a TALEN-modified endogenous αβ-TCR negative human cell according to any one of the above wherein said cell has been genetically modified to reduce or inactivate the expression of MT2A.

In particular embodiments, the invention provides a TALEN-modified endogenous αβ-TCR negative human cell according to any one of the above wherein said cell has been genetically modified to reduce or inactivate the expression of PTGER2.

In particular embodiments, the invention provides a TALEN-modified endogenous αβ-TCR negative human cell according to any one of the above wherein at least one additional endogenous genomic gene is overexpressed as in PCT/EP2017/058923 which is incorporated herein by reference in its entirety.

The present invention provides a TALEN-modified endogenous αβ-TCR negative human cell as above for use to alter the survival of pathological cells responsible for a pathological condition, said pathological condition may be for example a cancer, a viral infection, in an individual regardless of his MHC or TCR molecules, preferably said TALEN-modified endogenous αβ-TCR negative human cell induces no GVHD, more preferably said TALEN-modified endogenous αβ-TCR negative human cell induces no GVHD and no HVGD.

The present invention provides a TALEN-modified endogenous αβ-TCR negative human cell as above for use as a medicament that induces no GVHD.

The present invention provides a TALEN-modified endogenous αβ-TCR negative human cell as above for use as a medicament that induces no grade 1 GVHD.

The present invention provides a TALEN-modified endogenous αβ-TCR negative human cell as above for use as a medicament that induces no grade 2 GVHD.

The present invention provides a TALEN-modified endogenous αβ-TCR negative human cell as above for use as a medicament that induces no grade 3 GVHD.

The present invention provides a TALEN-modified endogenous αβ-TCR negative human cell as above for use as a medicament that induces no grade 4 GVHD.

The present invention provides a TALEN-modified endogenous αβ-TCR negative human cell as above for use as a medicament that induces no acute GVHD.

The present invention provides a TALEN-modified endogenous αβ-TCR negative human cell as above for use as a medicament that induces no chronical GVHD.

The present invention provides a TALEN-modified endogenous αβ-TCR negative human cell as above for use as a medicament that induces neither acute nor chronical GVHD.

The present invention provides a population of human cells comprising a TALEN-modified endogenous αβ-TCR negative human cell according to any one of the above embodiments.

The present invention provides a pharmaceutical composition comprising a TALEN-modified endogenous αβ-TCR negative human cell according to any one of the above or a population of human cells as above and a pharmaceutically acceptable excipient.

The present invention provides a TALEN-modified endogenous αβ-TCR negative human cell according to the above or a population of human cells as above or the pharmaceutical composition as above, for use as a medicament.

The present invention provides a TALEN-modified endogenous αβ-TCR negative human cell according to any one of the above or the population of human cells as above or the pharmaceutical composition according to the above for use in the treatment of cancer, in particular pediatric cancer.

The object of the present invention encompasses immunotherapy against a solid cancer; cells of the invention may be engineered to be resistant to hypoxia and/or for expressing a CAR under hypoxia as disclosed in WO2015092024 incorporated herein by reference.

The present invention provides a TALEN-modified endogenous αβ-TCR negative human cell according to any one of the above or the population of human cells as above or the pharmaceutical composition according to the above for use in the treatment of cancer, wherein said cancer is selected from the group consisting of a cancer of carcinoma, lymphoma, sarcoma, blastomas, and leukemia.

The present invention provides a TALEN-modified endogenous αβ-TCR negative human cell according to any one of the above or the population of human cells as above or the pharmaceutical composition according to the above for use in the treatment of a hematologic cancer, acute leukemia, B-cell acute lymphoid leukemia (BALL), T-cell acute lymphoid leukemia (TALL), small lymphocytic leukemia (SLL), acute lymphoid leukemia (ALL); chronic leukemia, chronic myelogenous leukemia (CML), chronic lymphocytic leukemia (CLL), non-Hodgkin lymphoma, or myeloma; or wherein the disease is a CD19-negative cancer, e.g., a CD19-negative relapsed cancer.

The present invention provides a TALEN-modified endogenous αβ-TCR negative human cell according to any one of the above or the population of human cells as above or the pharmaceutical composition according to the above for use in the treatment of cancer wherein the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma.

The present invention provides a TALEN-modified endogenous αβ-TCR negative human cell according to any one of the above or the population of human cells as above or the pharmaceutical composition according to the above for use in the treatment of cancer wherein the cancer of B-cell origin is selected from the group consisting of B cell lymphoma, B-lineage acute lymphoblastic leukemia, B-cell chronic lymphocytic leukemia, and B-cell non-Hodgkin's lymphoma.

The present invention provides a TALEN-modified endogenous αβ-TCR negative human cell according to any one of the above or the population of human cells as above or the pharmaceutical composition according to the above for use in the treatment of cancer wherein the cancer is AML, ALL, a T cell lymphoma.

MEANS for Detecting an Endonuclease Modified Primary Cell

The present invention provides a means or a degenerated means for detecting an endonuclease-modified endogenous αβ-TCR negative primary human cell wherein said endonuclease is selected from a TALEN, a Crispr/cas 9, meganuclease, TAL-nuclease, Zinc finger nuclease, In a Polymerase Chain Reaction (PCR), a primer is used to bind to the DNA to start the replication. Usually, the objective is to amplify a specific piece of DNA, so primers are designed to only bind around that sequence of DNA. In contrast, in degenerate oligonucleotide primed PCR (DOP-PCR), one uses primers that can potentially bind to many sequences. This is accomplished by two ways: degenerate base pairing and/or using a low annealing temperature in the first two or so cycles. Degenerate base pairing is also accomplished by using bases like deoxyinosine that can bind to any other base pair. The low initial annealing temperatures stabilize the binding of this primer to the DNA, despite the fact that with only a 6 bp match, the bond between the primer and the DNA is weak as compared to normal adequate condition with non degenerated primers The degenerated primer generally has 6 regular base pairs on the 3' end, a bunch of degenerate nucleotides, and 6 regular base pairs again on the 5' end. The specificity of the probe may be given by the 6 bps on the 3' end. Since it is much easier to match 6 bps than 16 or more, as in a regular PCR primer, this degenerate primer amplifies many more sequences in the genome than regular PCR primers do.

The present invention provides a means for detecting an endonuclease-modified endogenous αβ-TCR negative primary human cell wherein the constant region of the genomic TCR gene (TRAC gene) comprises a genetic modification generated by a rare a cutting endonuclease and affecting cell surface expression of the alpha beta TCR, said genomic TRAC gene further comprising from 5' to 3':

(a) a 5' region of said human genomic TRAC gene upstream
(b) a recognition domain for a rare cutting endonuclease,
(c) a gap or an insertion as compared to the wild type TRAC gene affecting the cell surface expression of the extracellular domain or transmembrane domain of the alpha beta TCR,
said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof,
(c') optionally a second rare cutting endonuclease recognition domain,
(d) a 3' region of the genomic TRAC gene.

The present invention provides a means according to the above for detecting potential off site and on site endonuclease-induced events (double strand DNA cut).

The present invention provides a means according to the above wherein said endonuclease is selected from the group consisting of: Crispr/Cas 9, Cpf1, TALEN, transposase, ZEN, Zinc finger endonuclease, meganuclease, or Mega-TAL.

The present invention provides a means according to the above wherein said endonuclease is selected from the group consisting of: Crispr/Cas 9, TALEN, transposase, Zinc finger endonuclease, meganuclease, MegaTAL, a combination thereof.

The present invention provides a means for identifying a TALEN-modified endogenous αβ-TCR negative human primary cell wherein the constant region of the genomic TCR gene (TRAC gene) comprises a genetic modification generated by a TALEN and affecting cell surface expression of the alpha beta TCR, said genomic TRAC gene comprising from 5' to 3':

(a) a 5' region of said human genomic TRAC gene upstream
(b) a recognition domain for a TALEN, preferably TTGTCCCACAGATATCC (nt 1-17 of SEQ ID NO: 38),
(c) a gap or an insertion as compared to the wild type TRAC gene affecting the cell surface expression of the extracellular domain or transmembrane domain of the alpha beta TCR,
said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof,
(c') optionally a second TALEN recognition domain,
(d) a 3' region of the genomic TRAC gene.

The present invention provides means according to the above wherein at least one means binds to a sequence inserted into the endonuclease modified TRAC gene and/or to the sequence upstream an endonuclease binding sequence.

The present invention provides a means according to the above for detecting off site and on site endonuclease-induced events in engineered human primary cells using at least one probe.

In the present invention, a probe may be designed based on known bona fide on-sites identified using a given endonuclease, preferably a TALEN, more preferably a TALEN binding to TTGTCCCACAGATATCCagaaccctgacc ctgCCGTGTACCAGCTGAGAGA (SEQ ID NO: 38).

Under this preferred aspect, a first half TALEN moiety binds to TTGTCCCACAGATATCC (nt 1-17 of SEQ ID NO: 38), the second binds to CCGTGTACCAGCT-GAGAGA (nt 33-51 of SEQ ID NO: 38) and the dsDNA cut occurs within: agaaccctgaccctg (nt 18-32 of SEQ ID NO: 38).

Any of the known methods allowing detecting and identifying off sites sequences may be used, preferably the adapted guide seq technique of the present invention and method of detection of an insertion of the present invention.

In particular embodiments, the present invention provides a means according to the above for detecting potential off site and on site endonuclease-induced events in engineered human primary cells using at least one probe binding to a sequence inserted into off sequence(s) during the process of engineering human primary cells.

Detection of said such off-site insertion would ultimately allow to put aside and discard engineered human primary cells with off sites as off site events are not desired in endonuclease-engineered human primary cells used as a medicament for immunotherapy in human.

Alternatively, off site events in an endonuclease-engineered human primary cell may be analyzed using lists of bona fide off-site sequences in the human genome identified using any one of the known method for measuring endonuclease-induced off site events in human primary cells.

The present invention provides a means according to the above for detecting potential off site and on site endonuclease-induced events in human primary cells using at least one probe binding to a se-quence corresponding to an endonuclease binding domain or a probe binding to a sequence upstream an endonuclease binding domain.

The complementary sequences may be used.

The present invention provides a means according to the above for detecting potential off site and on site endonuclease-induced events in human primary cells using at least one probe binding to a se-quence corresponding to a defined bona fide off site sequence.

Preferably, the present invention provides a means according to the above for detecting off site and on site TRAC gene-specific endonuclease-induced events in human primary cells.

Preferably, the present invention provides a means according to the above for detecting human cells comprising on site TRAC-specific TALEN-induced events in human primary cells.

Preferably, the present invention provides a means according to the above for detecting on site TRAC-specific TALEN-induced events in human primary cells said probe binds to TTGTCCCACAGATATC (SEQ ID NO: 36) and/or to CCGTGTACCAGCTGAGA (nt 33-51 of SEQ ID NO: 38).

Preferably, the present invention provides a means according to the above for detecting on site TRAC-specific TALEN-induced events in human primary cells said probe binds to ITGTCCCACAGATATC (SEQ ID NO: 36) or GGCACATGGTCGACTCT (SEQ ID NO: 159), preferably to TTGTCCCACAGATATC (SEQ ID NO: 36), and to AACAGGGTGTCTATAG (SEQ ID NO: 160).

The present invention takes advantage of lists of bona fide off-site sequences identified in prior art in the human genome for an endonuclease(s) Crispr, TALEN, meganucleases, Zn Finger nuclease targeting the TRAC gene.

The initial method is those disclosed in Hendel et al., 2015. Trends Biotechnol. February; 33 (2): 132-140; Pattanayak V. 2014. Methods Enzymol. 546:47-78, preferably a guide seq method adapted to TALEN. The present invention provides a means for identifying an endonuclease (preferably a TALEN-modified endogenous αβ-TCR negative human primary cell wherein at least one or at least two different endonucleases were used either together or successively as in PCT/EP2016/066355 and targeting the TRAC gene and at least one another gene selected from those listed in PA2016 70840 which is herein incorporated by reference.

The present invention provides a means for identifying an endonuclease modified αβ-TCR negative human primary cell, preferably a TALEN modified endogenous αβ-TCR negative human primary cell wherein at least one or at least two different endonucleases were used either together or successively as in PCT/EP2016/066355 and targeting the TRAC gene and at least one another gene selected from CD38, CD70, dCK, CD52, beta 2 microglobulin, CIITA, TRBC, PD1, CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, SERCA3, BCAT, IL27RA, STAT1, STAT3, ILT2, ILT4, SEMA7, SHARPIN, STAT1, PEA15, RICTOR, JAK2, AURKA, DNMT3,MT1A,MT2A,PT-GER2, gene generating miR101, gene generating mir26A, gene generating mir21, or gene generating miRNA31. The present invention provides a means for identifying a TALEN-modified endogenous αβ-TCR negative human primary cell wherein at least one or at least two different endonucleases were used either together or successively as in PCT/EP2016/066355 and targeting the TRAC gene and at least one another gene selected from CD38, CD70, dCK, CD52, beta 2 microglobulin, CIITA, TRAC, TRBC, PD1, CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, SERCA3, BCAT, IL27RA, STAT1, STAT3, ILT2, ILT4, SEMA7, SHARPIN, STAT1, PEA15, RICTOR, JAK2, AURKA, DNMT3,MT1A,MT2A,PTGER2, gene generating miR101, gene generating mir26A, gene generating mir21, or gene generating miRNA31.

The present invention provides a means for identifying a TALEN-modified endogenous αβ-TCR negative human primary cell wherein at least one or at least two different TALEN were used targeting the TRAC gene and at least one another gene selected from: dCK, CD52, beta 2 microglobulin, CIITA, TRBC, PD1, CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, SERCA3, BCAT, IL27RA, STAT1, STAT3, ILT2, ILT4, SEMA7, SHARPIN, STAT1, PEA15,RICTOR, JAK2, AURKA, DNMT3,MT1A, MT2A,PTGER2, gene generating miR101, gene generating mir26A, gene generating mir21, or gene generating miRNA31.

The present invention provides a means for identifying a TALEN-modified endogenous αβ-TCR negative human primary cell wherein at least one or at least two different TALEN were used targeting the TRAC gene and at least one another gene selected from: CD38, CD70, CS1, PD1 (Uniprot Q15116), CTLA4 (Uniprot P16410), PPP2CA (Uniprot P67775), PPP2CB (Uniprot P62714), PTPN6 (Uniprot P29350), PTPN22 (Uniprot Q9Y2R2), LAG3 (Uniprot P18627), HAVCR2 (Uniprot Q8TDQO), BTLA (Uniprot Q7Z6A9), CD160 (Uniprot 095971), TIGIT (Uniprot Q495A1), CD96 (Uniprot P40200), CRTAM (Uniprot 095727), LAIR1 (Uniprot Q6GTX8), SIGLEC7 (Uniprot Q9Y286), SIGLEC9 (Uniprot Q9Y336), CD244 (Uniprot Q9BZW8), TNFRSF10B (Uniprot 014763), TNFRSF10A (Uniprot 000220), CASP8 (Uniprot Q14790), CASP10 (Uniprot Q92851), CASP3 (Uniprot P42574), CASP6 (Uniprot P55212), CASP7 (Uniprot P55210), FADD (Uniprot Q13158), FAS (Uniprot P25445), TGFBRII (Uniprot P37173), TGFRBRI (Uniprot Q15582), SMAD2 (Uniprot Q15796), SMAD3 (Uniprot P84022), SMAD4 (Uniprot Q13485), SMAD10 (Uniprot B7ZSB5), SKI (Uniprot P12755), SKIL (Uniprot P12757), TGIF1 (Uniprot Q15583), IL10RA (Uniprot Q13651), IL10RB (Uniprot Q08334), HMOX2 (Uniprot P30519), IL6R (Uniprot P08887), IL6ST (Uniprot P40189), EIF2AK4 (Uniprot Q9P2K8), CSK (Uniprot P41240), PAG1 (Uniprot Q9NWQ8), SIT1 (Uniprot Q9Y3P8), FOXP3 (Uniprot Q9BZS1), PRDM1 (Uniprot Q60636), BATF (Uniprot Q16520), GUCY1A2 (Uniprot P33402), GUCY1A3 (Uniprot Q02108), GUCY1B2 (Uniprot Q8BXH3) and GUCY1B3 (Uniprot Q02153) and for those disclosed in PA201770603 that is to say, human SERCA3, human BCAT, human IL27RA, human STAT1, human STAT3, human ILT2, human ILT4, human SEMA7, human SHARPIN, human STAT1, human PEA15, human RICTOR, human JAK2, human AURKA, human DNMT3, human MT1A, human MT2A, human PTGER2, the human gene generating miR101, mir26A, mir21, or miRNA31 is part of the present invention.

Means for identifying the following TALEN-engineered genes: CD38, CD70, CS1, CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, SERCA3, BCAT, IL27RA, STAT1, STAT3, ILT2, ILT4, SEMA7, SHARPIN, STAT1, PEA15, RICTOR, JAK2, AURKA, DNMT3, MT1A,MT2A,PTGER2, gene generating miR101, mir26A, mir21, or miRNA31, TRAC were generated.

Particularly, meganuclease-induced bona fide off-site sequences in primary cells were identified, as well as CRISPR-induced bona fide off-site sequences were identified, using said endonucleases targeting one of the following human genes or a combination of TRAC and one of the following human genes: TRBC, CD40L, adenosine A2a receptor (A2aR); B7-related protein 1 (B7RP1); B and T lymphocyte attenuator (BTLA); galectin 9 (GAL9), herpesvirus entry mediator (HVEM); inducible T cell co-stimulator (ICOS); interleukin-12-, -IL-27 (IL-12, IL27); killer cell immunoglobulin-like receptor (KIR); lymphocyte activation gene 3 (LAG3); programmed cell death protein 1 (PD1); PD1 ligand (PDL); transforming growth factor-B (TGFB); T cell membrane protein 3 (TIM3), CD38, CD70, CS1, CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, SERCA3, BCAT, IL27RA, STAT1, STAT3, ILT2, ILT4, SEMA7, SHARPIN, STAT1, PEA15, RICTOR, JAK2, AURKA, DNMT3,MT1A,MT2A,PTGER2, gene generating miR101, mir26A, mir21, or miRNA31.

The present invention provides Means or Probe(s) for detecting off sites and/or on sites generated during cell engineering using an endonuclease, preferably an endonuclease selected from a TALEN, a Meganuclease, a Crispr/Cas 9, a Zinc Finger endonuclease, more preferably a TALEN and even more preferably a TALEN binding to the TRAC gene, preferably to a sequence in the exon 1 of the TRAC gene.

The present invention provides Means or Probe(s) for detecting off sites and/or on sites generated during cell engineering using a TALEN binding to the following sequence ttgtcccacagATATC.

The present invention provides Means or Probe(s) for detecting off sites and/or on sites generated during cell engineering using an endonuclease selected from a TALEN, a meganuclease, a Crispr/Cas 9, a Zinc Finger endonuclease, a megaTAL more preferably a TALEN and even more preferably a TAL-ENthat bind to a sequence located in any one of the genes identified in 62/410,187:

| symbol | description |
| --- | --- |
| Il21 | interleukin 21 |
| Il3 | interleukin 3 |
| Ccl4 | isopentenyl-diphosphate delta isomerase 2 |
| Il21 | granzyme C |
| Gp49a | chemokine (C-C motif) receptor 8 |
| Cxcl10 | interleukin 2 |
| Nr4a3 | interleukin 1 receptor, type 1 |
| Lilrb4 | tumor necrosis factor (ligand) superfamily, member 4 |
| Cd200 | neuronal calcium sensor 1 |
| Cdkn1a | CDK5 and Abl enzyme substrate 1 |
| Gzmc | transmembrane and tetratricopeptide repeat containing 2 |
| Nr4a2 | LON peptidase N-terminal domain and ring finger 1 |
| Cish | glycoprotein 49 A |
| Nr4a1 | polo-like kinase 2 |
| Tnf | lipase, endothelial |
| Ccr8 | cyclin-dependent kinase inhibitor 1A (P21) |
| Ladl | grainyhead-like 1 (*Drosophila*) |
| Slamf1 | cellular retinoic acid binding protein II |
| Crabp2 | adenylate kinase 4 |
| Furin | microtubule-associated protein 1B |
| Gadd45g | acyl-CoA synthetase long-chain family member 6 |
| Bcl2l1 | zinc finger E-box binding homeobox 2 |
| Ncs1 | CD200 antigen |
| Ciart | carboxypeptidase D |
| Ahr | thioredoxin reductase 3 |
| Spry1 | myosin IE |
| Tnfsf4 | RNA binding protein with multiple splicing 2 |
| Myo10 | mitogen-activated protein kinase kinase 3, opposite strand |
| Dusp5 | PERP, TP53 apoptosis effector |
| Myc | myosin X |
| Psrc1 | immediate early response 3 |
| St6galnac4 | folliculin interacting protein 2 |
| Nfkbid | leukocyte immunoglobulin-like receptor, subfamily B, member 4 |
| Bst2 | circadian associated repressor of transcription |
| Txnrd3 | RAR-related orphan receptor gamma |
| Plk2 | proline/serine-rich coiled-coil 1 |
| Gfi1 | cysteine rich protein 2 |
| Pim1 | cAMP responsive element modulator |
| Pvt1 | chemokine (C-C motif) ligand 4 |
| Nfkbib | nuclear receptor subfamily 4, group A, member 2 |
| Gnl2 | transglutaminase 2, C polypeptide |
| Cd69 | synapse defective 1, Rho GTPase, homolog 2 (*C, elegans*) |
| Dgat2 | sprouty homolog 1 (*Drosophila*) |
| Atf3 | activating transcription factor 3 |
| Tnfrsf21 | pogo transposable element with KRAB domain |
| Lonrf1 | tumor necrosis factor receptor superfamily, member 21 |
| Cables1 | cytokine inducible SH2-containing protein |
| Cpd | lymphotoxin A |

-continued

| symbol | description |
| --- | --- |
| Qtrtd1 | FBJ osteosarcoma oncogene |
| Polr3d | signaling lymphocytic activation molecule family member 1 |
| Kcnq5 | syndecan 3 |
| Fos | mitochondrial ribosomal protein L47 |
| Slc19a2 | ladinin |
| Hif1a | E2F transcription factor 5 |
| Il15ra | ISG15 ubiquitin-like modifier |
| Nfkb1 | aryl-hydrocarbon receptor |
| Phlda3 | diacylglycerol O-acyltransferase 2 |
| Mtrr | FBJ osteosarcoma oncogene B |
| Pogk | pleckstrin homology-like domain, family A, member 3 |
| Map2k3os | potassium voltage-gated channel, subfamily Q, member 5 |
| Egr2 | tumor necrosis factor receptor superfamily, member 10b |
| Isg15 | Mirl7 host gene 1 (non-protein coding) |
| Perp | glucose-fructose oxidoreductase domain containing 1 |
| Ipo4 | plexin A1 |
| Mphosph10 | heat shock factor 2 |
| Plk3 | carbohydrate sulfotransferase 11 |
| Ifitm3 | growth arrest and DNA-damage-inducible 45 gamma |
| Polr1b | solute carrier family 5 (sodium-dependent vitamin transporter), member 6 |
| Usp18 | interferon induced transmembrane protein 3 |
| Top1mt | DENN/MADD domain containing 5A |
| Dkc1 | plasminogen activator, urokinase receptor |
| Polr1c | solute carrier family 19 (thiamine transporter), member 2 |
| Cdk6 | ubiquitin domain containing 2 |
| Ier3 | nuclear receptor subfamily 4, group A, member 3 |
| Lta | zinc finger protein 52 |
| Ptprs | SH3 domain containing ring finger 1 |
| Fnip2 | dihydrouridine synthase 2 |
| Asna1 | cyclin-dependent kinase 5, regulatory subunit 1 (p35) |
| Mybbp1a | processing of precursor 7, ribonuclease P family, (S, cerevisiae) |
| Il1r1 | growth factor independent 1 |
| Dennd5a | interleukin 15 receptor, alpha chain |
| E2f5 | BCL2-like 1 |
| Rcl1 | protein tyrosine phosphatase, receptor type, s |
| Fosl2 | plasmacytoma variant translocation 1 |
| Atad3a | fos-like antigen 2 |
| Bax | BCL2-associated X protein |
| Phf6 | solute carrier family 4, sodium bicarbonate cotransporter, member 7 |
| Zfp52 | tumor necrosis factor receptor superfamily, member 4 |
| Crtam | chemokine (C-X-C motif) ligand 10 |
| Nop14 | polo-like kinase 3 |
| Rel | CD3E antigen, epsilon polypeptide associated protein |
| Gramd1b | tumor necrosis factor (ligand) superfamily, member 11 |
| Ifi27l2a | polymerase (RNA) III (DNA directed) polypeptide D |
| Tnfrsf10b | early growth response 2 |
| Rpl7l1 | DnaJ (Hsp40) homolog, subfamily C, member 2 |
| Eif1a | DNA topoisomerase 1, mitochondrial |
| Nfkb2 | tripartite motif-containing 30D |
| Heatr1 | DnaJ (Hsp40) homolog, subfamily C, member 21 |
| Utp20 | SAM domain, SH3 domain and nuclear localization signals, 1 |
| Chst11 | solute carrier family 5 (inositol transporters), member 3 |
| Ddx21 | mitochondrial ribosomal protein L15 |
| Hsf2 | dual specificity phosphatase 5 |
| Bccip | apoptosis enhancing nuclease |
| Tagap | ets variant 6 |
| Sdc3 | DIM1 dimethyladenosine transferase 1-like (S, cerevisiae) |

-continued

| symbol | description |
| --- | --- |
| Sytl3 | 2'-5' oligoadenylate synthetase-like 1 |
| Gtpbp4 | UTP18, small subunit (SSU) processome component, homolog (yeast) |
| Crip2 | BRCA2 and CDKN1A interacting protein |
| Sh3rf1 | synaptotagmin-like 3 |
| Nsfl1c | 5-methyltetrahydrofolate-homocysteine methyltransferase reductase |
| Gtf2f1 | URB2 ribosome biogenesis 2 homolog (S, cerevisiae) |
| Slc4a7 | ubiquitin-conjugating enzyme E2C binding protein |
| Etv6 | lysine (K)-specific demethylase 2B |
| Trim30d | queuine tRNA-ribosyltransferase domain containing 1 |
| Ddx27 | ubiquitin specific peptidase 31 |
| Pwp2 | eukaryotic translation initiation factor 2-alpha kinase 2 |
| Chchd2 | ATPase family, AAA domain containing 3A |
| Myo1e | adhesion molecule, interacts with CXADR antigen 1 |
| Eif5b | SUMO/sentrin specific peptidase 3 |
| Stat5a | ESF1, nucleolar pre-rRNA processing protein, homolog (S, cerevisiae) |
| Cops6 | deoxynucleotidyltransferase, terminal, interacting protein 2 |
| D19Bwg1357e | TGFB-induced factor homeobox 1 |
| Aatf | eukaryotic translation initiation factor 1A |
| Aen | interferon-stimulated protein |
| Amical | pleiomorphic adenoma gene-like 2 |
| Wdr43 | PWP2 periodic tryptophan protein homolog (yeast) |
| Cct4 | furin (paired basic amino acid cleaving enzyme) |
| Nifk | tumor necrosis factor |
| Tgm2 | apoptosis antagonizing transcription factor |
| Ero1l | interferon, alpha-inducible protein 27 like 2A |
| Gfod1 | ST6 (alpha-N-acetyl-neuraminyl-2,3-beta-galactosyl-1,3)-N-acetylgalactosaminide alpha-2,6-sialyltransferase 4 |
| Ak4 | methyltransferase like 1 |
| Sdad1 | notchless homolog 1 (Drosophila) |
| Dimt1 | mitochondrial ribosomal protein L3 |
| Esf1 | UBX domain protein 2A |
| Cd3eap | guanine nucleotide binding protein-like 2 (nucleolar) |
| Samsn1 | programmed cell death 11 |
| Tnfrsf4 | cyclin-dependent kinase 8 |
| Mettl1 | eukaryotic translation initiation factor 5B |
| Cd274 | RNA terminal phosphate cyclase-like 1 |
| Ubtd2 | NSFL1 (p97) cofactor (p47) |
| Icos | nuclear factor of kappa light polypeptide gene enhancer in B cells inhibitor, delta |
| Kdm2b | M-phase phosphoprotein 10 (U3 small nucleolar ribonucleoprotein) |
| Larp4 | GRAM domain containing 1B |
| Eif3d | ERO1-like (S, cerevisiae) |
| Tnfaip3 | nuclear receptor subfamily 4, group A, member 1 |
| Map1b | surfeit gene 2 |
| Cdv3 | N(alpha)-acetyltransferase 25, NatB auxiliary subunit |
| Plac8 | yrdC domain containing (E, coli) |
| Mrpl3 | La ribonucleoprotein domain family, member 4 |
| Surf2 | SDA1 domain containing 1 |
| Ubxn2a | importin 4 |
| Utp18 | inducible T cell co-stimulator |
| Isg20 | solute carrier family 7 (cationic amino acid transporter, y+ system), member 1 |
| Dnajc2 | arsA arsenite transporter, ATP-binding, homolog 1 (bacterial) |
| Jak2 | polymerase (RNA) I polypeptide C |
| Slc7a1 | spermatogenesis associated 5 |
| Syde2 | ubiquitin specific peptidase 18 |
| Slc5a6 | placenta-specific 8 |
| Dnttip2 | general transcription factor IIF, polypeptide 1 |
| Idi2 | nuclear factor of kappa light polypeptide gene enhancer in B cells inhibitor, beta |

-continued

| symbol | description |
|---|---|
| Dus2 | PHD finger protein 6 |
| Pitrm1 | RRN3 RNA polymerase 1 transcription factor homolog (yeast) |
| Plxna1 | cytotoxic and regulatory T cell molecule |
| Cdk5r1 | COP9 (constitutive photomorphogenic) homolog, subunit 6 (*Arabidopsis thaliana*) |
| Ube2cbp | asparagine-linked glycosylation 3 (alpha-1,3-mannosyltransferase) |
| Tnfsf11 | tryptophanyl-tRNA synthetase |
| Pop7 | hypoxia up-regulated 1 |
| Psme3 | family with sequence similarity 60, member A |
| Mir17hg | bone marrow stromal cell antigen 2 |
| Tsr1 | nuclear factor of kappa light polypeptide gene enhancer in B cells 2, p49/p100 |
| Rbpms2 | UTP20, small subunit (SSU) processome component, homolog (yeast) |
| Mrp147 | CD274 antigen |
| Rab8b | proviral integration site 1 |
| Plagl2 | signal transducer and activator of transcription 5A |
| Grhl1 | CD69 antigen |
| Zeb2 | pitrilysin metallepetidase 1 |
| sept-02 | cyclin-dependent kinase 6 |
| Slc5a3 | DEAD (Asp-Glu-Ala-Asp) box polypeptide 27 |
| Naa25 | polymerase (RNA) I polypeptide B |
| Plaur | tumor necrosis factor, alpha-induced protein 3 |
| Metap1 | nodal modulator 1 |
| Alg3 | NOP14 nucleolar protein |
| Mrpl15 | ribosomal protein L7-like 1 |
| Oasl1 | methionyl aminopeptidase 1 |
| Rorc | hypoxia inducible factor 1, alpha subunit |
| Nomo1 | Janus kinase 2 |
| Tgif1 | nuclear factor of kappa light polypeptide gene enhancer in B cells 1, p105 |
| Lipg | reticuloendotheliosis oncogene |
| Rrn3 | septin 2 |
| Dnajc21 | nucleolar protein interacting with the FHA domain of MKI67 |
| Yrdc | elongation factor Tu GTP binding domain containing 2 |
| Acsl6 | myelocytomatosis oncogene |
| Spata5 | dyskeratosis congenita 1, dyskerin |
| Urb2 | carnitine deficiency-associated gene expressed in ventricle 3 |
| Nle1 | GTP binding protein 4 |
| Wars | HEAT repeat containing 1 |
| Crem | proteaseome (prosome, macropain) activator subunit 3 (PA28 gamma, Ki) |
| Larp1 | La ribonucleoprotein domain family, member 1 |
| Eif2ak2 | DNA segment, Chr 19, Brigham & Women's Genetics 1357 expressed |
| Hyou1 | eukaryotic translation initiation factor 3, subunit D |
| Senp3 | TSR1 20S rRNA accumulation |
| Tmtc2 | MYB binding protein (P160) 1a |
| Fosb | T cell activation Rho GTPase activating protein |
| Pdcd11 | RAB8B, member RAS oncogene family |
| Usp31 | DEAD (Asp-Glu-Ala-Asp) box polypeptide 21 |
| Cdk8 | chaperonin containing Tcp1, subunit 4 (delta) |
| Eftud2 | coiled-coil-helix-coiled-coil-helix domain containing 2 |
| Fam60a | WD repeat domain 43 |

Selection of preferred endogenous genes that are constantly active during immune cell activation (dependent or independent from T-cell activation).

| Symbol | Gene description |
|---|---|
| CD3G | CD3 gamma |
| Rn28s1 | 28S ribosomal RNA |
| Rn18s | 18S ribosomal RNA |
| Rn7sk | RNA, 7SK, nuclear |
| Actg1 | actin, gamma, cytoplasmic 1 |

-continued

| Symbol | Gene description |
|---|---|
| B2m | beta-2 microglobulin |
| Rpl18a | ribosomal protein L18A |
| Pabpc1 | poly(A) binding protein, cytoplasmic 1 |
| Gapdh | glyceraldehyde-3-phosphate dehydrogenase |
| Rpl19 | ribosomal protein L19 |
| Rpl17 | ribosomal protein L17 |
| Rplp0 | ribosomal protein, large, P0 |
| Cfl1 | cofilin 1, non-muscle |
| Pfn1 | profilin 1 |

Selection of genes that are transiently upregulated upon T-cell activation.

| Symbol | Gene description |
|---|---|
| Il3 | interleukin 3 |
| Il2 | interleukin 2 |
| Ccl4 | chemokine (C-C motif) ligand 4 |
| Il21 | interleukin 21 |
| Gp49a | glycoprotein 49 A |
| Nr4a3 | nuclear receptor subfamily 4, group A, member 3 |
| Lilrb4 | leukocyte immunoglobulin-like receptor, subfamily B, member 4 |
| Cd200 | CD200 antigen |
| Cdkn1a | cyclin-dependent kinase inhibitor 1A (P21) |
| Gzmc | granzyme C |
| Nr4a2 | nuclear receptor subfamily 4, group A, member 2 |
| Cish | cytokine inducible SH2-containing protein |
| Ccr8 | chemokine (C-C motif) receptor 8 |
| Lad1 | ladinin |
| Crabp2 | cellular retinoic acid binding protein II |

Selection of genes that are upregulated over more than 24 hours upon T-cell activation.

| Symbol | Description |
|---|---|
| Gzmb | granzyme B |
| Tbx21 | T-box 21 |
| Pdcd1 | programmed cell death 1 |
| Plek | pleckstrin |
| Chek1 | checkpoint kinase 1 |
| Slamf7 | SLAM family member 7 |
| Zbtb32 | zinc finger and BTB domain containing 32 |
| Tigit | T cell immunoreceptor with Ig and ITIM domains |
| Lag3 | lymphocyte-activation gene 3 |
| Gzma | granzyme A |
| Wee1 | WEE 1 homolog 1 (*S. pombe*) |
| Il2rb2 | interleukin 12 receptor, beta 2 |
| Ccr5 | chemokine (C-C motif) receptor 5 |
| Eea1 | early endosome antigen 1 |
| Dtl | denticleless homolog (*Drosophila*) |

Selection of genes that are down-regulated upon immune cell activation.

| Symbol | Gene description |
|---|---|
| Spata6 | spermatogenesis associated 6 |
| Itga6 | integrin alpha 6 |
| Rcbtb2 | regulator of chromosome condensation (RCC1) and BTB (POZ) domain containing protein 2 |
| Cd1d1 | CD1d1 antigen |
| St8sia4 | ST8 alpha-N-acetyl-neuraminide alpha-2,8-sialyltransferase 4 |
| Itgae | integrin alpha E, epithelial-associated |
| Fam214a | family with sequence similarity 214, member A |
| Slc6a19 | solute carrier family 6 (neurotransmitter transporter), member 19 |

-continued

| Symbol | Gene description |
|--------|------------------|
| Cd55 | CD55 antigen |
| Xkrx | X Kell blood group precursor related X linked |
| Mturn | maturin, neural progenitor differentiation regulator homolog (Xenopus) |
| H2-Ob | histocompatibility 2, O region beta locus |
| Cnr2 | cannabinoid receptor 2 (macrophage) |
| Itgae | integrin alpha E, epithelial-associated |
| Raver2 | ribonucleoprotein, PTB-binding 2 |
| Zbtb20 | zinc finger and BTB domain containing 20 |
| Arrb1 | arrestin, beta 1 |
| Abca1 | ATP-binding cassette, sub-family A (ABC1), member 1 |
| Tet1 | tet methylcytosine dioxygenase 1 |
| Slc 16a5 | solute carrier family 16 (monocarboxylic acid transporters), member 5 |
| Trav14-1 | T cell receptor alpha variable 14-1 |
| Ampd3 | adenosine monophosphate deaminase 3 |
| Zfp640 | zinc finger protein 640 |
| LOC100038422 | uncharacterized LOC100038422 |
| Zfp600 | zinc finger protein 600 |
| Serpinb3a | serine (or cysteine) peptidase inhibitor, clade B (ovalbumin), member 3A |
| Tas2r106 | taste receptor, type 2, member 106 |
| Magea3 | melanoma antigen, family A, 3 |
| Omt2a | oocyte maturation, alpha |
| Cpxcr1 | CPX chromosome region, candidate 1 |
| Hsf3 | heat shock transcription factor 3 |
| Pbsn | Probasin |
| Sbp | spermine binding protein |
| Wfdc6b | WAP four-disulfide core domain 6B |
| Meiob | meiosis specific with OB domains |
| Dnm3os | dynamin 3, opposite strand |
| Skint22 | selection and upkeep of intraepithelial T cells 11 |

Selection of human genes that are silent upon T-cell activation (safe harbor gene targeted integration loci).

In particular, the present invention provides Means or Probe(s) for detecting off sites and/or on sites generated during cell engineering using a TALEN binding to the TCR alpha, the TCR beta, more preferably to the TCR alpha and to the following sequence ttgtcccacagATATC, even more preferably said means or probe comprise a sequence complementary to a sequence comprising tigtcccacagA-TATC (SEQ ID NO: 36) and a sequence complementary to a sequence in the TRAC gene after the initiation codon and downstream the sequence CCGTGTACCAGCTGAGA (SEQ ID NO: 26).

In the present invention off sites cut using a TALEN binding to the following sequence ttgtcccacagA-TATC (SEQ ID NO: 36), said means or probe comprising a sequence complementary to a sequence comprising ttgtcccacagA-TATC (SEQ ID NO: 36) and/or a sequence complementary to a sequence in the TRAC gene downstream the sequence CCGTGTACCAGCTGAGA (SEQ ID NO: 26), are below the level of detection using a guide seq analysis as adapted for TALEN.

In particular embodiments, the present invention provides means for detecting off site and on site of endonuclease-induced events wherein detecting off sites and on sites is performed by a guide-seq adapted technique implemented during the process of making said endogenous αβ-TCR negative human T cell comprising an endonuclease modified genomic TRAC gene.

In particular embodiments, the present invention provides a means according to any one of the above wherein said TALEN modified genomic TRAC gene comprises:

(a) a 5' region of said human genomic TRAC gene;

(b) a recognition domain for a TALEN, preferably a recognition domain for a TALEN comprising the following sequence ttgtcccacag.ATATC (SEQ ID NO: 36), or ttgtcccacagATATCCAG (SEQ ID NO: 37), or (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence, a stop codon, a sequence coding for a self-cleaving peptide in frame with the TRAC open reading frame, an IRES, a sequence coding a chimeric antigen receptor (CAR), a sequence coding a TCR, a sequence coding a protein conferring sensitivity to a drug, a sequence coding a protein conferring resistance to a drug, a termination sequence, a combination thereof, (c') optionally a second TALEN recognition domain, (d) a 3' region of the genomic TRAC gene;

and said means binds to said an endonuclease modified genomic TRAC gene and/or to off sites Degenerated oligonucleotides for adapted PCR are provided here as a probe binding to the engineered TRAC gene, optionally to off sites and further amplification by pcr.

A degenerate primer is defined as: "A mix of oligonucleotide sequences in which some positions contain a number of possible bases, giving a population of primers with similar sequences that cover all possible nucleotide combinations for a given protein sequence".

In particular embodiments, the present invention provides means for detecting a TALEN modified endogenous αβ-TCR negative human cell, said means binding to at least 5, 6, 7, 8, 9, 10 bases of the following sequence ttgtcccaca-gATATC (SEQ ID NO: 36).

In particular embodiments, the present invention provides means for detecting an endonuclease modified endogenous αβ-TCR negative human cell comprising a probe wherein said probe binds to a sequence in the modified genomic TRAC gene, said probe binds to a sequence upstream the first endonuclease binding domain or said probe binds to a sequence upstream said endonuclease recognition domain, and/or to a sequence encoding a tag.

In the case of endonucleases (TALENs, meganucleases) comprising at least two separated domains or monomers, the first endonuclease binding domain or recognition domain is the first binding domain or recognition domain in 5' and binds the left sequence.

In particular embodiments, the present invention provides means for detecting a TALEN modified endogenous αβ-TCR negative human cell comprising a probe wherein said probe binds to a sequence in the modified genomic TRAC gene, upstream a TALEN binding domain or TALEN recognition domain, and/or to a sequence encoding a tag.

In particular embodiments, the present invention provides means for detecting a TALEN modified endogenous αβ-TCR negative human cell comprising a probe wherein said probe binds to at least 10 bases of a sequence comprising ttgtcccacag.ATATC (SEQ ID NO: 36), or ttgtcccacagA-TATCCAG (SEQ ID NO: 37), in the modified genomic TRAC gene.

In particular embodiments, the present invention provides means for detecting an endonuclease-modified endogenous αβ-TCR negative human cell by polymerase chain reaction (pcr) and off sites modifications, preferably by guide sequence.

In particular embodiments, the present invention provides means for detecting an endonuclease-modified endogenous αβ-TCR negative human cell by deep sequencing and off sites modifications, preferably by guide sequence.

In particular embodiments, the present invention provides means comprising a sequence complementary to an inactivated genomic TCRA gene wherein an exogenous coding sequence was integrated using one or more endonucleases and/or a viral vector.

The present invention provides an endonuclease-modified endogenous αβ-TCR negative human cell as any one of the above comprising an inactivated genomic TCRA gene wherein an exogenous sequence coding a CAR was integrated into the genomic TCRA gene using a lentiviral vector or a AAV vector and said genomic disruptions are performed using a CRISPR/CAS9, meganuclease, a megaTAL or a TALEN endonuclease system.

The present invention provides a TALEN-modified endogenous αβ-TCR negative human cell according to any one of the above wherein an exogenous sequence coding a CAR was integrated into the genomic TCRA gene using a lentiviral vector or a AAV vector introduced by electroporation or nucleofection.

The present invention provides a TRAC-specific endonuclease engineered human cell with an endonuclease specific off site pattern engineered using an AAV6 vector.

The present invention provides a TRAC exon 1-specific endonuclease engineered human cell with an endonuclease specific off site pattern, engineered using an AAV6 vector.

The present invention provides a TRAC exon 1-specific endonuclease engineered human cell with an endonuclease specific off site pattern, engineered using an AAV6/AAV2 vector.

The present invention provides a TRAC exon 1-specific TALEN that binds to at least 10 bases of the sequence ttgtcccacagATATC (SEQ ID NO: 36) engineered human cell, engineered using an AAV6 vector and with a reduced specific off target pattern as compared to other TRAC exon 1-specific endonuclease engineered human cell.

The present invention provides a TALEN-modified endogenous αβ-TCR negative human cell wherein an exogenous sequence coding a CAR was integrated into the genomic TCRA gene using an AAV6/2 vector. The present invention provides a TALEN-modified endogenous αβ-TCR negative human cell wherein an exogenous sequence coding a CAR was integrated into the genomic TCRA gene using an AAV6/2 vector said vector was introduced by electroporation or by nucleofection.

The present invention provides a method for treating a patient in need thereof, the method comprising administering a cell according to any one of the preceding embodiments.

The present invention provides a kit comprising at least one TALEN that binds to the genomic TRAC gene, a TALEN that binds to an endogenous cytokine inducible SH2-containing (CISH) gene and a TALEN that binds to an endogenous gene selected from adenosine A2a receptor (ADORA), CD276, V-set domain containing T cell activation inhibitor 1 (VTCN1), B and T lymphocyte associated (BTLA), cytotoxic T-lymphocyte-associated protein 4 (CTLA4), indoleamine 2,3-dioxygenase 1 (IDOI), killer cell immunoglobulin-like receptor, three domains, long cytoplasmic tail, 1 (KIR3DL1), lymphocyte-activation gene 3 (LAG3), programmed cell death 1 (PD-1), hepatitis A virus cellular receptor 2 (HAVCR2), V-domain immunoglobulin suppressor of T-cell activation (VISTA), natural killer cell receptor 2B4 (CD244), hypoxanthine phosphoribosyltransferase 1 (HPRT), adeno-associated virus integration site (AAVS SITE (E.G. AAVS 1, AAVS2, ETC.)), or chemokine (C—C motif) receptor 5 (gene/pseudogene) (CCR5).

The present invention provides a method for producing a TALEN-modified endogenous αβ-TCR negative human primary cell said method comprising:
(a) introducing into a human primary cell:
(i) a first nucleic acid sequence encoding an engineered nuclease; or an engineered nuclease protein; wherein said engineered nuclease produces a cleavage at a recognition sequence within said human TCR alpha constant region gene; and
(b) a second nucleic acid sequence comprising an exogenous polynucleotide;
wherein the sequence of said exogenous polynucleotide is inserted into said human TCR alpha constant region gene at said cleavage site; and further wherein said genetically-modified primary cell has reduced cell-surface expression of the endogenous TCR when compared to an unmodified control primary cell.

The present invention provides a method as above wherein said exogenous polynucleotide comprises a nucleic acid sequence encoding a chimeric antigen receptor, wherein said chimeric antigen receptor comprises an extracellular ligand-binding domain and one or more intracellular signaling domains.

The present invention provides a method as above, wherein said exogenous polynucleotide comprises a first promoter sequence, such as a promoter which activity is conditional that drives expression of said exogenous polynucleotide.

The present invention provides a method as above, wherein at least said second nucleic acid sequence is introduced into said cell by contacting said cell with a recombinant adeno-associated virus (AAV6) vector comprising said second nucleic acid sequence.

The present invention provides a method as above, wherein said recombinant AAV vector is a self-complementary AAV vector.

The present invention provides a method as above, wherein said recombinant AAV vector derived at least in part from an AAV6.

The present invention provides a method as above, wherein said engineered nuclease is a meganuclease, a zinc-finger nuclease (ZFN), a transcription activator-like effector nuclease (TALEN), a CRISPR/Cas nuclease, or a megaTAL nuclease.

The present invention provides a method as above, wherein said engineered nuclease is a recombinant TALEN.

The present invention provides a method as above, wherein said recombinant TALEN comprises a first subunit and a second subunit, wherein said first subunit binds to a first recognition half-site, and wherein said second subunit binds to a second recognition half-site.

The present invention provides a method as above, wherein the first recognition half-site of the TALEN has the following sequence ttgtcccacagATATCCAG (SEQ ID NO: 37).

The present invention provides a method as above, wherein said engineered nuclease is a meganuclease.

The present invention provides a method as above, wherein said recombinant meganuclease recognizes and cleaves a recognition sequence within residues 93-208 of the wild-type human TCR alpha constant region, wherein said recombinant meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region.

The present invention provides a method as above, wherein said meganuclease is a single-chain meganuclease comprising a linker, wherein said linker covalently joins said first subunit and said second subunit.

The present invention provides a means of detection of cells obtained according to any of one the method above wherein a meganuclease recognizing and cleaving a recognition sequence within residues 93-208 of the wild-type human TCR alpha constant region, is used.

In particular embodiments, the present invention provides a human cell or a population of human cells wherein the constant region of the genomic TCR gene (TRAC gene) comprises a genetic modification generated by a meganuclease recognizing and cleaving a recognition domain or sequence within residues 93-208 of the wild-type human TCR alpha constant region and affecting cell surface expression of the alpha beta TCR, said genomic TRAC gene further comprising from 5' to 3':

(a) a 5' region of said human genomic TRAC gene upstream a recognition domain for meganuclease recognizing and cleaving a recognition domain or sequence within residues 93-208 of the wild-type human TCR alpha constant region, (b) a recognition domain for a meganuclease, within residues 93-208 of the wild-type human TCR alpha constant region, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence, a stop codon, a sequence coding for a self-cleaving peptide in frame with the TRAC open reading frame, an IRES, a sequence coding a chimeric antigen receptor (CAR), a sequence coding a TCR, a sequence coding a protein conferring sensitivity to a drug, a sequence coding a protein conferring resistance to a drug, a termination sequence, a combination thereof, (c') optionally a second megonuclease recognition domain, within residues 93-208 of the wild-type human TCR alpha constant region, (d) a 3' region of the genomic TRAC gene, In one embodiment, the present invention provides a mean of detecting a human cell produced using a meganuclease recognizing and cleaving a recognition domain or sequence within residues 93-208 of the wild-type human TCR alpha constant region.

In particular embodiments, the present invention provides a mean, means for detecting a human cell produced using a crispr/cas 9 system wherein said guide mRNA recognizes the following sequence in the TRAC exon 1: GGGC-TATAGGAGGTCTTGGGAC (SEQ ID NO: 164).

Thus, in one aspect, the invention provides a means for detecting a Crispr/cas 9-modified cell comprising in its genome a modified human TCR alpha constant region gene, wherein the modified human TCR alpha constant region gene comprises from 5' to 3': (a) a 5' region of the human TCR alpha constant region gene; (b) a PAM, (b') an exogenous polynucleotide; and (c) a 3' region of the human TCR alpha constant region gene.

The present invention provides therefore a means for detecting cells obtained according to any of one the method above.

The present invention provides a means of SEQ ID NO: 5, SEQ ID NO: 6, SEQ ID NO: 7, a combination thereof or any degenerated means derived from SEQ ID NO: 5, SEQ ID NO: 6, SEQ ID NO: 7, a combination thereof.

The present invention provides a means as above for detecting on site and/or off site cleavage by endonuclease, in particular as a step in a GUIDE SEQ method.

The present invention provides the means as above for detecting on site and/or off site cleavage by endonuclease.

The present invention provides means as above for detecting on site and/or off site cleavage by endonuclease of any one of SEQ ID N° 13 to 22, a combination thereof.

Figure 1:
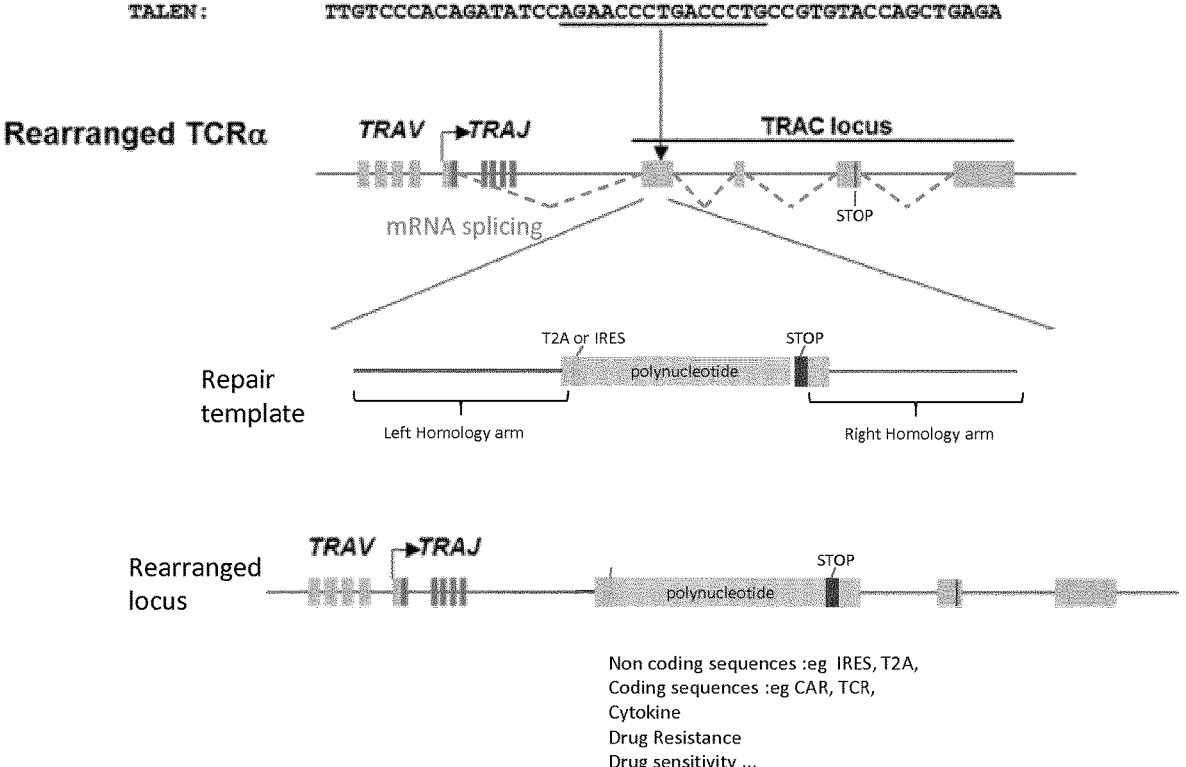
FIG. 1. TCR KO (SEQ ID NO: 38), exogenous gene such as a chimeric antigen receptor (CAR), expressed FIG. 2. Endogenous TCR maintained, exogenous gene, such as a chimeric antigen receptor (CAR), co-expressed FIG. 3. Endogenous TCR inactivated (SEQ ID NO: 38), Recombinant TCR expressed FIG. 4. TCR KO (SEQ ID NO: 38), exogenous gene expressed (IRES)
Figure 2:
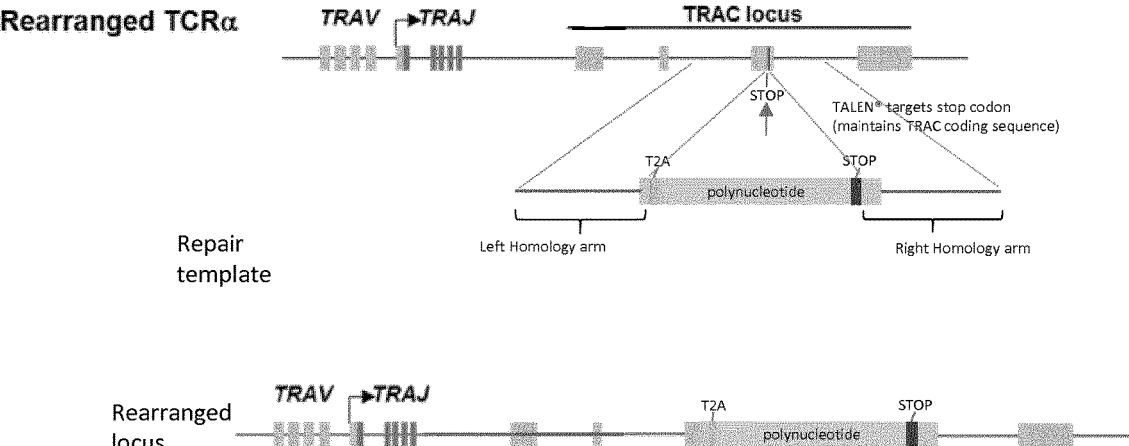
Figure 3:
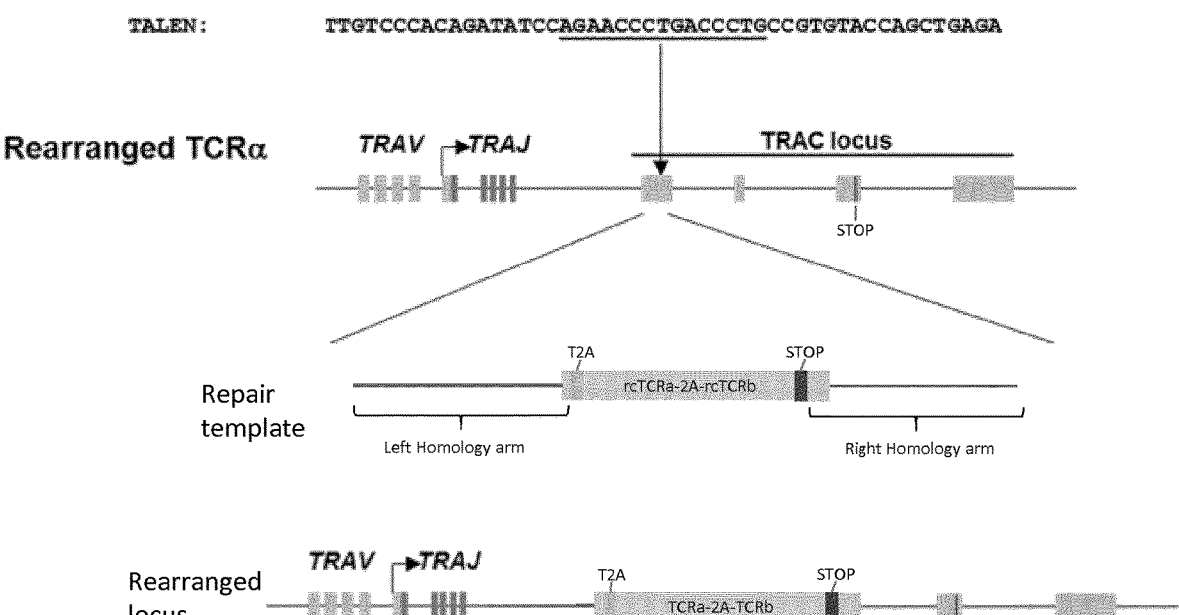
Figure 4:
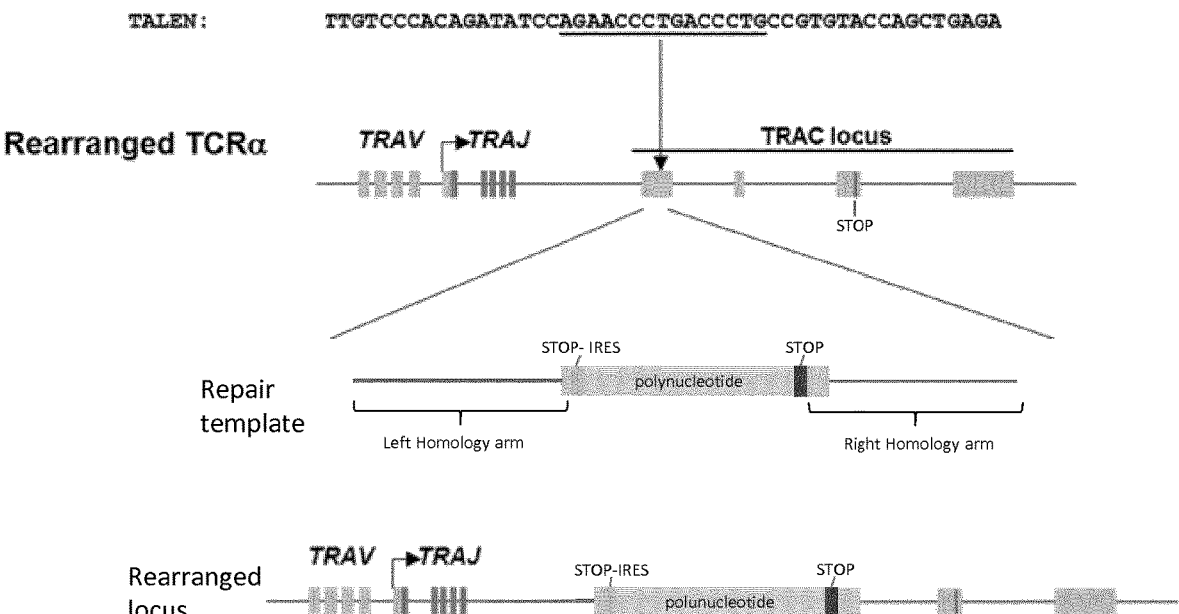
Figure 5:
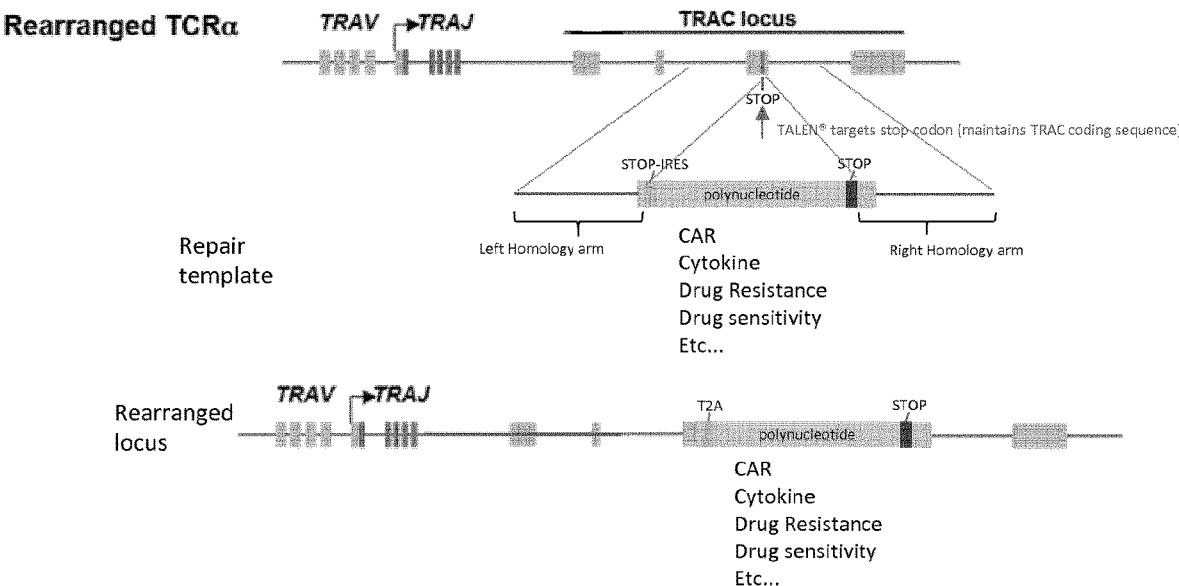
FIG. 5. Endogenous TCR maintained, exogenous gene co-expressed (IRES)
Figure 6:
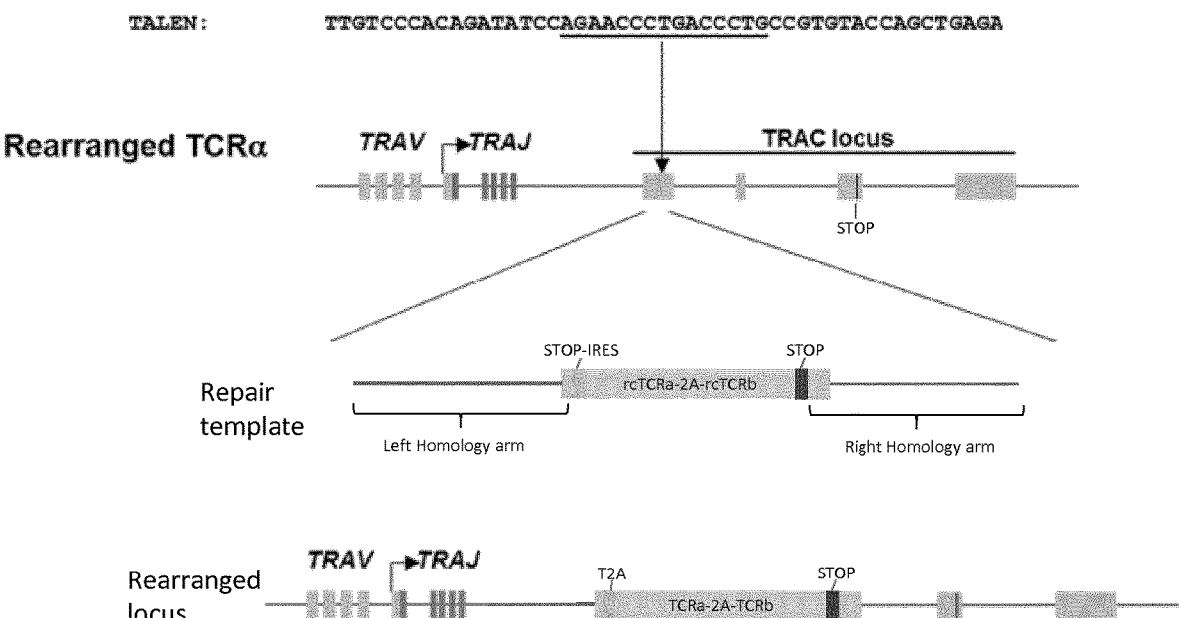
FIG. 6. Endogenous TCR inactivated (SEQ ID NO: 38), Recombinant TCR expressed (IRES)
Figure 7:
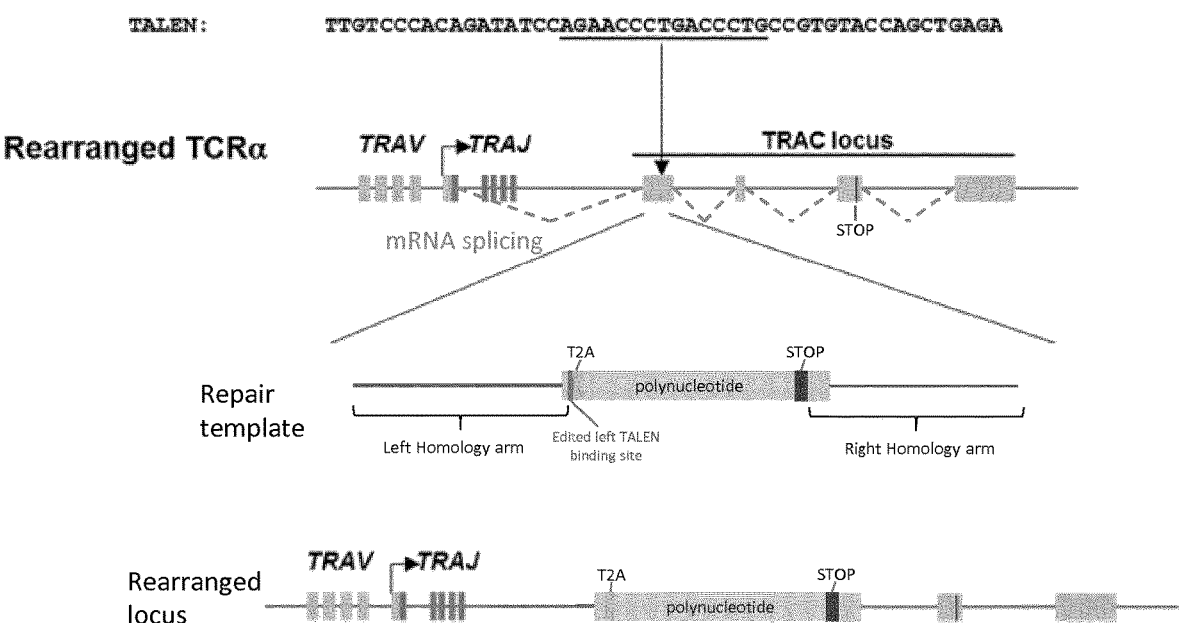
FIG. 7. TCR KO (SEQ ID NO: 38), exogenous gene expressed, TALEN target site edited
Figure 8:
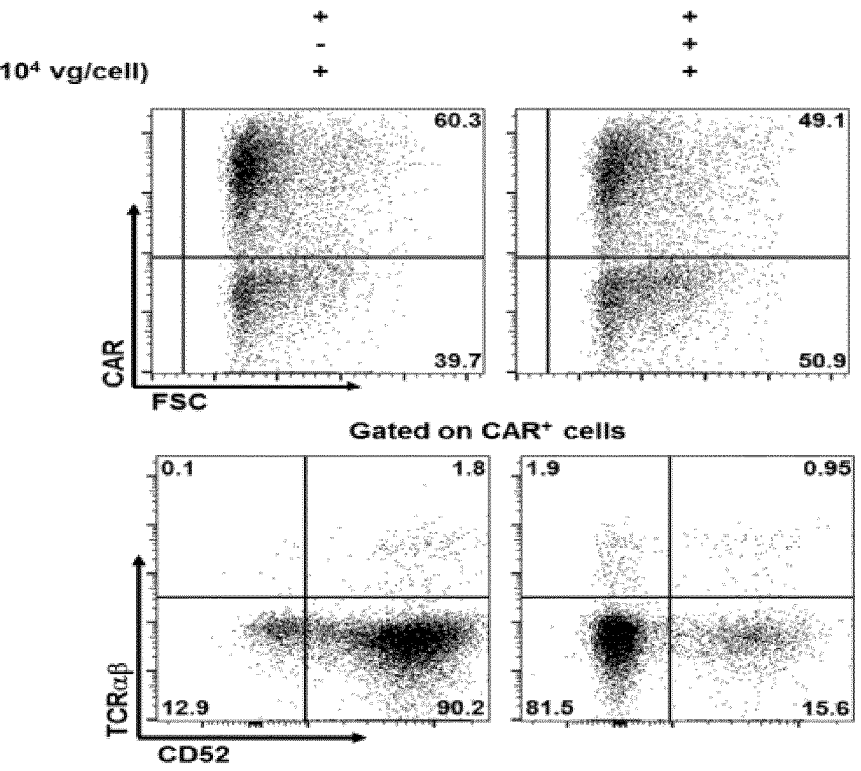
FIG. 8: Inactivation of CD52 gene and inactivation by insertion of a sequence coding a self cleaving peptide 2A, aCAR and a polyA terminator sequence into the TRAC gene.

DETAILED DESCRIPTION OF THE INVENTION 1.1 References and Definitions

The patent and scientific literature referred to herein establishes knowledge that is available to those of skill in the art. The issued patents, allowed applications, published foreign applications, and references, including GEN-BANK™ database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells, an homogenous population of cells.

As used herein, unless specifically indicated otherwise, the word "or" is used in the inclusive sense of "and/or" and not the exclusive sense of "either/or."

As used herein, the term "TALEN" or "TALE-nucleases" refers to an endonuclease comprising a DNA-binding domain comprising 14-20 or 16-22 TAL domain repeats fused to any portion of the FokI nuclease domain (WO2011072246).

TALE-nucleases, are fusion protein of a TALE binding domain with a cleavage catalytic domain. These endonucleases have been successfully applied to primary immune cells, in particular T-cells from peripheral blood mononuclear cell (PBMC). Such TALE-nucleases, marketed under the name TALEN, are those currently used to simultaneously inactivate gene sequences in T-cells originating from donors, in particular to produce allogeneic therapeutic T-Cells in which the genes encoding TCR (T-cell receptor) and CD52 are disrupted. These cells can be endowed with chimeric antigen receptors (CAR) for treating cancer patients (US2013/0315884). TALE-nucleases are very specific reagents because they need to bind DNA by pairs under obligatory heterodimeric form to obtain dimerization of the cleavage domain Fok-1. Left and right heterodimer members each recognizes a different nucleic sequence of about 14 to 20 bp, together spanning target sequences of 30 to 50 bp overall specificity.

Other endonuclease systems derived from homing endonucleases (ex: 1-Onul, or I-Crel), combined or not with TAL-nuclease (ex: MegaTAL) or zing-finger nucleases have also proven specificity, but to a lesser extend so far.

As used herein, the term "Compact TALEN" refers to an endonuclease comprising a DNA-binding domain with 16-22 TAL domain repeats fused in any orientation to any catalytically active portion of nuclease domain of the I-TevI homing endonuclease.

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-Crel, and can refer to an engineered variant of I-Crel that has been modified relative to natural I-Crel with respect to, for example, DNA-binding specificity, DNA cleavage activity, DNA-binding affinity, or dimerization properties. Methods for producing such modified variants of 1-Crel are known in the art (e.g., WO 2007/047859). A meganuclease as used herein binds to double-stranded DNA as a heterodimer or as a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" can refer to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. No. 8,445,251.

As used herein, the term "CRISPR" (Clustered Regularly Interspaced Short palindromic Repeats) refers to such as Cas9, and a guide RNA that directs DNA cleavage of the caspase by hybridizing to a recognition site in the genomic DNA.

Other endonucleases reagents have been developed based on the components of the type II prokaryotic CRISPR (Clustered Regularly Interspaced Short palindromic Repeats) adaptive immune system of the bacteria S. pyogenes. This multi-component system referred to as RNA-guided nuclease system (Gasiunas, Barrangou et al. 2012; Jinek, Chylinski et al. 2012), involves members of Cas9 or Cpf1 endonuclease families coupled with a guide RNA molecules that have the ability to drive said nuclease to some specific genome sequences (Zetsche et al. (2015). Cpf1 is a single RNA-guided endonuclease that provides immunity in bacteria and can be adapted for genome editing in mammalian cells. Cell 163:759-771). Such programmable RNA-guided endonucleases are easy to produce because the cleavage specificity is determined by the sequence of the RNA guide, which can be easily designed and cheaply produced. The specificity of CRISPR/Cas9 although stands on shorter sequences than TAL-nucleases of about 10 pb, which must be located near a particular motif (PAM) in the targeted genetic sequence.

As used herein, the term "megaTAL" refers to a single-chain nuclease comprising a transcription activator-like effector (TALE) DNA binding domain with an engineered, sequence-specific homing endonuclease.

As used herein, with respect to a protein, the term "recombinant" means having an altered amino acid sequence as a result of the application of genetic engineering techniques to nucleic acids that encode the protein, and cells or organisms that express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

The following documents are entirely incorporated herein by reference WO2017062451, WO2015057980, WO2017106528, in particular for a method of preparing a crispr or meganuclease-TRAC modified human cells.

As used herein, the term "wild-type" or "native" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases.

As used herein, the term "modification" means any insertion, deletion or substitution of an amino acid residue in the sequence relative to a reference sequence (e.g., a wild-type or a native or genomic sequence).

As used herein, the term "recognition sequence" or "recognition domain" refers to a DNA sequence that is bound and cleaved by an endonuclease. In the case of a meganuclease, a recognition sequence comprises a pair of inverted, 9 base pair "half sites" that are separated by four base pairs.

In the case of a single-chain meganuclease, the N-terminal domain of the protein contacts a first half-site and the C-terminal domain of the protein contacts a second half-site.

Cleavage by a meganuclease produces four base pair 3'"overhangs", "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 bases pair recognition sequence.

In the case of a Compact TALEN, the recognition sequence comprises a first CNNNGN sequence that is recognized by the I-TevI domain, followed by a nonspecific spacer 4-16 base pairs in length, followed by a second sequence 16-22 bp in length that is recognized by the TAL-effector domain (this sequence typically has a 5' T base). Cleavage by a Compact TALEN produces two base pair 3' overhangs.

In the case of a CRISPR, the recognition sequence is the sequence, typically 16-24 basepairs, to which the guide RNA binds to direct Cas9 cleavage. Cleavage by a CRISPR produced blunt ends.

As used herein, the term "target site" or "target sequence" refers to a region of the chromosomal DNA of a cell comprising a recognition sequence for a nuclease.

As used herein, the term "DNA-binding affinity" or "binding affinity" means the tendency of a nuclease to non-covalently associate with a reference DNA molecule (e.g., a recognition sequence or an arbitrary sequence). Binding affinity is measured by a dissociation constant, 3%. As used herein, a nuclease has "altered" binding affinity if the Kd of the nuclease for a reference recognition sequence is increased or decreased by a statistically significant percent change relative to a reference nuclease.

As used herein, the term "homologous recombination" or "HR" refers to the natural, cellular process in which a double-stranded DNA-break is repaired using a homologous DNA sequence as the repair template (see, e.g., Cahill et al.

(2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006), Front. Biosci. 1 1:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knockout a gene in a population of cells.

CAR

As used herein, a "chimeric antigen receptor" or "CAR" refers to an engineered receptor that confers or grafts specificity for an antigen onto an immune effector cell (e.g., a human T cell). A chimeric antigen receptor typically comprises an extracellular ligand-binding domain or moiety and an intracellular domain that comprises one or more stimulatory domains that transduce the signals necessary for T cell activation. In some embodiments, the extracellular ligand-binding domain or moiety can be in the form of single-chain variable fragments (scFvs) derived from a monoclonal antibody, which provide specificity for a particular epitope or antigen (e.g., an epitope or antigen preferentially present on the surface of a cancer cell or other disease-causing cell or particle). The extracellular ligand-binding domain can be specific for any antigen or epitope of interest.

In a particular embodiment, the ligand-binding domain is specific for CD22. In another particular embodiment, the ligand-binding domain is specific for CD123.

SCFV

In particular embodiments, the CAR encoded by the exogenous polynucleotide inserted into the TRAC gene comprises a scfv. The scfvs of the invention can be attached via a linker sequence.

HINGE

The extracellular domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region is used to provide more flexibility and accessibility for the extracellular ligand-binding domain. A hinge region may comprise up to 300 amino acids, preferably 10 to 100 amino acids and most preferably 10 to 50 amino acids. Hinge region may be derived from all or part of naturally occurring molecules, such as from all or part of the extracellular region of CD8, or CD4, or from all or part of an antibody constant region. Alternatively, the hinge region may be a synthetic sequence that corresponds to a naturally occurring hinge sequence, or may be an entirely synthetic hinge sequence. In a preferred embodiment said hinge domain comprises a part of a human CD8 alpha chain, FcRIIIα receptor or IgG1, respectively.

A Hinge from IgG4 or from PD1 is part of the present invention and disclosed in WO2016120216 and may be used in the construction of a CAR according to the invention.

A CAR according to the present invention is anchored into the membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, or δ, polypeptide constituting CD3 complex, IL2 receptor p55 (α chain), p75 (β chain) or chain, subunit chain of Fc receptors, in particular Fc receptor Ill or CD proteins. Alternatively the transmembrane domain can be synthetic and can comprise predominantly hydrophobic residues such as leucine and valine.

MIMOTOPE—Suicide Switch

In the present invention, the extracellular domain of a chimeric antigen receptor may also comprise a monoclonal antibody epitope that can be recognized by a monoclonal antibody such as those described in WO2016120216. In a preferred embodiment? a CAR of the invention is a "QR3", "QR2", "QR1", "Q", "R", "R2" or "R3" CAR with Q is an epitope recognized by Q ben10 antibody and R an epitope recognized by rituximab as described in WO2016120216A1 which is incorporated herein by reference.

The extracellular domain of a chimeric antigen receptor can also comprise an autoantigen (see, Payne et al. (2016), Science 353 (6295): 179-184), that can be recognized by an autoantigen-specific B cell receptor on B lymphocytes. The autoantibody allows directing T cells to specifically target and kill autoreactive B lymphocytes in antibody-mediated autoimmune diseases. Such CARs can be referred to as chimeric autoantibody receptors (CAARs), and their use is encompassed by the invention.

one or several monoclonal antibody epitope(s) can be inserted into the scFv and/or the hinge of the CAR, and their use is encompassed by the invention for eliminating cells in vivo for example.

Intracellular Domain

The signal transducing domain or intracellular signaling domain of a CAR according to the present invention is responsible for intracellular signaling following the binding of extracellular ligand binding domain to the target resulting in the activation of the immune cell and immune response (cytolytic activity against the target cell). In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function and directs the cell to perform a specialized function.

Preferred examples of signal transducing domain in a CAR of the invention can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d.

The intracellular stimulatory domain can include one or more cytoplasmic signaling domains that transmit an activation signal to the immune effector cell following antigen binding. In one embodiment, a cytoplasmic signaling domains includes, a CD3-zeta intracellular stimulatory domain.

In another embodiment, the signaling transducing domain of the CAR of the invention consists in a CD3zeta signaling domain and excludes any sequence from human CD28 signaling domain.

In particular embodiments, the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In one embodiment, the signal transduction domain of the CAR of the present invention comprises a part of co-stimulatory signal molecule consisting of fragment of 4-1BB (GENBANK™: AAA53133). In another embodiment, the signal transduction domain of a CAR according to the present invention comprises no sequence from CD28 (NP_006130.1).

In one embodiment, all the embodiments of the present invention comprise no sequence from CD28 (NP_006130.1).

In one embodiment, the signal transduction domain of a CAR of the present invention comprises a part of co-stimulatory signal molecule 4-1BB (GENBANK™: AAA53133) and no sequence from CD28 (NP_006130.1).

In one embodiment, the signal transduction domain of a CAR of the present invention comprises a part of co-stimulatory signal molecule 4-1BB (GENBANK™: AAA53133) and CD3 zeta signaling domain.

In one embodiment, the signal transduction domain of a CAR of the present invention comprises a part of co-stimulatory signal molecule 4-1BB (GENBANK™: AAA53133) and CD3 zeta intracellular signaling domain and CD28 intracellular signaling domain.

The intracellular stimulatory domain can also include one or more intracellular co-stimulatory domains that transmit a proliferative and/or cell-survival signal after ligand binding. Such intracellular co-stimulatory domains can include, without limitation, a CD28 domain, an OX40 domain, or a combination thereof. A chimeric antigen receptor can further include additional structural elements, including a trans-membrane domain that is attached to the extracellular ligand-binding domain via a hinge or spacer sequence.

MULTICHAIN CAR

The insertion in the TRAC gene may comprise a sequence encoding a multichain CAR are those described in WO2014039523 A1.

EXOGENOUS TCR or Recombinant Exogenous TCR

As used herein, an "exogenous T cell receptor (TCR)" or "recombinant TCR" refers to a TCR whose sequence is introduced into the genome of an immune effector cell (e.g., a human T cell) which does not express the endogenous TCR. Expression of an exogenous TCR in an immune effector cell can confer specificity for a specific and known epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest as those listed herein.

As used herein, the term "undetectable expression" of an antigen refers to a reduction in the expression at the cell surface, in a genetically-modified cell, to the level measured using a negative control cell that do not express said antigen.

Term "undetectable expression" of the T cell receptor at the cell surface of a genetically-modified cell corresponds to the level of the endogenous alpha and beta chains of the TCR in genetically-modified cell measured using a control cell that does not express the endogenous alpha and beta chains of the T cell receptor (and an Ab specific for the alpha beta TCR).

The term reduced can also refer to a reduction in the percentage of cells in a population of cells that express an endogenous polypeptide (i.e., an endogenous alpha and beta T cell receptor and a chimeric antigen receptor) at the cell surface when compared to a population of control cells.

Such a reduction may be up to 5%, 10%, 20%, 30%, 40%, 50%, 60%, 70%, 80%, 90%, 95%, or up to 100% (unde-tectable). Accordingly, the term "reduced" encompasses both a partial knockdown and a complete knockdown (unde-tectable) of the endogenous T cell receptor, and undetectable cell surface expression of the endogenous alpha beta TCR.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and that is a function of the number of identical or similar residues or nucleotides, the number of total residues or nucleotides, and the presence and length of gaps in the sequence alignment. A variety of algorithms and computer programs are available for deter-mining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden ei a/. (1996), Meth. Enzymol.266: \3\-U\; Altschul et al. (1997), Nucleic Acids Res. 25:33 89-3402); Zhang et al. (2000), J. Comput. Biol. 7 (1-2): 203-14.

As used herein, percent similarity of two amino acid sequences is the score based upon the following parameters for the BLASTp algorithm: word size=3; gap opening penalty=–I 1; gap extension penalty=–I; and scoring matrix=BLOSUM62. As used herein, percent similarity of two nucleic acid sequences is the score based upon the following parameters for the BLASTn algorithm: word size=I 1; gap opening penalty=–5; gap extension penalty=–2; match reward=1; and mismatch penalty=–3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corre-sponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue 'Y" to amino acid "A" in the second protein if residues X and Y correspond to each other in a sequence alignment, and despite the fact that X and Y may be different numbers.

As used herein, the term "recognition half-site," "recog-nition sequence half-site," or simply "half-site" means a nucleic acid sequence in a double-stranded DNA molecule of the TRAC gene that is recognized by a monomer of a homodimeric or heterodimeric TALEN.

The first "recognition half-site," or "first recognition site" or "first recognition domain" means the nucleic acid sequence in a double-stranded DNA molecule recognized by the a monomer ((the left monomer)) located in 5' as com-pared to the second monomer ((the right monomer) of a TALEN As used herein, the term "recognition half-site," "recognition sequence half-site," or simply "half-site" for a meganuclease means a nucleic acid sequence in a double-stranded DNA molecule that is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues.

A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity TCR ALPHA GENE Gene ID: 6955, as Updated on 9 Jul. 2017 (NCBI).

As used herein, the terms "T cell receptor alpha gene" refers to the human TCR alpha gene on the chromosome 14. from TRA in Genome Data Viewer Map ViewerLocation: 14q11.2.

T cell receptors recognize foreign antigens which have been processed as small peptides and bound to major histocompatibility complex (MHC) molecules at the surface of antigen presenting cells (APC). Each T cell receptor is a dimer consisting of one alpha and one beta chain or one delta and one gamma chain. In a single cell, the T cell receptor loci are rearranged and expressed in the order delta, gamma, beta, and alpha.

If both delta and gamma rearrangements produce functional chains, the cell expresses delta and gamma. If not, the cell proceeds to rearrange the beta and alpha loci. This region represents the germline organization of the T cell receptor alpha and delta loci. Both the alpha and delta loci include V (variable), J (joining), and C (constant) segments and the delta locus also includes diversity (D) segments. The delta locus is situated within the alpha locus, between the alpha V and J segments. During T cell development, the delta chain is synthesized by a recombination event at the DNA level joining a D segment with a J segment; a V segment is then joined to the D-J gene.

The alpha chain is synthesized by recombination joining a single V segment with a J segment. For both chains, the C segment is later joined by splicing at the RNA level. Recombination of many different V segments with several J segments provides a wide range of antigen recognition. Additional diversity is attained by junctional diversity, resulting from the random additional of nucleotides by terminal deoxynucleotidyltransferase. Five variable segments can be used in either alpha or delta chains and are described by TRAV/DV symbols. Several V and J segments of the alpha locus are known to be incapable of encoding a protein and are considered pseudogenes.

The constant region of the (T cell receptor alpha gene) TCRA or TRAC gene is identified by NCBI Gen ID NO. 28755. The regions of the TCR alpha gene targeted by the TALEN endonucleases of the invention correspond to a sequence that codes for an extracellular or intramembrane part of the T cell receptor alpha protein. The genetic modification (deletion, mutation or insertion) ultimately results in an alteration of cell surface expression of the alpha beta TCR.

In particular embodiments, the genetic modification alters cell surface expression of the delta gamma of the TCR.

In particular embodiments, the region(s) of the TCR alpha gene targeted by the nuclease is (are) as in WO2017062451 or as in WO2015057980 or as in WO2017106528.

In one embodiment, the genetic modification of the T cell receptor alpha constant region is located in a region corresponding to the c1, c2 or c3 region, preferably C1, of human T cell receptor alpha constant region, before the stop codon, and as defined in WO2017106528, preferably the genetic modification of the T cell receptor alpha constant region is located in a region corresponding to the c1 region of human T cell receptor alpha constant region.

In one embodiment, the genetic modification of the T cell receptor alpha constant region is located in a region corresponding to

```
                                    (SEQ ID NO: 38)
        TTGTCCCACAGATATCCagaaccctgaccc tgCCGTGTACCAGCTGAGAGA.
```

"T cell receptor alpha constant region gene" "TRAC gene" refers to the constant region of the human gene, in particular to the sequence identified by NCBI Gen ID NO. 28755. This is also referred as wild type (wt) TRAC gene and its sequence may slightly vary from one individual to another (slightly vary means 0.001% sequence change with no impact on the protein sequence (silent substitution deletion or insertion).

Genomic means that belongs to the genome (chromosomal DNA of the cells) and was not integrated into the genome as part of the experiments as a transgene or an exogenous polynucleotide performed in the present invention. In other words, the TRAC gene of the invention is not a transgene, or an exogenous polynucleotide.

CELL

In one aspect, described herein is a cell (e.g., a eukaryotic cell such as a human cell including a lymphoid cell, a stem cell (e.g., iPSC, embryonic stem cell, MSC or HSC), or a progenitor cell) in which expression of a TCR gene is modulated.

In one aspect, described herein is a human cell (e.g., a eukaryotic cell such as a human cell including a lymphoid cell, a stem cell (e.g., iPSC, embryonic stem cell, MSC or HSC), or a progenitor cell) in which cell surface expression of a alpha beta TCR gene is inhibited by modification (mutation, deletion, or insertion, preferably an insertion) of exon c1, c2 and/or c3 of the TRAC gene.

In one aspect, described herein is a cell (e.g., a eukaryotic cell such as a human cell including a lymphoid cell, a stem cell (e.g., iPSC, embryonic stem cell, MSC or HSC), or a progenitor cell) in which expression of endogenous alpha beta TCR gene is modulated by insertion or an exogenous sequence into a TCR gene sequence coding for an extracellular domain of the TCR or a transmembrane domain so that cell surface expression of a functional alpha beta TCR can be compromised.

TAG

A tag is meant to be a sequence including a noncoding sequence or a coding sequence used as a marker or label and integrated into on-site (optionally in off sites) and can be detected.

Engineering

The TRAC-deficient human cell of the invention may include further genomic modifications, for example an inactivated T-cell receptor beta gene, and inactivated PD1, CD52 and/or CTLA4 gene. The TRAC-deficient human cell of the invention may include further genomic modifications, for example an inserted transgene or an inserted exogenous polynucleotide sequence such as a gene encoding a chimeric antigen receptor (CAR), a gene encoding a T-cell Receptor (TCR) and/or a gene encoding an antibody, a transgene encoding a cytokine selected from IL-2, IL-7, IL-3, IL-12, IL-15, IL-17, IL-27, a protein conferring resistance to a drug, a protein conferring sensitivity to a drug, a combination thereof.

In a preferred embodiment, said transgene or polynucleotide is inserted in the TRAC gene.

Pharmaceutical Composition

Pharmaceutical compositions comprising a pharmaceutically acceptable vehicle (or carrier) and any cell or cell population as described herein are also provided as well as methods of using the cells and pharmaceutical compositions in ex vivo therapies for the treatment of a disorder (e.g., a cancer) in a subject.

In the present invention described herein are cells in which the expression of a TCR gene is inactivated. In preferred embodiments, exon c1, c2 and/or c3 of a TCR gene is inactivated. In other embodiments, the activity of the endogenous TCR promotor is not inactivated and may be activated. The activation of the endogenous TCR promotor may be by an exogenous molecule (e.g., engineered transcription factor comprising a DNA-binding domain and a transcriptional activation domain) that binds to the TCR gene and activates TCR expression.

In some embodiments, cells are described that comprise a transiently expressed engineered nuclease to cause a knockout of a TRAC gene, knock-in of said TRAC gene, knock-in of said TRAC gene without a knockout of a TRAC gene, preferably knock-in of said TRAC gene with a knockout of a TRAC gene, more preferably knock-in of said TRAC gene with a knockout of a TRAC gene and expression of a CAR specific for an antigen expressed on a pathological cell.

Further, the human TRAC-deficient human cells of the invention described are cells wherein the expression of an endogenous TCR gene is reduced and TCR alpha beta expression at the cell surface is undetectable.

Further, the human TRAC-modified human cells of the invention described are cells wherein the expression of a known and selected TCR gene, which may be a known and selected alpha beta TCR gene, is maintained and the known TCR alpha beta expression at the cell surface is detectable.

Also provided here, cells wherein the expression of a TCR gene is reduced (as compared to a non engineered cells) and TCR alpha beta expression at the cell surface is undetectable (as compared to a positive control) and wherein the cells are further engineered to comprise a least one exogenous transgene and/or an additional knock out of at least one endogenous gene (e.g., beta 2 microglobulin (B2M) and/or immunological checkpoint gene such as PD1 and/or CTLA4) or combinations thereof. The exogenous transgene may be integrated into a TCR gene (e.g., when the TCR gene is knocked out) and/or may be integrated into a non-TCR gene such as a safe harbor gene. In some cases, the exogenous transgene encodes an ACTR and/or a CAR. The transgene construct may be inserted by either HDR- or NITEJ-driven processes.

In some aspects, the cells with undetectable TCR expression comprise an exogenous TCR or an exogenous CAR. Cells of the invention further comprise a knockout of one or more check point inhibitor genes. In some embodiments, the check point inhibitor is PD1. In other embodiments, the check point inhibitor is CTLA4 or any of the immune check points disclosed in WO2014191128 selected from the list consisting of CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1 B2 and GUCY1 B3, In some aspects, the cells with undetectable TCR expression comprise an exogenous TCR or an exogenous CAR and at least two inactivated genes selected from the group consisting of PD1 and TCR alpha, PD1 and TCR beta, CTLA-4 and TCR alpha, CTLA-4 and TCR beta, LAG 3 and TCR alpha, LAG 3 and TCR beta, Tim3 and TCR alpha, Tim3 and TCR beta, BTLA and TCR alpha, BTLA and TCR beta, BY55 and TCR alpha, BYS5 and TCR beta, TIGIT and TCR alpha, TIGIT and TCR beta, B7H5 and TCR alpha, B7H5 and TCR beta, LAIR1 and TCR alpha, LAIR1 and TCR beta, SIGLEC10 and TCR alpha, SIGLEC10 and TCR beta, 2B4 and TCR alpha, 2B4 and TCR beta.

In further aspects, the TCR alpha KO cell of the invention comprises a PD1 knockout and a CTLA4 knockout. In some embodiments, another TCR gene inactivated is a gene encoding TCR β (TCRB). In some embodiments, this is achieved via targeted cleavage of the constant region of this gene (TCR β Constant region, or TRBC). In all embodiments, the TCR gene encoding TCR alpha (TCRA) is modified, and contain an insertion, a mutation and/or a deletion that affect(s) or not the cell surface of the TCRalpha beta. In further embodiments, insertion is achieved via targeted cleavage of the constant region of a TCR gene C1. In some embodiments, the TCR gene modified cells are further modified at the B2M gene, the HLA-A, -B, -C genes, or the TAP gene, or any combination thereof. In other embodiments, the regulator for HLA class II, CTLA, is also modified.

In further aspects, the TCR alpha KO cell of the invention comprises a CD25 KO with an insertion of a cytokine encoding sequence, preferably IL-2, IL-7, -12, 15, -17, -27, -27.

In a preferred embodiment, the TRAC gene modified human cells are further modified at the B2M gene, and/or the TAP gene, ant at the regulator for HLA class II, CTLA.

In a more preferred embodiment the TRAC gene KO human cells are further KO at the B2M gene, and/or the TAP gene, ant at the regulator for HLA class II, CTLA.

In certain embodiments, the cells described herein comprise a modification (e.g., deletion and/or insertion) to a TRAC gene (e.g., modification of exon c1, using a TALEN). In certain embodiments, the modification comprises binding of an engineered Transcription Factor as described herein such that a TCRA gene expression is modulated, for example, repressed or activated. In other embodiments, the modification is a genetic modification (change of the native nucleotide sequence) at or near nuclease(s) binding (target) and/or cleavage site(s), including but not limited to, modifications to sequences within 1-300 (or any number of base pairs therebetween) base pairs upstream, downstream and/or including 1 or more base pairs of the site(s) of cleavage and/or binding site; modifications within 1-100 base pairs (or any number of base pairs therebetween) of including and/or on either side of the binding and/or cleavage site(s); modifications within 1 to 50 base pairs (or any number of base pairs therebetween) including and/or on either side (e.g., 1 to 5, 1 to 10, 1 to 20 or more base pairs) of the binding and/or cleavage site(s); and/or modifications to one or more base pairs within the nuclease binding site and/or cleavage site.

In preferred embodiments, means for detecting a cell comprising Zinc-finger mediated TRAC designs as described in WO 2017106528, or in U.S. Patent Publication 20150132269.

Guide RNAs for the *S. pyogenes* CRISPR Cas9 system were also constructed to target the TCRA gene as in U.S. Publication No. 201500566705 or as in table 2 of WO2017106528.

The modified cell of the invention is a human cell such as lymphoid cell (e.g., a human T-cell), a human stem/progenitor cell (e.g., an induced human pluripotent stem cell (iPSC), a human embryonic stem cell (e.g., human ES), a human mesenchymal stem cell (MSC), or a human hematopoietic stem cell (HSC). The human stem cells may be totipotent or pluripotent (e.g., partially differentiated such as an HSC that is a pluripotent myeloid or lymphoid stem cell). In other embodiments, the invention provides methods for producing human cells that have a null genotype for TCR expression. Any of the modified human stem cells described herein (modified at the TCRA locus) may then be differentiated to generate a differentiated (in vivo or in vitro) cell descended from a stem cell as described herein with modified TCRA gene expression.

In another aspect, the cells, population of cells or pharmaceutical compositions, means of detection of said cells or of said pharmaceutical composition described herein can be used, for example, in the treatment or prevention or amelioration of a disorder. The methods typically comprise (a) cleaving or down regulating an endogenous TCR gene in an isolated human cell (e.g., progenitor, dedifferentiated or differentiated T-cell or lymphocyte) using a TALEN such that the TCR gene is inactivated or down modulated, cell surface expression of the TCR alpha beta is undetectable and cell express a molecule to redirect its specificity and (b) introducing the cell into the subject, thereby treating or preventing the disorder.

In some embodiments, the gene encoding TCR β (TCRB) is inactivated or down modulated, as are the B2M gene, and the regulator for HLA class II gene, CIITA.

The methods typically comprise (a) cleaving or down regulating an endogenous TCR gene in an isolated cell (e.g., progenitor, dedifferentiated or differentiated T-cell or lymphocyte) using a nuclease (a TALEN) such that the TCR gene is modified such as inactivated (insertion stopping the expression of the TCR alpha protein) so that cell surface expression of the TCR alpha beta is undetectable and cell express a molecule (insertion in frame) to redirect its specificity, preferably a CAR and (b) detecting and identifying the nuclease TALEN-modified cells as compared to other nuclease modified cells using a CRISPR/Cas or engineered transcription factor (e.g. ZFN-TF, TALE-TF, Cfpl-TF or Cas9-TF) used to modify the TCR gene expression (c) identifying the (lack of) off sites as a signature and as a quality control of the engineered cells.

In some embodiments inactivation is achieved via targeted cleavage of the constant region of the beta gene (TCR B Constant region, or TRBC). In preferred embodiments, the gene encoding TCR alpha (TCRA) is modified such as comprises an insertion that inactivates the expression of TCR alpha beta at the cell surface.

In further preferred embodiments, the disorder is a cancer or an infectious disease. In further preferred embodiments inactivation is achieved via targeted cleavage of the constant region of this gene (TCR a Constant region, or abbreviated as TRAC). In some embodiments, additional genes are modulated (knocked-out), for example, B2M, PD1 and/or CTLA4 and/or one or more therapeutic transgenes are present in the cells (integrated via targeted integration such as nuclease-mediated integration using a vector).

The transcription factor(s) and/or nuclease(s) can be introduced into a cell or the surrounding culture media as mRNA, in protein form and/or as a DNA sequence encoding the nuclease(s). In certain embodiments, the isolated cell introduced into the subject further comprises additional genomic modification, for example, an integrated exogenous sequence (into the cleaved TCR gene or a different gene, for example a safe harbor gene or locus) and/or inactivation (e.g., nuclease-mediated) of additional genes, for example one or more HLA genes. The exogenous sequence or protein may be introduced via a vector (e.g. Ad, AAV, LV), or by using a technique such as electroporation. In some embodiments, the proteins are introduced into the cell by cell squeezing (see Kollmannsperger et al (2016) Nat Comm 7, 10372 doi: 10.1038/ncomms10372).

Preferably, nucleases preferably mRNA encoding nucleases, even more preferably mRNA encoding TALEN are introduced into human primary cells by electroporation as described in US20130315884.

Cell Therapy

In some aspects, the human engineered cells of the invention may be used for therapy, for example, for adoptive cell transfer, immunotherapy. In other embodiments, the cells for use in T cell transplant contain another gene modification of interest. In one aspect, the T cells contain an inserted chimeric antigen receptor (CAR) specific for a cancer marker. In a further aspect, the inserted CAR is specific for the CD22 marker characteristic of B cells, including B cell malignancies.

In one aspect, the T cells contain an inserted chimeric antigen receptor (CAR) specific for a cancer marker. In a further aspect, the inserted CAR is specific for the CD38 marker characteristic of B cells, including B cell malignancies and comprises a genomic inactivated CD38 gene.

In one aspect, the T cells contain an inserted chimeric antigen receptor (CAR) specific for a cancer marker. In a further aspect, the inserted CAR is specific for the CD123 marker characteristic of immune cells, including immune cell malignancies, AML, BPDCN.

In one aspect, the T cells contain an inserted chimeric antigen receptor (CAR) specific for a cancer B cell marker. In a further aspect, the inserted CAR is specific for the CD22 marker characteristic of immune cells, including immune B cell malignancies.

Such cells would be useful in a therapeutic composition administered several times (repeated administration) for treating patients with match or partial match HLA, and so that unmatched HLA are never the same in the successive doses administered and so would be able to be used as an "off-the-shelf therapeutic for any patient in need thereof.

In another aspect, the TCR-modulated (modified) T cells contain an inserted Antibody-coupled T-cell Receptor (ACTR) donor sequence. In some embodiments, the ACTR donor sequence is inserted into a TCR gene to disrupt expression of that TCR gene following nuclease induced cleavage. In other embodiments, the donor sequence is inserted into a "safe harbor" locus, such as the AAVS 1, HPRT, albumin and CCR5 genes. In some embodiments, the ACTR sequence is inserted via targeted integration where the ACTR donor sequence comprises flanking homology arms that have homology to the sequence flanking the cleavage site of the engineered nuclease. In some embodiments, the ACTR donor sequence further comprises a promoter and/or other transcriptional regulatory sequences. In other embodiments, the ACTR donor sequence lacks a promoter. In some embodiments, the ACTR donor is inserted into a TCR β encoding gene (TCRB). In some embodiments insertion is achieved via targeted cleavage of the constant region of this gene (TCR β Constant region, or TRBC). In preferred embodiments, the ACTR donor is inserted into a TCR a encoding gene (TCRA). In further preferred embodiments insertion is achieved via targeted cleavage of the constant region of this gene (TCR a Constant region, abbreviated TRAC). In some embodiments, the donor is inserted into an exon sequence in TCRA, while in others, the donor is inserted into an intronic sequence in TCRA. In some embodiments, the TCR-modulated cells further comprise a CAR. In still further embodiments, the TCR-modulated cells are additionally modulated at an HLA gene or a checkpoint inhibitor gene.

Also provided are pharmaceutical compositions comprising the modified cells as described herein (e.g., T cells or stem cells with inactivated TCR gene), or pharmaceutical compositions comprising one or more of the TCR gene binding molecules (e.g., engineered transcription factors and/or nucleases) and a pharmaceutically acceptable vehicle or excipient as described herein. In certain embodiments, the pharmaceutical compositions further comprise one or more pharmaceutically acceptable excipients. The modified cells, TCR gene binding molecules (or polynucleotides encoding these molecules) and/or pharmaceutical compositions comprising these cells or molecules are introduced into the subject via methods known in the art, e.g. through intravenous infusion, infusion into a specific vessel such as the hepatic artery, or through direct tissue injection (e.g. muscle). In some embodiments, the subject is an adult human with a disease or condition that can be treated or ameliorated with the composition. In other embodiments, the subject is a pediatric subject where the composition is administered to prevent, treat or ameliorate the disease or condition (e.g., cancer, graft versus host disease, etc.).

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of single or double-stranded polynucleotides, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "vector" can also refer to adeno-associated viral vector, with AAV6 capsid protein and AAV2 sequences allowing guidance.

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "human T cell" or "T cell" refers to a T cell isolated from a human donor. Human T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration that resulted in the genetically-modified cell; (b) a cell of the same genotype as the genetically-modified cell but that has been transformed with a null construct (i.e., with a construct that has no known effect on the trait of interest); or, (c) a cell genetically identical to the genetically-modified cell but that is not exposed to conditions or stimuli or further genetic modifications that would induce expression of altered genotype or phenotype.

T cell expressing alpha beta TCR. T cell with a native TCR gene (eg as described in NCBI reference as above), that may include silent mutation(s).

Therapeutic Applications 2.1 Principle of the Invention

The present invention is based, in part, on the discovery that different engineered nucleases recognize and cleave recognition sequences found within the human TCR alpha gene, and depending on the nuclease used, off sites sequences. The sequence(s) cleaved (of sites and on sites) is (are) specific for the nuclease used and linked to the frequency and number of off target sites making the final product more or less reliable as a stable medicament. This is especially important to be provided due to the fact that a medicament must be stable in a host and resist the immune system that exerts constant pressure.

Moreover, according to the invention, an exogenous polynucleotide sequence can be inserted specifically into the TCR alpha constant region gene at the nuclease cleavage site, and may be used as a tag to detect engineered cells, even in cells with additional edited genes, such as CD52 or dCK KO gene. Insertion takes place for example by homologous recombination, such that a sequence of interest is concurrently expressed in the cell. Such exogenous sequences can be noncoding sequence and/or encode, for example, a chimeric antigen receptor, an exogenous TCR receptor, or any other polypeptide of interest. Ultimately the TRAC gene modification results in a specific sequence as compared to the wt TRAC non-engineered sequence.

The inventors provided human cells engineered for immunotherapy with no or reduced side effects (GVHD, . . . ) with stable phenotypes and genotypes (that is to say with undetectable level of off sites) comprising the following sequence:

(SEQ ID NO: 24)

```
AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

TCCGGTGAGGGCAGAGGAAGTCTTCTAACATGCGGTGACGTGGAGGAGAATCCGGGCCCCGGATCCcodingsequence
```

(SEQ ID NO: 25)

```
TCTAGAGGGCCCGTTTAAACCCGCTGATCAGCCTCGACTGTGCCTTCTAGTTGCCAGC

CATCTGTTGTTTGCCCCTCCCCCGTGCCTTCCTTGACCCTGGAAGGTGCCACTCCCACTGTCCTTTCCTAATAAAAT

GAGGAAATTGCATCGCATTGTCTGAGTAGGTGTCATTCTATTCTGGGGGGTGGGGTGGGGCAGGACAGCAAGG

GGGAGGATTGGGAAGACAATAGCAGGCATGCTGGGGATGCGGTGGGCTCTATGACTAGTGGCGAATTCCCGTGT

ACCAGCTGAGAGACTCTAAATCCAGTGACAAGTCTGTCTGCCTATTCACCGATTTTGATTCTCAAACAAATGTGTC

ACAAAGTAAGGATTCTGATGTGTATATCACAGACAAAACTGTGCTAGACATGAGGTCTATGGACTTCAAGAGCAA

CAGTGCTGTGGCCTGGAGCAACAAATCTGACTTTGCATGTGCAAACGCCTTCAACAACAGCATTATTCCAGAAGA

CACCTTCTTCCCCAGCCCAGGTAAGGGCAGCTTTGGTGCCTTCGCAGGCTGTTTCCTTGCTTCAGGAA,
```

Preferably said insertion in the genomic TRAC comprises the following sequence:

AAGTAGCCCTGCATTTCAGGTTTCCTTGAGTG GCAGGCCAGGCCTGGCCGTGAACGTTCACT- GAAATCATGGCC TCTTGGCCAAGATTGA- TAGCTTGTGCCTGTCCCTGAGTCCCAGTCCAT- CACGAGCAGCTGGTTTCTAAGATGCTAT TTC CCGTATAAAGCATGAGACCGTGACTT GCCA GCCCCACAGAGCCCCGCCCTTGTCCAT- CACTGGCATCTGGAC TCCAGCCTGG GTTGG GGCAAAGAGGGAAATGAGATCATGTCCT AACCCTGATCCTCTTGTCCCACAGATATCCAG TCCGGTGAGGGCAGAGGAAGTCTTCTAA- CATGCGGTGACGTGGAGGAGAATCCG GGCCCCGGATCCGCTCTGC CCGTCACCG CTCTGCTGCTGCCACTGGCCCTGCTGCTGCAC GCAGCAAGACCAGGAGGGGGAGGCAGCT GCCC CTACAGCAACCCCAGCCTGTGCAGCG- GAGGCGGCGGCAGCGGCGGAGGGGGTAGCC AGGTGCAGCTGCAGC AGAGCGGCCCTGGCCT GGTGAAGCCAAGCCAGACACTGTCCCTGACC TGCGCCATCAGCGGCGATTCCGTGAG CTC- CAACTCCGCCGCCTGGAATTGGATCAGG CAGTCCCCTTCTCGGGGCCTGGAGTGGCTGG- GAAGGACATACT ATCGGTCTAAGTGGTACAAC- GATTATGCCGTGTCTGTGAAGAGCAGAAT- CACAATCAACCCTGACACCTCCAAGA ATCAG TTCTCTCTGCAGCTGAATAGCGTGACACCAG AGGACACCGCCGTGTACTATTGCGCCAGG- GAGGTGACC GGCGACCTGGAGGATGCCTT TGACATCTGGGGCCAGGGCACAATGGTGACC GTGTCTAGCGGAGGAGGAGGA TCCGGAGGAG GAGGATCTGGCGGCGGCGGCAGCGATATCCA- GATGACACAGTCCCCATCCTCTCTGAGCGC CTC CGTGGGCGACAGAGTGACAATCACCTG TAGGGCCTCCCAGACCATCGGTCTTACCT- GAACTGGTATCAGCAGA GGCCCGGCAAGGCC CCTAATCTGCTGATCTACGCAGCAAGCTCCC TGCAGAGCGGAGTGCCATCCAGATTCTCTG GCAGGGGCTCCGGCACAGACTTCACCCTGAC- CATCTCTAGCCTGCAGGCCGAGGACTTCGC- CACCTACTATTGCC AGCAGTCTTATAGCATCC

CCCAGACATTTGGCCAGGGCACCAAGCTG- GAGATCAAGGGAAGCGGAGGGGGAG GCAG CTGCCCCTACAGCAACCCCAGCCTGT GCAG CGGAGGCGGCGGCAGCGAGCTGCCCACCCA GGGCACCTT CTCCAACGTGTCCACCAACGTGA GCCCAGCCAAGCCCACCACCACCGCCTGT CCTTATTCCAATCCTTCCCTGTGT GCTCCCAC- CACAACCCCAGCACCAAGGCCACCTACACCT GCACCAACCATCGCCTCTCAGCCCCTGAGCCT- GAGA CCTGAGGCATGTAGGCCAGCAGCAG- GAGGAGCAGTCCATACAAGGGGTCTGGAT- TTTGCATGCGACATCTACAT CTGGGCACCT CTGGCAGGAACATGTGGCGTGCTCCTGCT CAGCCTGGTCATCACCCTGTACTG CAAGA GAGGCA GGAAGAAGCTGCTGTATATCTT- CAAGCAGCCCTTCATGCGCCCCGTGCAGAC AACCCAGGAGGAGGATGGCTGC TCCTGTAG GTTCCCAGAAGAGGAGGAGGGGAGGATGT- GAGCTGCGCGTGAAGTTTTCCCGGTCTGCC GACGCAC CTGCATACCAGCAGGGCCAGAAC CAGCTGTATAACGAGCTGAATCTGGGCCG- GAGAGAGGAGTACGATGTGCT GGACAAGA GGCGCGGCAGAGATCCAGAGATGGGCGGCA- AGCCCCGGAGAAAGAACCCTCAGGAGGGC CTGT ACAATGAGCTGCAGAAGGATAAGATG GCCGAGGCCTATTCTGAGATCGGCATGAAGG- GAGAGAGGCGCCGGG GCAAGGGACACGA CGGACTGTACCAGGGACTGAGCACAGCCAC- CAAGGATACCTATGACGCCCTGCATATGCAG GCACTGCCTCCAAGGTGATCTAGAGGGC CCGTTTAAACCCGCTGATCAGCCTCGACTGT GCCTTCTAGTTGCCAG CCATCTGTTGTTTGC CCC TCCCCCGTGCCTTCCTTGACCCTGGAAG GTGCCACTCCCACTGTCCTTTCCTAATAAAA TGAGGAAATTGCATCGCATTGTCTGAGTAG GTGTCATTCTATTCTGGGGGGTGGGGT GGGG CAGGACAGCAAG GGGGAGGATTGGGAAGA CAATAGCAGGCATGCTGGGGATGCGGTGGG CTCTATGACTAGTGGCGAATTCCCGT GTAC CAGCTGAGAGACTCTAAATCCAGTGACAAGT CTGTCTGCCTATTCACCGATTTTGATTCT- CAAACAAATGTG TCACAAAGTAAGGATTCT-

GATGTGTATATCACAGACAAAACTGTGCTAGA-
CATGAGGTCTATGGACTTCAAGAGC AACAGTG
CTGTGGCCTGGAGCAACAAATCTGACTTTG-
CATGTGCAAACGCCTTCAACAACAGCATTAT-
TCCAGAA GACACCTTCTTCCCCAGCCCAGGT
AAGGGCAGCTTTGGTGCCTTCGCAGGCTGTT-
TCCTTGCTTCAGGAA, (SEQ ID NO: 9). or
AAGTAGCCCTGCATTTCAGGTTTCCTTGAG
TGGCAGGCCAGGCCTGGCCGTGAACGTT-
CACTGAAATCATGGCC TCTTGGCCAAGATTGA-
TAGCTTGTGCCTGTCCCTGAGTCCCAGTCCAT-
CACGAGCAGCTGGTTTCTAAGATGCTAT TTC
CCGTATAAAGCATGAGACCGTGACTT GCCAG
CCCCACAGAGCCCCGCCCTTGTCCATCACTGG-
CATCTGGAC TCCAGCCTGGGTTGGGGCAAAG
AGGGAAATGAGATCATGTCCTAACCCTGATC
CTCTTGTCCCACAGATATCCAG TCCGGTGAG
GGCAGAGGAAGTCTTCTAACATGCGGT GAC
GTGGAGGAGAATCCGGGCCCCGGATCCG
CTCTGC CCGTCACCGCTCTGCTGCTGCCACTG
GCCCTGCTGCTGCACGCCGCCAGACCCGGCG-
GAGGAGGCTCTTGCCCC TACAGCAACCCCAG
CCTGTGCTCTGGCGGCGGCGGCAGCGGAG
GCGGCGGCTCCCAGGTGCAGCTGCAGCAG
AGCGGCCCTGGCCTGGTGGAGCCAAGCCA-
GACACTGTCCCTGACCTGCGCCATC TCTG
GCGACAGCGTGAGCTC CAACAGCGCCGCATG-
GAATTGGATCAGGCAGTCCCCATCTCGG
GGCCTGGAGTGGCTGGGCAGAACATACTATA
GGTCCACCTGGTACAACGACTATGCCGGC
TCCGTGAAGTCTCGCATCACAATCAACCCCGA-
TACCAGCAAGAATC AGTTCTCCCTGC AGCTG
ACATCTGTGACCCCTGAGGACACAGCCGTG
TACTATTGCACCAGAAGCAGGCACAATA CAT-
TTCGGGGAATGGACGTGTGGGGACAGGGC
ACACTGGTGACCGTGAGCGGAGGAGGAG-
GATCCGGCGGA GGAGGCTCTGGCG GCGGCGG
CAGCGACATCCAGCTGACCCAGTCCCC TTC
TAGCCTGAGCGCCTCCGTGGGCG ATAGAGTGA
CAATCACCTGTAGGGCCTCTCAGAGCATCTC
CTCTTACCTGAACTGGTATCAGCAGAA GCC
CGGCA AGGCCCCTAAGCTGCTGATCTACGC
AGCAAGCTCCCTGCAGTCTGGAGTGCCAAGC
AGATTCTCCGGCTCTGGC AGCGGCACCGACTT-
TACACTGACCATCTCTAGCCTGCAGCCTGAG-
GATTTCGCCACATACTATTGCCAGCAGTCCT
ATTCTACACCACTGACCTTTGGCGGCGGCAC-
CAAGGTGGAGATCAAGGGAAGCGGC GGC
GGCGGAAGTTGTCC ATATTCAAACCCAAGTCT
GTGCAGCGGCGGAGGAGGAAGCGAACTGCC-
TACTCAGGGAACCTTCAGCAACGTG TCCAC-
CAATGTGAGCCCAGCAAAGCCTACCACAACC
GCATGCCCATACTCTAACCCCAGCCTGTG
CACAACCACA CCAGCACCCAGGCCCCCTAC
CCCTGCACCAACAATCGCCTCCCAGCCTC
TGTCTCTGCGGCCAGAGGCCTGCAGA
CCCGCCGCCGGCGGAGCAGTGCACACA
CGGGGCCTGGACTTTGCCTGTGATATC-
TATATCTGGGCACCACTGGC CGGAACATGTG
GCGTGCTGCTGCTGTCACTGGTCATTACACTGT
ACTGTAAGCGAGGCCGGAAGAAACTGCTGT
ATATTTTCAAACAGCCCTTTATGAGACC TGT
GCAGACTACCCAGGAGGAAGACGG CTGC
AGCTGTAGGTTCCCCG AGGAAGAGGAAG GCG
GGTGTGAGCTGAGGGTCAAGTTTAGCCGCTC
CGCAGATGCCCCTGCTTACCAGCAGG GGCA
GAATCAGCTGTATAACGAGCTGAATCT

GGGACGGAGAGAGGAATACGACGTGCTGGA-
TAAAAGGCGCGG GAGAGACCCCGAAATGG-
GAGGCAAGCCACGACGGAAAAACCCCCAG-
GAGGGCCTGTACAATGAACTGCAGAA GGAC
AAAATGGCAGAGGCCTATAGTGAAATCGGGAT-
GAAGGGAGAGAGAAGGCGCGGCA AAGG GC
ACGATG GCCTGTACCAGGGGCTGTCTACTGC-
CACCAAGGACACCTATGATGCTCTGCATATGC
AGGCACTGCCTCCAAGGT GATCTAGAGG GC
CC GTTTAAACCCGCTGATCAGCCTCGACTGT
GCCTTCTAGTTGCCAGCCATCTGTTGTTTGCCC
CTCCCCCGTGCCTTCCTTGACCCTGGAAGGT
GCCACTCCCACTGTCCTTTCCTAATAAAAT-
GAGGAAATTGCATCG CATTGTCTGAGTAGGTG
TCATTCTATTCTGGGGGGTGGGGTGGGGCA
GGACAGCAAGGGGGAGGATTGGGAA GACAA
TAGCAGGCATGCTGGGGATGCGGTGGGCTC-
TATGACTAGTGGCGAATTCCCGTGTACCAGCT-
GAGAGAC TCTAAATCCAGTGACAAGTCTGTC
TGCCTATTCACCGATTTTGATTCTCAAACAA
ATGTGTCACAAAGTAAGGATTC TGATGTGTAT
ATCACAGACAAAACTGTGCTAGACATGAGGT
CTATGGACTTCAAGAGCAACAGTGCTGT
GGCCTG GAGCAACAAATCTGACTTTGCATGTG
CAAACGCCTTCAACAACAGCATTATTCCAGAA-
GACACCTTCTTCCCCAG CCCAGGTAAGGG
CAG CT TTGGTGCCTTCGCAGGCTGTTTCCT
TGCTTCAGGAA (SEQ ID NO: 10).), or
AAGTAGCCCTGCATTTCAGGTTTCCTTGAGTGG
CAGGCCAGGCCTGGCCGTGAACGTTCACT-
GAAATCATGGCC TCTTGGCCAAGATTGA-
TAGCTTGTGCCTGTCCCTGAGTCCCAGTCCAT-
CACGAGCAGCTGGTTTCTAAGATGCTAT TTCC
CGTATAAAGCATGAGACCGTGACTTGCC
AGCCCCACAGAGCCCCGCCCTTGTCCAT-
CACTGGCATCTGGAC TCCAGCCTGGGTTG
GGGCAAAGAGGGAAATGAGATCATGTC
CTAACCCTGATCCTCTTGTCCCACAGA-
TATCCAG TCCGGTGAGGGCAGAGGAAGTC
TTCTAACATGCGGTGACGTGGAGGAGAATCCG
GGCCCCGGATCCGCTCTGC CCGTCACCG CTCT
GCTGCTGCCACTGGCCCTGCTGCTG CACGCC
GCCAGACCCGGCGGAGGAGGCTCTTGCCCC
TACAGCAACCCCAGCCTGTGCTCTGGCGGC-
GGCGGCAGCGGAGGCGGCGGCTC CCAG GT
GCAGCTGCAGCAG AGCGGCCCCGGCCTGGT-
GAAGCCTAGCCAGACACTGTCCCTGAC
CTGCGC AATCTCCGGCGACAGCGTGTCCGG
AAACAGGGCCACATGGAATTGGATCAGACAG
TCTCCAAGCAGGGCCTGGAGTGGCTGG-
GAAGGACCTACTAT CGGTCCGCCTGGTACAA
CGACTATGCCGTGTCTGTGAAGGGCCGCATCA-
CATTCAACCCAGATACCAGCAAGAAT CAG
TTTTCCCTGCAGCTGAATTCTGTGACACC
CGAGGATACCGCCGTGTACTATTGCGCCAG
AGGCGAGAGCGG AGCAGCAGCAGACGCCT
TCGATATCTGGGGCCAGGGCACCACA GTGA
CAGTGAGCGGAGGAGGAGGATCCGG CGGAG-
GAGGCTCTGGCGGCGGCGGCAGCGACATC
CAGCTGACCCAGAGCCCACCTTCCCTG
TCTGCCAGCGTG GGCGATCGCGTGACAAT-
CACCTGTCGGGCCTCCCAGTCTATCAGCTCC-
TACCTGAACTGGTATCAGCAGAAGCCA
GGCAAGGCCCCCAAGCTGCTGATCTACGCAG-
CATCTAGCCTGCAGTCTGGAGTGCCAAGCA-
GATTCAGCGGATC CGGATTCGGCACAGACTT-
TACACTGACCATCTCCTCTCTGCAGCCCGAGG-

ATTTCGCCACCTACTATTGCCAGCAG TCT-
TATAGCACACCTCAGACCTTTGGCCAGGGCAC-
CAAGGTGGACATCAAGGGAAGTGGAGGAG-
GAGGAAGTT GTCCCTACTCAAACC
CATCTCTGTGCTCAGGAGGAGGAGGAAGT-
GAACTGCCTACTCAGGGAACATTCAGCAAC
GTGTCCACCAATGTGAGCCCAGCAAAGCC-
TACCACAACCGCATGCCCATACTCTAACC
CCAGCCTGTGCACAACC ACACCAGCACCCAG
GCCCCCTACCCCTGCACCAACAATCGCCTCCC
AGC CTCTGTCTCTGCGGCCAGAGGCCTGC
AGACCCGCCGCCGGCGGAGCAGTGCACAC
ACGGGGCCTGGACTTTGCCTGTGATATC-
TATATCTGGGCACCACT GGCCGGAACATGT
GGCGTGCTGCTGCTGTCACTGGTCATTA-
CACTGTACTGTAAGCGAGGCCGGAAGAA
ACTGC TGTATATTTTCAAACAGCCCTTTATGA-
GACCTGTGCAGACTACCCAGGAGGAAGAC
GGCTGCAGCTGTAGGTTCC CCGAGGAAGAG-
GAAGGCGGGTGTGAGCTGAGGGTCAAGTT-
TAGCCGCTCCGCAGATGCCCCTGCTTACCA
GCA GGGGCAGAATCAGCTGTATAACGAGCT-
GAATCTGGGACGGAGGAGGAATACGACG
TGC TGGATAAAAGGCGC GGGGAGAGACCC
CGAAATGGGAGGCAAGCCACGACGGAAAA
ACCCCCAGGAGGGCCTGTACAATGAACTGCAG
AAGGACAAAATGGCAGAGGCCTATAGTGAA
ATCGGGATGAAGGGAGAGAGAAGGCGC
GGCAAAGGGCACGA TGGCCTGTACCAGG
GGCTGTCTACTGCCACCAAGGACACCTAT-
GATGCTCTGCATATGCAGGCACTGCCTCCAAG
GTGATCTAGAGGGCCCGTTTAAACCCGCT-
GATCAGCCTCGACTGTGCCTTCTAGTTGCCAG-
CCATCTGTTGTTTGC CCCTCCCCGTGCCT
TCCTTGACCCTGGAAGGTGCCACTCC-
CACTGTCCTTTCCTAATAAAATGAGGAAATTG-
CAT CGCATTGTCTGAGTAGGTGTCATTCTAT-
TCTGGGGGGTGGGGTGGGGCAGGACAGCAA-
GGGGGAGGATTGGG AAGACAATAGCAGG-
CATGCTGGGGATGCGGTGGGCTCTATGACT
AGTGGCGAATTCCCGTGTACCAGCTGAGAG
ACTCTAAATCCAGTGACAAGTCTGTCTGCCT-
ATTCACCGATTTTGATTCTCAAACAAATGTGT-
CACAAAGTAAGGA TTCTGATGTGTATATCACA-
GACAAAACTGTGCTAGACATGAGGTCTATGG-
ACTTCAAGAGCAACAGTGCTGTGGC CTGGA
GCAACAAATCTGACTTTGCATGTGCAAAC
GCCTTCAACAACAGCATTATTCCAGAAGACAC
CTTCTTCCCC AGCCCAGGTAAGGGCAG CTTT
GGTG CCTTCGCAGGCTGTTTCCTTGCTTCAG-
GAA, (SEQ ID NO: 11), or
AAGTAGCCCTGCATTTCAGGTTTCCTTGAGT
GGCAGGCCAGGCCTGGCCGTGAACGTTCACT-
GAAATCATGGCC TCTTGGCCAAGATTGA-
TAGCTTGTGCCTGTCCCTGAGTCCCAGTCCAT-
CACGAGCAGCTGGTTTCTAAGATGCTAT
TTCCCGTATAAAGCATGAGACCGTGAC
TTGCCAGCCCCACAGAGCCCCGCCCTTGTC-
CATCACTGGCATCTGGAC TCCAGCCTGGG
TTGGGGCAAAGAGGGAAATGAGATCATGTC
CTAACCCTGATCCTCTTGTCCCACAGATAT
CCAG TCCGGTGACGTGGAGGAGAATCCGGG
CCCCGGATCCGCTCTGC CCGTCACCGCTCTG
CTGCTGCCTCTGGCCCTGCTGCTGCACGCAGC-
CAGACCAGGCGGAGGAGGCTCCTGCCCT
TACTCTAACCCAAGCCTGTGCTCCGGAGGAG-

GAGGATCCGGCGGAGGAGGCTCTGAGGT-
GAAGCTGGTGGAG AGCGGAGGAGGCC TG
GTGCAGCCTGGCGGCTCCCTGTCTCTGAG
CTGCGCAGCATCCGGCTTCACCTTTACAGA
CTACTATATGTCTTGGGTGAGACAGCCCCC
TGGCAAGGCCCTGGAGTGGCTGGCCCT-
GATCAGGTCCAAGGCCG ATGGCTACACCAC
AGAGTATTCCGCCTCTGTGAAGGGCAGATT-
CACCCTGTCTAGGGACGATAGCCAGTCCATCC
TGTACCTGCAGATGAATGCACTGCGCCC
CGAGGACAGCGCCACATACTATTGTGCCAGA-
GACGCCGCCTACTATT CTTACTATAGCCCTGA
GGGCGCTATGGACTACTGGGGCCAGGGCA
CCTCCGTGACAGTGAGCTCCGGAGGAGG
AGGAAGCGGAGGAGGAGGCTCCGGCGGCGG
CGGCTCTATGGCCGACTATAAGGATATCGT-
GATGACCCAGAGC CACAAGTTTATGTCTA-
CAAGCGTGGGCGACCGCGTGAACATCACC
TGCAAGGCCAGCCAGAATGTGGATTCCGC
CGTGGCCTGGTACCAGCAGAAGCCTGGCCA-
GAGCCCTAAGGCCCTGATCTATTCCGCCTCT-
TACCGGTATAGCGG AGTGCCTGACCGCTT-
CACCGGAAGGGGATCCGGAACAGACTT-
CACCCTGACAATCTCTAGCGTGCAGGCCGAG
GATCTGGCCGTGTACTATTGTCAGCAGTAC-
TATAGCACCCCCTGGACCTTCGGCGGAG-
GAACCAAGCTGGAGATC AAGAGAGGATCTG-
GAGGAGGAGGAAGCTGCCCATACTCCAACC-
CCTCTCTGTGCAGCGGAGGAGGAGGATCTG
AGCTGCCAACCCAGGGCACATTTTCCAACG
TGTCTACAAATGTGAGCCCAGCAAAGCCAAC-
CACAACCGCATGC CCTTATAGCAATCCATC
CCTGTGCACAACCACACCTGCACCAAGAC-
CACCAACCCCAGCACCTACAATCGCCTCTC
AGCCACTGAGCCTGCGCCCCGAGGCATGCC
GGCCTGCAGCAGGCGGCGCCGTGCACACCA-
GGGGCCTGGACT TCGCCTGCGATATCTACATC
TGGGCACCTCTGGCAGGAACCTGTGGCGTGCT
GCTGCTGAGCCTGGTCATCACCC TGTACTGC
AAGAGAGGCAGGAAGAAGCTGCTGTATATCTT-
CAAGCAGCCCTTTATGCGCCCTGTGCAGAC-
CACAC AGGAGGAGGACGAGCTGCAGCTG TCG
GTTCCCAGAAGAGGAGGAGGGCGGCTGT-
GAGCTGAGAGTGAAGTTT AGCAGGTCCGCC-
GATGCACCAGCATACCAGCAGGGACAGAA
CCA- GCTGTATAACGAGCTGAATCTGGGC
CGGA GAGAGGAGTACGACGTGCTGGA-
TAAGAGGAGGGGAAGGGACCCCGAGATGG-
GAGGCAAGCCACGGAGAAA GAACCCCCAG-
GAGGGCCTGTACAATGAGCTGCAGAAGGACAA-
GATGGCCGAGGCCTATTCCGAGATCGGCATG
AAGGGAGAGAGGCGCCGGGGCAAGGGACAC-
GATGGCCTGTACCAGGGCCTGTCTACCGC-
CACAAAGGACACC TATGATGCCCTGCATA
TGCAGGCACTGCCTCCAAGGTGATCTAGAGG
GCCCGTTTAAACCCGCTGATCAGCCTCG
ACTGTGCCTTCTAGTTGCCAGCCATCT
GTTGTTTG CCCCTCCCCGTGCCT TCCTTG
ACCCTGGAAGGTGCCACTC CCACTGTCCTTTC
CTAATAAAATGAGGAAATTGCATCGCATTGTCT-
GAGTAGGTGTCATTCTATTCTGGGGGGTGG
GGTGGGGCAGGACAGCAAGGGGGAGGAT-
TGGGAAGACAATAGCAGGCATGCTGGGGAT
GCGGTGGGCTCTAT GACTAGTGGCGAATTC
CCGTGTACCAGCTGAGAGACTCTAAATCCAG
TGACAAGTCTGTCTGCCTATTCACCGATT

TTGATTCTCAAACAAATGTGTCACAAAG TAAG
GATTCTGATGTGTATATCACAGACA AAACTGT
GCTAGACATGAG      GTCTATGGACTTCAAGAG
CAACAGTGCTGTGGCCTGGAGC      AACAAATC
TGACTTTGCATGTGCAAACGCCTTCAA CAA CA
GCATTATTCCAGAAGACACCTTC      TTCCCCAG
CCCAGGTAAGGGCAGCTTTGGTG    CCTTCGCA
GGCTGTTT CCTTGCTTCAGGAA (SEQ ID NO: 12)
wherein underlined sequences are sequence of the
genomic TRAC (homology arm), Italic bold sequence
is a sequence coding for a 2A peptide, Italic is a
sequence corresponding to a ply A termination
sequence (BGH polyA).

In frame is a sequence coding for a CAR sequence, in
particular for an anti-CD22 CAR, an anti-CD123 CAR
sequence, preferably anti-CD22 CAR, anti-CD123 CAR.

The inventors also provided means for detecting and
identifying said engineered cells (TALEN-modified endog-
enous αβ-TCR negative human primary cell). This is an
essential step for making a medicament and useful to
provide quality controlled cells.

Thus, the present invention allows for both the knockout
of the endogenous alpha beta T cell receptor and the
expression of an exogenous nucleic acid sequence (e.g., a
chimeric antigen receptor or exogenous TCR) by targeting a
single recognition site with a single engineered nuclease in
one cell.

Accordingly, the present invention provides a homog-
enous population of CAR-expressing cells.

In particular embodiments where a sequence encoding a
chimeric antigen receptor is inserted into the TCR alpha
constant region gene, the invention provides a simplified
method for producing an "allogeneic" T cell that expresses
an antigen-specific CAR and has reduced TCR alpha beta
expression, or complete knockout, of the endogenous TCR.
Such cells can exhibit reduced or no induction of graft-
versus-host-disease (GVHD) when administered to an allo-
geneic subject and no rejection by T cells of the host.
(HvGD).

TALEN for Recognizing and Cleaving Recognition
Sequences in the T Cell Receptor Alpha Constant Region
Gene and Comparative Nucleases Doing the Same In particular embodiments, the invention can be practiced
using a TALEN or a Compact TALEN.

It is known in the art that it is possible to use a site-specific
nuclease to make a DNA break in the genome of a living
cell, and that such a DNA break can result in permanent
modification of the genome via mutagenic NHEJ repair or
via homologous recombination with a transgenic DNA
sequence. NHEJ can produce mutagenesis at the cleavage
site, resulting in inactivation of the allele. NHEJ-associated
mutagenesis may inactivate an allele via generation of early
stop codons, frameshift mutations producing aberrant non-
functional proteins, or could trigger mechanisms such as
nonsense-mediated mRNA decay. The use of nucleases to
induce mutagenesis via NHEJ can be used to target a specific
mutation or a sequence present in a wild-type allele.

The use of nucleases to induce a double-strand break in a
target locus is known to stimulate homologous recombina-
tion, particularly of transgenic DNA sequences flanked by
sequences that are homologous to the genomic target. In this
manner, exogenous nucleic acid sequences can be inserted
into a target locus. Such exogenous nucleic acids can be
non-coding sequence or encode, for example, a chimeric
antigen receptor, an exogenous TCR, or any sequence or
polypeptide of interest. For said polypeptide of interest to be
expressed, said open reading frame or encoding sequence must be in frame with the TCR promotor or have its own
promoter. In case the encoding sequence is in frame with the
TCR promotor it has to comprise a sequence encoding a
self-cleaving peptide such as a 2A peptide, for the subse-
quent polypeptide to be expressed on its own, by itself.

IRES

In one embodiment said polypeptide encoded by an
exogenous sequence comprises an IRES.

An IRES means Internal ribosome entry sites and may be
any IRES that allows the transcription and then translation
of a coding sequence inserted in the gene of the invention.

(SEQ ID NO: 23)
Gcccctctccctcccccccccctaacgttactggccgaagccgcttggaa taaggccggtgtgcgtttgtctatatgttattttccaccatattgccgtc ttttggcaatgtgagggcccggaaacctggccctgtcttcttgacgagca ttcctaggggtctttccctctcgccaaaggaatgcaaggtctgttgaat gtcgtgaaggaagcagttcctctggaagcttcttgaagacaaacaacgtc tgtagcgaccctttgcaggcagcggaaccccccacctggcgacaggtgcc tctgcggccaaaagccacgtgtataagatacacctgcaaaggcggcacaa ccccagtgccacgttgtgagttggatagttgtggaaagagtcaaatggct ctcctcaagcgtattcaacaaggggctgaaggatgcccagaaggtacccc attgtatgggatctgatctggggcctcggtgcacatgctttacatgtgtt tagtcgaggttaaaaaaacgtctaggcccccgaaccacggggacgtggt tttcctttgaaaaacacgatgataatatggccacaacc In an advantageous embodiment the invention may be
practiced using a TALEN.

In an advantageous embodiment the invention may be
practiced using a TALEN encoded by ATGGGCGAT
CCTAAAAAGAAACGTAAGGTCATCGATATCGCC-
GATCTACGCACGCTCGGCTACAGCCAGCAGCAA
CAGGAGAAGATCAAACCGAAGGTTCGTTCGACA
GTGGCGCAGCACCACGAGGCACTGGTCGGC-
CACGGGTTTA CACACGCGCACATCGTTGCGTTAAG
CCAACACCCGGCAGCGTTAGGGACCGTCGCTGT-
CAAGTATCAGGACATG          ATCGCAGCGTTGCCA
GAGGCGACACACGAAGCGATCGTTGGCGTCGG
CAAA  CAGTGGTCCGGCGCACGCGCTC  TGGAGG
CCT  TGCTCACGGTGGCGGGAGAGTTGAGAGGTC-
CACCGTTACAGTTGGACACAGGCCAACTTCTCAA
GATTGCAAAACGTGGCGGCGTGACCGCAGTG-
GAGGCAGTGCATGCATGGCGCAATGCACTGA
CGGGTGCCCCG  CTCAACTTGACCCCCCA  GCAG
GTGGTGGCCATCGCCAGCAATGGCGGTGGC  AAGC
AGGCGCTGGAGACGGTCC  AGCGGCTGTTGCCGG
TGCTGTGCCAGGCCCACGGCTTGACCCCCCAGC
AGGTGGTGGCCATCGCCAGCAATAAT       GGTGGC
AAGCAGGCGCTGGAGACGGTCCAGCGGCTGTTGC
CGGTGCTGTGCCAGGCCCACGGCTTGACCCCC
CAGCAGGTGGTGGCCATCGCCAGCAATGGCG GTG
GCAAGCAGGCGCTGGAGACGGTCCAGCGGCTGT
TGCCG     GTGCTGTGCCAGGCCCACGGCTTGACCC
CGG           AGCAGGTGGTGGCCATCGCCAGCCAC- GATGGCGGCAAGCAG GCGCTGGAGACGGTC
CAGCGGCTGTTGCCGGTGCTGTGCCAGGCCCACGG
CTTGACCCCGGAGCAGGTGGTG GCCATCGCCAGC-
CACGATGGCGGCAAGCAGGCGCTGGAGACGGTCC
AGCGGCTGTTGCCGGTGCTGTGCCAG GCC- 5
CACGGCTTGACCCCGGAGCAGGTGGTGGC-
CATCGCCAGCCACGATGGCGGCAAGCAGGCGCTG-
GAGACG GTCCAGCGGCTGTTGCCGGTG CTGTG
CCAGGCCCACGGCTTGACCCCGGAGCAGGTG
GTGGCCATCGCCAGCA ATATTGGTGGCAAG CAGG 10
CG CTGGAGACGGTGCAGGCGCTGTTGCC GGT
GCTGTGCCAGGCCCACGGCTTGAC CCCGGAGCA
GGTGGTGGCCATCGCCAGCCACGATGGCGG
CAAGCAGGCGCTGGAGACGGTCCAGCGGCTGTT
GCCGGTGCTGTGCCAGGCCCACGGCTTGACCCCG- 15
GAGCAGGTGGTGGCCATCGCCAGCAATAT-
TGGTGGCAAG CAGGCGCTGGAGACGGTGCAG
GCGCTGTTGCCGGTGCTGTGCCAGGCCCACG
GCTTGACCCCCCAGCAGGTG GTGGCCATCG
CCAGCAATAATGGTGGCAAGCAGGCGCTGGA- 20
GACGGTCCAGCGGCTGTTGCCGGTGCTGTGCC
AGGCCCACGGCTTGACCCCGGAGCAGGTGGTGGC-
CATCGCCAGCAATATTGGTGGCAAGCAGGCGCTG-
GAGAC GGTGCAGGCGCTGTTGCCGGTGCTGT
GCCAGGCCCACGGCTTGACCCCCCAGCAGGTGG 25
TGGCCATCGCCAGC AATGGCGGTGGCAAGCAGGC
GCTGGAGACGGTCCAGCGGCTGTTGCCGGTGCTG
TGCCAGGCCCACGGCTTG ACCCCGGAGCA
GGTGGTGGCCATCGCCAGCAATATTGGTGGC
AAGCAG GCGCTGGAGACGGTGCAGGCGCTG 30
TTGCCGGTGCTGTGCCAGGCCCACGGCTTGACCC
CCC AGCAGGTGGTGGCCATCGCCAGCAATGGCGG
TGGCA AGCAGGCGCTGGAGACGGTCCAGC
GGCTGT TGCCGGTGCTGTGCCAGGCCCACGGCTT
GACCCCGGAGCAGG TGGTGGCCATCGCCAGCCAC-
GATGGCGGCAAGCAGGCGCTGGAGACGGTCCAGC
GGCTGTTGCCGGTGCTGTG CCAGGCCCACGG
CTTGACCCCTCAGCAGGTGGTGGCCATCGCCAGC
AATGGCGGCGGCAGGCCGGCGCTGGA GAGCAT-
TGTTGCCCAGTTATCTCGCCCTGATCCGGCG 40
TTGGCCGCGTTGACCAACGACCACCTCGTCGC
CTTGGC CTGCCTCGGCGGGCGTCCTGCGCTG-
GATGCAGTGAAAAAGGGATTGGGGGATCC-
TATCAGCCGTTCCCAGCTGG TGAAGTCCGAGCTG-
GAGGAGAAGAAATCCGAGTTGAGGCACAAGCT- 45
GAAGTACGTGCCCCACGAGTACATCGA GCT-
GATCGAGATCGCCCGGAACAGCACCCAGG ACC
GTATCCTGGAGATGAAGGTGATGGAGTTCTTCAT-
GAAGG TGTACGGCTACAGGGGCAAGCACCTGG
GCGGCTCCAGGAAGCCCGACGGCGCCATCTA- 50
CACCGTGGGCTCCCC CATCGACTACGGCGTGAT
CGTGGACACCAAGGCCTACTCCGGCGGCTACAA
CCTGCCCATCGGCCAGGCCGACG AAATGCAG
AGGTACGTGGAGGAGAACCAGACCAGGAAC
AAGCACATCAACCCCAACGAGTGGTGGAAGGTGT 55
ACCCCTCCAGCGTGACCGAGTTCAAGTTCCT
GTTCGTGTCCGGCCACTTCAAGGGCAACTA-
CAAGGCCCAGCTG ACCAGGCTGAACCACATCAC-
CAACTGCAACGGCGCCGTGCTGTCCGTGGAG-
GAGCTCCTGATCGGCGGCGAGA TGATCAAG
GCCGGCACCCTGACCCTGGAGGAGGTGAGGAG-
GAAGTTCAACAACGGCGAGATCAACTTCGCGG
CCGACTGATAA (SEQ ID NO: 1), resulting for example in
the sequence:

MGDPKKKRKVIDIADLRTLGYSQQQQEKIKPKV
      RSTVAQHHEALVGHGFTHAHIVALSQHPAAL-
      GTVAVKYQDMIA ALPEATHEAIVGVGKQWSGA-

RALEALLTVAGELRGPPLQLDTGQLLKI-
AKRGGVTAVEAVHAWRNALTGAPLNLTPQ
QVVAIASNGGGKQALETVQRLLP VLCQAHG
LTPQQVVAIASNNGGKQALETVQRLLPVLCQAH
GLTPQQVVAIASN GGGKQALETVQRLLPVLCQA
HGLTPEQVVAIASHDGGKQALETVQRLLPVL
CQAHGLTPEQVVAIASHDGGKQALE TVQRL
LPVLCQAHGLTPEQVVAIASHDGGKQALETVQ
RLLPVLCQAHGLTPEQVVAIASNIGGKQAL
ETVQALLPVLC QAHGLTPEQVVAIASHDGGKQ
AL ETVQRLLPVLCQAHGLTPEQVVAIASNIGGK
QALETVQALLPVLCQAHGLTPQ QVVAIASNN
GGKQALETVQRLLPVLCQAHGLTPEQVVA-
IASNIGGKQALETVQALLPVLCQAHGLTPQQVVA-
IASN GGGKQALETVQRLLPVLCQAHGLTPEQVV
AIASNIGGKQALETVQALLPVLCQAHGLTPQQ-
VVAIASNGGGKQALE TVQRLLPVLCQAHGLTPE
Q VVAIASHDGGKQALETVQRLLPVLCQAHG
TPQQVVAIASNGGGRPALESIVAQLSRP DPA-
LAALTNDHLVALACLGGRPALDAVKKGLGDPIS-
RSQLVKSELEEKKSELRHKLKYVPHEYIELIE-
IARNSTQDRILEM KVMEFFMKVYGY RGKHLG
GSRKPDGAIYTVGSPIDYGVIVDTKAYSGGY-
NLPIGQADEMQRYVEENQTRNKHINP NEWW
KVYPSSVTEFKFLFVSGHFKGNYKAQLTRLN-
HITNCNGAVLSVEELLIGGEMIKAGTLTLE
EVRRKFNNGEINF AAD (SEQ ID NO: 3)
and
ATGGGCGATCCTAAAAAGAAACGTAAGGTCATC-
GATATCGCCGATCTACGCACGCTCGGCTACA
GCCAGCAGCAA CAGGAGAAGATCAAACCGA
AGGTTCGTTCGACAGTGGCGCAGCACCACGA
GGCACTGGTCGGCCACGGGTTTA CACACGC
GCACATCGTTGCGTTAAGCCAACACCCG
GCAGCGTTAGGGACCGTCGCTGTCAAGTA
TCAGGACATG ATCGCAGCGTTGCCAGAGGCG
ACACACGAAGCGATCGTTGGCGTCGGCAA
ACA GT GGTCC GGCGCACGCGCTC TGGAGG
CCTTGCTCACGGTGGCGGGAGAGTTGAGAG
GTCCACCGTTACAGTTGGACACAGGC-
CAACTTCTCAA GATTGCAAAACGTGGCG
GCGTGA CCGCAGTGGAGGCAGTGCATGCATG
GCGCAATGCACTGACGGGTGCCCCG CTCAA
CTTGACCCCGGAGCAGGTGGTGGCCATCG
CCAGCCACGATGGCGGCAAGCAGGCGCTGGA-
GACGGTCC AGCGGCTGTTGCCGGTG CTGT
GCCAGGCCCACGGCTTGACCCCCCAG CAGGT
GGTGGCCATCGCCAGCAATGG CGGTGGC AAG
CAGGCGCTGGAGACGGTCCAGCGGCTGTTGCC
GGTGCTGTGCCAGGCCCACGGCTTGACCCC
GGAGCAGGTGGTGGCCATCGCCAGCCAC-
GATGGCGGCAAGCAGGCGCTGGAGAC GG TC
CAGCGGCTGTTGCC GGTGCTGTGCCAGGCC-
CACGGCTTGACCCCGGAGCAGGTGGTGGC-
CATCGCCAGCAATATTGGTGGCAAGCAG
GCGCTGGAGACGGTGCAGGCGCTGTTGC
CGGTGCTGTGCCAGGCCCACGGCTTGACCCCC
CAGCAGGTGGTG GCCATCGCCAGCAATA ATG
GTG GCAAGCAGGCGCTGGAGACGGTCCAG
CGGCTGTTGCCGGTGCTGTGCCAGG CCCAC
GG CTTGACCCCGGAGCAGGTGGTGGCCAT
CGCCAGCCACGATGGCGGCAAGCAGGCGCTG-
GAGACGG TCCAGCGGCTGTTGCCGGT GCTGT
GCCAGGCCCACGGCTTGACCCCCCAGCA GGT
GGTGGCCATCGCCAGCAAT GGCGGTGGCAAG
CAGGCGCTGGAGACGGTCCAGCGGCTGTTGCC
GGTGC TGTGCCAGGCCCACGGCTTGACC CCCCAGCAGGTGGTGGCCATCGCCAGCAAT AA
TGGTGGCAAGCAGGCGCTGGAGACGGTCCA
GCGGCTGTTGC CGGTGCTGTGCCAGGCCCAC
GGCTTGACCCCCCAGCAGGTGGTGGCCATCG
CCAGCAATAATGGTGGCAAGCA GGCGCTGGA-
GACGGTCCAGCGGCTGTTGCCGGTGCTGTGC-
CAGGCCCACGGCTTGACCCCCCAG CAGGT GG
TG GCCATCGCCAGCAATGGCGGTGGCAAGC
AGGCGCTGGAGACGGTCCAGCGGCTGTTGCC
GGTGCTGTGCCAG GCCCACGGCTTGACCCCG- 10
GAGCAGGTGGTGGCCATCGCCAGCAATATTG
GTGGCAAGCAGGCGCTGGAGACG GTGCAGG
CGCTGTTGCCGGTGCTGTGCCAGGCCCACG
GCTTGACCCCGGAGCAGGTGGTGGCCATC
GCCAGCC ACGATGGCGGCAAGCAGGCGCTG- 15
GAGACGGTCCAGCGGCTGTTGCCGGTGCTGT-
GCCAGGCCCACGGCTTGA CCCCGGAGCA GG
TGGTGGCCATCGCCAGCAATATTGGTGGCA
AGC AGGCGCTGGAGACGGTGCAGGCGCTGTT
GCCGGTGCTGTGCCAGGCCCACGGCTTG
ACCCCGGAGCAGGTGGTGGCCATCGCCAGC-
CACGATGGCGGCAA GCAGGCGCTGGAGACG
GTCCAGCGGCTGTTGCCGGTGCTGTGCCAGG-
CCCACGGCTTGACCCCCCAGCAGGTG GTGGC-
CATCGCCAGCAATAATGGTGGCAAGCAGGCG-
CTGGAGACGGTCCAGCGGCTGTTGCCGGTG
CTGTGCCAGGCCCACGGCTTGACCCCT CAGC
AGGTGGTGGCCATCGCCAGCAATGGCGGCG
GCAGGCCGGCGCTGGAGA GCATTGTTGCCCA
GTTATCTCGCCCTGATCCGGCGTTG GCCGCG 30
TTGACCAACGACCACCTCGTCGCCTTGGCCT
GCCTCGGCGGGCGTCCTGCGCTGGATGCAGT-
GAAAAAGGGATTGGGGGATCCTATCAGCC GT
TCCCAGCTGGT GAAGTCCGAGCTGGAGGAG
AAGAAATCCGAGTTGAGGCACAAGCTGAA G 35
TACGTGCCCCACGAGTACATCGAG CTGAT
CGAGATCGCCCGGAACAGCACCCAGGACCGT
ATCCTGGAGATGAAGGTGATGGAGTTCTTCAT-
GAAGGT GTACGGCTACAGGGGCAAGCAC
CTGGGCGGCTCCAGGAAGCCCGACGGCGC- 40
CATCTACACCGTGGGCTCCCCC ATCGACTAC
GGCGTGATCGTGGACACCAAGGCCTACTC CG
GCGGCTACAACCTGCCCATCGGCCAGGCC
GACGA AATGCAGAGGTACGTGGAGGAGAA
CCAGACCAGGAACAAGCACATCAACCCCAA 45
CGAGTGGTGGAAGGTGTA CCCCTCCAGCGTG
ACCGAGTTCAAGTTCCTGTTCGTGTCCGGC-
CACTTCAAGGGCAACTACAAGGCCCAGCTGA
CCAGGCTGAACCACATCACCAACTGCA AC
GGCGCCGTGCTGTCCGTGGAGGAGCTCCT-
GATCGGCGGCGAGAT GATCAAGGCCGGCA
CCCTGACCCTGGAGGAGGTGAGGAGGAAGTT-
CAACAACGGCGAGATCAACTTCGCGGC
CGACTGATAA (SEQ ID NO: 2), encoding for
example:
MGDPKKKRKVIDIADLRTLGYSQQQQEKIKPKV
RSTVAQHHEALVGHGFTHAHIVALSQHPAAL-
GTVAVKYQDMIA ALPEATHEAIVGVGKOWSGA-
RALEALLTVAGELRGPPLQLDTGQLLKIAKRGG
VTAVEAVHAWRNALTGAPLNLTPE QVVAIAS HD
GGKQALETVQRLLPVLCQAHGLTPQQVVAIA
SNGGGKQALETVQRLLPVLCQAHGLTPEQVVA-
IASH DGGKQALETVQRLLPVLCQAHGLTPE QV
VAIASNIGGKQALETVQALLPVLCQAHGLTPQQ
VVAIASNNGGKQALE TVQRLLPVLCQAHGLT-
PEQ VVAIASHDGGKQALETVQRLLPVLCQ
AHGLT PQQVVAIASNGGGKQALETVQRLLPVL CQAH GLTPQQVVAIASNNGGKQALETVQRL
LPVLCQA HGLTPQQVVAIASNNGGKQAL-
ETVQRLL PVLC QAHGLT PQQVVAIASNG-
GGKQALETVQRLLPVL CQ AHGLTPEQVVA-
IASNIGGKQALETVQALLPV LCQAHGLTPEQ-
VVAIASHDGGKQALETVQRL LPVLCQAHGLT-
PEQVVAIASNIGGKQALET VQALLPVLCQA-
HGLTPEQVVAIASHDGGKQALE TVQRLLPV-
LCQAHGLTPQQVVAIASNNGGK QALETVQRL-
LPVLCQAHGLTPQQVVAIASNGGGRPALE-
SIVAQLSRP DPALAALTNDHLVALACLGGRPAL-
DAVKKGLGDPISRSQLVKSELEEKKSEL
RHKLKYVPHEYIELIEIARNSTQDRILEM KVMEF
FMKVVYGYRGKHLGGSRKPDGAIYTVGSPIDY
GVIVDTKAYSGGYNLPIGQADEMQRYVEENQ
TRNKHINP NEWWKVYPSSVTEFKFLFVSGHFK
GNYKAQLTRLNHITNCNGAVLSVEELLIGGEMI-
KAGTLTLEEVRRKFNNGEINF AAD, (SEQ ID NO:
4), For the right TALEN.

In an advantageous embodiment, the invention can be practiced using a TALEN recognizing the following sequence:

```
                                    (SEQ ID NO: 38)
          TTGTCCCACAGATATCCagaaccctgaccc tgCCGTGTACCAGCTGAGAGA.
```

Methods for making TALEN domains that bind to pre-determined DNA sites are known in the art, for example Reyon et al. (2012) Nat Biotechnol. 30:460-5.

An Improved method of the invention allows making endonucleases inducing below detection off target cleavage.

An Improved method of the invention allows making TALEN endonucleases inducing no or very limited and silent off target cleavage.

In particular embodiments, the nucleases used to compare the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs as discloses in WO2017106528.

The present invention provides means for detecting such cells (on and off-sites dsDNA cut induced by said mega-nucleases).

Recombinant meganucleases used here comprise a first subunit, comprising a first hypervariable (HVR1) region, and a second subunit, comprising a second hypervariable (HVR2) region. Further, the first subunit binds to a first recognition half-site in the recognition sequence (e.g., the TRC 1, TRC3, or TRC7 half-site), and the second subunit binds to a second recognition half-site in the recognition sequence (e.g., the TRC2, TRC4, or TRC8 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which com-prises the HVR2 region and binds the second half-site, is positioned as the C-terminal subunit. In alternative embodi-ments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Comparative exemplary TRC 1-2 meganucleases, TRC 3-4 meganucleases and TRC 7-8 meganucleases are disclosed in WO2017106528.

A variety of different types of nuclease are useful for practicing the invention. In one embodiment, the invention can be practiced using recombinant meganucleases. In another embodiment, the invention can be practiced using a CRISPR nuclease or CRISPR Nickase. Methods for making CRISPRs and CRISPR Nickases that recognize pre-determined DNA sites are known in the art, for example Ran, et al. (2013) Nat Protoc. 8:2281-308.

General Methods for Producing Genetically-Modified Cells

The invention provides methods for producing genetically-modified cells using engineered TALEN nucleases that recognize and cleave recognition sequences found within the human TCR alpha constant region gene.

In one embodiment, the invention provides methods for producing genetically-modified cells using engineered TALEN nucleases that recognize and cleave recognition sequences found within the human TCR alpha constant region gene,

```
                                      (SEQ ID NO: 38)
TTGTCCCACAGATATCCagaaccctgaccctgCCGTGTACCAGCTGAGA
GA.
```

In one embodiment, the invention provides methods for producing genetically-modified cells using engineered TALEN nucleases that recognize and cleave sequence having at least 80% identity with sequence recognition sequences found within the human TCR alpha constant region gene

```
                                      (SEQ ID NO: 38)
    TTGTCCCACAGATATCCagaaccctgaccc tgCCGTGTACCAGCTGAGAGA.
```

In one embodiment, the invention provides methods for producing genetically-modified cells using engineered TALEN nucleases that recognize and cleave sequence having at least 90% identity with sequence recognition sequences found within the human TCR alpha constant region gene

```
                                      (SEQ ID NO: 38)
    TTGTCCCACAGATATCCagaaccctgaccc tgCCGTGTACCAGCTGAGAGA.
```

In one embodiment, the invention provides methods for producing genetically-modified cells using engineered TALEN nucleases that recognize and cleave sequence having at least 91% identity with sequence recognition sequences found within the human TCR alpha constant region gene

```
                                      (SEQ ID NO: 38)
    TTGTCCCACAGATATCCagaaccctgaccc tgCCGTGTACCAGCTGAGAGA.
```

In one embodiment, the invention provides methods for producing genetically-modified cells using engineered TALEN nucleases that recognize and cleave sequence having at least 92% identity with sequence recognition sequences found within the human TCR alpha constant region gene

```
                                      (SEQ ID NO: 38)
    TTGTCCCACAGATATCCagaaccctgaccc tgCCGTGTACCAGCTGAGAGA.
```

In one embodiment, the invention provides methods for producing genetically-modified cells using engineered TALEN nucleases that recognize and cleave sequence having at least 93% identity with sequence recognition sequences found within the human TCR alpha constant region gene

```
                                      (SEQ ID NO: 38)
    TTGTCCCACAGATATCCagaaccctgaccc tgCCGTGTACCAGCTGAGAGA.
```

In one embodiment, the invention provides methods for producing genetically-modified cells using engineered TALEN nucleases that recognize and cleave sequence having at least 94% identity with sequence recognition sequences found within the human TCR alpha constant region gene

```
                                      (SEQ ID NO: 38)
    TTGTCCCACAGATATCCagaaccctgaccc tgCCGTGTACCAGCTGAGAGA.
```

In one embodiment, the invention provides methods for producing genetically-modified cells using engineered TALEN nucleases that recognize and cleave sequence having at least 95% identity with sequence recognition sequences found within the human TCR alpha constant region gene

```
                                      (SEQ ID NO: 38)
TTGTCCCACAGATATCCagaaccctgaccctgCCGTGTACCAGCT-
GAGAGA.
```

In one embodiment, the invention provides methods for producing genetically-modified cells using engineered TALEN nucleases that recognize and cleave sequence having at least 96% identity with sequence recognition sequences found within the human TCR alpha constant region gene (TTGTCCCACAGATATCCagaaccct gaccctgCCGTGTACCAGCTGAGAGA (SEQ ID NO: 38).

In one embodiment, the invention provides methods for producing genetically-modified cells using engineered TALEN nucleases that recognize and cleave sequence having at least 97% identity with sequence recognition sequences found within the human TCR alpha constant region gene TTGTCCCACAGATATCCagaaccctgaccct gCCGTGTACCAGCTGAGAGA (SEQ ID NO: 38).

In one embodiment, the invention provides methods for producing genetically-modified cells using engineered TALEN nucleases that recognize and cleave sequence having at least 98% identity with sequence recognition sequences found within the human TCR alpha constant region gene TTGTCCCACAGATATCCagaaccctgacc ctgCCGTGTACCAGCTGAGAGA (SEQ ID NO: 38).

In one embodiment, the invention provides methods for producing genetically-modified cells using engineered TALEN nucleases that recognize and cleave sequence having at 99% identity with sequence recognition sequences found within the human TCR alpha constant region gene (TTGTCCCACAGA-TATCCagaaccctgaccctgCCGT GTACCAGCTGAGAGA (SEQ ID NO: 38).

In one embodiment, the invention provides methods for producing genetically-modified cells using engineered TALEN nucleases that recognize and cleave sequence having 100% identity with sequence recognition sequences found within the human TCR alpha constant region gene (TTGTCCCACAGA-TATCCagaaccctgaccctgCCGTGT ACCAGCTGAGAGA (SEQ ID NO: 38).

Cleavage at such recognition sequences can allow for NHEJ at the cleavage site and disrupted expression of the human T cell receptor alpha chain subunit, leading to reduced expression and/or function of the T cell receptor at the cell surface. Additionally, cleavage at such recognition sequences can further allow for homologous recombination of exogenous nucleic acid sequences directly into the TCR alpha constant region gene.

RNA Encoding Nucleases

Engineered TALEN nucleases of the invention can be delivered into a cell in the form of a protein or, preferably, as a nucleic acid encoding the engineered nuclease. Such nucleic acid can be DNA (e.g., circular or linearized plasmid DNA or PCR products) or RNA or a combination of RNAs.

Such RNA may have various stability, various lengths and be delivered in various amounts.

For embodiments in which the engineered TALEN nuclease coding sequence is delivered in DNA form, it should be operably linked to a promoter to facilitate transcription of the nuclease, (TALEN or meganuclease gene). Mammalian promoters suitable for the invention include constitutive promoters such as the cytomegalovirus early (CMV) promoter (Thomsen et al. (1984), Proc Natl Acad Sci USA. 81 (3): 659-63) or the SV40 early promoter (Benoist and Chambon (1981), Nature. 290 (5804): 304-10) as well as inducible promoters such as the tetracycline-inducible promoter (Dingermann ei a/. (1992), Mol Cell Biol. 12 (9): 4038-45).

In some embodiments, mRNA encoding the engineered nuclease is delivered to the cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methylguanosine. In some embodiments, the mRNA may be polyadenylated. in other embodiments, the mRNA may have different lengths of poly A tail.

In particular embodiments, an mRNA encoding an engineered nuclease of the invention can be a polycistronic mRNA encoding two or more nucleases (or half) that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (/'. e., cistrons) from the same mRNA molecule including, but not limited to, an IRES element, a T2A element, a P2A element, an E2A element, and an F2A element.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (/'. e., cistrons) from the same mRNA molecule including, but not limited to, an IRES element, a T2A element, a P2A element, an E2A element, and an F2A element.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (/'. e., cistrons) from the same mRNA molecule including, but not limited to, an IRES element, a T2A element, a P2A element, an E2A element, and an F2A element.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (/'. e., cistrons) from the same mRNA molecule including, but not limited to, an IRES element, a T2A element, a P2A element, an E2A element, and an F2A element.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic m'RNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (/'. e., cistrons) from the same mRNA molecule including, but not limited to, an IRES element, a T2A element, a P2A element, an E2A element, and an F2A element.

In particular embodiments, an mRNA encoding an engineered nuclease of the invention can be a polycistronic mRNA encoding two or more nucleases that are simultaneously expressed in the cell and no coding regulatory RNA. A polycistronic mRNA can encode two or more nucleases of the invention that target different recognition sequences in the same target gene and activates program(s) of T cell differentiation or dedifferentiation. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes and a non coding ARN regulating the maturing state of the cell as described (Neilson.R. Genes Dev. 2007 Mar. 1; 21 (5): 578-589. doi: 10.1101/gad.1522907).

A polycistronic mRNA comprising any element known in the art to allow for the translation of two or more genes (/'. e., cistrons) from the same mRNA molecule including, but not limited to, an IRES element, a T2A element, a P2A element, an E2A element, and an F2A element.

Purified nuclease proteins can be delivered into cells to cleave genomic DNA, which allows for homologous recombination or non-homologous end-joining at the cleavage site with a sequence of interest, by a variety of different mechanisms known in the art.

In some embodiments, engineered nuclease proteins, or DNA/mRNA encoding engineered nucleases, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25:679-736), MPG (Simeoni, et al. (2003) Nucleic Acids Res. 31:2717-2724), Pep-1 (Deshayes et al. (2004) Biochemistry 43:7698-7706, and HSV-1 VP-22 (Deshayes et al. (2005) Cell Mol Life Sci. 62:1839-49. In an alternative embodiment, engineered nucleases, or DNA/mRNA encoding engineered nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall, et al. (2014) Tissue Barriers. 2 (4): e944449; Dinda, et al. (2013) Curr Pharm Biotechnol. 14:1264-74; Kang, et al. (2014) Curr Pharm Biotechnol. 15 (3): 220-30; Qian et al. (2014) Expert Opin Drug Metab Toxicol. 10 (11): 1491-508).

In some embodiments, engineered nuclease proteins, or DNA/mRNA encoding engineered nucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1μ η, preferably <100 nm. Such nanoparticles may be designed using a core composed of metal, lipid, polymer, or biological macromolecule, and multiple copies of the recombinant meganuclease proteins, mRNA, or DNA can be attached to or encapsulated with the nanoparticle core. This increases the copy number of the protein/mRNA/DNA that is delivered to each cell and, so, increases the intracellular expression of each engineered nuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33 (30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the engineered nucleases or DNA/mRNA encoding the engineered nucleases, are encapsulated within liposomes or complexed using cationic lipids (see, e.g., Lipofectamine™, Life Technologies Corp., Carlsbad, CA; Zuris et al. (2015) Nat Biotechnol. 33:73-80; Mishra et al. (201 1) J Drug Deliv. 201 1:863734). The liposome and lipoplex formulations can protect the payload from degradation, and facilitate cellular uptake and delivery efficiency through fusion with and/or disruption of the cellular membranes of the cells.

In some embodiments, engineered nuclease proteins, or DNA/mRNA encoding engineered nucleases, are encapsulated within polymeric scaffolds (e.g., PLGA) or complexed using cationic polymers (e.g., PEI, PLL) (Tamboli et al. (201 1) Ther Deliv. 2 (4): 523-536).

In some embodiments, engineered nuclease proteins, or DNA/mRNA encoding engineered nucleases, are combined with amphiphilic molecules that self-assemble into micelles (Tong et al. (2007) J Gene Med. 9 (11): 956-66). Polymeric micelles may include a micellar shell formed with a hydrophilic polymer (e.g., polyethyleneglycol) that can prevent aggregation, mask charge interactions, and reduce nonspecific interactions outside of the cell.

In some embodiments, engineered nuclease proteins, (also called nuclease or endonuclease in the present invention) or DNA/mRNA encoding engineered nucleases, are formulated into an emulsion or a nanoemulsion (i.e., having an average particle diameter of <1 nm) for delivery to the cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, engineered nuclease proteins, or DNA/mRNA encoding engineered nucleases, are covalently attached to, or non-covalently associated with, multifunctional polymer conjugates, DNA dendrimers, and polymeric dendrimers (Mastorakos et al. (2015) Nanoscale. 7 (9): 3845-56; Cheng et al. (2008) J. Pharm Sci. 97 (1): 123-43).

The dendrimer generation can control the payload capacity and size, and can provide a high payload capacity. Moreover, display of multiple surface groups can be leveraged to improve stability and reduce nonspecific interactions.

In some embodiments, genes encoding an engineered nuclease are introduced into a cell using a viral vector. Such vectors are known in the art and include lentiviral vectors, adenoviral vectors, and adeno-associated virus (AAV) vectors (reviewed in Vannucci, et al. (2013 New Microbiol. 36:1-22). Recombinant AAV vectors useful in the invention can be derived from any AAV that allows for transduction of the virus into the cell and insertion of the nuclease gene into the cell genome. In particular embodiments, recombinant AAV vectors encode AAV6 capsid protein, and structural elements from AAV2 allowing genetic material encapsidation in particules with AAV6 capsid protein.

Recombinant AAV vectors can also be self-complementary such that they do not require second-strand DNA synthesis in the host cell (McCarty, et al. (2001) Gene Ther. 8:1248-54).

If the engineered TALEN nuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, nuclease genes are operably linked to a promoter that drives gene expression preferentially in the target cell (e.g., a human T cell).

Similarly, a polynucleotide encoding a gene such as a CAR or a TCR may be delivered as a vector (e.g. *lenti*, AAV, preferably AAV, more preferably AAV6 and even more preferably AAV6 and AAV2 ITR)

The invention further provides for the introduction of an exogenous nucleic acid into the cell, such that the exogenous nucleic acid sequence is inserted into the TRAC constant region gene at a nuclease cleavage site. In some embodiments, the exogenous nucleic acid comprises a 5' homology arm and a 3' homology arm to promote recombination of the nucleic acid sequence into the cell genome at the nuclease cleavage site.

Exogenous nucleic acids or polynucleotides of the invention may be introduced into the cell by any of the means previously disclosed. In a particular embodiment, exogenous nucleic acids are introduced by way of a viral vector, such as a lentivirus, retrovirus, adenovirus, or preferably a recombinant AAV vector, more preferably a recombinant AAV6 vector, with AAV2 inverted terminal repeat (ITR). Recombinant AAV vectors useful for introducing an exogenous nucleic acid can have any serotype that allows for transduction of the virus into the cell and insertion of the exogenous nucleic acid sequence into the cell genome. In particular embodiments, the recombinant AAV vectors have a serotype AAV6. The recombinant AAV vectors can also be self-complementary such that they do not require second-strand DNA synthesis in the host cell.

In another particular embodiment, an exogenous nucleic acid can be introduced into the cell using a single-stranded DNA template. The single-stranded DNA can comprise the exogenous nucleic acid and, in preferred embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV2 ITR sequence 3' downstream of the 3' homology arm.

In another particular embodiment, genes encoding an endonuclease of the invention and/or an exogenous nucleic acid sequence of the invention (e;g. a CAR) can be introduced into the cell by transfection with a linearized DNA template. In some examples, a plasmid DNA encoding an endonuclease and/or an exogenous nucleic acid sequence can be digested by one or more restriction enzymes such that the circular plasmid DNA is linearized prior to transfection into the cell.

When delivered to a cell, an exogenous nucleic acid of the invention can be operably linked to any promoter suitable for expression of the encoded polypeptide in the cell, including those mammalian promoters and inducible promoters previously discussed. An exogenous nucleic acid of the invention can also be operably linked to a synthetic promoter. Synthetic promoters can include, without limitation, the JeT promoter (WO 2002/012514).

Activation

In examples where the genetically-modified cells of the invention are human T cells, or cells derived therefrom, such cells may require activation prior to introduction of a nuclease and/or an exogenous nucleic acid sequence. For example, T cells can be contacted with anti-CD3 and anti-CD28 antibodies that are soluble or conjugated to a support (i.e., beads) for a period of time sufficient to activate the cells.

Suicide Gene

Genetically-modified cells of the invention can be further modified to express one or more inducible suicide genes, the induction of which provokes cell death and allows for selective destruction of the cells in vitro or in vivo. In some examples, a suicide gene can encode a cytotoxic polypeptide, a polypeptide that has the ability to convert a non-toxic prodrug into a cytotoxic drug, and/or a polypeptide that activates a cytotoxic gene pathway within the cell. That is, a suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). A suicide gene can also encode a polypeptide that is expressed at the surface of the cell that makes the cells sensitive to therapeutic and/or cytotoxic monoclonal antibodies. In further examples, a suicide gene can encode recombinant antigenic polypeptide comprising an antigenic motif recognized by the anti-CD20 mAb Rituximab and an epitope that allows for selection of cells expressing the suicide gene. See, for example, the RQR8 polypeptide described in WO2013153391, which comprises two Rituximab-binding epitopes and a QBEndIO-binding epitope. For such a gene, Rituximab can be administered to a subject to induce cell depletion when needed.

In one embodiment two Rituximab-binding epitopes are inserted directly into the chimeric antigen receptor, such as in an anti-CD22 CAR, or an anti-CD123 CAR, or in an anti-CD30 CAR in the linker of the scfv and/or in the hinge linking the scfv to the transmembrane domain.

In one embodiment two Rituximab-binding epitopes and a QBEndIO-binding epitope are inserted directly into the chimeric antigen receptor, such as in an anti-CD22 CAR, or an anti-CD123 CAR, or in an anti-CD30 CAR, in the linker between the VH and the VL of the scfv and/or in the hinge linking the scfv to the transmembrane domain.

In some embodiments, the invention provides a pharmaceutical composition comprising a genetically-modified cell of the invention (a TALEN-modified endogenous αβ-TCR negative human primary cell wherein the constant region of the genomic TCR gene (TRAC gene) comprises a genetic modification generated by a TALEN and affecting cell surface expression of the alpha beta TCR, said genomic TRAC gene comprising from 5' to 3':

(a) a 5' region of said human genomic TRAC gene upstream (b) a recognition domain for a TALEN, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a sequence coding such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a second TALEN recognition domain, (d) a 3' region of the genomic TRAC gene), or a population of said genetically-modified cells of the invention, and a pharmaceutical carrier, and another medicament, such as a PNA for dCK KO cells, alemtuzumab for CD52 KO, glucocorticoid for a GR KO cell . . .

Such pharmaceutical compositions can be prepared in accordance with known techniques. See, e.g., Remington, The Science And Practice of Pharmacy (21s ed. 2005). In the manufacture of a pharmaceutical formulation according to the invention, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents useful in the treatment of a disease in the subject. In additional embodiments, where the genetically-modified cell is a genetically-modified human T cell (or a cell derived therefrom), pharmaceutical compositions of the invention can further include biological molecules, such as cytokines (e.g., IL-2, IL-7, IL-15, and/or IL-21, IL-27), which promote in vivo cell proliferation and engraftment. Pharmaceutical compositions comprising genet-ically-modified cells of the invention can be administered in the same composition as an additional agent or biological molecule or, alternatively, can be co-administered in separate compositions.

Therapeutic Applications

Pharmaceutical compositions of the invention can be useful for treating any disease state that can be targeted by adoptive immunotherapy. The disease that may be treated using the object of the present invention (engineered primary human cells expressing a CAR or a TCR) may or may not be characterized by cells or tissue expressing the target of the CAR expressed at the cells surface of the said objects.

In a particular embodiment, the pharmaceutical compositions of the invention are useful in the treatment of cancer. Such cancers can include, without limitation, carcinoma, lymphoma, sarcoma, blastomas, leukemia, cancers of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In certain embodiments, cancers of B-cell origin include, without limitation, B-lineage acute lymphoblastic leukemia, B-cell chronic lymphocytic leukemia, and B-cell non-Hodgkin's lymphoma.

In particular embodiments, the object of the invention may be used as a function of the CAR expressed at the surface of the cell of the invention to treat a disease characterized in the expression of the CAR target.

Doses of cells genetically modified cells (engineered cells of the invention), useful for the treatment of cancer may range from 1 to $10^8$ cells.

MEANS for DETECTING the Cells of the Invention

The present invention provides means for detecting engineered cells. Such means of the invention encompasses any means capable of recognizing and detecting a modified TCR gene that underwent a deletion, a mutation, an insertion. Such means of the invention encompasses any means capable of recognizing and detecting a modified TCR gene that underwent a deletion, a mutation, an insertion of the TRAC gene and off sites, if any.

The means may be an oligonucleotide, a degenerated oligonucleotide, a probe, a DNA probe, a RNA probe, a labeled endonuclease, a labeled TALEN, a combination thereof.

The present invention provides a method for detecting engineered cells, in particular for detecting a wt TRAC gene, a TRAC gene with a deletion, a TRAC gene with an insertion of from 05.kb, 1 kb, 2, kb, 3 kb, 4 kb to 5 kb insertion into the TRAC gene. Such method of the invention comprises means recognizing, binding to a wt TRAC gene, means recognizing, binding to a modified TRAC gene that underwent a deletion, a mutation, or an insertion.

The engineered TRAC gene may have kept an endonuclease binding site. Thus, in particular embodiment, a means of the present invention comprises a sequence that is or is complementary to the binding sequence of the endonuclease.

In particular embodiments, a means of the present invention comprises a polynucleotide sequence that binds to the 10 to 15 first nucleotides in 5' of the TRAC gene and another polynucleotide sequence binding to the 10 to 15 last nucleotides in 3' of the TRAC gene. The present invention provides a method for detecting a wt TRAC gene or a modified TRAC gene comprising a deletion, a mutation or an insertion.

The present invention provides a method for detecting a wt TRAC gene or a modified TRAC gene comprising a deletion, a mutation or an insertion comprising:

(i) Purifying the DNA of a TRAC-modified cell, and of a cell used as an appropriate control, (ii) Incubating said DNA with means for detecting a modified TRAC gene of the invention or a wt TRAC gene, resulting in a mixture;

(iii) Submitting the mixture to a pcr (iv) Sequencing the pcr product.

In particular embodiments, a means of the present invention comprises a sequence that is complementary to the binding sequence of the TALEN, preferably complementary to TTGTCCCACAGATATCC (nt 1-17 of SEQ ID NO: 38), CCGTGTACCAGCTGAGAGA (nt 33-51 of SEQ ID NO: 38) or comprising TTGTCCCACAGATATCC (nt 1-17 of SEQ ID NO: 38), CCGTGTACCAGCTGAGAGA (nt 33-51 of SEQ ID NO: 38).

In particular embodiments, a means of the present invention comprises a sequence that is or is complementary to the binding sequence of a meganuclease.

In particular embodiments, a means of the present invention comprises a sequence that is complementary to the binding sequence of a compact TALEN nuclease.

In particular embodiments, a means of the present invention comprises a sequence that is complementary to the binding sequence of a megaTAL nuclease.

In particular embodiments, a means of the present invention comprises a sequence that is complementary to the sequence to which the guide of the Crispr/Cas9 system binds to or comprise the guide used to engineer the TRAC gene.

In all cases, the means can comprise a sequence designed to recognize the sequence in the engineered TRAC gene just upstream the sequence recognized by the endonuclease (homology arm) that is or was recognized by the first monomer of the endonuclease (if the binding domain of the nuclease is cut, then the sequence just upstream subsists in the engineered TRAC gene).

As used herein, the term "recognition sequence" refers to a DNA sequence that is bound and cleaved by an endonuclease.

In the case of a TALEN, a recognition sequence comprises two sites, ie from 5' to 3': the left recognition sequence followed by the right recognition sequence, more preferably TTGTCCCACAGATATC (SEQ ID NO: 36) and CCGTGTACCAGCTGAGA (SEQ ID NO: 26).

Preferred TALEN of the Invention:

As used herein, the term "DNA-binding affinity" or "binding affinity" means the tendency of a nuclease to non-covalently associate with a reference DNA molecule (e.g., a recognition sequence or an arbitrary sequence). Binding affinity is measured by a dissociation constant, 3/4. As used herein, a nuclease has "altered" binding affinity if the Kd of the nuclease for a reference recognition sequence is increased or decreased by a statistically significant percent change relative to a reference nuclease.

In the present invention a TALEN may associate preferentially to the following sequence: 5' TGATCCTCTTGTcc-cacagatatccagaaccctgaccctgcccgtgtaccagctgagaga (SEQ ID NO: 123) 3' Or from 5'to 3': TTGTCCCACAGA-TATCAGAACCCTGACCCTGCCGTGTACCAGCT-GAGA (SEQ ID NO: 124) with TTGTCCCACAGATATC (SEQ ID NO: 36) (first or left binding site, first or left recognition domain) CCGTGTACCAGCTGAGA (SEQ ID NO: 26) (second or right binding site-second or right recognition domain).

In a preferred embodiment, the means comprise a sequence that binds to a TAG inserted into the engineered TRAC gene and/or part of the TRAC gene upstream the recognition sequence of the nuclease.

The underlined sequence below corresponds to a possible sequence used as a base for designing a probe or a mean of the invention for the detection of an engineered cells.

DDDDDDDDDD TTGTCCCACAGATATCAGAACCCTGACCCTGCCGTGTACCAGCTGAGA DDDDDDDDDD
DDDDDDDDDD (SEQ ID NO: 125):

In the case of a meganuclease, a recognition sequence comprises a pair of inverted, 9 basepair "half sites" that are separated by four basepairs. In the case of a single-chain meganuclease, the N-terminal domain of the protein contacts a first half-site and the C-terminal domain of the protein contacts a second half-site. Cleavage by a meganuclease produces four basepair 3 '"overhangs". "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a Compact TALEN, the recognition sequence comprises a first CNNNGN sequence that is recognized by the I-Tevi domain, followed by a nonspecific spacer 4-16 basepairs in length, followed by a second sequence 16-22 bp in length that is recognized by the TAL-effector domain (this sequence typically has a 5' T base). Cleavage by a Compact TALEN produces two basepair 3'overhangs. In the case of a CRISPR, the recognition sequence is the sequence, typically 16-24 basepairs, to which the guide RNA binds to direct Cas9 cleavage. Cleavage by a CRISPR produced blunt ends.

As used herein, the term "target site" or "target sequence" or "on site" or "on site target" refers to a region of the chromosomal DNA of a cell comprising a recognition sequence for a nuclease, that is intended to be modified or edited (for introducing a mutation, a deletion or an insertion).

Off target site or off target sequence refers to a region of the chromosomal DNA of a cell comprising a secondary recognition sequence for a nuclease which is not the expected target sequence (intended to be edited) and may bind less specifically and/or with a lower affinity the tested TALEN.

sequence of the TRAC gene upstream (in 5' of the first recognition domain) or down stream the second recognition domain.

According to another embodiment, a probe or a mean according to the present invention may comprise part of a sequence of the TRAC gene and part of the first recognition domain of a TALEN.

According to another embodiment, a probe or a mean according to the present invention may comprise part of the first recognition domain of a TALEN or the entire first recognition domain of a TALEN.

According to another embodiment, a probe or a mean according to the present invention may comprise the first recognition domain of a TALEN.

According to another embodiment, a probe or a mean according to the present invention may comprise the first recognition domain of a TALEN part of the sequence of the integrated polynucleotide.

According to another embodiment, a probe or a mean according to the present invention may comprise a sequence or a domain that binds to the genome-integrated polynucleotide, to the sequence encoding a self-cleaving peptide, to the sequence coding an IRES, to the sequence coding a CAR, said sequence may be one of those as follows:

(SEQ ID NO: 126)
DDDDDDDDDDDDTTGTCCCACAGATATCAGAACCCTGACCCTGCCGTGTACCAGCTGAGADDDDDDDDDDDD, (SEQ ID NO: 126)
DDDDDDDDDDDDTTGTCCCACAGATATCAGAACCCTGACCCTGCCGTGTACCAGCTGAGADDDDDDDDDDDD, (SEQ ID NO: 126
DDDDDDDDDDDDTTGTCCCACAGATATCAGAACCCTGACCCTGCCGTGTACCAGCTGAGADDDDDDDDDDDD (SEQ ID NO: 126)
DDDDDDDDDDDDTTGTCCCACAGATATCAGAACCCTGACCCTGCCGTGTACCAGCTGAGADDDDDDDDDDDD, (SEQ ID NO: 129)
DDDDDDDDDDDDTTGTCCCACAGATATC (XXX)n (SEQ ID NO: 130)
CCGTGTACCAGCTGAGADDDDDDDDDDDD with (XXX)n is an with (XXX) n is an integrated polynucleotide comprising a tag, said tag may be a non coding sequence, a sequence encoding protein such as a self-cleaving peptide, a CAR, D represents a base, successive Ds represent an homology with the genomic wt TRAC gene.

Means of the invention were designed based on the "recognition sequence" of the nucleases in WO2017062451 or disclosed in WO 2017106528 but also based on other recognition sequence identified herewith and for which the frequency of off site either calculated or calculated and measured in silico would not be superior to those generated using the nucleases generated so far, preferably The TALEN of the present invention have no detectable off site target, using any one of the method disclosed so far to detect said off target, including guide-seq method adapted to TALEN.

The TALEN of the present invention target and cleave an active gene in a human cell genome, (active means that the gene is expressed in a normal cell, a in normal adult cell, in a normal progenitor cell in a normal embryonic cell.

In a preferred embodiment, the TALEN of the present invention target and cleave a component of the TCR gene, more preferably a TCRalpha or a TCR beta, a TCR delta or a TCR gamma, even more preferably a TCR alpha and/or beta.

TALEN cleaving stop codon of TCR alpha or beta constant region.

TCR beta constant region has two possible genes (TRBC1 and TRBC2).

TALEN TRAC on Stop hsTRAC_ex1
(SEQ ID NO: 131)
gatacgaacctaaactttcaaaacctgtcag-tgattggg ttccgaatcctcctcctgaaagtggccgggtttaatctgc tcatgacgctgcggctgtggtccagcTGAggtgaggggcc ttgaagctggg Four TALEN were identified (SEQ ID NO: 132)
TCTGCTCATGACGCTGCGGCTGTGGTCCAGCTGAGGTGAGGGGCCTTGAA

TCTGCTCATGACGCTGC GGCTGTGGTCCAGCTG AGGTGAGGGGCCTTG

AA

-continued
(SEQ ID NO: 133)
TGCTCATGACGCTGCGGCTGTGGTCCAGCTGAGGTGAGGGGCCTTGAA

TGCTCATGACGCTGCGG CTGTGGTCCAGCTG AGGTGAGGGGCCTTG

AA (SEQ ID NO: 134)
TGACGCTGCGGCTGTGGTCCAGCTGAGGTGAGGGGCCTTGAAGCTGGGA

TGACGCTGCGGCTGTGG TCCAGCTGAGGTGAG GGGCCTTGAAGCTGG

GA (SEQ ID NO: 135)
TGGTCCAGCTGAGGTGAGGGGCCTTGAAGCTGGGAGTGGGGTTTAGGGA

TGGTCCAGCTGAGGTGA GGGGCCTTGAAGCTG GGAGTGGGGTTTAGG

GA

Best TALEN based on specificity results is TALEN 2

(SEQ ID NO: 133)
TGCTCATGACGCTGCGGCTGTGGTCCAGCTGAGGTGAGGGGCCTTGAA

TGCTCATGACGCTGCGG CTGTGGTCCAGCTG AGGTGAGGGGCCTTG

AA (SEQ ID NO: 127)
hsTRBC1_stop
taacccccaaaactttctcttctgcagGTCAAGAGAAAGGATTTCtg aAGGCAGCCCTG-GAAGTGGAGTTAGGAGCTTCTAACCCGTCATGGT

TTCAATA

Three TALEN were identified (SEQ ID NO: 128)
TCTGCAGGTCAAGAGAAAGGATTTCTGAAGGCAGCCCTGGAAGTGGA

TCTGCAGGTCAAGAGAA AGGATTTCTGAAG GCAGCCCTGGAAGTG

GA (SEQ ID NO: 136)
TTTCTCTTCTGCAGGTCAAGAGAAAGGATTTCTGAAGGCAGCCCTGG

AATTTCTCTTCTGCAGGTC AAGAGAAAGGATTTC TGAAGGCAGCC

CTGGAA

-continued (SEQ ID NO: 137)
TTCTGAAGGCAGCCCTGGAAGTGGAGTTAGGAGCTTCTAACCCGTCA

TTCTGAAGGCAGCCCTG GAAGTGGAGTTAG GAGCTTCTAACCCGT

CA

Best TALEN identified based on specificity results is the TALEN (SEQ ID NO: 137)
TTCTGAAGGCAGCCCTGGAAGTGGAGTTAGGAGCTTCTAACCCG

TCATTCTGAAGGCAGCCCTG GAAGTGGAGTTAG GAGCTTCTA

ACCCGTCA hsTRBC2_stop
(SEQ ID NO: 138)
tagcccctgaaaccctgaaaatgttctctcttccacagGTCAAG AGAAAGGAT-TCCAGAGGCtagCTCCAAAACCATCCCAGGTCAT

TCTTCATCCTCACCCACTCCAAAACCATCCCAGGTCATTCTTCA

TCC

Four TALEN were identified:

(SEQ ID NO: 139)
TGAAAATGTTCTCTCTTCCACAGGTCAAGAGAAAGGATTCCAG

AGGCTATGAAAATGTTCTCTCTT CCACAGGTCAAGAGA AAG

GATTCCAGAGGCTA (SEQ ID NO: 140)
TTCTCTCTTCCACAGGTCAAGAGAAAGGATTCCAGAGGCTAGC

TCCAAATTCTCTCTTCCACAGGT CAAGAGAAAGGATTC CAG

AGGCTAGCTCCAAA (SEQ ID NO: 141)
TTCTCTCTTCCACAGGTCAAGAGAAAGGATTCCAGAGGCTAGC

TCCAAATCTCTCTTCCACAGGTC AAGAGAAAGGATTCC AGA

GGCTAGCTCCAAAA (SEQ ID NO: 142)
TAGCTCCAAAACCATCCCAGGTCATTCTTCATCCTCACCCACT

CCAAAATAGCTCCAAAACCATCC CAGGTCATTCTTCAT CCT

CACCCACTCCAAAA

Best TALEN based on specificity TALEN 2 (or 4)
(SEQ ID NO: 140)
TTCTCTCTTCCACAGGTCAAGAGAAAGGATTCCAGAGGCTAGC

TCCAAATTCTCTCTTCCACAGGT CAAGAGAAAGGATTC CAG

AGGCTAGCTCCAAA

In other embodiments, the TALEN of the present invention targets and cleaves any one of the gene disclosed in patent application 62/410,187 (KO/KI).

For the purpose of making a drug or medication administrable in human (universal TCR-negative CART cells_or off the shelve) that would be stable once administered and wherein a frequency of off site cutting would be near zero, the present inventors analyzed systematically the frequency of off sites that would be generated when using TALEN of the invention and compared the data to those obtained with a meganuclease, aMegaTAL, a crispr/cas system, reported to target the same sequences (or successive sequences) of the human TRAC gene coding for extracellular or transmembrane domain of the TCRalpha beta protein (those which, when inactivated by deletion insertion, would result in a decrease in cell surface expression of functional TCR alpha beta).

To measure the stability of such cells an in vitro system was set up wherein cells were challenges everyday for weeks at least 5) with immune cells and with cells expressing targeted antigen as described as in USP 62/537,435.

Blood sample from two healthy individuals (human) individuals that received "allogenic therapy" with the cells of the present invention were also analyzed four weeks after the first injection for the presence of cells in the blood.

A TAG means a element, preferably a genetic element such as a sequence that allows detecting an engineered human cell comprising it.

The TAG of the invention may comprise, an endonuclease recognition domain, a sequence or part of a sequence encoding a self-cleaving peptide, an IRES, and/or a sequence or part of a sequence just downstream the sequence upstream the recognition sequence of an rare cutting endonuclease such as a TALEN, a CRISPR, a meganuclease, a megatal, a zinc finger.

Detection is achieved using a mean of detection, that may be a specific antibody, a oligonucleotide, preferably two nucleotides, an RNA, a DNA, a combination thereof.

According to the present invention, a means can comprise a sequence designed to recognize the tag inserted into the engineered TRAC gene and/or part of the TRAC gene in 5' of the insertion, part of the sequence inserted into the TRAC gene (CAR, exogenous TCR, gene making cells sensitive to a drug).

In one embodiment, the tag inserted into the TRAC gene may comprise a sequence encoding a self-cleaving peptide, and/or another chosen sequence such as GAC TAC AAA GAC GAT GAC GAC AAG (SEQ ID NO: 141), TAC CCA TAC GAT GTT CCA GAT TAC GCT, CAC CAC CAC CAC CAC CAC, GAA CAA AAA CTC ATC TCA GAA GAG GAT CTG (SEQ ID NO: 142), or any one of those disclosed in Costea PI, Lundeberg J, Akan P (2013) TagGD: Fast and Accurate Software for DNA Tag Generation and Demultiplexing. PLOS ONE 8 (3): e57521. doi.org/10.1371/journal.pone.0057521.

A means for detecting any one of these tags, is part of the present invention.

In addition, the inventors have determined appropriate target sequences within the 3 exons of the TCR alpha, allowing to prevent TCR expression at the cell surface if cleaved and engineered by insertion of a CAR and off site above detection.

The invention provides therefore at least one means for detecting a TCR engineered cell of the invention comprising one of the following sequences:

GAGAATCAAAATCGGTGAATAGG (SEQ ID NO: 70), TTCAAAACCTGTCAGTGATTGGG (SEQ ID NO: 94), TGTGCTAGACATGAGGTCTATGG (SEQ ID NO: 71), CGTCATGAGCAGATTAAACCCGG (SEQ ID NO: 95), TCAGGGTTCTGGA-TATCTGTGGG (SEQ ID NO: 72), GTCAGGGTTCTGGATATCTGTGG (SEQ ID NO: 73), TTCGGAACCCAATCACTGACAGG (SEQ ID NO: 96), TAAACCCGGCCACTTTCAGGAGG (SEQ ID NO: 97), AAAGTCAGATTTGTTGCTCCAGG (SEQ ID NO: 74), AACAAATGTGT-CACAAAGTAAGG (SEQ ID NO: 75), TGGATT-TAGAGTCTCTCAGCTGG (SEQ ID NO: 76),

TAGGCAGACAGACTTGTCACTGG (SEQ ID NO: 77), AGCTGGTACACGGCAGGGTCAGG (SEQ ID NO: 78), GCTGGTACACGGCAGGGTCAGGG (SEQ ID NO: 79), TCTCTCAGCTGGTACACGGCAGG (SEQ ID NO: 80), TTT-CAAAACCTGTCAGTGATTGG (SEQ ID NO: 98), GATTAAACCCGGCCACTTTCAGG (SEQ ID NO: 99), CTCGACCAGCTTGACATCACAGG (SEQ ID NO: 100), AGAGTCTCTCAGCTGGTACACGG (SEQ ID NO: 81), CTCTCAGCTGGTA-CACGGCAGGG (SEQ ID NO: 82), AAGTTCCTGT-GATGTCAAGCTGG (SEQ ID NO: 101), ATCCTCCTCCTGAAAGTGGCCGG (SEQ ID NO: 102), TGCTCATGACGCTGCGGCTGTGG (SEQ ID NO: 103), ACAAAACTGTGCTAGACATGAGG (SEQ ID NO: 83), ATTTGTTTGAGAAT-CAAAATCGG (SEQ ID NO: 84), CATCACAG-GAACTTTCTAAAAGG (SEQ ID NO: 104), GTCGAGAAAAGCTTTGAAACAGG (SEQ ID NO: 105), CCACTTTCAGGAGGAGGATTCGG (SEQ ID NO: 106), CTGACAGGTTTTGAAAGTTTAGG (SEQ ID NO: 107), AGCTTTGAAACAGGTAA-GACAGG (SEQ ID NO: 108), TGGAATAATGCTGTTGTTGAAGG (SEQ ID NO: 85), AGAGCAACAGTGCTGTGGCCTGG (SEQ ID NO: 86), CTGTGGTCCAGCTGAGGTGAGGG (SEQ ID NO: 109), CTGCGGCTGTGGTCCAGCTGAGG (SEQ ID NO: 110), TGTGGTCCAGCTGAGGT-GAGGGG (SEQ ID NO: 111), CTTCTTCCCCAGCCCAGGTAAGG (SEQ ID NO: 87), ACACGGCAGGGTCAGGGTTCTGG (SEQ ID NO: 88), CTTCAAGAGCAACAGTGCTGTGG (SEQ ID NO: 89), CTGGGGAAGAAGGTGTCTTCTGG (SEQ ID NO: 90), TCCTCCTCCT-GAAAGTGGCCGGG (SEQ ID NO: 112), TTAATCTGCTCATGACGCTGCGG (SEQ ID NO: 113), ACCCGGCCACTTTCAGGAGGAGG (SEQ ID NO: 114), TTCTTCCCCAGCCCAGGTAAGGG (SEQ ID NO: 91), CTTACCTGGGCTGGG-GAAGAAGG (SEQ ID NO: 92), GACACCTTCTTCCCCAGCCCAGG (SEQ ID NO: 93), GCTGTGGTCCAGCTGAGGTGAGG (SEQ ID NO: 115), CCGAATCCTCCTCCTGAAAGTGG (SEQ ID NO: 116), a complementary sequence thereof; said mean may be associated for example for a mean binding to the CAR sequence of peptide 2A sequence, and allowing a PCR according to the present invention.

In other embodiments, the present invention also provides a mean for detecting engineered immune cells (cell were engineered using various endonucleases Crispr/Cas9) comprising a sequence comprising at least one of the following sequences: AGAGTCTCTCAGCTGGTACA (SEQ ID NO: 39), GCACCAAAGCTGCCCTTACC (SEQ ID NO: 40), AAGTTCCTGTGATGTCAAGC (SEQ ID NO: 41), TTCG-GAACCCAATCACTGAC (SEQ ID NO: 42), GAT-TAAACCCGGCCACTTTC (SEQ ID NO: 43), CGTCAT-GAGCAGATTAAACC (SEQ ID NO: 44), CTCAAGGTTCAGATCAGAAG (SEQ ID NO: 45), TAGGCAGACAGACTTGTCAC (SEQ ID NO: 46), AACAAATGTGTCACAAAGTA (SEQ ID NO: 47), CAC-CAAAGCTGCCCTTACCT (SEQ ID NO: 48), CTGACAGGTTTTGAAAGTTT (SEQ ID NO: 49), TTCAAAACCTGTCAGTGATT (SEQ ID NO: 50), CCGAATCCTCCTCCTGAAAG (SEQ ID NO: 51), CCACTTTCAGGAGGAGGATT (SEQ ID NO: 52), TAAACCCGGCCACTTTCAGG (SEQ ID NO: 53), TCT-CAAACAAATGTGTCACAAAGTA (SEQ ID NO: 54), CTTACAATCTTGCAGATCTGGAATG (SEQ ID NO: 55), TTAATCTGCTCATGACGCTG (SEQ ID NO: 56), GGAGAAGAGGGGCAATGCAG (SEQ ID NO: 57), TCTTCTCCCTCTCCAAACAG (SEQ ID NO: 58), AGCAGCTTTCACCTCCTTGG (SEQ ID NO: 59), GTAGCAGCTTTCACCTCCTT (SEQ ID NO: 60), AGTTGGTGGCATTGCCGGGG (SEQ ID NO: 61), TCTGTGATATACACATCAGAATC (SEQ ID NO: 62), TCTGTGATATACACATCAGAATCC (SEQ ID NO: 63), GAGTCTCTCAGCTGGTACACGGC (SEQ ID NO: 64), GAGTCTCTCAGCTGGTACACGGCA (SEQ ID NO: 65), ATTCTCAAACAAATGTGTCACAA (SEQ ID NO: 66), ATTCTCAAACAAATGTGTCACAAA (SEQ ID NO: 67), GTCTGTGATATACACATCAGAAT (SEQ ID NO: 68), GTCTGTGATATACACATCAGAATC (SEQ ID NO: 69), GAGAATCAAAATCGGTGAATAGG (SEQ ID NO: 70), TGTGCTAGACATGAGGTCTATGG (SEQ ID NO: 71), TCAGGGTTCTGGATATCTGTGGG (SEQ ID NO: 72), GTCAGGGTTCTGGATATCTGTGG (SEQ ID NO: 73), AAAGTCAGATTTGTTGCTCCAGG (SEQ ID NO: 74), AACAAATGTGTCACAAAGTAAGG (SEQ ID NO: 75), TGGATTTAGAGTCTCTCAGCTGG (SEQ ID NO: 76), TAGGCAGACAGACTTGTCACTGG (SEQ ID NO: 77), AGCTGGTACACGGCAGGGTCAGG (SEQ ID NO: 78), GCTGGTACACGGCAGGGTCAGGG (SEQ ID NO: 79), TCTCTCAGCTGGTACACGGCAGG (SEQ ID NO: 80), AGAGTCTCTCAGCTGGTACACGG (SEQ ID NO: 81), CTCTCAGCTGGTACACGGCAGGG (SEQ ID NO: 82), ACAAAACTGTGCTAGACATGAGG (SEQ ID NO: 83), ATTTGTTTGAGAATCAAAATCGG (SEQ ID NO: 84), TGGAATAATGCTGTTGTTGAAGG (SEQ ID NO: 85), AGAGCAACAGTGCTGTGGCCTGG (SEQ ID NO: 86), CTTCTTCCCCAGCCCAGGTAAGG (SEQ ID NO: 87), ACACGGCAGGGTCAGGGTTCTGG (SEQ ID NO: 88), CTTCAAGAGCAACAGTGCTGTGG (SEQ ID NO: 89), CTGGGGAAGAAGGTGTCTTCTGG (SEQ ID NO: 90), TTCTTCCCCAGCCCAGGTAAGGG (SEQ ID NO: 91), CTTACCTGGGCTGGGGAAGAAGG (SEQ ID NO: 92), GACACCTTCTTCCCCAGCCCAGG (SEQ ID NO: 93), TTCAAAACCTGTCAGTGATTGGG (SEQ ID NO: 94), CGTCATGAGCAGATTAAACCCGG (SEQ ID NO: 95), TTCGGAACCCAATCACTGACAGG (SEQ ID NO: 96), TAAACCCGGCCACTTTCAGGAGG (SEQ ID NO: 97), TTTCAAAACCTGTCAGTGATTGG (SEQ ID NO: 98), GATTAAACCCGGCCACTTTCAGG (SEQ ID NO: 99), CTCGACCAGCTTGACATCACAGG (SEQ ID NO: 100), AAGTTCCTGTGATGTCAAGCTGG (SEQ ID NO: 101), ATCCTCCTCCTGAAAGTGGCCGG (SEQ ID NO: 102), TGCTCATGACGCTGCGGCTGTGG (SEQ ID NO: 103), CATCACAGGAACTTTCTAAAAGG (SEQ ID NO: 104), GTCGAGAAAAGCTTTGAAACAGG (SEQ ID NO: 105), CCACTTTCAGGAGGAGGATTCGG (SEQ ID NO: 106), CTGACAGGTTTTGAAAGTTTAGG (SEQ ID NO: 107), AGCTTTGAAACAGGTAAGACAGG (SEQ ID NO: 108), CTGTGGTCCAGCTGAGGTGAGGG (SEQ ID NO: 109), CTGCGGCTGTGGTCCAGCTGAGG (SEQ ID NO: 110), TGTGGTCCAGCTGAGGTGAGGGG (SEQ ID NO: 111), TCCTCCTCCTGAAAGTGGCCGGG (SEQ ID NO: 112), TTAATCTGCTCATGACGCTGCGG (SEQ ID NO: 113), ACCCGGCCACTTTCAGGAGGAGG (SEQ ID NO: 114), GCTGTGGTCCAGCTGAGGTGAGG (SEQ ID NO: 115), CCGAATCCTCCTCCTGAAAGTGG (SEQ ID NO: 116) and complementary sequence of any one thereof.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

A list of bona fide off sites induced by a meganuclease, a Crispr/cas9, a Zn finger or a MegaTAL was established using the respective TRAC-specific endonucleases as previously described in WO2014153470A2, WO2017062451, WO2015057980, WO2017106528.

To establish these lists, different donors of different genetic background origin can be tested. Said off sites sequences were identified using an adapted guide seq method.

Example 1: TALEN binding sequences (or recognition sequence) in the TRAC gene and sequences in engineered TRAC gene for insertion of a polynucleotide comprising a self-cleaving peptide, a CAR, and a termination signal (poly A).

Frame for the design of any means, probe, oligonuleotides of the invention for detecting alpha beta TCR deficient cells of the invention TRAC exon1 (capital letter)

```
                                    (SEQ ID NO: 117)
ttggccaagattgatagcttgtgcctgtccctgag tcccagtccatcacgag-cagctggtttctaagat gctatttcccgtataaagcatgagaccgtgacttg ccagccccacagagccccgcccttgtccatcactg gcatctggactccagcctgggttggggcaaagagg gaaatgagatcatgtcctaaccctgatcctctt-g tcccacagATATCCAGAACCCTGACCCTGCCGTGT

ACCAGCTGAGAGACTCTAAATCCAGTGACAAGTCT

GTCTGCCTATTCACCGATTTTGATTCTCAAACAAA

TGTGTCACAAAGTAAGGATTCTGATGTG-TATATC

ACAGACAAAACTGTGCTAGACATGAGGTCTATGGA

CTTCAAGAGCAACAGTGCTGTGGCCTGGAGCAACA

AATCTGACTTTGCATGTGCAAACGCCTTCAACAAC

AGCATTATTCCAGAAGACAC-CTTCTTCCCCAGCC

CAGGtaagggcagctttggtgccttcgcaggctgt ttccttgcttcaggaatggccaggttctgcccaga gctctggtcaatgatgtctaaaactcctctgattg gtggtctcggccttatccattgccac-caaaaccc tcttttttactaagaaacagtgagccttgttctggc agtccagagaatgacacgggaaaaaagcagatgaa gagaaggtggcaggagagggcacgtggcccagcct cagtctctccaactgagttcctgcctgcctgcctt t-gctcagactgtttgcccttactgctcttctag gcctcattctaagcccccttctccaagttgcctctc
```

-continued

```
cttatttctccctgtctgccaaaaaatctttccca gctcactaagtcagtctcacgcagtcactcattaa cccaccaatcactgattgtgccggcacatgaatgc ac
                                    (SEQ ID NO: 161)
```

Integration site preferred:
```
                                    (SEQ ID NO: 143)
ttggccaagattgatagcttgtgcctgtccctgag tcccagtccatcacgag-cagctggtttctaagat gctatttcccgtataaagcatgagaccgtgacttg ccagccccacagagccccgcccttgtccatcactg gcatctggactccagcctgggttggggcaaagagg gaaatgagatcatgtcctaaccctgatcctcttgt cccacagATATCCAG
```

XXX

```
                                    (SEQ ID NO: 118)
CCGTGTACCAGCTGAGAGACTCTAAATCCAGTGACA

AGTCTGTCTGCCTATTCACCGATTTTGATTCTCAA

ACAAATGTGTCACAAAGTAAGGATTCTGATGTGTA

TATCACAGACAAAACTGTGCTAGACATGAGGTCTA

TGGACTTCAAGAGCAACAGTGCTGTGGCCTGGAGC

AACAAATCTGACTTTGCATGTGCAAACGCCTTCAA

CAACAGCATTATTCCAGAAGACACCTTCTTCCCCA

GCCCAGGtaagggcagctttggtgccttcgcaggc tgtttccttgcttcaggaatggccaggttctgccc agagctctggtcaatgatgtctaaaactcctctga ttggtggtctcggccttatccattgccaccaaaac cctctttttactaagaaacagtgagccttgttctg gcagtccagagaatgacacgggaaaaaagcagatg aagagaaggtggcaggagagggcacgtggcccagc ctcagtctctccaactgagttcctgcctgcctgcc tttgctcagactgtttgcccttactgctcttcta ggcctcattctaagcccccttctccaagttgcctct ccttatttctccctgtctgccaaaaaatctttccc agctcactaagtcagtctcacgcagtcactcatta acccaccaatcactgattgtgccggcacatgaatg
```
XXX represents a polynucleotide inserted.

Sequences detected after dsDNA cleavage (5')

Most preferred sequence in TRAC:

```
                                   (SEQ ID NO: 37)
ttgtcccacagATATCCAG
-2A sequence in frame with TCR-CAR sequence-pA-
right homology alternatives:

(nt 1-22 of SEQ. ID NO: 38)
ttgtcccacagATATCCAGAAC
-2A sequence-CAR sequence-pA-right homology (nt 1-25 of SEQ ID NO: 38)
ttgtcccacagATATCCAGAACCCT
-2A sequence-CAR sequence-pA-right homology (nt 1-28 of SEQ ID NO: 38)
ttgtcccacagATATCCAGAACCCTGAC
-2A sequence-CAR sequence-pA-right homology (nt 1-31 of SEQ ID NO: 38)
ttgtcccacagATATCCAGAACCCTGACCCT
-2A sequence-CAR sequence-pA-right homology (nt 1-34 of SEQ ID NO: 38)
ttgtcccacagATATCCAGAACCCTGACCCTGCC
-2A sequence-CAR sequence-pA-right homology (nt 1-37 of SEQ ID NO: 38)
ttgtcccacagATATCCAGAACCCTGACCCTGCCGTG
-2A sequence-CAR sequence-pA-right homology (nt 1-40 of SEQ ID NO: 38)
ttgtcccacagATATCCAGAACCCTGACCCTGCCGTGTAC
-2A sequence-CAR sequence-pA-right homology (nt 1-43 of SEQ ID NO: 38)
ttgtcccacagATATCCAGAACCCTGACCCTGCCGTGTACCAG
-2A sequence-CAR sequence-pA-right homology
```

Possible sequence in 3': no restriction, underlined sequence may be absent:

```
Left homology -2A sequence-CAR sequence-pA-
                               (SEQ ID NO: 144)
CCTGACCCTGCCGTGTACCAGCTGAGAGACTCTAA Left homology -2A sequence-CAR sequence-pA-
                     (nt 2-35 of SEQ ID NO: 144)
CTGACCCTGCCGTGTACCAGCTGAGAGACTCTAA Left homology -2A sequence-CAR sequence-pA-
                     (nt 3-35 of SEQ ID NO: 144)
TGACCCTGCCGTGTACCAGCTGAGAGACTCTAA Left homology -2A sequence-CAR sequence-pA-
                     (nt 4-35 of SEQ ID NO: 144)
GACCCTGCCGTGTACCAGCTGAGAGACTCTAA Left homology -2A sequence-CAR sequence-pA-
                     (nt 5-35 of SEQ ID NO: 144)
ACCCTGCCGTGTACCAGCTGAGAGACTCTAA Left homology -2A sequence-CAR sequence-pA-
                     (nt 6-35 of SEQ ID NO: 144)
CCCTGCCGTGTACCAGCTGAGAGACTCTAA Left homology -2A sequence-CAR sequence-pA-
                     (nt 7-35 of SEQ ID NO: 144)
CCTGCCGTGTACCAGCTGAGAGACTCTAA Left homology -2A sequence-CAR sequence-pA-
                     (nt 8-35 of SEQ ID NO: 144)
CTGCCGTGTACCAGCTGAGAGACTCTAA Left homology -2A sequence-CAR sequence-pA-
                     (nt 9-35 of SEQ ID NO: 144)
TGCCGTGTACCAGCTGAGAGACTCTAA
```

-continued

```
Left homology -2A sequence-CAR sequence-pA-
                    (nt 10-35 of SEQ ID NO: 144)
GCCGTGTACCAGCTGAGAGACTCTAA Left homology -2A sequence-CAR sequence-pA-
                    (nt 11-35 of SEQ ID NO: 144)
CCGTGTACCAGCTGAGAGACTCTAA
(most preferred sequence).

Left homology -2A sequence-CAR sequence-pA-
                    (nt 12-35 of SEQ ID NO: 144)
CGTGTACCAGCTGAGAGACTCTAA Left homology -2A sequence-CAR sequence-pA-
                    (nt 13-35 of SEQ ID NO: 144)
GTGTACCAGCTGAGAGACTCTAA Left homology -2A sequence-CAR sequence-pA-
                    (nt 14-35 of SEQ ID NO: 144)
TGTACCAGCTGAGAGACTCTAA Left homology -2A sequence-CAR sequence-pA-
                    (nt 13-35 of SEQ ID NO: 144)
GTACCAGCTGAGAGACTCTAA Left homology -2A sequence-CAR sequence-pA-
                    (nt 14-35 of SEQ ID NO: 144)
TGTACCAGCTGAGAGACTCTAA Left homology -2A sequence-CAR sequence-pA-
                    (nt 15-35 of SEQ ID NO: 144)
GTACCAGCTGAGAGACTCTAA Left homology -2A sequence-CAR sequence-pA-
                    (nt 16-35 of SEQ ID NO: 144)
TACCAGCTGAGAGACTCTAA Left homology -2A sequence-CAR sequence-pA-
                    (nt 17-35 of SEQ ID NO: 144)
ACCAGCTGAGAGACTCTAA Left homology -2A sequence-CAR sequence-pA-
                    (nt 18-35 of SEQ ID NO: 144)
CCAGCTGAGAGACTCTAA Left homology -2A sequence-CAR sequence-pA-
                    (nt 19-35 of SEQ ID NO: 144)
CAGCTGAGAGACTCTAA Left homology -2A sequence-CAR sequence-pA-
                    (nt 20-35 of SEQ ID NO: 144)
AGCTGAGAGACTCTAA Left homology -2A sequence-CAR sequence-pA-
                    (nt 21-35 of SEQ ID NO: 144)
GCTGAGAGACTCTAA Left homology -2A sequence-CAR sequence-pA-
                    (nt 22-35 of SEQ ID NO: 144)
CTGAGAGACTCTAA Left homology -2A sequence-CAR sequence-pA-
                    (nt 23-35 of SEQ ID NO: 144)
TGAGAGACTCTAA Left homology -2A sequence-CAR sequence-pA
                    (nt 24-35 of SEQ ID NO: 144)
GAGAGACTCTAA Left homology -2A sequence-CAR sequence-pA-
                    (nt 25-35 of SEQ ID NO: 144)
AGAGACTCTAA Left homology -2A sequence-CAR sequence-pA-
                    (nt 26-35 of SEQ ID NO: 144)
GAGACTCTAA Left homology -2A sequence-CAR sequence-pA-
                    (nt 27-35 of SEQ ID NO: 144)
AGACTCTAA
```

-continued

Left homology -2A sequence-CAR sequence-pA-
                     (nt 28-35 of SEQ ID NO: 144)
GACTCTAA

OTHER TALEN Studied in TRAC
  In Exon1:

(SEQ ID NO: 145)
TCCAGTGACAAGTCTGTctgcctattcaccgaTTTTGATTCTCAAACAA
Combination in 5' (with 2A sequence in frame with TRAC)

(nt 1-58 of SEQ ID NO: 146)
ttgtcccacagATATCCAGAACCCTGACCCTGCCGTGTACCAGCTGAGAGACTCTAAA
2A sequence-CAR sequence-pA-right homology (nt 1-61 of SEQ ID NO: 146)
ttgtcccacagATATCCAGAACCCTGACCCTGCCGTGTACCAGCTGAGAGACTCTAAATCC
2A sequence-CAR sequence-pA-right homology (nt 1-64 of SEQ ID NO: 146)
ttgtcccacagATATCCAGAACCCTGACCCTGCCGTGTACCAGCTGAGAGACTCTAAATCCAGT
2A sequence-CAR sequence-pA-right homology (nt 1-67 of SEQ ID NO: 146)
ttgtcccacagATATCCAGAACCCTGACCCTGCCGTGTACCAGCTGAGAGACTCTAAATCCAGTGAC
2A sequence-CAR sequence-pA-right homology (nt 1-70 of SEQ ID NO: 146)
ttgtcccacagATATCCAGAACCCTGACCCTGCCGTGTACCAGCTGAGAGACTCTAAATCCAGTGACAAG
-2A sequence-CAR sequence-pA-right homology (nt 1-73 of SEQ ID NO: 146)
ttgtcccacagATATCCAGAACCCTGACCCTGCCGTGTACCAGCTGAGAGACTCTAAATCCAGTGACAAGTCT
-2A sequence-CAR sequence-pA-right homology (nt 1-76 of SEQ ID NO: 146)
ttgtcccacagATATCCAGAACCCTGACCCTGCCGTGTACCAGCTGAGAGACTCTAAATCCAGTGACAAGTCTGTC-
-2A sequence-CAR sequence-pA-right homology (nt 1-79 of SEQ ID NO: 146)
ttgtcccacagATATCCAGAACCCTGACCCTGCCGTGTACCAGCTGAGAGACTCTAAATCCAGTGACAAGTCTGTCTGC
-2A sequence-CAR sequence-pA-right homology (nt 1-82 of SEQ ID NO: 146)
ttgtcccacagATATCCAGAACCCTGACCCTGCCGTGTACCAGCTGAGAGACTCTAAATCCAGTGACAAGTCTGTCTGCCTA
-2A sequence-CAR sequence-pA-right homology (nt 1-85 of SEQ ID NO: 146)
ttgtcccacagATATCCAGAACCCTGACCCTGCCGTGTACCAGCTGAGAGACTCTAAATCCAGTGACAAGTCTGTCTGCCTATTC
-2A sequence-CAR sequence-pA-right homology (nt 1-88 of SEQ ID NO: 146)
ttgtcccacagATATCCAGAACCCTGACCCTGCCGTGTACCAGCTGAGAGACTCTAAATCCAGTGACAAGTCTGTCTG
CCTATTCACC 2A sequence-CAR sequence-pA-right homology (nt 1-91 of SEQ ID NO: 146)
ttgtcccacagATATCCAGAACCCTGACCCTGCCGTGTACCAGCTGAGAGACTCTAAATCCAGTGACAAGTCTGTCTG
CCTATTCACCGAT-2A sequence-CAR sequence-pA-right homology (nt 1-94 of SEQ ID NO: 146)
ttgtcccacagATATCCAGAACCCTGACCCTGCCGTGTACCAGCTGAGAGACTCTAAATCCAGTGACAAGTCTGTCTG
CCTATTCACCGATTTT-2A sequence-CAR sequence-pA-right homology (nt 1-97 of SEQ ID NO: 146)
ttgtcccacagATATCCAGAACCCTGACCCTGCCGTGTACCAGCTGAGAGACTCTAAATCCAGTGACAAGTCTGTCTG
CCTATTCACCGATTTTGAT-2A sequence-CAR sequence-pA-right homology (nt 100 of SEQ ID NO: 146)
ttgtcccacagATATCCAGAACCCTGACCCTGCCGTGTACCAGCTGAGAGACTCTAAATCCAGTGACAAGTCTGTCTG
CCTATTCACCGATTTTGATTCT-2A sequence-CAR sequence-pA-right homology (SEQ ID NO: 146)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAA-2A sequence-CAR sequence-pA-right homology Possible combination in 3'
Left homology-2A sequence-CAR sequence-pA-
                              (SEQ ID NO: 147)
TTCACCGATTTTGATTCTCAAACAAATGTGTCACAA -continued Left homology-2A sequence-CAR sequence-pA-
TCACCGATTTTGATTCTCAAACAAATGTGTCACAA      (nt 2-36 of SEQ ID NO: 147)

Left homology-2A sequence-CAR sequence-pA-
CACCGATTTTGATTCTCAAACAAATGTGTCACAA      (nt 3-36 of SEQ ID NO: 147)

Left homology-2A sequence-CAR sequence-pA-
ACCGATTTTGATTCTCAAACAAATGTGTCACAA      (nt 4-36 of SEQ ID NO: 147)

Left homology-2A sequence-CAR sequence-pA-
CCGATTTTGATTCTCAAACAAATGTGTCACAA      (nt 5-36 of SEQ ID NO: 147)

Left homology-2A sequence-CAR sequence-pA-
CGATTTTGATTCTCAAACAAATGTGTCACAA      (nt 6-36 of SEQ ID NO: 147)

Left homology-2A sequence-CAR sequence-pA-
GATTTTGATTCTCAAACAAATGTGTCACAA      (nt 7-36 of SEQ ID NO: 147)

Left homology-2A sequence-CAR sequence-pA-
ATTTTGATTCTCAAACAAATGTGTCACAA      (nt 8-36 of SEQ ID NO: 147)

Left homology-2A sequence-CAR sequence-pA-
TTTTGATTCTCAAACAAATGTGTCACAA      (nt 9-36 of SEQ ID NO: 147)

Left homology-2A sequence-CAR sequence-pA-
TTTGATTCTCAAACAAATGTGTCACAA      (nt 10-36 of SEQ ID NO: 147)

Left homology-2A sequence-CAR sequence-pA-
TTGATTCTCAAACAAATGTGTCACAA      (nt 11-36 of SEQ ID NO: 147)

Left homology-2A sequence-CAR sequence-pA-
TGATTCTCAAACAAATGTGTCACAA      (nt 12-36 of SEQ ID NO: 147)

Left homology-2A sequence-CAR sequence-pA-
GATTCTCAAACAAATGTGTCACAA      (nt 13-36 of SEQ ID NO: 147)

Left homology-2A sequence-CAR sequence-pA-
ATTCTCAAACAAATGTGTCACAA      (nt 14-36 of SEQ ID NO: 147)

Left homology-2A sequence-CAR sequence-pA-
TTCTCAAACAAATGTGTCACAA      (nt 15-36 of SEQ ID NO: 147)

Left homology-2A sequence-CAR sequence-pA-
TCTCAAACAAATGTGTCACAA      (nt 16-36 of SEQ ID NO: 147)

Left homology-2A sequence-CAR sequence-pA-
CTCAAACAAATGTGTCACAA      (nt 17-36 of SEQ ID NO: 147)

Left homology-2A sequence-CAR sequence-pA-
TCAAACAAATGTGTCACAA      (nt 18-36 of SEQ ID NO: 147)

Left homology-2A sequence-CAR sequence-pA-
CAAACAAATGTGTCACAA      (nt 19-36 of SEQ ID NO: 147)

Left homology-2A sequence-CAR sequence-pA-
AAACAAATGTGTCACAA      (nt 20-36 of SEQ ID NO: 147)

Left homology-2A sequence-CAR sequence-pA-
AACAAATGTGTCACAA      (nt 21-36 of SEQ ID NO: 147)

-continued

```
Left homology-2A sequence-CAR sequence-pA-
                                                    (nt 22-36 of SEQ ID NO: 147)
ACAAATGTGTCACAA Left homology-2A sequence-CAR sequence-pA-
                                                    (nt 23-36 of SEQ ID NO: 147)
CAAATGTGTCACAA Left homology-2A sequence-CAR sequence-pA-
                                                    (nt 24-36 of SEQ ID NO: 147)
AAATGTGTCACAA Left homology-2A sequence-CAR sequence-pA-
                                                    (nt 25-36 of SEQ ID NO: 147)
AATGTGTCACAA Left homology-2A sequence-CAR sequence-pA-
                                                    (nt 26-36 of SEQ ID NO: 147)
ATGTGTCACAA Left homology-2A sequence-CAR sequence-pA-
                                                    (nt 27-36 of SEQ ID NO: 147)
TGTGTCACAA Left homology-2A sequence-CAR sequence-pA-
                                                    (nt 28-36 of SEQ ID NO: 147)
GTGTCACAA Left homology-2A sequence-CAR sequence-pA-
                                                    (nt 29-36 of SEQ ID NO: 147)
TGTCACAA Left homology-2A sequence-CAR sequence-pA-
                                                    (nt 30-36 of SEQ ID NO: 147)
GTCACAA TRAC_T04 that binds to
                                                    (SEQ ID NO: 149)
TATATCACAGACAAAACtgtgctagacatgagGTCTATGGACTTCAAGA (nt 1-136 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTG-
2A sequence-CAR sequence-pA-right homology (nt 1-139 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTAT-
-2A sequence-CAR sequence-pA-right homology (nt 1-142 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATC
-2A sequence-CAR sequence-pA-right homology (nt 1-145 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACA
-2A sequence-CAR sequence-pA-right homology (nt 1-148 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGAC-
2A sequence-CAR sequence-pA-right homology (nt 1-151 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAA
-2A sequence-CAR sequence-pA-right homology (nt 1-154 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACT-
2A sequence-CAR sequence-pA-right homology (nt 1-157 of SEQ ID NO: 148)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TG-2A sequence-CAR sequence-pA-right homology
```

-continued (nt 1-160 of SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTA-2A sequence-CAR sequence-pA-right homology (nt 1-163 of SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGAC-2A sequence-CAR sequence-pA-right homology (nt 1-166 of SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATG-2A sequence-CAR sequence-pA-right homology (nt 1-169 of SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGG-2A sequence-CAR sequence-pA-right homology (nt 1-172 of SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCT-2A sequence-CAR sequence-pA-right homology (nt 1-175 of SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATG-2A sequence-CAR sequence-pA-right homology (SEQ ID NO: 148)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGAC-2A sequence-CAR sequence-pA-right homology TRAC_T05 (underlined sequence): Talen binding site.

(nt 1-175 of SEQ ID NO: 150)

TGAGGTCTATGGACTTCaagagcaacagtgctGTGGCCTGGAGCAACAA (nt 1-178 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGAC-2A sequence-CAR sequence-pA-right homology (nt 1-181 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTC-2A sequence-CAR sequence-pA-right homology (nt 1-184 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAG-2A sequence-CAR sequence-pA-right homology (nt 1-187 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGC-2A sequence-CAR sequence-pA-right homology (nt 1-190 of SEQ. ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAAC-2A sequence-CAR sequence-pA-right homology (nt 1-193 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAACAGT-2A sequence-CAR sequence-pA-right homology (nt 1-196 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAACAGTGCT-2A sequence-CAR sequence-pA-right homology (nt 1-199 of SEQ ID NO: 151)

ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAACAGTGCTGTG-2A sequence-CAR sequence-pA-right
homology -continued

```
                                              (nt 1-202 of SEQ ID NO: 151)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAACAGTGCTGTGGCC-2A sequence-CAR sequence-pA-right
homology (nt 1-205 of SEQ ID NO: 151)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAACAGTGCTGTGGCCTGG-2A sequence-CAR sequence-pA-right
homology (SEQ ID NO: 151)
ttgtcccacagATATCCAGAACCCTGACCCTGCCGTGTACCAGCTGAGAGACTCTAAATCCAGTGACAAGTCTGTCTG
CCTATTCACCGATTTTGATTCTCAAACAAATGTGTCACAAAGTAAGGATTCTGATGTGTATATCACAGACAAAACTG
TGCTAGACATGAGGTCTATGGACTTCAAGAGCAACAGTGCTGTGGCCTGGAGC-2A sequence-CAR sequence-pA-
right
homology hsTRAC_T01

(SEQ ID NO: 152)

TATCCAGAACCCTGACCctgccgtgtaccagctGAGAGACTCTAAATCCA (SEQ ID NO: 37)

ttgtcccacagATATCCAG-2A sequence-CAR sequence-pA-right homology (nt 1-22 of SEQ ID NO: 153)
ttgtcccacagATATCCAGAAC-2A sequence-CAR sequence-pA-right homology (nt 1-25 of SEQ ID NO: 153)
ttgtcccacagATATCCAGAACCCT-2A sequence-CAR sequence-pA-right homology (nt 1-28 of SEQ ID NO: 153)
ttgtcccacagATATCCAGAACCCTGAC-2A sequence-CAR sequence-pA-right homology (nt 1-31 of SEQ ID NO: 153)
ttgtcccacagATATCCAGAACCCTGACCCT-2A sequence-CAR sequence-pA-right homology (nt 1-34 of SEQ ID NO: 153)
ttgtcccacagATATCCAGAACCCTGACCCTGCC-2A sequence-CAR sequence-pA-right homology (nt 1-37 of SEQ ID NO: 153)
ttgtcccacagATATCCAGAACCCTGACCCTGCCGTG-2A sequence-CAR sequence-pA-right homology (nt 1-40 of SEQ ID NO: 153)
ttgtcccacagATATCCAGAACCCTGACCCTGCCGTGTAC-2A sequence-CAR sequence-pA-right homology (nt 1-43 of SEQ ID NO: 153)
ttgtcccacagATATCCAGAACCCTGACCCTGCCGTGTACCAG-2A sequence-CAR sequence-pA-right homology (nt 1-46 of SEQ ID NO: 153)
ttgtcccacagATATCCAGAACCCTGACCCTGCCGTGTACCAGCTG- 2A sequence-CAR sequence-pA-right
homology (nt 1-49 of SEQ ID NO: 153)
ttgtcccacagATATCCAGAACCCTGACCCTGCCGTGTACCAGCTGAGA-2A sequence-CAR sequence-pA-right
homology (nt 1-52 of SEQ ID NO: 153)
ttgtCCcacagATATCCAGAACCCTGACCCTGCCGTGTACCAGCTGAGAGAC-2A sequence-CAR sequence-pA-right
homology (SEQ ID NO: 153)
ttgtcccacagATATCCAGAACCCTGACCCTGCCGTGTACCAGCTGAGAGACTCT-2A sequence-CAR sequence-pA-
right homology Example of TALEN targeting Exon2
TRAC_T02:
                                              (SEQ ID NO: 154)
that binds to TTTAGAAAGTTCCTGTGatgtcaagctggtcgAGAAAAGCTTTGAAACA
```

Example 2: Production of UCART cells by inserting a CAR to the TRAC locus with a TALEN

Experimental Protocol

To disrupt the TRAC locus and place a CAR (ex: CD22-specific m971 QR3 or CD123-specific K43 QR3) under its transcriptional control (TRAC-CAR), a TRAC TALEN targeting the first exon of TRAC locus and an adeno-associated virus (AAV) vector repair matrix encoding a self-cleaving T2A peptide followed by the CAR cDNA were prepared. PBMCs were thawed and activated using Transact human T activator CD3/CD28 beads. 3 days after their activation, T cells were passed to be transfected 4 hours later at the earliest. T cells were then transfected by electrotransfer of 1 µg of mRNA encoding TRAC TALEN per million cells using an AGILEPULSE system (Harvard Apparatus) into a 0.4 cm cuvette. Following electroporation, cells were immediately diluted in X-VIVO-15 media supplemented by 20 ng/ml IL-2 and 5% CTS™ Immune Cell SR at the concentration of $4\times10^6$ cells/mL and incubated in 12 well-plates (500 µl per well) at 37° C. in the presence of 5% CO2.

A Recombinant AAV6 donor vector comprising 300 kb homology arms in 5' and 3' was added to the culture (1.5h after electroporation at the multiplicity of infection of $3\times10^4$ vg/cell). Subsequently, edited cells were cultured overnight at 30° C. in X-Vivo-15 media supplemented by 20 ng/ml IL-2 and 5% CTS™ Immune Cell SR and cultured back in the standard conditions starting from the day after (37° C., $1\times10^6$ cells/mL, X-VIVO-15 media supplemented by 20 ng/ml IL-2 and 5% CTS™ Immune Cell SR). Cells were then expanded in the standard conditions and passed every 2 to 3 days. 10 days after transfection/transduction TRAC knock-out and CAR expression were assessed by flow cytometry. Then, 10 days post-transduction, CAR+ T cells cytolytic capacities towards antigen presenting cells were assessed in a flow-based cytotoxicity assay after a 4h or overnight coculture at 37° C. in the presence of 5% CO2.

The target cells that were chosen for their level of expression in antigen (CD22 or CD123). CART and target cells were cocultured in X-VIVO-15 medium at effector (CAR+):target ratios of 1:1, 2:1, 5:1 and 10:1 for the 4h experiment and 0.1:1, 0.2:1, 0.5:1 and 1:1. Culture medium is supplemented with 5% CTS™ Immune Cell SR. To distinguish positive (Daudi or Raji) and negative (SUP-T1) tumor cell lines, positive target cells were stained with CFSE while SUP-T1 were stained with the CELLTRACE violet proliferation marker. At the end of the coculture, cell viability was measured and the percentage of specific lysis was calculated after normalization to non-specific target cell lysis.

A simultaneous editing of the TRAC and CD52 genes or TRAC dCK genes results in TCR/CD52-deficient T cells, or TCR/dCK-deficient T cells which can be administered with, or following, alemtuzumab treatment or PNA treatment, respectively. Alemtuzumab mediates lymphodepletion/immunosuppression thereby promoting engraftment. The same protocol as described previously was used, with the only difference that T cells were transfected by electrotransfer of 1 µg of mRNA encoding TRAC TALEN and 1 µg of mRNA encoding CD52 TALEN or dCK TALEN per million cells.

In parallel, cells were transfected with different plasmids encoding the different CARs of interest and a control CAR (CAR1). Supernatants were harvested 48h later and concentrated by ultracentrifugation. Titration was performed using Jurkat cells transduced with different quantities (µl) of supernatant. 4 days later CAR expression was assessed by flow cytometry on viable RQR8+ cells in combination with a live/dead cell marker and viral titers were determined.

TALEN-targeted CAR gene integration into the TRAC locus. rAAV6 contained a CAR cassette flanked by 1000 bp to 100 homology arms and the bottom panel the edited TRAC locus.

3 days after activation, T cells were transfected or not preferably by electrotransfer, at a dose of 1 µg of mRNA encoding TRAC TALEN per million cells. 1.5h later, rAAV6 donor vector was added or not to the culture at the multiplicity of infection of $3\times10^4$ vg/cell. TCR and CAR expressions were assessed by flow cytometry on viable T cells using CD4, CD8, TCRαβ mAb, CD22 or CD123 recombinant protein (full length) in combination with a live/dead cell marker.

The results show that the population of CAR$^+$ cells after rAAV transduction is more homogenous than after rLv transduction.

Using this 2-in-1 strategy of TCR KO and CAR KI, the integration of the CAR at the TRAC locus is highly efficient since the frequency of CAR$^+$TCR$^-$ cells reached more than 42%.

Total cells or CAR$^+$ T cells cytolytic capacities towards antigen presenting cells was assessed in a flow-based cytotoxicity assay. The cell viability was measured after 4h or after an overnight coculture with CAR T cells at effector/target ratios set at 10:1, 5:1, 2:1 and 1:1 or 1:1, 0.5:1, 0.2:1 and 0.1:1 respectively.

The results show that TRAC-CART cells produced after rAAV6 transduction are as cytotoxic in vitro as UCART cells produced after rLV transduction.

3 days after activation, T cells were transfected or not by electrotransfer of 1 µg of each mRNA encoding TRAC and CD52 TALEN per million cells. 1.5h later, rAAV6 donor vector was added or not to the culture at the multiplicity of infection of $3\times10^4$ vg/cell. TCR, CD52 and CAR expressions were assessed by flow cytometry on viable T cells using CD4, CD8, TCRαβ mAb, CD22 or CD123 recombinant protein (full length) in combination with a live/dead cell marker.

The results show that this 2-in-1 strategy of TCR KO and CAR KI can be extended to the use of more than one TALEN. As previously demonstrated, the integration of the CAR at the TRAC locus is highly efficient and specific since the frequency of CAR+TCR" cells reached more than 47%. Importantly, no CAR expression was detected at the CD52 locus when T cells were transfected only with 1 µg of mRNA encoding CD52 TALEN. More than 80% of the population of CAR+ T cells is knocked-out for both TCRαβ and CD52.

Characterization of TALEN, meganuclease, Zn finger engineered primary cell—TRAC Recognition Sequences—off site measurements.

Recombinant nucleases engineered to recognize recognition sequences of the human TRAC gene (all in the human T cell receptor alpha constant region) were previously disclosed in WO2017062451 Precision TRAC, WO2015057980 or in WO2017106528. The activity of said endonucleases results in a disablement of the extracellular part of the endogenous TCR alpha beta and ultimately to a down regulation of cell surface of the endogenous alpha beta TCR. Comparative Zn finger were those disclosed in US2011158957. all nucleases were compared to the reference TALEN as disclosed in WO2013176915.

To determine whether nucleases could recognize and cleave their respective recognition sequences, primary cells isolated from leukapheresis were used.

Cells were engineered as below and cell surface expression of alpha beta TCR was measured as a read out.

In particular experiments, purified cell populations were used to test whether TRAC gene editing could be different in whole blood cells, purified naive T cells, purified memory T cells etc.

Means for detecting the engineered TRAC gene is a probe, oligonucleotides, oligonucleotides designed for PCR amplification of the DNA in the TRAC gene greater than 1 kb. A labelled (P32) may be prepared as an alternative.

Any PCR method may be adapted such as real time PCR, TaqMan one-step reverse transcription-quantitative PCR (qRT-PCR) targeting conserved regions of the TRAC gene upstream the recognition sequence and are part of the present invention.

The following sequence was amplified to quantify on target integration:

(SEQ ID NO: 8)

```
GCTGGGGTTTTGAAGAAGATCCTATTAAATAAAAGAATAAGCAGTATTA

TTAAGTAGCCCTGCATTTCAGGTTTCCTTGAGTGGCAGGCCAGGCCTGG

CCGTGAACGTTCACTGAAATCATGGCCTCTTGGCCAAGATTGATAGCTT

GTGCCTGTCCCTGAGTCCCAGTCCATCACGAGCAGCTGGTTTCTAAGAT

GCTATTTCCCGTATAAAGCATGAGACCGTGACTTGCCAGCCCCACAGAG

CCCCGCCCTTGTCCATCACTGGCATCTGGACTCCAGCCTGGGTTGGGGC

AAAGAGGGAAATGAGATCATGTCCTAACCCTGATCCTCTTGTCCCACAG

ATATCCAGTCCGGTGAGGGCAGAGGAAGTCTTCTAACATGCGGTGACGT

GGAGGAGAATCCGGGCCCC
```

Using the following means:

```
Forward:
                             (SEQ ID NO: 5)
GCTGGGGTTTTGAAGAAGATCC

Reverse:
                             (SEQ ID NO: 6)
GACTTCCTCTGCCCTCACC

Probe:
                             (SEQ ID NO: 7)
CCCTTGTCCATCACTGGCAT
```

Cells were harvested at different time points of their expansion.

Two steps of washes are performed in X-VIVO15 medium before one additional wash performed in the presence of 140U/ml of benzonase for 30 min at 37° C.

Two following washes are necessary to remove the excess of benzonase.

Cells are then dry pelleted and stored at −20° C.

Genomic DNA is extracted using the DNEASY Blood & Tissue Kit (QIAGEN) following manufacturer's guidelines.

gDNA concentration was assessed using the Quant-iT™ PicoGreen™ dsDNA Assay Kit (ThermoFisher Scientific).

For qPCR assay, primers and probe (FAM) are designed to amplify a sequence of 373 bp, the forward primer being located in the TRAC locus outside of the left homology sequence and the reverse primer in the T2A sequence. A mix of primers and probe is prepared in TE buffer containing 300 nM of forward primer, 900 nM of reverse primer and 250 nM of probe (IDT Technologies).

In another preferred embodiment the mix of primers and probe is prepared in TE buffer containing 300 nM of forward primer, 900 nM of reverse primer and 220 nM of probe (IDT Technologies).

In another preferred embodiment, the mix of primers and probe is prepared in TE buffer containing 300 nM of forward primer, 900 nM of reverse primer and 220 nM of probe (IDT Technologies) and the optimal quantity of gDNA to use ranges from 100 to 200 ng (10 µl), preferably between 20 and 30 ng (10 µl).

Target amplification is performed using the TaqMan Gene Expression Master Mix (Thermo Fisher 4369514) and run on a C1000 Touch™ Thermal Cycler (BioRad). Gene expression is normalized to RPP30 gene expression (ddPCR™ CNV Assay, Validated (HEX)) and the number of copies is calculated from the dilution ($10^6$ copies/µl down to $10^0$ copies/µl) of a standard plasmid that includes the sequence of interest as previously described, extended in 5' by some nucleotides corresponding to the TRAC locus sequence.

To amplify a sequence according to the present invention, the concentration of primers/probe was adjusted and the annealing/extension step was increased by 2, such as from 45 sec to 1 min 30 sec.

Preferably, the annealing/extension step was increased from 45 sec to 1 min 30 sec and performed at 61.5° C.

On site and/or off sites cleavage determination by GUIDE SEQ for the following genes:

CD28 Talen, CD28 Talen, CD28 Crispr and PD1 TALEN, TRAC Talen (two conditions of stringency) CS1, CS1+TRAC Talen, CD52+TRAC Talen, CS1+TRAC Talen Sequence of the dsODN:

GTTTAATTGAGTTGTCATATGTTAATAACGGTAT (SEQ ID NO: 20) used for insertion in off sites and onsite in the presence or absence of (SEQ ID NO: 154)

```
AAGTAGCCCTGCATTTCAGGTTTCCTTGAGTGGCAGGCCAGGCCTGGCCGTGAACGTTCACTGAAATCATGGCC

TCTTGGCCAAGATTGATAGCTTGTGCCTGTCCCTGAGTCCCAGTCCATCACGAGCAGCTGGTTTCTAAGATGCTAT

TTCCCGTATAAAGCATGAGACCGTGACTTGCCAGCCCCACAGAGCCCCGCCCTTGTCCATCACTGGCATCTGGAC

TCCAGCCTGGGTTGGGGCAAAGAGGGAAATGAGATCATGTCCTAACCCTGATCCTCTTGTCCCACAGATATCCAG

TCCGGTGAGGGCAGAGGAAGTCTTCTAACATGCGGTGACGTGGAGGAGAATCCGGGCCCCGGATCCGCTCTG

CCCGTCACCGCTCTGCTGCTGCCTCTGGCCCTGCTGCTGCACGCAGCCAGACCAGGCGGAGGAGGCTCCTGCCC

TTACTCTAACCCAAGCCTGTGCTCCGGAGGAGGAGGATCCGGCGGAGGAGGCTCTGAGGTGAAGCTGGTGGA

GAGCGGAGGAGGCCTGGTGCAGCCTGGCGGCTCCCTGTCTCTGAGCTGCGCAGCATCCGGCTTCACCTTTACAG

ACTACTATATGTCTTGGGTGAGACAGCCCCCTGGCAAGGCCCTGGAGTGGCTGGCCCTGATCAGGTCCAAGGCC

GATGGCTACACCACAGAGTATTCCGCCTCTGTGAAGGGCAGATTCACCCTGTCTAGGGACGATAGCCAGTCCATC

CTGTACCTGCAGATGAATGCACTGCGCCCCGAGGACAGCGCCACATACTATTGTGCCAGAGACGCCGCCTACTAT

TCTTACTATAGCCCTGAGGGCGCTATGGACTACTGGGGCCAGGGCACCTCCGTGACAGTGAGCTCCGGAGGAGG

AGGAAGCGGAGGAGGAGGCTCCGGCGGCGGCGGCTCTATGGCCGACTATAAGGATATCGTGATGACCCAGAGC
```

-continued

```
CACAAGTTTATGTCTACAAGCGTGGGCGACCGCGTGAACATCACCTGCAAGGCCAGCCAGAATGTGGATTCCGC

CGTGGCCTGGTACCAGCAGAAGCCTGGCCAGAGCCCTAAGGCCCTGATCTATTCCGCCTCTTACCGGTATAGCGG

AGTGCCTGACCGCTTCACCGGAAGGGGATCCGGAACAGACTTCACCCTGACAATCTCTAGCGTGCAGGCCGAG

GATCTGGCCGTGTACTATTGTCAGCAGTACTATAGCACCCCCTGGACCTTCGGCGGAGGAACCAAGCTGGAGATC

AAGAGAGGATCTGGAGGAGGAGGAAGCTGCCCATACTCCAACCCCTCTCTGTGCAGCGGAGGAGGAGGATCTG

AGCTGCCAACCCAGGGCACATTTTCCAACGTGTCTACAAATGTGAGCCCAGCAAAGCCAACCACAACCGCATGC

CCTTATAGCAATCCATCCCTGTGCACAACCACACCTGCACCAAGACCACCAACCCCAGCACCTACAATCGCCTCTC

AGCCACTGAGCCTGCGCCCCGAGGCATGCCGGCCTGCAGCAGGCGGCGCCGTGCACACCAGGGGCCTGGACT

TCGCCTGCGATATCTACATCTGGGCACCTCTGGCAGGAACCTGTGGCGTGCTGCTGCTGAGCCTGGTCATCACCC

TGTACTGCAAGAGAGGCAGGAAGAAGCTGCTGTATATCTTCAAGCAGCCCTTTATGCGCCCTGTGCAGACCACAC

AGGAGGAGGACGGCTGCAGCTGTCGGTTCCCAGAAGAGGAGGAGGGCGGCTGTGAGCTGAGAGTGAAGTTT

AGCAGGTCCGCCGATGCACCAGCATACCAGCAGGGACAGAACCAGCTGTATAACGAGCTGAATCTGGGCCGGA

GAGAGGAGTACGACGTGCTGGATAAGAGGAGGGGAAGGGACCCCGAGATGGGAGGCAAGCCACGGAGAAA

GAACCCCCAGGAGGGCCTGTACAATGAGCTGCAGAAGGACAAGATGGCCGAGGCCTATTCCGAGATCGGCATG

AAGGGAGAGAGGCGCCGGGGCAAGGGACACGATGGCCTGTACCAGGGCCTGTCTACCGCCACAAAGGACACC

TATGATGCCCTGCATATGCAGGCACTGCCTCCAAGGTGATCTAGAGGGCCCGTTTAAACCCGCTGATCAGCCTCG

ACTGTGCCTTCTAGTTGCCAGCCATCTGTTGTTTGCCCCTCCCCCGTGCCTTCCTTGACCCTGGAAGGTGCCACTCC

CACTGTCCTTTCCTAATAAAATGAGGAAATTGCATCGCATTGTCTGAGTAGGTGTCATTCTATTCTGGGGGGTGGG

GTGGGGCAGGACAGCAAGGGGGAGGATTGGGAAGACAATAGCAGGCATGCTGGGGATGCGGTGGGCTCTATG

ACTAGTGGCGAATTCCCGTGTACCAGCTGAGAGACTCTAAATCCAGTGACAAGTCTGTCTGCCTATTCACCGATTT

TGATTCTCAAACAAATGTGTCACAAAGTAAGGATTCTGATGTGTATATCACAGACAAAACTGTGCTAGACATGAGG

TCTATGGACTTCAAGAGCAACAGTGCTGTGGCCTGGAGCAACAAATCTGACTTTGCATGTGCAAACGCCTTCAAC

AACAGCATTATTCCAGAAGACACCTTCTTCCCCAGCCCAGGTAAGGGCAGCTTTGGTGCCTTCGCAGGCTGTTTC

CTTGCTTCAGGAA
```

Samples.

Primary T cells were electroporated either with a TRAC endonuclease or nothing plus 1000 pmol of a DS oligonucleotide.

Two samples of each condition were done, and the genomic DNA extracted. Each genomic DNA was divided in 3 aliquots which were individually processed using the GUIDE-seq protocol.

The genomic DNA was extracted and submitted to standard GUIDE-seq procedure:

shearing of the DNA by sonication.

end repair to have blunt extremities.

ligation of a Y-shape adaptor blunt on one side, and with overhangs on the other (so that it can ligate only on one side):

successive PCRs between the DS oligo and the adaptor above: these can be done either using the sequence of the oligo ("plus" amplification that will amplify one side of the flanking region) or the reverse complement sequence of the oligo ("minus" amplification that will amplify the other side of the flanking region).

each PCR product is then sequenced on both sides (R1 and R2)

All samples were amplified on both strands minus and plus, and sequenced in both extremities R1 and R2.

Nuclease:

The arms of the TALENs are the following (with TO included)

for TRAC: TRACL=TTGTCCCACAGATAT (SEQ ID NO: 162) and TRACR=TCTCAGCTGGTACAC (SEQ ID NO: 163)

Locations of the sites on the v37.1 of the genome:

onsite TRAC: contig NT_026437.12, starting on position 4016436 (middle of spacer on 4016460)

Primers used for the PCR

The primers used on the side of the oligo were:

for the plus strand, ATACCGTTATTAACATATGACA (SEQ ID NO: 13) for the first PCR, and then CATATGACAACTCAATTAAAC (SEQ ID NO: 14) for the second PCR:

ATACCGTTATTAACATATGACAACTCAATTAAAC (SEQ ID NO: 15) oligo (rev compl)

ATACCGTTATTAACATATGACA 1st PCR (SEQ ID NO: 16).

CATATGACAACTCAATTAAAC 2nd PCR (SEQ ID NO: 17)

for the minus strand, GTTAATTGAGTTGTCATATGTTAATAAC (SEQ ID NO: 18) for the first PCR, and then TTGAGTTGTCATATGTTAATAACGGTA (SEQ ID NO: 19) for the second PCR:

GTTTAATTGAGTTGTCATATGTTAATAACGGTAT (SEQ ID NO: 20) oligo

GTTTAATTGAGTTGTCATATGTTAATAAC 1st PCR (SEQ ID NO: 21)

TTGAGTTGTCATATGTTAATAACGGTA 2nd PCR (SEQ ID NO: 22.

Structure of the Product

The structure of the waited products should be the following, with the DS oligonucleotide being in uppercase, the primers that should remain after the PCRs in lowercase, and the unknown genomic sequence represented by NNNNN NNNNN:

for "plus" PCRs: R1→aatgatacggcgaccaccgagatct acact cttt ccctacacgacgctcttccgatct-NNNNNNNNNNGTT TA ATTGAGTTGTCATATG-tatcaccgactgcccataga gaggactccagtcac-taaggcgaatctcgtatgccgtcttctgcttg←R2 (SEQ ID NO: 155)

for "minus" PCRs: R2→caagcagaagacggcatacga gat-tcgccttagtgactggagtcctctctatgggcag-tcggtgat-TTGA GTTGTCATATGTTAATAACGGTATNNNNNNN NNNNN-agatcggaagagcgtcgtgtaggaaagagtgtagat ctcggtggtcgccgtatcatt←R1 (SEQ ID NO: 156)

Sequence data processing:

Reads were first tested for the presence of the expected primer:

for minus_R2 reads, the presence of the sequence TGAGTIGTCATATGTTAATAACGGTAT (nt 8-36 of SEQ ID NO: 20) which is the sequence of the second primer without the first T was checked, for plus_R2 reads, the presence of the sequence CATATGACAACTCAATTAAAC (SEQ ID NO: 17) which is the sequence of the second PCR primer was checked.

when the R2 read had not this sequence, R2 was eliminated. Remaining reads were then successively trimmed in 3' and 5' for adaptor presence with a minimum required overlap length of 20 bp and remaining sequences shorter than 10 bp were discarded. The counts are represented with:

the initial number of reads the number of filtered reads (for the required oligo)

the final number of trimmed reads once short trimmed sequences are discarded.

A GUIDE-Seq read count or GUIDE-Seq score for a given site in the TRAC gene by a given endonuclease, represents a quantitative measurement of the cleavage efficiency of that sequence by an RNA or protein guided nuclease. Preferably the RNA or protein guided nuclease of the invention affecting the TRAC gene have a score near zero (undetectable).

The results indicated on site cleavage for 4 TALENs tested affecting the TRAC gene and cell surface expression of alpha beta TCR. Offsite cleavages were below detection in TALEN edited primary cells using the guide-seq analysis adapted to TALEN.

At 48, 72, 96 hours post-transfection, cells were evaluated by flow cytometry to determine the percentage of TCR alpha beta-positive and negative cells as compared to the appropriate control. All meganucleases and crispr tested were found to produce TCR-negative cells.

Insertion of an anti-CD22 or anti-CD123 chimeric antigen receptor sequence was confirmed by pcr and sequencing of the TCR alpha constant region gene.

Cell-surface expression of the chimeric antigen receptor confirmed by flow cytometry, using an anti-Fab or rituximab. Knockout of the endogenous T cell receptor at the cell surface was verified by flow cytometry as previously described.

These studies demonstrated that TALEN, meganucleases and Crispr can recognize and cleave the TRAC gene in T cells obtained from a human donor. Further, these studies demonstrated that NHEJ occurs at the cleavage site, as evidenced by the appearance of indels in 3' of the insertion. Moreover, TRAC TALEN were shown to reduce cell-surface expression of the T cell receptor in human T cells obtained from a donor, even in the presence of a CD52 TALEN in cells with a CAR inserted into the genomic TRAC gene.

These studies demonstrate that AAV vectors can be used in conjunction with recombinant TALENs or Crispr to incorporate specifically an exogenous nucleic acid sequence into a cleavage site in the TCR alpha constant region via homologous recombination without insertion in other sites (CD52, dCK).

Example 3

TALEN®-Mediated Double Targeted Integration of IL-15 and CAR Encoding Matrices in T-Cells This example describes methods to improve the therapeutic outcome of CAR T-cell therapies by integrating an IL-15/soluble IL-15 receptor alpha heterodimer (IL15/sIL15rα) expression cassette under the control of the endogenous T-cell promoters regulating PD1 and CD25 genes. Because both genes are known to be upregulated upon tumor engagement by CAR T-cells, they could be hijacked to re-express IL-IL15/sIL15rα only in vicinity of a tumor. This method would reduce the potential side effects of IL15/sIL15rα systemic secretion while maintaining its capacity to reduced activation induced T-cell death (AICD), promote T-cell survival, enhance T-cell antitumor activity and to reverse T-cell anergy.

The method developed to integrate IL15/sIL15rα at PD1 and CD25 loci consisted in generating a double-strand break at both loci using TALEN in the presence of a DNA repair matrix vectorized by AAV6. This matrix consists of two homology arms embedding IL15/sIL15rα coding regions separated by a 2A cis acting elements and regulatory elements (stop codon and polyA sequences). Depending on the locus targeted and its involvement in T-cell activity, the targeted endogenous gene could be inactivated or not via specific matrix design.

When CD25 gene was considered as targeted locus, the insertion matrix was designed to knock-in (KI) IL15/sIL15rα without inactivating CD25 because the protein product of this gene is essential for T-cell function. In contrary, because PD1 is involved in T-cell inhibition/exhaustion of T-cells, the insertion matrix was designed to prevent its expression while enabling the expression and secretion of IL15/sIL15rα.

To illustrate this approach and demonstrate the feasibility of multiple targeted insertion in primary T-cells, three different matrices were designed. The first one named CARm was designed to insert an anti-CD22 CAR cDNA at the TRAC locus in the presence of TRAC TALEN. The second one, IL-15_CD25m that was designed to integrate IL15, sIL15rα and the surface marker named ΔLNGFR cDNAs separated by 2A cis-acting elements just before the stop codon of CD25 endogenous coding sequence using CD25 TALEN®. The third one, IL-15_PD1m, contained the same expression cassette and was designed to integrate in the middle of the PD1 open reading frame using PD1 TALEN. The three matrices contained an additional 2A cis-acting element located upstream expression cassettes to enable co-expression of IL15/sIL15rα and CAR with the endogenous gene targeted.

We first assessed the efficiency of double targeted insertion in T-cells by transducing them with one of the AAV6 encoding IL15/sIL15rα matrices along with the one encoding the CAR and subsequently transfected the corresponding TALEN®. AAV6-assisted vectorization of matrices in the presence of mRNA encoding TRAC TALEN and PD1 or CD25 TALEN enabled expression of the anti CD22 CAR more than 46% of engineered T-cells.

To determine the extent of IL15m integration at CD25 and PD1 locus, engineered T-cells were activated with either antiCD3/CD28 coated beads or with CD22 expressing Raji tumor cells. 2 days post activation, cells were recovered and analyzed by FACS using LNGFR expression as IL15/sIL15rα secretion surrogate. Our results showed that antiCD3/CD28 coated beads induced expression of ΔLNGFR by T-cells containing IL-15m_CD25 or IL-15m_PD1, independently of the presence of the anti CD22 CAR. Tumor cells however, only induced expression of ΔLNGFR by T-cell treated by both CARm and IL-15m. This indicated that expression of ΔLNGFR could be specifically induced through tumor cell engagement by the CAR.

As expected the endogenous CD25 gene was still expressed in activated treated T-cells while PD1 expression was strongly impaired.

To verify that expression of ΔLNGFR correlated with secretion of IL15 in the media, T-cells expressing the anti-CD22 CAR and ΔLNGFR were incubated in the presence of CD22 expressing Raji tumor cells (E:T ratio=1:1) for a total of 10 days. Supernatant were recovered at day 2, 4, 7 and 10 and the presence of IL15 was quantified by ELISA assay. Our results showed that (L15 was secreted in the media only by T-cells that were co-treated by both CARm and IL15m matrices along with their corresponding TALEN. T-cell treated with either one of these matrices were unable to secrete any significant level of IL15 with respect to resting T-cells.

To assess whether the level of secreted IL-15 could impact CAR T-cell activity, CAR T-cell were cocultured in the presence of tumor cells at E:T ratio of 5:1 for 4 days. Their antitumor activity was challenged everyday by pelleting and resuspended them in a culture media lacking IL-2 and containing fresh tumor cells. Antitumor activity of CAR T-cell was monitored everyday by measuring the luminescence of the remaining Raji tumor cells expressing luciferase. Our results showed that CAR T-cells co-expressing IL-15 had a higher antitumor activity than those lacking IL15 at all time points considered.

Thus, together our results showed a simultaneous targeted insertions of CAR and IL15 cDNA at TRAC and CD25 or PD1 loci. This double targeted insertion led to robust expression of an antiCD22 CAR and to the secretion of IL15 in the media. Levels of secreted IL15 were sufficient to enhance the activity of CAR T-cells.

The present invention encompasses a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a half TALEN, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a coding sequence such as a sequence coding for a self-dleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a) a recognition domain for another half TALEN, (d) a 3' region of the genomic TRAC gene further comprising another inactivated genomic gene, such as any one of the following encoding genes: a gene encoding interleukin 3, interleukin 2, chemokine (C—C motif) ligand 4, interleukin 21, glycoprotein 49 A, nuclear receptor subfamily 4, group A, member 3, leukocyte immunoglobulin-like receptor, subfamily B, member 4, CD200 antigen, cyclin-dependent kinase inhibitor 1A (P21), granzyme c, nuclear receptor subfamily 4, group A, member 2, cytokine inducible SH2-containing protein, chemokine (C—C motif) receptor 8, ladinin, cellular retinoic acid binding protein II, granzyme B, T-box 21, programmed cell death 1, pleckstrin, checkpoint kinase 1, SLAM family member 7, zinc finger and BTB domain containing 32, T cell immunoreceptor with Ig and ITIM domains, lymphocyte-activation gene 3, granzyme A, WEE 1 homolog 1 (S. pombe), interleukin 12 receptor, beta 2, chemokine (C—C motif) receptor 5, early endosome antigen 1, and denticleless homolog (Drosophila).

The present invention encompasses a TALEN-modified endogenous αβ-TCR negative human primary cell wherein the constant region of the genomic TCR gene (TRAC gene) comprises a genetic modification generated by a TALEN and affecting cell surface expression of the endogenous alpha beta TCR, said genomic TRAC gene comprising from 5' to 3':

(a) a 5' region of said human genomic TRAC gene upstream, (b) a recognition domain for a half TALEN, (c) a gap or an insertion as compared to the wild type TRAC gene affecting the cell surface expression of the extracellular domain or transmembrane domain of the alpha beta TCR, said insertion comprising an exogenous polynucleotide selected from a noncoding sequence such as, a stop codon, an IRES, a coding sequence such as a sequence coding for a self-cleaving peptide in frame with the TRAC open reading frame, a sequence coding a chimeric antigen receptor (CAR), a sequence coding a TCR, a sequence coding a protein conferring sensitivity to a drug, a sequence coding a protein conferring resistance to a drug, a cytokine, a termination sequence, a combination thereof, (c') optionally a) a recognition domain for another half TALEN, (d) a 3' region of the genomic TRAC gene further comprising another inactivated genomic gene, such as any one of the following encoding genes: CXCL13, NFRSF1B, RGS2, TIGIT, CD27, NFRSF9, SLA, NF19A, NPP5F, XCL2, HLA-DMA, FAM3C, QCRC1, WARS, EIF3L, KCNKS, TMBIM6, CD200, C3H7A, SH2D1A, ATP1B3, YO7A, THADA, PARK7, EGR2, FDFT1, CRTAM and IFI16.

In one particular embodiment the second inactivated gene is comprising an insertion wherein said insertion comprises a cytokine, in particular IL-3, IL-7, IL-12 and IL-15.

The invention claimed is:

1. A method for producing an endonuclease-modified endogenous αβ-TCR negative human T cell said method comprising introducing into a human T cell:

(i) an engineered nuclease or a first nucleic acid molecule encoding the engineered nuclease, wherein said engineered nuclease is a meganuclease, a zinc-finger nuclease (ZFN), a transcription activator-like effector nuclease (TALE-Nuclease), or a CRISPR/Cas nuclease, or a megaTAL nuclease;

wherein said engineered nuclease produces a cleavage at a recognition site within an endogenous genomic human T cell receptor (TCR) alpha constant region gene in the human T cell; and (ii) a second nucleic acid molecule comprising an exogenous polynucleotide encoding a chimeric antigen receptor (CAR) comprising an scFv, a transmembrane domain from CD8 alpha, and one or more intracellular signaling domains from CD3 zeta and costimulatory domain from 4-1BB or a recombinant TCR, wherein said exogenous polynucleotide is inserted into said endogenous genomic human TCR alpha constant region gene at said cleavage at said recognition site by homologous recombination to generate a genetically-modified T cell;

wherein insertion of said exogenous polynucleotide into said endogenous genomic human TCR alpha constant region gene results in a recombinant genomic nucleic acid molecule comprising the sequence:

gctggggttt tgaagaagat cctattaaat aaaagaataa gcagtattat taagtagccc tgcatttcag gtttccttga gtggcaggcc aggcctggcc gtgaacgttc actgaaatca tggcctcttg gccaagattg atagcttgtg cctgtccctg agtcccagtc catcacgagc agctggtttc taagatgcta tttcccgtat aaagcatgag accgtgactt gccagcccca cagagccccg cccttgtcca tcactggcat ctggactcca gcctgggttg gggcaaagag ggaaatgaga tcatgtccta accctgatcc tcttgtccca cagatatcca gtccggtgag ggcagaggaa gtcttctaac atgcggtgac gtggaggaga atccgggccc c (SEQ ID NO: 8), wherein said genetically-modified T cell has no cell-surface expression of the endogenous TCR.

2. The method of claim 1, further comprising detecting endonuclease cleavage at a site other than at said recognition site by PCR.

3. The method of claim 1, wherein said engineered nuclease is a TALE-Nuclease.

4. The method of claim 1, wherein said second nucleic acid molecule is introduced into said cell by contacting said cell with a recombinant adeno-associated virus (AAV) vector comprising said second nucleic acid sequence.

5. The method of claim 4, wherein said recombinant AAV vector is a self-complementary AAV vector.

6. The method of claim 3, wherein said TALE-Nuclease recognizes the sequence TTGTCCCACAGATATC (SEQ ID NO: 36) in the endogenous genomic human TCR alpha constant region gene.

7. The method of claim 1, wherein said endonuclease is a Zinc finger nuclease that recognizes from 5' to 3' TGCTGTGGCCTGGAGCAAC (SEQ ID NO: 157) and GACTTTGCATGTGCA (SEQ ID NO: 158) and cleaves within ATATC (aa 12-16 of SEQ ID NO: 36), or a Crispr/Cas 9 that recognizes a complementary sequence to any one of the following sequences:

```
                                         (SEQ ID NO: 39)
AGAGTCTCTCAGCTGGTACA, (SEQ ID NO: 40)
GCACCAAAGCTGCCCTTACC, (SEQ ID NO: 41)
AAGTTCCTGTGATGTCAAGC, (SEQ ID NO: 42)
TTCGGAACCCAATCACTGAC, (SEQ ID NO: 43)
GATTAAACCCGGCCACTTTTC, (SEQ ID NO: 44)
CGTCATGAGCAGATTAAACC, (SEQ ID NO: 45)
CTCAAGGTTCAGATCAGAAG, (SEQ ID NO: 46)
TAGGCAGACAGACTTGTCAC, (SEQ ID NO: 47)
AACAAATGTGTCACAAAGTA,
```

-continued (SEQ ID NO: 48)
CACCAAAGCTGCCCTTACCT, (SEQ ID NO: 49)
CTGACAGGTTTTGAAAGTTT, (SEQ ID NO: 50)
TTCAAAACCTGTCAGTGATT, (SEQ ID NO: 51)
CCGAATCCTCCTCCTGAAAG, (SEQ ID NO: 52)
CCACTTTCAGGAGGAGGATT, (SEQ ID NO: 53)
TAAACCCGGCCACTTTCAGG, (SEQ ID NO: 54)
TCTCAAACAAATGTGTCACAAAGTA, (SEQ ID NO: 55)
CTTACAATCTTGCAGATCTGGAATG, (SEQ ID NO: 56)
TTAATCTGCTCATGACGCTG, (SEQ ID NO: 57)
GGAGAAGAGGGGCAATGCAG, (SEQ ID NO: 58)
TCTTCTCCCTCTCCAAACAG, (SEQ ID NO: 59)
AGCAGCTTTCACCTCCTTGG, (SEQ ID NO: 60)
GTAGCAGCTTTCACCTCCTT, (SEQ ID NO: 61)
AGTTGGTGGCATTGCCGGGG, (SEQ ID NO: 62)
TCTGTGATATACACATCAGAATC, (SEQ ID NO: 63)
TCTGTGATATACACATCAGAATCC, (SEQ ID NO: 64)
GAGTCTCTCAGCTGGTACACGGC, (SEQ ID NO: 65)
GAGTCTCTCAGCTGGTACACGGCA, (SEQ ID NO: 66)
ATTCTCAAACAAATGTGTCACAA, (SEQ ID NO: 67)
ATTCTCAAACAAATGTGTCACAAA, (SEQ ID NO: 68)
GTCTGTGATATACACATCAGAAT, (SEQ ID NO: 69)
GTCTGTGATATACACATCAGAATC, (SEQ ID NO: 70)
GAGAATCAAAATCGGTGAATAGG, (SEQ ID NO: 71)
TGTGCTAGACATGAGGTCTATGG, (SEQ ID NO: 72)
TCAGGGTTCTGGATATCTGTGGG, (SEQ ID NO: 73)
GTCAGGGTTCTGGATATCTGTGG, (SEQ ID NO: 74)
AAAGTCAGATTTGTTGCTCCAGG, -continued (SEQ ID NO: 75)
AACAAATGTGTCACAAAGTAAGG, (SEQ ID NO: 76)
TGGATTTAGAGTCTCTCAGCTGG, (SEQ ID NO: 77)
TAGGCAGACAGACTTGTCACTGG, (SEQ ID NO: 78)
AGCTGGTACACGGCAGGGTCAGG, (SEQ ID NO: 79)
GCTGGTACACGGCAGGGTCAGGG, (SEQ ID NO: 80)
TCTCTCAGCTGGTACACGGCAGG, (SEQ ID NO: 81)
AGAGTCTCTCAGCTGGTACACGG, (SEQ ID NO: 82)
CTCTCAGCTGGTACACGGCAGGG, (SEQ ID NO: 83)
ACAAAACTGTGCTAGACATGAGG, (SEQ ID NO: 84)
ATTTGTTTGAGAATCAAAATCGG, (SEQ ID NO: 85)
TGGAATAATGCTGTTGTTGAAGG, (SEQ ID NO: 86)
AGAGCAACAGTGCTGTGGCCTGG, (SEQ ID NO: 87)
CTTCTTCCCCAGCCCAGGTAAGG, (SEQ ID NO: 88)
ACACGGCAGGGTCAGGGTTCTGG, (SEQ ID NO: 89)
CTTCAAGAGCAACAGTGCTGTGG, (SEQ ID NO: 90)
CTGGGGAAGAAGGTGTCTTCTGG, (SEQ ID NO: 91)
TTCTTCCCCAGCCCAGGTAAGGG, (SEQ ID NO: 92)
CTTACCTGGGCTGGGGAAGAAGG, (SEQ ID NO: 93)
GACACCTTCTTCCCCAGCCCAGG, (SEQ ID NO: 94)
TTCAAAACCTGTCAGTGATTGGG, (SEQ ID NO: 95)
CGTCATGAGCAGATTAAACCCGG, (SEQ ID NO: 96)
TTCGGAACCCAATCACTGACAGG, (SEQ ID NO: 97)
TAAACCCGGCCACTTTCAGGAGG, (SEQ ID NO: 98)
TTTCAAAACCTGTCAGTGATTGG, (SEQ ID NO: 99)
GATTAAACCCGGCCACTTTCAGG, (SEQ ID NO: 100)
CTCGACCAGCTTGACATCACAGG, (SEQ ID NO: 101)
AAGTTCCTGTGATGTCAAGCTGG, -continued (SEQ ID NO: 102)
ATCCTCCTCCTGAAAGTGGCCGG, (SEQ ID NO: 103)
TGCTCATGACGCTGCGGCTGTGG, (SEQ ID NO: 104)
CATCACAGGAACTTTCTAAAAGG, (SEQ ID NO: 105)
GTCGAGAAAAGCTTTGAAACAGG, (SEQ ID NO: 106)
CCACTTTCAGGAGGAGGATTCGG, (SEQ ID NO: 107)
CTGACAGGTTTTGAAAGTTTAGG, (SEQ ID NO: 108)
AGCTTTGAAACAGGTAAGACAGG, (SEQ ID NO: 109)
CTGTGGTCCAGCTGAGGTGAGGG, (SEQ ID NO: 110)
CTGCGGCTGTGGTCCAGCTGAGG, (SEQ ID NO: 111)
TGTGGTCCAGCTGAGGTGAGGGG, (SEQ ID NO: 112)
TCCTCCTCCTGAAAGTGGCCGGG, (SEQ ID NO: 113)
TTAATCTGCTCATGACGCTGCGG, (SEQ ID NO: 114)
ACCCGGCCACTTTCAGGAGGAGG, (SEQ ID NO: 115)
GCTGTGGTCCAGCTGAGGTGAGG, -continued (SEQ ID NO: 116)
CCGAATCCTCCTCCTGAAAGTGG a MegaTAL, a meganuclease that recognizes and cleaves a recognition sequence within residues 93-208 of the wild-type human TCR alpha constant region, wherein said recombinant meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region.

8. The method of claim 7, wherein said meganuclease is a single-chain meganuclease comprising a linker, wherein said linker covalently joins said first subunit and said second subunit.

9. An endonuclease-modified endogenous αβ-TCR negative human cell obtained by the method of claim 1.

10. An endonuclease-modified endogenous αβ-TCR negative human cell obtained by the method of claim 3.

11. The endonuclease-modified endogenous αβ-TCR negative human cell according to claim 9, wherein said CAR is an anti-CD22 CAR, which comprises the amino acid sequence of to SEQ ID NO: 9, SEQ ID NO: 10 or SEQ ID NO: 11.

12. The endonuclease-modified endogenous αβ-TCR negative human cell, according to claim 9, wherein said exogenous polynucleotide comprises a sequence encoding anti-CD123 CAR, which is at least 80% identical to SEQ ID NO: 12.

13. The method of claim 1, wherein said engineered nuclease produces a cleavage at a recognition site within the nucleotide sequence TTGTCCCACAGATATCCAGA ACCCTGACCCTGCCGTGTACCAGCTGAGAGA (SEQ ID NO: 38).

\* \* \* \* \*